(12) United States Patent
Du et al.

(10) Patent No.: US 12,129,223 B2
(45) Date of Patent: Oct. 29, 2024

(54) LIPIDS FOR USE IN LIPID NANOPARTICLE FORMULATIONS

(71) Applicant: Acuitas Therapeutics, Inc., Vancouver (CA)

(72) Inventors: Xinyao Du, Richmond (CA); Steven M. Ansell, Vancouver (CA); Jason Samuel Tan, Vancouver (CA); Polina Blagojevic, Vancouver (CA); Stephen Paul Arns, Vancouver (CA); Julia Gatenyo, Vancouver (CA)

(73) Assignee: Acuitas Therapeutics, Inc., Vancouver (CA)

( * ) Notice: Subject to any disclaimer, the term of this patent is extended or adjusted under 35 U.S.C. 154(b) by 0 days.

(21) Appl. No.: 18/066,954

(22) Filed: Dec. 15, 2022

(65) Prior Publication Data

US 2023/0295075 A1    Sep. 21, 2023

Related U.S. Application Data

(60) Provisional application No. 63/290,398, filed on Dec. 16, 2021.

(51) Int. Cl.
| | |
|---|---|
| *C07C 237/06* | (2006.01) |
| *A61K 9/51* | (2006.01) |
| *A61K 31/7105* | (2006.01) |
| *C07C 237/22* | (2006.01) |
| *C07D 233/64* | (2006.01) |

(52) U.S. Cl.
CPC .......... *C07C 237/06* (2013.01); *A61K 9/5123* (2013.01); *A61K 31/7105* (2013.01); *C07C 237/22* (2013.01); *C07D 233/64* (2013.01); *C07C 2601/04* (2017.05)

(58) Field of Classification Search
CPC .................................................. C07C 237/06
See application file for complete search history.

(56) References Cited

U.S. PATENT DOCUMENTS

| | | |
|---|---|---|
| 2,411,662 A | 11/1946 | Martin |
| 2,856,420 A | 10/1958 | Crawford, Jr. |
| 3,340,299 A | 9/1967 | Weintraub et al. |
| 3,594,224 A | 7/1971 | Blackman |
| 3,729,564 A | 4/1973 | Chang et al. |
| 3,838,991 A | 10/1974 | Garth |
| 3,931,430 A | 1/1976 | Tada et al. |
| 3,951,581 A | 4/1976 | Nakayama et al. |
| 4,121,898 A | 10/1978 | Kirschnek et al. |
| 4,450,282 A | 4/1984 | Ritzer et al. |
| 4,491,583 A | 1/1985 | Cronin et al. |
| 4,639,468 A | 1/1987 | Roncucci et al. |
| 4,687,661 A | 8/1987 | Kikuchi et al. |
| 4,897,355 A | 1/1990 | Eppstein et al. |
| 4,946,787 A | 8/1990 | Eppstein et al. |
| 5,049,386 A | 9/1991 | Eppstein et al. |
| 5,176,996 A | 1/1993 | Hogan et al. |
| 5,420,032 A | 5/1995 | Marshall et al. |
| 5,422,251 A | 6/1995 | Fresco |
| 5,478,860 A | 12/1995 | Wheeler et al. |
| 5,552,157 A | 9/1996 | Yagi et al. |
| 5,653,996 A | 8/1997 | Hsu |
| 5,705,385 A | 1/1998 | Bally et al. |
| 5,744,335 A | 4/1998 | Wolff et al. |
| 5,756,785 A | 5/1998 | O'Lenick, Jr. |
| 5,759,230 A | 6/1998 | Chow et al. |
| 5,789,538 A | 8/1998 | Rebar et al. |
| 5,885,613 A | 3/1999 | Holland et al. |
| 5,919,743 A | 7/1999 | O'Lenick, Jr. |
| 5,925,523 A | 7/1999 | Dove et al. |
| 5,965,542 A | 10/1999 | Wasan et al. |
| 5,976,567 A | 11/1999 | Wheeler et al. |
| 5,981,501 A | 11/1999 | Wheeler et al. |
| 6,007,988 A | 12/1999 | Choo et al. |
| 6,008,336 A | 12/1999 | Hanson et al. |
| 6,013,453 A | 1/2000 | Choo et al. |

(Continued)

FOREIGN PATENT DOCUMENTS

| | | |
|---|---|---|
| CN | 102604115 A | 7/2012 |
| CN | 104876831 A | 9/2015 |

(Continued)

OTHER PUBLICATIONS

American Cancer Society, "Can Cancer Be Prevented?," *Cancer Facts & Figures 2009*, retrieved from www.cancer.org, Feb. 2009.
Akinc et al., "A combinatorial library of lipid-like materials for delivery of RNAi therapeutics," Nature Biotechnology 26(5):561-569, May 2008.
Akinc et al., "Targeted delivery of RNAi therapeutics with endogenous and exogenous ligand- based mechanisms," *Mol. Ther.* 18(7): 1357-1364, 2010.
Alabi et al., "Multiparametric approach for the evaluation of lipid nanoparticles for siRNA delivery," PNAS 110(32): 12881-12886, Aug. 6, 2013.

(Continued)

*Primary Examiner* — Golam M Shameem
(74) *Attorney, Agent, or Firm* — Seed IP Law Group LLP

(57) ABSTRACT

Compounds are provided having the following structure:

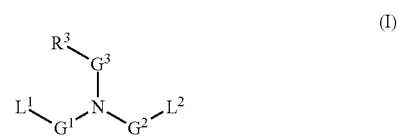

(I)

or a pharmaceutically acceptable salt, tautomer or stereoisomer thereof, wherein $R^3$, $L^1$, $L^2$, $G^1$, $G^2$ and $G^3$ are as defined herein. Use of the compounds as a component of lipid nanoparticle formulations for delivery of a therapeutic agent, compositions comprising the compounds and methods for their use and preparation are also provided.

26 Claims, No Drawings

(56) References Cited

U.S. PATENT DOCUMENTS

| | | |
|---|---|---|
| 6,013,813 A | 1/2000 | O'Lenick, Jr. |
| 6,020,526 A | 2/2000 | Schwartz et al. |
| 6,034,137 A | 3/2000 | Belloni et al. |
| 6,077,509 A | 6/2000 | Weiner et al. |
| 6,093,348 A | 7/2000 | Kowalski et al. |
| 6,107,286 A | 8/2000 | Byk et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,300,321 B1 | 10/2001 | Scherman et al. |
| 6,333,433 B1 | 12/2001 | Banerjee et al. |
| 6,410,248 B1 | 6/2002 | Greisman et al. |
| 6,410,328 B1 | 6/2002 | Maclachlan et al. |
| 6,453,242 B1 | 9/2002 | Eisenberg et al. |
| 6,458,381 B1 | 10/2002 | Sourovoi et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,534,484 B1 | 3/2003 | Wheeler et al. |
| 6,586,410 B1 | 7/2003 | Wheeler et al. |
| 6,599,692 B1 | 7/2003 | Case et al. |
| 6,607,882 B1 | 8/2003 | Cox, III et al. |
| 6,620,794 B1 | 9/2003 | O'Lenick, Jr. et al. |
| 6,689,558 B2 | 2/2004 | Case |
| 6,723,551 B2 | 4/2004 | Kotin et al. |
| 6,794,136 B1 | 9/2004 | Eisenberg et al. |
| 6,815,432 B2 | 11/2004 | Wheeler et al. |
| 6,824,978 B1 | 11/2004 | Cox, III et al. |
| 6,833,252 B1 | 12/2004 | Dujon et al. |
| 6,835,395 B1 | 12/2004 | Semple et al. |
| 6,843,942 B2 | 1/2005 | Katinger et al. |
| 6,858,224 B2 | 2/2005 | Wheeler et al. |
| 6,903,185 B2 | 6/2005 | Kim et al. |
| 6,933,113 B2 | 8/2005 | Case et al. |
| 6,979,539 B2 | 12/2005 | Cox, III et al. |
| 6,986,902 B1 | 1/2006 | Chen et al. |
| 6,989,264 B2 | 1/2006 | Atkinson et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,112,337 B2 | 9/2006 | Huang et al. |
| 7,153,949 B2 | 12/2006 | Kim et al. |
| 7,163,824 B2 | 1/2007 | Cox, III et al. |
| 7,217,509 B2 | 5/2007 | Wolffe et al. |
| 7,253,273 B2 | 8/2007 | Collingwood |
| 7,262,054 B2 | 8/2007 | Jamieson et al. |
| 7,271,002 B2 | 9/2007 | Kotin et al. |
| 7,341,738 B2 | 3/2008 | Semple et al. |
| 7,361,635 B2 | 4/2008 | Miller et al. |
| 7,404,969 B2 | 7/2008 | Chen et al. |
| 7,419,817 B2 | 9/2008 | Chiorini et al. |
| 7,470,781 B2 | 12/2008 | Crouzet et al. |
| 7,641,915 B2 | 1/2010 | Chen et al. |
| 7,691,405 B2 | 4/2010 | Chen et al. |
| 7,745,651 B2 | 6/2010 | Heyes et al. |
| 7,785,792 B2 | 8/2010 | Wolffe et al. |
| 7,799,565 B2 | 9/2010 | MacLachlan et al. |
| 7,803,397 B2 | 9/2010 | Heyes et al. |
| 7,811,602 B2 | 10/2010 | Cullis et al. |
| 7,888,121 B2 | 2/2011 | Urnov et al. |
| 7,893,302 B2 | 2/2011 | Chen et al. |
| 7,901,708 B2 | 3/2011 | MacLachlan et al. |
| 7,914,796 B2 | 3/2011 | Miller et al. |
| 7,923,542 B2 | 4/2011 | Wolffe et al. |
| 7,951,925 B2 | 5/2011 | Ando et al. |
| 7,972,854 B2 | 7/2011 | Miller et al. |
| 7,982,027 B2 | 7/2011 | MacLachlan et al. |
| 8,034,376 B2 | 10/2011 | Manoharan et al. |
| 8,034,598 B2 | 10/2011 | Miller |
| 8,071,370 B2 | 12/2011 | Wolffe et al. |
| 8,110,379 B2 | 2/2012 | DeKelver et al. |
| 8,153,773 B2 | 4/2012 | Jemielity et al. |
| 8,158,601 B2 | 4/2012 | Chen et al. |
| 8,206,747 B2 | 6/2012 | Zale et al. |
| 8,278,036 B2 | 10/2012 | Kariko et al. |
| 8,283,333 B2 | 10/2012 | Yaworski et al. |
| 8,293,276 B2 | 10/2012 | Troiano et al. |
| 8,318,208 B1 | 11/2012 | Zale et al. |
| 8,318,211 B2 | 11/2012 | Zale et al. |
| 8,329,070 B2 | 12/2012 | MacLachlan et al. |
| 8,409,861 B2 | 4/2013 | Guschin et al. |
| 8,466,122 B2 | 6/2013 | Heyes et al. |
| 8,563,314 B2 | 10/2013 | Gregory et al. |
| 8,569,256 B2 | 10/2013 | Heyes et al. |
| 8,575,123 B2 | 11/2013 | Manoharan et al. |
| 8,586,526 B2 | 11/2013 | Gregory et al. |
| 8,597,912 B2 | 12/2013 | Collingwood et al. |
| 8,623,618 B2 | 1/2014 | Doyon et al. |
| 8,642,076 B2 | 2/2014 | Manoharan et al. |
| 8,691,750 B2 | 4/2014 | Constien et al. |
| 8,697,359 B1 | 4/2014 | Zhang |
| 8,703,489 B2 | 4/2014 | Wang |
| 8,722,082 B2 | 5/2014 | Manoharan et al. |
| 8,748,089 B2 | 6/2014 | Kariko et al. |
| 8,754,062 B2 | 6/2014 | De Fougerolles et al. |
| 8,771,985 B2 | 7/2014 | Cui et al. |
| 8,772,453 B2 | 7/2014 | Paschon et al. |
| 8,802,644 B2 | 8/2014 | Chen et al. |
| 8,822,668 B2 | 9/2014 | Yaworski et al. |
| 8,835,108 B2 | 9/2014 | Kariko et al. |
| 8,945,868 B2 | 2/2015 | Collingwood et al. |
| 8,956,828 B2 | 2/2015 | Bonini et al. |
| 8,962,281 B2 | 2/2015 | Doyon et al. |
| 9,005,973 B2 | 4/2015 | Cost et al. |
| 9,012,498 B2 | 4/2015 | Manoharan et al. |
| 9,045,763 B2 | 6/2015 | DeKelver et al. |
| 9,139,554 B2 | 9/2015 | Hope et al. |
| 9,150,847 B2 | 10/2015 | Rebar |
| 9,200,266 B2 | 12/2015 | Wang |
| 9,234,016 B2 | 1/2016 | Gregory et al. |
| 9,254,265 B2 | 2/2016 | Geall et al. |
| 9,255,250 B2 | 2/2016 | Gregory et al. |
| 9,352,042 B2 | 5/2016 | Heyes et al. |
| 9,394,545 B2 | 7/2016 | Miller |
| 9,458,205 B2 | 10/2016 | Gregory et al. |
| 9,604,908 B2 | 3/2017 | Stanton et al. |
| 9,682,922 B2 | 6/2017 | Manoharan et al. |
| 9,737,619 B2 | 8/2017 | Ansell et al. |
| 9,738,593 B2 | 8/2017 | Ansell et al. |
| 9,750,824 B2 | 9/2017 | Kariko et al. |
| 9,770,463 B2 | 9/2017 | Geall et al. |
| 9,795,566 B2 | 10/2017 | Oya et al. |
| 9,801,897 B2 | 10/2017 | Geall et al. |
| 10,106,490 B2 | 10/2018 | Du |
| 10,117,941 B2 | 11/2018 | Manoharan et al. |
| 10,144,725 B2 | 12/2018 | Brown |
| 10,166,298 B2 | 1/2019 | Ansell et al. |
| 10,221,127 B2 | 3/2019 | Du et al. |
| 10,682,374 B2 | 6/2020 | Dong et al. |
| 11,040,112 B2 | 6/2021 | Ansell et al. |
| 11,168,051 B2 | 11/2021 | Du et al. |
| 11,241,490 B2 | 2/2022 | Weissman et al. |
| 11,357,856 B2 | 6/2022 | Ansell et al. |
| 11,453,639 B2 | 9/2022 | Du |
| 11,524,932 B2 * | 12/2022 | Du ................ C07C 229/24 |
| 11,542,225 B2 * | 1/2023 | Du ................ A61K 47/28 |
| 11,583,504 B2 * | 2/2023 | Brader ............ A61K 9/19 |
| 11,597,698 B2 * | 3/2023 | Benenato ........ C07C 229/16 |
| 11,639,329 B2 * | 5/2023 | Du ................ A61K 47/543 |
| | | 514/44 A |
| 2002/0062044 A1 | 5/2002 | Banerjee et al. |
| 2003/0031704 A1 | 2/2003 | Huang et al. |
| 2003/0049310 A1 | 3/2003 | Gao |
| 2003/0073640 A1 | 4/2003 | Beigelman et al. |
| 2003/0077829 A1 | 4/2003 | MacLachlan |
| 2003/0124033 A1 | 7/2003 | Baker et al. |
| 2003/0153081 A1 | 8/2003 | Tagawa et al. |
| 2003/0232410 A1 | 12/2003 | Liljedahl et al. |
| 2004/0002092 A1 | 1/2004 | Arnould et al. |
| 2004/0037874 A1 | 2/2004 | Hong et al. |
| 2004/0142025 A1 | 7/2004 | MacLachlan et al. |

(56) References Cited

U.S. PATENT DOCUMENTS

| | | |
|---|---|---|
| 2004/0142474 A1 | 7/2004 | Mahato et al. |
| 2005/0026157 A1 | 2/2005 | Baltimore et al. |
| 2005/0064474 A1 | 3/2005 | Urnov et al. |
| 2005/0064595 A1 | 3/2005 | MacLachlan et al. |
| 2005/0208489 A1 | 9/2005 | Carroll et al. |
| 2005/0222064 A1 | 10/2005 | Vargeese et al. |
| 2005/0250723 A1 | 11/2005 | Hoerr et al. |
| 2005/0267061 A1 | 12/2005 | Martin |
| 2006/0058249 A1 | 3/2006 | Tong et al. |
| 2006/0063231 A1 | 3/2006 | Li et al. |
| 2006/0078552 A1 | 4/2006 | Arnould et al. |
| 2006/0083780 A1 | 4/2006 | Heyes et al. |
| 2006/0100177 A1 | 5/2006 | Nishimura et al. |
| 2006/0153836 A1 | 7/2006 | Bailly et al. |
| 2006/0188490 A1 | 8/2006 | Hoerr et al. |
| 2006/0188987 A1 | 8/2006 | Guschin et al. |
| 2006/0206949 A1 | 9/2006 | Arnould et al. |
| 2006/0240554 A1 | 10/2006 | Chen et al. |
| 2006/0251620 A1 | 11/2006 | Ivanova et al. |
| 2007/0042031 A1 | 2/2007 | MacLachlan et al. |
| 2007/0117128 A1 | 5/2007 | Smith et al. |
| 2007/0218528 A1 | 9/2007 | Miller |
| 2008/0020058 A1 | 1/2008 | Chen et al. |
| 2008/0025944 A1 | 1/2008 | Hoerr et al. |
| 2008/0131962 A1 | 6/2008 | Miller |
| 2008/0159996 A1 | 7/2008 | Ando et al. |
| 2008/0200417 A1 | 8/2008 | Semple et al. |
| 2008/0249296 A1 | 10/2008 | Chung et al. |
| 2009/0023718 A1 | 1/2009 | Miller et al. |
| 2009/0068164 A1 | 3/2009 | Segal et al. |
| 2009/0086558 A1 | 4/2009 | Do |
| 2009/0136465 A1 | 5/2009 | Merenick et al. |
| 2009/0191259 A1 | 7/2009 | Li et al. |
| 2009/0209037 A1 | 8/2009 | Tagawa et al. |
| 2009/0247608 A1 | 10/2009 | Manoharan et al. |
| 2009/0263407 A1 | 10/2009 | Dande et al. |
| 2009/0285881 A1 | 11/2009 | Dande et al. |
| 2009/0305346 A1 | 12/2009 | Miller |
| 2009/0324584 A1 | 12/2009 | Hoerr et al. |
| 2010/0036115 A1 | 2/2010 | Beigelman et al. |
| 2010/0068285 A1 | 3/2010 | Zale et al. |
| 2010/0068286 A1 | 3/2010 | Troiano et al. |
| 2010/0069426 A1 | 3/2010 | Zale et al. |
| 2010/0087337 A1 | 4/2010 | Dewitt |
| 2010/0104645 A1 | 4/2010 | Ali et al. |
| 2010/0104655 A1 | 4/2010 | Zale et al. |
| 2010/0189729 A1 | 7/2010 | Hoerr et al. |
| 2010/0196492 A1 | 8/2010 | Green et al. |
| 2010/0203076 A1 | 8/2010 | Fotin-Mleczek et al. |
| 2010/0218264 A1 | 8/2010 | Cui et al. |
| 2010/0285112 A1 | 11/2010 | Novobrantseva et al. |
| 2010/0291156 A1 | 11/2010 | Barner et al. |
| 2010/0305196 A1 | 12/2010 | Probst et al. |
| 2010/0324120 A1 | 12/2010 | Chen et al. |
| 2011/0045473 A1 | 2/2011 | De Fougerolles et al. |
| 2011/0091525 A1 | 4/2011 | Heyes et al. |
| 2011/0097720 A1 | 4/2011 | Ciufolini et al. |
| 2011/0145940 A1 | 6/2011 | Voytas et al. |
| 2011/0200582 A1 | 8/2011 | Baryza et al. |
| 2011/0201055 A1 | 8/2011 | Doyon et al. |
| 2011/0250225 A1 | 10/2011 | Fotin-Mleczek et al. |
| 2011/0256175 A1 | 10/2011 | Hope et al. |
| 2011/0262491 A1 | 10/2011 | Keegan et al. |
| 2011/0262527 A1 | 10/2011 | Heyes et al. |
| 2011/0265198 A1 | 10/2011 | Gregory et al. |
| 2011/0274759 A1 | 11/2011 | Troiano et al. |
| 2011/0294717 A1 | 12/2011 | Ali et al. |
| 2011/0301073 A1 | 12/2011 | Gregory et al. |
| 2011/0305727 A1 | 12/2011 | Swanson et al. |
| 2011/0305770 A1 | 12/2011 | Zhao et al. |
| 2011/0311582 A1 | 12/2011 | Manoharan et al. |
| 2011/0311583 A1 | 12/2011 | Manoharan et al. |
| 2012/0004293 A1 | 1/2012 | Zale et al. |
| 2012/0009222 A1 | 1/2012 | Nguyen et al. |
| 2012/0017290 A1 | 1/2012 | Cui et al. |
| 2012/0021043 A1 | 1/2012 | Kramps et al. |
| 2012/0027796 A1 | 2/2012 | Manoharan et al. |
| 2012/0027803 A1 | 2/2012 | Manoharan et al. |
| 2012/0040398 A1 | 2/2012 | Miller |
| 2012/0046478 A1 | 2/2012 | Manoharan et al. |
| 2012/0058144 A1 | 3/2012 | Manoharan et al. |
| 2012/0058188 A1 | 3/2012 | Manoharan et al. |
| 2012/0060230 A1 | 3/2012 | Collingwood et al. |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0172411 A1 | 7/2012 | Heyes et al. |
| 2012/0177724 A1 | 7/2012 | Irvine et al. |
| 2012/0178702 A1 | 7/2012 | Huang et al. |
| 2012/0183602 A1 | 7/2012 | Chen et al. |
| 2012/0195936 A1 | 8/2012 | Rudolph et al. |
| 2012/0202871 A1 | 8/2012 | Heyes et al. |
| 2012/0207845 A1 | 8/2012 | Sung et al. |
| 2012/0225434 A1 | 9/2012 | Ciufolini et al. |
| 2012/0244207 A1 | 9/2012 | Fitzgerald et al. |
| 2012/0251618 A1 | 10/2012 | Schrum et al. |
| 2012/0264810 A1 | 10/2012 | Lin et al. |
| 2012/0276209 A1 | 11/2012 | Cullis et al. |
| 2012/0288541 A1 | 11/2012 | Zale et al. |
| 2012/0295832 A1 | 11/2012 | Constien et al. |
| 2013/0017223 A1 | 1/2013 | Hope et al. |
| 2013/0022649 A1 | 1/2013 | Yaworski et al. |
| 2013/0064894 A1 | 3/2013 | Martin et al. |
| 2013/0108685 A1 | 5/2013 | Kuboyama et al. |
| 2013/0122104 A1 | 5/2013 | Yaworski et al. |
| 2013/0122591 A1 | 5/2013 | Cost et al. |
| 2013/0123338 A1 | 5/2013 | Heyes et al. |
| 2013/0129754 A1 | 5/2013 | Thess et al. |
| 2013/0129811 A1 | 5/2013 | Kuboyama et al. |
| 2013/0137104 A1 | 5/2013 | Cost et al. |
| 2013/0149375 A1 | 6/2013 | Geall |
| 2013/0177639 A1 | 7/2013 | Geall et al. |
| 2013/0177640 A1 | 7/2013 | Geall et al. |
| 2013/0177690 A1 | 7/2013 | Regar |
| 2013/0177983 A1 | 7/2013 | Rebar |
| 2013/0189351 A1 | 7/2013 | Geall |
| 2013/0195968 A1 | 8/2013 | Geall et al. |
| 2013/0195969 A1 | 8/2013 | Geall et al. |
| 2013/0196373 A1 | 8/2013 | Gregory et al. |
| 2013/0202684 A1 | 8/2013 | Geall et al. |
| 2013/0259879 A1 | 10/2013 | Baumhof et al. |
| 2013/0261172 A1 | 10/2013 | Kariko et al. |
| 2013/0266640 A1 | 10/2013 | De Fougerolles et al. |
| 2013/0280283 A1 | 10/2013 | Lorenz et al. |
| 2013/0280305 A1 | 10/2013 | Kuboyama et al. |
| 2013/0295043 A1 | 11/2013 | Kallen et al. |
| 2013/0323269 A1 | 12/2013 | Manoharan et al. |
| 2013/0336998 A1 | 12/2013 | Kallen et al. |
| 2013/0338210 A1 | 12/2013 | Manoharan et al. |
| 2014/0017212 A1 | 1/2014 | Rebar et al. |
| 2014/0030292 A1 | 1/2014 | Franti et al. |
| 2014/0044772 A1 | 2/2014 | MacLachlan et al. |
| 2014/0045913 A1 | 2/2014 | Kuboyama et al. |
| 2014/0120622 A1 | 5/2014 | Gregory et al. |
| 2014/0121393 A1 | 5/2014 | Manoharan et al. |
| 2014/0134260 A1 | 5/2014 | Heyes et al. |
| 2014/0179761 A1 | 6/2014 | Manoharan et al. |
| 2014/0193484 A1 | 7/2014 | Bertholet Girardin et al. |
| 2014/0227346 A1 | 8/2014 | Geall et al. |
| 2014/0242152 A1 | 8/2014 | Geall et al. |
| 2014/0255472 A1 | 9/2014 | Geall et al. |
| 2014/0256785 A1 | 9/2014 | Manoharan et al. |
| 2014/0294937 A1 | 10/2014 | MacLachlan et al. |
| 2014/0295449 A1 | 10/2014 | Ciufolini et al. |
| 2014/0308304 A1 | 10/2014 | Manoharan et al. |
| 2014/0309277 A1 | 10/2014 | Barzya et al. |
| 2014/0323548 A1 | 10/2014 | Budzik et al. |
| 2015/0037326 A1 | 2/2015 | Butler-Ransohoff et al. |
| 2015/0050302 A1 | 2/2015 | Thess |
| 2015/0056705 A1 | 2/2015 | Conway et al. |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |

(56) References Cited

U.S. PATENT DOCUMENTS

| | | |
|---|---|---|
| 2015/0140068 A1 | 5/2015 | Barnett et al. |
| 2015/0159172 A1 | 6/2015 | Miller et al. |
| 2015/0165006 A1 | 6/2015 | Thess et al. |
| 2015/0184195 A1 | 7/2015 | Thess et al. |
| 2015/0203446 A1 | 7/2015 | Manoharan et al. |
| 2015/0218554 A1 | 8/2015 | Thess |
| 2015/0306249 A1 | 10/2015 | Baumhof et al. |
| 2015/0329474 A1 | 11/2015 | Shintou et al. |
| 2015/0335708 A1 | 11/2015 | Kwak et al. |
| 2016/0009637 A1 | 1/2016 | Manoharan et al. |
| 2016/0024474 A1 | 1/2016 | Cost et al. |
| 2016/0095924 A1 | 4/2016 | Hope et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0235864 A1 | 8/2016 | Schlake et al. |
| 2016/0263278 A1 | 9/2016 | Grinstaff et al. |
| 2016/0304883 A1 | 10/2016 | Grund et al. |
| 2016/0326548 A1 | 11/2016 | Cost |
| 2016/0361411 A1 | 12/2016 | Gindy et al. |
| 2017/0027803 A1 | 2/2017 | Agrawal et al. |
| 2017/0029847 A1 | 2/2017 | Thess |
| 2017/0119667 A1 | 5/2017 | Oya et al. |
| 2017/0173080 A1 | 6/2017 | Lee et al. |
| 2017/0211075 A1 | 7/2017 | Lee et al. |
| 2017/0252430 A1 | 9/2017 | Fotin-Mleczek et al. |
| 2017/0266292 A1 | 9/2017 | Luo et al. |
| 2017/0326225 A1 | 11/2017 | Rauch et al. |
| 2018/0044687 A1 | 2/2018 | Thess et al. |
| 2018/0064827 A1 | 3/2018 | Conway et al. |
| 2018/0087072 A1 | 3/2018 | Miller et al. |
| 2018/0125952 A1 | 5/2018 | Fotin-Mleczek et al. |
| 2018/0126003 A1 | 5/2018 | Hoerr |
| 2018/0148727 A1 | 5/2018 | Grund et al. |
| 2018/0185516 A1 | 7/2018 | Ansell et al. |
| 2018/0214537 A1 | 8/2018 | Mutzke et al. |
| 2018/0237786 A1 | 8/2018 | Schlake et al. |
| 2018/0296663 A1 | 10/2018 | Hipp et al. |
| 2018/0303925 A1 | 10/2018 | Weissman et al. |
| 2018/0312545 A1 | 11/2018 | Baumhof et al. |
| 2019/0022247 A1 | 1/2019 | Ansell et al. |
| 2019/0024096 A1 | 1/2019 | Schmid et al. |
| 2019/0160164 A1 | 5/2019 | Rauch et al. |
| 2019/0249219 A1 | 8/2019 | Reichert et al. |
| 2019/0274968 A1 | 9/2019 | Weissman et al. |
| 2020/0046838 A1 | 2/2020 | Ansell et al. |
| 2020/0093936 A1 | 3/2020 | Muzykantov et al. |
| 2020/0121809 A1 | 4/2020 | Hope et al. |
| 2020/0163878 A1 | 5/2020 | Baumhof et al. |
| 2020/0172472 A1 | 6/2020 | Du |
| 2020/0283372 A1 | 9/2020 | Du |
| 2020/0368254 A1 | 11/2020 | Xu et al. |
| 2021/0069336 A1 | 3/2021 | Dong et al. |
| 2021/0107861 A1 | 4/2021 | Ansell et al. |
| 2021/0122702 A1 | 4/2021 | Du |
| 2021/0122703 A1 | 4/2021 | Du |
| 2021/0128488 A1 | 5/2021 | Du |
| 2021/0251898 A1 | 8/2021 | Baumhof et al. |
| 2021/0395188 A1 | 12/2021 | Ansell |
| 2022/0040285 A1 | 2/2022 | Weissman et al. |
| 2022/0072155 A1 | 3/2022 | Ansell et al. |
| 2022/0081392 A1 | 3/2022 | Du et al. |
| 2022/0106257 A1 | 4/2022 | Gatenyo et al. |
| 2022/0204439 A1 | 6/2022 | Du et al. |
| 2022/0273567 A1 | 9/2022 | Barbosa et al. |
| 2023/0097090 A1 | 3/2023 | Tam et al. |

FOREIGN PATENT DOCUMENTS

| | | |
|---|---|---|
| CN | 113387825 A | 9/2021 |
| DE | 707 279 C | 6/1941 |
| DE | 25 15 146 A1 | 10/1976 |
| EP | 0 055 576 A1 | 7/1982 |
| EP | 0 784 056 A1 | 7/1997 |
| EP | 1 013 268 A1 | 6/2000 |
| EP | 1 083 232 B1 | 2/2005 |
| EP | 2 852 381 B1 | 10/2020 |
| FR | 1 386 626 A | 1/1965 |
| GB | 1 277 947 A | 6/1972 |
| GB | 2 338 237 A | 12/1999 |
| JP | S45-38429 B | 12/1970 |
| JP | S49 76939 A | 7/1974 |
| JP | H05-331118 A | 12/1993 |
| JP | H09-255638 A | 9/1997 |
| JP | H10-3643 A | 1/1998 |
| JP | 2001-338416 A | 12/2001 |
| JP | 2003 081776 A | 3/2003 |
| JP | 2004-262867 A | 9/2004 |
| JP | 4681425 B2 | 5/2011 |
| PL | 210 199 B1 | 12/2011 |
| WO | 85/05047 A1 | 11/1985 |
| WO | 87/07183 A1 | 12/1987 |
| WO | 89/07929 A1 | 9/1989 |
| WO | 91/16039 A1 | 10/1991 |
| WO | 95/19431 A1 | 7/1995 |
| WO | 96/06166 A1 | 2/1996 |
| WO | 96/40964 A2 | 12/1996 |
| WO | 97/03939 A1 | 2/1997 |
| WO | 98/16599 A1 | 4/1998 |
| WO | 98/37186 A1 | 8/1998 |
| WO | 98/53057 A1 | 11/1998 |
| WO | 98/53058 A1 | 11/1998 |
| WO | 98/53059 A1 | 11/1998 |
| WO | 98/53060 A1 | 11/1998 |
| WO | 98/54311 A1 | 12/1998 |
| WO | 99/05094 A1 | 2/1999 |
| WO | 99/33493 A1 | 7/1999 |
| WO | 00/27878 A1 | 5/2000 |
| WO | 00/29103 A1 | 5/2000 |
| WO | 00/30444 A1 | 6/2000 |
| WO | 01/05373 A1 | 1/2001 |
| WO | 01/07548 A1 | 2/2001 |
| WO | 01/48233 A1 | 7/2001 |
| WO | 01/60970 A2 | 8/2001 |
| WO | 01/88197 A2 | 11/2001 |
| WO | 02/016536 A1 | 2/2002 |
| WO | 02/43699 A2 | 6/2002 |
| WO | 02/099084 A2 | 12/2002 |
| WO | 03/016496 A2 | 2/2003 |
| WO | 03/053409 A1 | 7/2003 |
| WO | 2004/002453 A1 | 1/2004 |
| WO | 2005/060934 A1 | 7/2005 |
| WO | 2006/138380 A2 | 12/2006 |
| WO | 2007/014275 A2 | 2/2007 |
| WO | 2007/024708 A2 | 3/2007 |
| WO | 2007/107304 A2 | 9/2007 |
| WO | 2008/103276 A2 | 8/2008 |
| WO | 2008/121949 A1 | 10/2008 |
| WO | 2009/086558 A1 | 7/2009 |
| WO | 2009/127060 A1 | 10/2009 |
| WO | 2009/132131 A1 | 10/2009 |
| WO | 2009/146867 A1 | 12/2009 |
| WO | 2010/005721 A2 | 1/2010 |
| WO | 2010/005723 A2 | 1/2010 |
| WO | 2010/005725 A2 | 1/2010 |
| WO | 2010/005726 A2 | 1/2010 |
| WO | 2010/005740 A2 | 1/2010 |
| WO | 2010/021865 A1 | 2/2010 |
| WO | 2010/030763 A2 | 3/2010 |
| WO | 2010/042877 A1 | 4/2010 |
| WO | 2010/048536 A2 | 4/2010 |
| WO | 2010/054384 A1 | 5/2010 |
| WO | 2010/054401 A1 | 5/2010 |
| WO | 2010/054405 A1 | 5/2010 |
| WO | 2010/054406 A1 | 5/2010 |
| WO | 2010/057150 A1 | 5/2010 |
| WO | 2010/062322 A2 | 6/2010 |
| WO | 2010/079430 A1 | 7/2010 |
| WO | 2010/080724 A1 | 7/2010 |
| WO | 2010/088537 A2 | 8/2010 |
| WO | 2010/129709 A1 | 11/2010 |

(56) References Cited

FOREIGN PATENT DOCUMENTS

| | | |
|---|---|---|
| WO | 2011/022460 A1 | 2/2011 |
| WO | 2011/043913 A2 | 4/2011 |
| WO | 2011/075656 A1 | 6/2011 |
| WO | 2011/076807 A2 | 6/2011 |
| WO | 2011/084513 A2 | 7/2011 |
| WO | 2011/084521 A2 | 7/2011 |
| WO | 2011/090965 A1 | 7/2011 |
| WO | 2011/094198 A1 | 8/2011 |
| WO | 2011/106688 A1 | 9/2011 |
| WO | 2011/127255 A1 | 10/2011 |
| WO | 2011/140627 A1 | 11/2011 |
| WO | 2011/141703 A1 | 11/2011 |
| WO | 2011/141705 A1 | 11/2011 |
| WO | 2011/143230 A1 | 11/2011 |
| WO | 2011/149733 A2 | 12/2011 |
| WO | 2011/153120 A1 | 12/2011 |
| WO | 2012/000104 A1 | 1/2012 |
| WO | 2012/006378 A1 | 1/2012 |
| WO | 2012/006380 A2 | 1/2012 |
| WO | 2012/016184 A2 | 2/2012 |
| WO | 2012/019630 A1 | 2/2012 |
| WO | 2012/030901 A1 | 3/2012 |
| WO | 2012/031043 A1 | 3/2012 |
| WO | 2012/031046 A2 | 3/2012 |
| WO | 2012/040184 A2 | 3/2012 |
| WO | 2012/044638 A1 | 4/2012 |
| WO | 2012/054365 A2 | 4/2012 |
| WO | 2012/054923 A2 | 4/2012 |
| WO | 2012/061259 A2 | 5/2012 |
| WO | 2012/068176 A1 | 5/2012 |
| WO | 2012/133737 A1 | 10/2012 |
| WO | 2013/014073 A1 | 1/2013 |
| WO | 2013/016058 A1 | 1/2013 |
| WO | 2013/044008 A2 | 3/2013 |
| WO | 2013/059496 A1 | 4/2013 |
| WO | 2013/086322 A1 | 6/2013 |
| WO | 2013/086354 A1 | 6/2013 |
| WO | 2013/086373 A1 | 6/2013 |
| WO | 2013/143555 A1 | 10/2013 |
| WO | 2014/008334 A1 | 1/2014 |
| WO | 2014/028487 A1 | 2/2014 |
| WO | 2014/089239 A1 | 6/2014 |
| WO | 2014/153163 A1 | 9/2014 |
| WO | 2014/160243 A1 | 10/2014 |
| WO | 2014/160284 A1 | 10/2014 |
| WO | 2015/074085 A1 | 5/2015 |
| WO | 2015/123576 A2 | 8/2015 |
| WO | 2015/130584 A2 | 9/2015 |
| WO | 2015/164674 A1 | 10/2015 |
| WO | 2015/177752 A1 | 11/2015 |
| WO | 2016/010840 A1 | 1/2016 |
| WO | 2016/014794 A1 | 1/2016 |
| WO | 2016/168469 A1 | 10/2016 |
| WO | 2016/176330 A1 | 11/2016 |
| WO | 2016/183298 A1 | 11/2016 |
| WO | 2016/210190 A1 | 12/2016 |
| WO | 2017/004143 A1 | 1/2017 |
| WO | 2017/021546 A1 | 2/2017 |
| WO | 2017/048770 A1 | 3/2017 |
| WO | 2017/049245 A2 | 3/2017 |
| WO | 2017/070616 A3 | 4/2017 |
| WO | 2017/070626 A2 | 4/2017 |
| WO | 2017/072590 A1 | 5/2017 |
| WO | 2017/074526 A1 | 5/2017 |
| WO | 2017/075531 A1 | 5/2017 |
| WO | 2017/112865 A1 | 6/2017 |
| WO | 2017/117528 A1 | 7/2017 |
| WO | 2017/140905 A1 | 8/2017 |
| WO | 2017/173054 A1 | 10/2017 |
| WO | 2017/182634 A1 | 10/2017 |
| WO | 2017/194454 A1 | 11/2017 |
| WO | 2017/201332 A1 | 11/2017 |
| WO | 2018/078053 A1 | 5/2018 |
| WO | 2018/081480 A1 | 5/2018 |
| WO | 2018/081638 A1 | 5/2018 |
| WO | 2018/107026 A1 | 6/2018 |
| WO | 2018/191657 | 10/2018 |
| WO | 2018/191719 | 10/2018 |
| WO | 2018/200943 | 11/2018 |
| WO | 2019/036000 | 2/2019 |
| WO | 2019/089828 | 5/2019 |

OTHER PUBLICATIONS

Alexidis et al., "Novel 1,4 Substituted Piperidine Derivatives. Synthesis and Correlation of Antioxidant Activity with Structure and Lipophilicity," *J. Pharm. Pharmacol.* 47: 131-137, 1995.
Anderson et al., "Incorporation of pseudouridine into mRNA enhances translation by diminishing PKR activation," *Nucleic Acids Res.* 38(17):5884-5892, 2010.
Anderson et al., "Nucleoside modifications in RNA limit activation of 2'-5'-oligoadenylate synthetase and increase resistance to cleavage by RNase L.," *Nucleic Acids Research* 39(21):9329-9338, 2011.
Ansell et al., "Application of Oligo-(14-amino-3,6,9,12-tetraoxatetradecanoic acid) Lipid Conjugates as Steric Barrier Molecules in Liposomal Formulations," *Bioconjugate Chem.* 10:653-666, 1999.
Aroua et al., "C60 Pyrrolidine Bis-carboxylic Acid Derivative as a Versatile Precursor for Biocompatible Fullerenes," *Org. Lett.* 16:1688-1691, 2014.
Aroua et al., "Essential Factors for Control of the Equilibrium in the Reversible Rearrangement of $M_3N@I_n$-$C_{80}$ Fulleropyrrolidines: Exohedral Functional Groups versus Endohedral Metal Clusters," *Chem. Eur. J.* 20:14032-14039, 2014. (with Supporting Information).
Basha et al., "Influence of cationic lipid composition on gene silencing properties of lipid nanoparticle formulations of siRNA in antigen-presenting cells," *Mol. Ther.* 19(12):2186-2200, 2011.
Belliveau et al., "Microfluidic Synthesis of Highly Potent Limit-size Lipid Nanoparticles for In Vivo Delivery of siRNA," *Mol. Ther. Nucleic Acids* 1:e37, 2012 (9 pages).
Bhattacharya et al., "Synthesis, Thermotropic Behavior, and Permeability Properties of Vesicular Membranes Composed of Cationic Mixed-Chain Surfactants," *Langmuir* 11:4748-4757, 1995.
Brito et al., "A Cationic Nanoemulsion for the Delivery of Next-generation RNA Vaccines," *Molecular Therapy* 22(12): 2118-2129, 2014.
Bruner et al., "3,5,5-Trimethylhexanol and Its Derivatives," *Industrial & Engineering Chemistry* 41(12):2860-2864, Jan. 1949. (5 pages).
CAS Registry No. 87973-08-8, Nov. 16, 1984, 1 page.
CAS Registry No. 92829-26-0, Dec. 17, 1984, 1 page.
CAS Registry No. 719993-61-0, Jul. 30, 2004, 1 page.
CAS Registry No. 745775-87-5, Sep. 16, 2004, 1 page.
CAS Registry No. 749830-60-2, Sep. 23, 2004, 1 page.
CAS Registry No. 1851849-79-0, Jan. 24, 2016, 1 page.
CAS Registry No. 1872489-33-2, Feb. 24, 2016, 1 page.
Cattanach et al., "Studies in the Indole Series. Part IV. Tetrahydro-1H-pyrido[4,3-b]-indoles as Serotonin Antagonists," *J. Chem Soc.* (C): 1235-1243, 1968.
Chaves et al., "A novel tripodal tris-hydroxypyrimidinone sequestering agent for trivalent hard metal ions: synthesis, complexation and in vivo studies," *Dalton Transactions* 42(17):6033-6045, 2013.
Chen et al., "Influence of particle size on the in vivo potency of lipid nanoparticle formulations of siRNA," *Journal of Controlled Release* 235:236-244, 2016.
Chen et al., "Rapid Discovery of Potent siRNA-Containing Lipid Nanoparticles Enabled by Controlled Microfluidic Formulation," *J. Am. Chem. Soc.* 134:6948-6951, 2012.
Chevalier et al., "Design, Activity, and Structure of a Highly Specific Artificial Endonuclease," *Molecular Cell* 10:895-905, 2002.
Choo et al., "Advances in Zinc Finger Engineering," *Current Opinion in Structural Biology* 10:411-416, 2000.
Cook et al., "Synthesis and Characterization of cis-Dioxomolybdenum(VI) Complexes with Sterically Bulky Tripodal Tetradentate Ligands," *Inorganica Chimica Acta* 144:81-87, 1988.

(56) References Cited

OTHER PUBLICATIONS

Durbin et al., "RNAs Containing Modified Nucleotides Fail to Trigger RIG-I Conformational Changes for Innate Immune Signaling," *mBio* 7(5):e00833-16, 2016 (11 pages).
Ernsting et al., "Factors controlling the pharmacokinetics, biodistribution and intratumoral penetration of nanoparticles," *Journal of Controlled Release* 172:782-794, 2013.
Fagerlund et al., "The Cpf1 CRISPR-Cas Protein Expands Genome-Editing Tools," *Genom Bio* 16:251, 2015 (3 pages).
Falcone et al., "Both the 5' Untranslated Region and the Sequences Surrounding the Start Site Contribute to Efficient Initiation of Translation In Vitro," *Molecular and Cellular Biology* 11(5):2656-2664, 1991.
Frisch et al. "A New Triantennary Galactose-Targeted PEGylated Gene Carrier, Characterization of Its Complex with DNA, and Transfection of Hepatoma Cells," *Bioconjugate Chem.* 15: 754-764, 2004.
Gronquist et al., "Synthesis of Unsaturated Polyazamacrolides from the Ladybird Beetle *Subcoccinella vigintiquatuorpunctata*," J. Org. Chem. 66:1075-1081, 2001.
Haft et al., "A Guild of 45 CRISPR-Associated (Cas) Protein Families and Multiple CRISPR/Cas Subtypes Exist in Prokaryotic Genomes," *PLoS Computational Biology* 1(6):e60, 2005.
Han et al., "Synthesis and Properties of Di-Chain Esterquat Surfactants," *J. Surfact Deterg.* 18: 91- 95, 2015.
Hancock et al., "Monoalkylaminopropanols and Butanols and their Esters," *J. Am. Chem. Soc.* 66(10):1738-1747, 1944.
Hekele et al., "Rapidly produced SAM® vaccine against H7N9 influenza is immunogenic in mice," *Emerging Microbes and Infections* 2:e52, 2013 (7 pages).
Heuer et al., "Repeat Domain Diversity of avrBs3-Like Genes in Ralstonia Solancearum Strains and Association with Host Preferences in the Field," *Applied and Environmental Microbiology* 73(13):4379-4384, 2007.
Higashi et al., "Novel lipidated sorbitol-based molecular transporters for non-viral gene delivery," *Journal of Controlled Release* 136:140-147, 2009.
Jasin, "Genetic Manipulation of Genomes with Rare-Cutting Endonucleases," *Trends Genet* 12:224-228, 1996.
Jayaraman et al., "Maximizing the Potency of siRNA Lipid Nanoparticles for Hepatic Gene Silencing In Vivo," *Angew. Chem. Int. Ed.* 51(34):8529-8533, XP055063645, 2012.
Karikó et al., "Incorporation of Pseudouridine into mRNA Yields Superior Nonimmunogenic Vector With Increased Translational Capacity and Biological Stability," *Mol. Ther.* 16(11):1833- 1840, 2008.
Karikó et al., "Increased Erythropoiesis in Mice Injected with Submicrogram Quantities of Pseudouridine-containing mRNA Encoding Erythropoietin," *Mol. Ther.* 20(5):948-953, 2012.
Karikó et al., "Suppression of RNA Recognition by Toll-like Receptors: The Impact of Nucleoside Modification and the Evolutionary Origin of RNA," *Immunity* 23:165-175, 2005.
Kay et al., "A Bacterial Effector Acts as a Plant Transcription Factor and Induces a Cell Size Regulator," *Science* 318:648-651, 2007.
Kim et al., "Hybrid restriction enzymes: zinc finger fusions to Fok I cleavage domain," *PNAS USA* 93(3): 1156-1160, 1996.
Kim et al., "Highly Efficient RNA-Guided Genome Editing in Human Cells via Delivery of Purified Cas9 Ribonucleoproteins," *Genome Research* 24(6): 1012-1019, 2014.
Kim et al., "Synthesis of Novel Poly(amido ethylenimine) (PAMEIM) Dendrimer and Its Self-assembly with Plasmid DNA," *Bull. Korean Chem. Soc.* 27(11): 1894-1896, 2006.
Lee et al., "Lipid nanoparticle siRNA systems for silencing the androgen receptor in human prostate cancer in vivo," *Int. J. Cancer* 131(5):E781-E790, 2012.
Leriche et al., "Investigation of Dendriplexes by Ion Mobility-Mass Spectrometry," *Molecules* 19(12):20731-20750, Dec. 12, 2014.
Leroueil et al., "Wide Varieties of Cationic Nanoparticles Induce Defects in Supported Lipid Bilayers," *Nano Letters* 8(2):420-424, 2008.
Leung et al., "Lipid Nanoparticles Containing siRNA Synthesized by Microfluidic Mixing Exhibit an Electron-Dense Nanostructured Core," *J. Phys. Chem. C. Nanomater. Interfaces* 116(34):18440-18450, 2012.
Leung et al., "Microfluidic Mixing: A General Method for Encapsulating Macromolecules in Lipid Nanoparticle Systems," *J. Phys. Chem. B* 119:8698-8706, 2015.
Li et al., "ATRP in Waterborne Miniemulsion via a Simultaneous Reverse and Normal Initiation Process," *Macromolecules* 37(6): 2106-2112, 2004.
Mahon et al., "A combinatorial approach to determine functional group effects on lipidoid- mediated siRNA delivery," *Bioconjug Chem.* 21(8): 1448-1454, 2010. (17 pages).
Maier et al., "Biodegradable lipids enabling rapidly eliminated lipid nanoparticles for systemic delivery of RNAi therapeutics," *Mol. Ther.* 21(8): 1570-1578, 2013.
Makarova et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," *Biology Direct* 1:7, 2006.
Marchi-Artzner et al., "Adhesion of Arg-Gly-Asp (RGD) Peptide Vesicles onto an Integrin Surface: Visualization of the Segregation of RGD Ligands into the Adhesion Plaques by Fluorescence," *Langmuir* 19:835-841, 2003.
Masuda et al., "Envelope-type lipid nanoparticles incorporating a short PEG-lipid conjugate for improved control of intracellular trafficking and transgene transcription," *Biomaterials* 30:4806- 4814, 2009.
Mendonça et al., "New tris-3,4-HOPO lanthanide complexes as potential imaging probes: complex stability and magnetic properties," *Dalton Transactions* 42(17):6046-6057, 2013.
Mui et al., "Influence of Polyethylene Glycol Lipid Desorption Rates on Pharmacokinetics and Pharmacodynamics of siRNA Lipid Nanoparticles," *Mol. Ther. Nucleic Acids* 2:e139, 2013 (8 pages).
Nguyen et al., "Lipid-derived nanoparticles for immunostimulatory RNA adjuvant delivery", Proceedings of the National Academy of Sciences 109(14): E797-E803, 2012.
Nishida, "Disk-shaped magnetic recording medium," Caplus Database, Accession No. 2001:881906, 2001 (1 page).
Pabo et al., "Design and Selection of Novel Cys2-His2 Zinc Finger Proteins," *Ann. Rev. Biochem.* 70:313-340, 2001.
Pardi et al., "Expression kinetics of nucleoside-modified mRNA delivered in lipid nanoparticles to mice by various routes," *Journal of Controlled Release* 217:345-351, 2015.
Patani et al., "Bioisosterism: A Rational Approach in Drug Design," *Chem. Rev.* 96(8):3147-3176, 1996.
Petsch et al., "Protective efficacy of in vitro synthesized, specific mRNA vaccines against influenza A virus infection," *Nature Biotechnology* 30(12): 1210-1216, 2012 (9 pages).
Perler et al., "Protein splicing elements: inteins and exteins a definition of terms and recommended nomenclature," *Nucleic Acids Research* 22:1125-1127, 1994.
Rajesh et al., "Dramatic Influence of the Orientation of Linker between Hydrophilic and Hydrophobic Lipid Moiety in Liposomal Gene Delivery," *Journal of the American Chemical Society* 129(37): 11408-11420, 2007.
Reed et al., "Behavior of Plasticizers in Vinyl Chloride-Acetate Resins," *Industrial & Engineering Chemistry* 35:896-904, Aug. 1943. (9 pages).
Russell et al., "The Stability of Human 8-Globin mRNA is Dependent on Structural Determinants Positioned Within Its 3' Untranslated Region," *Blood* 87:5314-5323, 1996.
Santo et al., "Hydrogen bonding interactions between Starburst dendrimers and several molecules of biological interest," *J Phys Org Chem* 12(4):293-307, Apr. 1999.
Schar et al., "Long Chain Linear Fatty Alcohols from ZIEGLER-Synthesis, their Mixtures, Derivatives and Use," IP.com Prior Art Database Technical Disclosure, Jan. 17, 2011, 39 pages.
Schnee et al., "An mRNA Vaccine Encoding Rabies Virus Glycoprotein Induces Protection against Lethal Infection in Mice and Correlates of Protection in Adult and Newborn Pigs," *PLoS Negl. Trop. Dis.* 10(6): e0004746, 2016 (20 pages).

(56) References Cited

OTHER PUBLICATIONS

Semple et al., "Interactions of liposomes and lipid-based carrier systems with blood proteins: Relation to clearance behaviour in vivo," Advanced Drug Delivery Reviews 32:3-17, 1998.
Semple et al., "Rational design of cationic lipids for siRNA delivery," *Nature Biotechnology* 28(2): 172-176, 2010. (26 pages).
Szebeni et al., "Activation of complement by therapeutic liposomes and other lipid excipient-based therapeutic products: Prediction and prevention," *Advanced Drug Delivery Reviews* 63:1020-1030, 2011.
Szebeni et al., "Complement activation as a bioequivalence issue relevant to the development of generic liposomes and other nanoparticulate drugs," *Biochemical and Biophysical Research Communications* 468:490-497, 2015.
Szebeni, "Complement activation-related pseudoallergy: A stress reaction in blood triggered by nanomedicines and biologicals," *Molecular Immunology* 61:163-173, 2014.
Szolcsányi et al., "Short racemic syntheses of calvine and epicalvine," *Tetrahedron Letters* 49:1357-1360, 2008.
Tam et al., "Advances in Lipid Nanoparticles for siRNA Delivery," *Pharmaceutics* 5:498-507, 2013.
Tam et al., "Small molecule ligands for enhanced intracellular delivery of lipid nanoparticle formulations of siRNA," *Nanomedicine* 9(5):665-674, 2013.
Tas et al., "Poly(methyl methacrylate) Copolymers Containing Multiple, Pendent Plasticizing Groups," *Journal of Polymer Science: Part A: Polymer Chemistry* 48(11):2302-2310, Jun. 2010. (10 pages).
Tekmira Pharmaceuticals Corp, Form 20-F, Edgar Online, filed Mar. 27, 2013, 298 pages.
Tekmira, "Tekmira and Alnylam Restructure Relationship and Settle All Litigation," Tekmira Pharmaceuticals Corporation, Nov. 12, 2012, 3 pages.
Torrecilla et al., "Lipid Nanoparticles as Carriers for RNAi against Viral Infections: Current Status and Future Perspectives," BioMed Research International 2014: Article ID 161794, 17 pages.
Van Doren et al., "Structure-Property Relationships in D-Glucitol Derivatives with Two Geminal Hydrocarbon Chains," J. Mater. Chem. 5(12):2153-2160, 1995.
Vanderah et al., "Oligo(ethylene oxide) Self-Assembled Monolayers with Self-Limiting Packing Densities for the Inhibition of Nonspecific Protein Adsorption," *Langmuir* 25(9):5026-5030, 2009.
Vogel et al., "A Bacterial Seek-and-Destroy System for Foreign DNA," *Science* 344(6187): 972-73, 2014.
Wang et al., "Composite Nanoparticles for Gene Delivery," *Adv. Genet.* 88:111-137, 2014.
Whitehead et al., "Synergistic Silencing: Combinations of Lipid-like Materials for Efficacious siRNA Delivery," *Molecular Therapy* 19(9): 1688-1694, 2011.
Wilson et al., "The Combination of Stabilized Plasmid Lipid Particles and Lipid Nanoparticle Encapsulated CpG Containing Oligodeoxynucleotides as Systemic Genetic Vaccine," *The Journal of Gene Medicine* 11(1): 14-25, 2009.
Xue et al., "Lipid-Based Nanocarriers for RNA Delivery," *Current Pharmaceutical Design* 21:3140-3147, 2015.
Yoshimura et al., "Solution Properties of Tadpole-type Cationic Amphiphilic Dendrimers Consisting of an Alkyl Chain, a Quaternary Ammonium, and a Poly(amidoamine) Dendron," Journal of Oleo Science 62(4):213-221, 2013.
Zhang et al., "Fighting against Skin Aging: The Way from Bench to Bedside," *Cell Transplantation* 27(5): 729-738, 2018.
Zhang et al., "Biodegradable Amino-Ester Nanomaterials for Cas9 mRNA Delivery in Vitro and in Vivo," ACS *Appl. Mater. Interfaces* 9(30): 25481-25487, 2017. (15 pages).
Zhang et al., "Lipid-modified spermine derivatives and liposome prepared with said derivatives," Caplus Database, Accession No. 2015:1437089, 2015. (2 pages).

* cited by examiner

LIPIDS FOR USE IN LIPID NANOPARTICLE FORMULATIONS

BACKGROUND

Technical Field

Embodiments of the present invention generally relate to novel lipids that can be used in combination with other lipid components, such as neutral lipids, cholesterol and polymer conjugated lipids, to form lipid nanoparticles for delivery of therapeutic agents, such as nucleic acids (e.g., oligonucleotides, messenger RNA), both in vitro and in vivo.

Description of the Related Art

There are many challenges associated with the delivery of nucleic acids to affect a desired response in a biological system. Nucleic acid based therapeutics have enormous potential but there remains a need for more effective delivery of nucleic acids to appropriate sites within a cell or organism in order to realize this potential. Therapeutic nucleic acids include, e.g., messenger RNA (mRNA), antisense oligonucleotides, ribozymes, DNAzymes, plasmids, immune stimulating nucleic acids, antagomir, antimir, mimic, supermir, and aptamers. Some nucleic acids, such as mRNA or plasmids, can be used to effect expression of specific cellular products as would be useful in the treatment of, for example, diseases related to a deficiency of a protein or enzyme. The therapeutic applications of translatable nucleotide delivery are extremely broad as constructs can be synthesized to produce any chosen protein sequence, whether or not indigenous to the system. The expression products of the nucleic acid can augment existing levels of protein, replace missing or non-functional versions of a protein, or introduce new protein and associated functionality in a cell or organism.

Some nucleic acids, such as miRNA inhibitors, can be used to effect expression of specific cellular products that are regulated by miRNA as would be useful in the treatment of, for example, diseases related to deficiency of protein or enzyme. The therapeutic applications of miRNA inhibition are extremely broad as constructs can be synthesized to inhibit one or more miRNA that would in turn regulate the expression of mRNA products. The inhibition of endogenous miRNA can augment its downstream target endogenous protein expression and restore proper function in a cell or organism as a means to treat disease associated to a specific miRNA or a group of miRNA.

Other nucleic acids can down-regulate intracellular levels of specific mRNA and, as a result, down-regulate the synthesis of the corresponding proteins through processes such as RNA interference (RNAi) or complementary binding of antisense RNA. The therapeutic applications of antisense oligonucleotide and RNAi are also extremely broad, since oligonucleotide constructs can be synthesized with any nucleotide sequence directed against a target mRNA. Targets may include mRNAs from normal cells, mRNAs associated with disease-states, such as cancer, and mRNAs of infectious agents, such as viruses. To date, antisense oligonucleotide constructs have shown the ability to specifically down-regulate target proteins through degradation of the cognate mRNA in both in vitro and in vivo models. In addition, antisense oligonucleotide constructs are currently being evaluated in clinical studies.

However, two problems currently face the use of oligonucleotides in therapeutic contexts. First, free RNAs are susceptible to nuclease digestion in plasma. Second, free RNAs have limited ability to gain access to the intracellular compartment where the relevant translation machinery resides. Lipid nanoparticles formed from lipids formulated with other lipid components, such as neutral lipids, cholesterol, PEG, PEGylated lipids, and oligonucleotides have been used to block degradation of the RNAs in plasma and facilitate the cellular uptake of the oligonucleotides.

There remains a need for improved lipids and lipid nanoparticles for the delivery of oligonucleotides. Preferably, these lipid nanoparticles would provide optimal drug:lipid ratios, protect the nucleic acid from degradation and clearance in serum, be suitable for systemic or local delivery, and provide intracellular delivery of the nucleic acid. In addition, these lipid-nucleic acid particles should be well-tolerated and provide an adequate therapeutic index, such that patient treatment at an effective dose of the nucleic acid is not associated with unacceptable toxicity and/or risk to the patient. The present invention provides these and related advantages.

BRIEF SUMMARY

In brief, embodiments of the present invention provide lipid compounds, including stereoisomers, pharmaceutically acceptable salts, prodrugs or tautomers thereof, which can be used alone or in combination with other lipid components such as neutral lipids, charged lipids, steroids (including for example, all sterols) and/or their analogs, and/or polymer conjugated lipids to form lipid nanoparticles for the delivery of therapeutic agents. In some instances, the lipid nanoparticles are used to deliver nucleic acids such as antisense and/or messenger RNA. Methods for use of such lipid nanoparticles for treatment of various diseases or conditions, such as those caused by infectious entities and/or insufficiency of a protein, are also provided.

In one embodiment, compounds having the following structure (I) are provided:

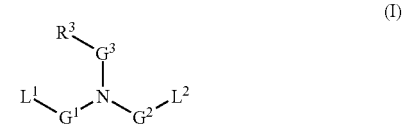

or a pharmaceutically acceptable salt, tautomer, prodrug or stereoisomer thereof, wherein $R^3$, $L^1$, $L^2$, $G^1$, $G^2$, and $G^3$ are as defined herein.

Pharmaceutical compositions comprising one or more of the foregoing compounds of structure (I) and a therapeutic agent are also provided. Also provided are lipid nanoparticles (LNPs) comprising one or more compounds of structure (I). In some embodiments, the pharmaceutical compositions and/or LNPs further comprise one or more components selected from neutral lipids, charged lipids, steroids and polymer conjugated lipids. The disclosed compositions are useful for formation of lipid nanoparticles for the delivery of the therapeutic agent.

In other embodiments, the present invention provides a method for administering a therapeutic agent to a patient in need thereof, the method comprising preparing a composition of lipid nanoparticles comprising the compound of structure (I) and a therapeutic agent and delivering the composition to the patient. In some embodiments the method for administering a therapeutic agent to a patient in need thereof comprises administering an LNP comprising one or more compounds of structure (I) and the therapeutic agent to the patient.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that embodiments of the invention may be practiced without these details.

Embodiments of the present invention are based, in part, upon the discovery of novel lipids that provide advantages when used in lipid nanoparticles for the in vivo delivery of an active or therapeutic agent such as a nucleic acid into a cell of a mammal. In particular, embodiments the present invention provides nucleic acid-lipid nanoparticle compositions comprising one or more of the novel lipids described herein that provide increased activity of the nucleic acid and improved tolerability of the compositions in vivo, resulting in a significant increase in the therapeutic index as compared to nucleic acid-lipid nanoparticle compositions previously described. For example, embodiments provide a lipid nanoparticle comprising one or more compounds of structure (I).

In particular embodiments, the present invention provides novel lipids that enable the formulation of improved compositions for the in vitro and in vivo delivery of mRNA and/or other oligonucleotides. In some embodiments, these improved lipid nanoparticle compositions are useful for expression of protein encoded by mRNA. In other embodiments, these improved lipid nanoparticles compositions are useful for upregulation of endogenous protein expression by delivering miRNA inhibitors targeting one specific miRNA or a group of miRNA regulating one target mRNA or several mRNA. In other embodiments, these improved lipid nanoparticle compositions are useful for down-regulating (e.g., silencing) the protein levels and/or mRNA levels of target genes. In some other embodiments, the lipid nanoparticles are also useful for delivery of mRNA and plasmids for expression of transgenes. In yet other embodiments, the lipid nanoparticle compositions are useful for inducing a pharmacological effect resulting from expression of a protein, e.g., increased production of red blood cells through the delivery of a suitable erythropoietin mRNA, or protection against infection through delivery of mRNA encoding for a suitable antigen or antibody.

The lipid nanoparticles and compositions of embodiments of the present invention may be used for a variety of purposes, including the delivery of encapsulated or associated (e.g., complexed) therapeutic agents such as nucleic acids to cells, both in vitro and in vivo. Accordingly, embodiments of the present invention provide methods of treating or preventing diseases or disorders in a subject in need thereof by contacting the subject with a lipid nanoparticle that encapsulates or is associated with a suitable therapeutic agent, wherein the lipid nanoparticle comprises one or more of the novel lipids described herein.

As described herein, embodiments of the lipid nanoparticles of the present invention are particularly useful for the delivery of nucleic acids, including, e.g., mRNA, antisense oligonucleotide, plasmid DNA, microRNA (miRNA), miRNA inhibitors (antagomirs/antimirs), messenger-RNA-interfering complementary RNA (micRNA), DNA, multivalent RNA, dicer substrate RNA, complementary DNA (cDNA), etc. Therefore, the lipid nanoparticles and compositions of embodiments of the present invention may be used to induce expression of a desired protein both in vitro and in vivo by contacting cells with a lipid nanoparticle comprising one or more novel lipids described herein, wherein the lipid nanoparticle encapsulates or is associated with a nucleic acid that is expressed to produce the desired protein (e.g., a messenger RNA or plasmid encoding the desired protein) or inhibit processes that terminate expression of mRNA (e.g., miRNA inhibitors). Alternatively, the lipid nanoparticles and compositions of embodiments of the present invention may be used to decrease the expression of target genes and proteins both in vitro and in vivo by contacting cells with a lipid nanoparticle comprising one or more novel lipids (e.g., a compound of structure (I)) described herein, wherein the lipid nanoparticle encapsulates or is associated with a nucleic acid that reduces target gene expression (e.g., an antisense oligonucleotide or small interfering RNA (siRNA)). The lipid nanoparticles and compositions of embodiments of the present invention may also be used for co-delivery of different nucleic acids (e.g., mRNA and plasmid DNA) separately or in combination, such as may be useful to provide an effect requiring colocalization of different nucleic acids (e.g., mRNA encoding for a suitable gene modifying enzyme and DNA segment(s) for incorporation into the host genome).

Nucleic acids for use with embodiments of this invention may be prepared according to any available technique. For mRNA, the primary methodology of preparation is, but not limited to, enzymatic synthesis (also termed in vitro transcription) which currently represents the most efficient method to produce long sequence-specific mRNA. In vitro transcription describes a process of template-directed synthesis of RNA molecules from an engineered DNA template comprised of an upstream bacteriophage promoter sequence (e.g., including but not limited to that from the T7, T3 and SP6 coliphage) linked to a downstream sequence encoding the gene of interest. Template DNA can be prepared for in vitro transcription from a number of sources with appropriate techniques which are well known in the art including, but not limited to, plasmid DNA and polymerase chain reaction amplification (see Linpinsel, J. L and Conn, G. L., General protocols for preparation of plasmid DNA template and Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012)

Transcription of the RNA occurs in vitro using the linearized DNA template in the presence of the corresponding RNA polymerase and adenosine, guanosine, uridine and cytidine ribonucleoside triphosphates (rNTPs) under conditions that support polymerase activity while minimizing potential degradation of the resultant mRNA transcripts. In vitro transcription can be performed using a variety of commercially available kits including, but not limited to RiboMax Large Scale RNA Production System (Promega), MegaScript Transcription kits (Life Technologies) as well as with commercially available reagents including RNA polymerases and rNTPs. The methodology for in vitro transcription of mRNA is well known in the art. (see, e.g., Losick, R., 1972, In vitro transcription, Ann Rev Biochem v. 41 409-46; Kamakaka, R. T. and Kraus, W. L. 2001. In Vitro Transcription. Current Protocols in Cell Biology. 2:11.6:11.6.1-11.6.17; Beckert, B. And Masquida, B., (2010) Synthesis of RNA by In Vitro Transcription in RNA in Methods in Molecular Biology v. 703 (Neilson, H. Ed), New York, N.Y.

Humana Press, 2010; Brunelle, J. L. and Green, R., 2013, Chapter Five—In vitro transcription from plasmid or PCR-amplified DNA, Methods in Enzymology v. 530, 101-114; all of which are incorporated herein by reference).

The desired in vitro transcribed mRNA is then purified from the undesired components of the transcription or associated reactions (including unincorporated rNTPs, protein enzyme, salts, short RNA oligos, etc.). Techniques for the isolation of the mRNA transcripts are well known in the art. Well known procedures include phenol/chloroform extraction or precipitation with either alcohol (ethanol, isopropanol) in the presence of monovalent cations or lithium chloride. Additional, non-limiting examples of purification procedures which can be used include size exclusion chromatography (Lukav sky, P. J. and Puglisi, J. D., 2004, Large-scale preparation and purification of polyacrylamide-free RNA oligonucleotides, RNA v. 10, 889-893), silica-based affinity chromatography and polyacrylamide gel electrophoresis (Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012). Purification can be performed using a variety of commercially available kits including, but not limited to SV Total Isolation System (Promega) and In Vitro Transcription Cleanup and Concentration Kit (Norgen Biotek).

Furthermore, while reverse transcription can yield large quantities of mRNA, the products can contain a number of aberrant RNA impurities associated with undesired polymerase activity which may need to be removed from the full-length mRNA preparation. These include short RNAs that result from abortive transcription initiation as well as double-stranded RNA (dsRNA) generated by RNA-dependent RNA polymerase activity, RNA-primed transcription from RNA templates and self-complementary 3' extension. It has been demonstrated that these contaminants with dsRNA structures can lead to undesired immunostimulatory activity through interaction with various innate immune sensors in eukaryotic cells that function to recognize specific nucleic acid structures and induce potent immune responses. This in turn, can dramatically reduce mRNA translation since protein synthesis is reduced during the innate cellular immune response. Therefore, additional techniques to remove these dsRNA contaminants have been developed and are known in the art including but not limited to scaleable HPLC purification (see, e.g., Kariko, K., Muramatsu, H., Ludwig, J. And Weissman, D., 2011, Generating the optimal mRNA for therapy: HPLC purification eliminates immune activation and improves translation of nucleoside-modified, protein-encoding mRNA, Nucl Acid Res, v. 39 e142; Weissman, D., Pardi, N., Muramatsu, H., and Kariko, K., HPLC Purification of in vitro transcribed long RNA in Synthetic Messenger RNA and Cell Metabolism Modulation in Methods in Molecular Biology v. 969 (Rabinovich, P. H. Ed), 2013). HPLC purified mRNA has been reported to be translated at much greater levels, particularly in primary cells and in vivo.

A significant variety of modifications have been described in the art which are used to alter specific properties of in vitro transcribed mRNA, and improve its utility. These include, but are not limited to modifications to the 5' and 3' termini of the mRNA. Endogenous eukaryotic mRNA typically contain a cap structure on the 5'-end of a mature molecule which plays an important role in mediating binding of the mRNA Cap Binding Protein (CBP), which is in turn responsible for enhancing mRNA stability in the cell and efficiency of mRNA translation. Therefore, highest levels of protein expression are achieved with capped mRNA transcripts. The 5'-cap contains a 5'-5'-triphosphate linkage between the 5'-most nucleotide and guanine nucleotide. The conjugated guanine nucleotide is methylated at the N7 position. Additional modifications include methylation of the ultimate and penultimate most 5'-nucleotides on the 2'-hydroxyl group.

Multiple distinct cap structures can be used to generate the 5'-cap of in vitro transcribed synthetic mRNA. 5'-capping of synthetic mRNA can be performed co-transcriptionally with chemical cap analogs (i.e. capping during in vitro transcription). For example, the Anti-Reverse Cap Analog (ARCA) cap contains a 5'-5'-triphosphate guanine-guanine linkage where one guanine contains an N7 methyl group as well as a 31-O-methyl group. However, up to 20% of transcripts remain uncapped during this co-transcriptional process and the synthetic cap analog is not identical to the 5'-cap structure of an authentic cellular mRNA, potentially reducing translatability and cellular stability. Alternatively, synthetic mRNA molecules may also be enzymatically capped post-transcriptionally. These may generate a more authentic 5'-cap structure that more closely mimics, either structurally or functionally, the endogenous 5'-cap which have enhanced binding of cap binding proteins, increased half-life, reduced susceptibility to 5' endonucleases, and/or reduced 5' decapping. Numerous synthetic 5'-cap analogs have been developed and are known in the art to enhance mRNA stability and translatability (see, e.g., Grudzien-Nogalska, E., Kowalska, J., Su, W., Kuhn, A. N., Slepenkov, S. V., Darynkiewicz, E., Sahin, U., Jemielity, J., and Rhoads, R. E., Synthetic mRNAs with superior translation and stability properties in Synthetic Messenger RNA and Cell Metabolism Modulation in Methods in Molecular Biology v. 969 (Rabinovich, P. H. Ed), 2013).

On the 3'-terminus, a long chain of adenine nucleotides (poly-A tail) is normally added to mRNA molecules during RNA processing. Immediately after transcription, the 3' end of the transcript is cleaved to free a 3' hydroxyl to which poly-A polymerase adds a chain of adenine nucleotides to the RNA in a process called polyadenylation. The poly-A tail has been extensively shown to enhance both translational efficiency and stability of mRNA (see Bernstein, P. and Ross, J., 1989, Poly (A), poly (A) binding protein and the regulation of mRNA stability, Trends Bio Sci v. 14 373-377; Guhaniyogi, J. And Brewer, G., 2001, Regulation of mRNA stability in mammalian cells, Gene, v. 265, 11-23; Dreyfus, M. And Regnier, P., 2002, The poly (A) tail of mRNAs: Bodyguard in eukaryotes, scavenger in bacteria, Cell, v. 111, 611-613).

Poly (A) tailing of in vitro transcribed mRNA can be achieved using various approaches including, but not limited to, cloning of a poly (T) tract into the DNA template or by post-transcriptional addition using Poly (A) polymerase. The first case allows in vitro transcription of mRNA with poly (A) tails of defined length, depending on the size of the poly (T) tract, but requires additional manipulation of the template. The latter case involves the enzymatic addition of a poly (A) tail to in vitro transcribed mRNA using poly (A) polymerase which catalyzes the incorporation of adenine residues onto the 3' termini of RNA, requiring no additional manipulation of the DNA template, but results in mRNA with poly(A) tails of heterogeneous length. 5'-capping and 3'-poly (A) tailing can be performed using a variety of commercially available kits including, but not limited to Poly (A) Polymerase Tailing kit (EpiCenter), mMESSAGE mMACHINE T7 Ultra kit and Poly (A) Tailing kit (Life Technologies) as well as with commercially available reagents, various ARCA caps, Poly (A) polymerase, etc.

In addition to 5' cap and 3' poly adenylation, other modifications of the in vitro transcripts have been reported to provide benefits as related to efficiency of translation and stability. It is well known in the art that pathogenic DNA and RNA can be recognized by a variety of sensors within eukaryotes and trigger potent innate immune responses. The ability to discriminate between pathogenic and self DNA and RNA has been shown to be based, at least in part, on structure and nucleoside modifications since most nucleic acids from natural sources contain modified nucleosides In contrast, in vitro synthesized RNA lacks these modifications, thus rendering it immunostimulatory which in turn can inhibit effective mRNA translation as outlined above. The introduction of modified nucleosides into in vitro transcribed mRNA can be used to prevent recognition and activation of RNA sensors, thus mitigating this undesired immunostimulatory activity and enhancing translation capacity (see e.g. Kariko, K. And Weissman, D. 2007, Naturally occurring nucleoside modifications suppress the immunostimulatory activity of RNA: implication for therapeutic RNA development, Curr Opin Drug Discov Devel, v. 10 523-532; Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013); Kariko, K., Muramatsu, H., Welsh, F. A., Ludwig, J., Kato, H., Akira, S., Weissman, D., 2008, Incorporation of Pseudouridine Into mRNA Yields Superior Nonimmunogenic Vector With Increased Translational Capacity and Biological Stability, Mol Ther v. 16, 1833-1840. The modified nucleosides and nucleotides used in the synthesis of modified RNAs can be prepared monitored and utilized using general methods and procedures known in the art. A large variety of nucleoside modifications are available that may be incorporated alone or in combination with other modified nucleosides to some extent into the in vitro transcribed mRNA (see e.g. US2012/0251618). In vitro synthesis of nucleoside-modified mRNA have been reported to have reduced ability to activate immune sensors with a concomitant enhanced translational capacity.

Other components of mRNA which can be modified to provide benefit in terms of translatability and stability include the 5' and 3' untranslated regions (UTR). Optimization of the UTRs (favorable 5' and 3' UTRs can be obtained from cellular or viral RNAs), either both or independently, have been shown to increase mRNA stability and translational efficiency of in vitro transcribed mRNA (see e.g. Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013).

In addition to mRNA, other nucleic acid payloads may be used for embodiments of this invention. For oligonucleotides, methods of preparation include but are not limited to chemical synthesis and enzymatic, chemical cleavage of a longer precursor, in vitro transcription as described above, etc. Methods of synthesizing DNA and RNA nucleotides are widely used and well known in the art (see, e.g. Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

For plasmid DNA, preparation for use with embodiments of this invention commonly utilizes but is not limited to expansion and isolation of the plasmid DNA in vitro in a liquid culture of bacteria containing the plasmid of interest. The presence of a gene in the plasmid of interest that encodes resistance to a particular antibiotic (penicillin, kanamycin, etc.) allows those bacteria containing the plasmid of interest to selectively grow in antibiotic-containing cultures. Methods of isolating plasmid DNA are widely used and well known in the art (see, e.g. Heilig, J., Elbing, K. L. and Brent, R (2001) Large-Scale Preparation of Plasmid DNA. Current Protocols in Molecular Biology. 41:II:1.7:1.7.1-1.7.16; Rozkov, A., Larsson, B., Gillstrom, S., Björnestedt, R. and Schmidt, S. R. (2008), Large-scale production of endotoxin-free plasmids for transient expression in mammalian cell culture. Biotechnol. Bioeng., 99: 557-566; and U.S. Pat. No. 6,197,553B1). Plasmid isolation can be performed using a variety of commercially available kits including, but not limited to Plasmid Plus (Qiagen), GenJET plasmid MaxiPrep (Thermo) and PureYield MaxiPrep (Promega) kits as well as with commercially available reagents.

Various exemplary embodiments of the lipids of the present invention, lipid nanoparticles and compositions comprising the same, and their use to deliver active (e.g. therapeutic agents), such as nucleic acids, to modulate gene and protein expression, are described in further detail below.

As used herein, the following terms have the meanings ascribed to them unless specified otherwise.

Unless the context requires otherwise, throughout the present specification and claims, the word "comprise" and variations thereof, such as, "comprises" and "comprising" are to be construed in an open and inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

The phrase "induce expression of a desired protein" refers to the ability of a nucleic acid to increase expression of the desired protein. To examine the extent of protein expression, a test sample (e.g. a sample of cells in culture expressing the desired protein) or a test mammal (e.g. a mammal such as a human or an animal model such as a rodent (e.g. mouse) or a non-human primate (e.g., monkey) model) is contacted with a nucleic acid (e.g. nucleic acid in combination with a lipid of the present invention). Expression of the desired protein in the test sample or test animal is compared to expression of the desired protein in a control sample (e.g. a sample of cells in culture expressing the desired protein) or a control mammal (e.g., a mammal such as a human or an animal model such as a rodent (e.g. mouse) or non-human primate (e.g. monkey) model) that is not contacted with or administered the nucleic acid. When the desired protein is present in a control sample or a control mammal, the expression of a desired protein in a control sample or a control mammal may be assigned a value of 1.0. In particular embodiments, inducing expression of a desired protein is achieved when the ratio of desired protein expression in the test sample or the test mammal to the level of desired protein expression in the control sample or the control mammal is greater than 1, for example, about 1.1, 1.5, 2.0. 5.0 or 10.0. When a desired protein is not present in a control sample or a control mammal, inducing expression of a desired protein is achieved when any measurable level of the desired protein in the test sample or the test mammal is detected. One of ordinary skill in the art will understand appropriate assays to determine the level of protein expression in a sample, for example dot blots, northern blots, in situ hybridization, ELISA, immunoprecipitation, enzyme function, and phenotypic assays, or assays based on reporter proteins that can produce fluorescence or luminescence under appropriate conditions.

The phrase "inhibiting expression of a target gene" refers to the ability of a nucleic acid to silence, reduce, or inhibit the expression of a target gene. To examine the extent of gene silencing, a test sample (e.g. a sample of cells in culture expressing the target gene) or a test mammal (e.g. a mammal such as a human or an animal model such as a rodent (e.g. mouse) or a non-human primate (e.g. monkey) model) is contacted with a nucleic acid that silences, reduces, or inhibits expression of the target gene. Expression of the target gene in the test sample or test animal is compared to expression of the target gene in a control sample (e.g. a sample of cells in culture expressing the target gene) or a control mammal (e.g. a mammal such as a human or an animal model such as a rodent (e.g. mouse) or non-human primate (e.g. monkey) model) that is not contacted with or administered the nucleic acid. The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the nucleic acids are capable of silencing, reducing, or inhibiting the expression of a target gene by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the nucleic acid. Suitable assays for determining the level of target gene expression include, without limitation, examination of protein or mRNA levels using techniques known to those of skill in the art, such as, e.g., dot blots, northern blots, in situ hybridization, ELISA, immunoprecipitation, enzyme function, as well as phenotypic assays known to those of skill in the art.

An "effective amount" or "therapeutically effective amount" of an active agent or therapeutic agent such as a therapeutic nucleic acid is an amount sufficient to produce the desired effect, e.g. an increase or inhibition of expression of a target sequence in comparison to the normal expression level detected in the absence of the nucleic acid. An increase in expression of a target sequence is achieved when any measurable level is detected in the case of an expression product that is not present in the absence of the nucleic acid. In the case where the expression product is present at some level prior to contact with the nucleic acid, an in increase in expression is achieved when the fold increase in value obtained with a nucleic acid such as mRNA relative to control is about 1.05, 1.1, 1.2, 1.3, 1.4, 1.5, 1.75, 2, 2.5, 3, 4, 5, 6, 7, 8, 9, 10, 15, 20, 25, 30, 40, 50, 75, 100, 250, 500, 750, 1000, 5000, 10000 or greater. Inhibition of expression of a target gene or target sequence is achieved when the value obtained with a nucleic acid such as antisense oligonucleotide relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, fluorescence or luminescence of suitable reporter proteins, as well as phenotypic assays known to those of skill in the art.

The term "nucleic acid" as used herein refers to a polymer containing at least two deoxyribonucleotides or ribonucleotides in either single- or double-stranded form and includes DNA, RNA, and hybrids thereof. DNA may be in the form of antisense molecules, plasmid DNA, cDNA, PCR products, or vectors. RNA may be in the form of small hairpin RNA (shRNA), messenger RNA (mRNA), antisense RNA, miRNA, micRNA, multivalent RNA, dicer substrate RNA or viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, single nucleotide polymorphisms, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are generally characterized by being poorly soluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "steroid" is a compound comprising the following carbon skeleton:

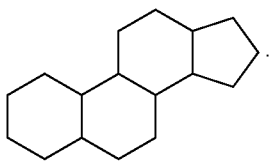 [SMILES: C1CCC2C(C1)CCC1C3CCCC3CCC21]

Non-limiting examples of steroids include cholesterol, and the like.

A "cationic lipid" refers to a lipid capable of being positively charged. Exemplary cationic lipids include one or more amine group(s) which bear the positive charge. Preferred cationic lipids are ionizable such that they can exist in a positively charged or neutral form depending on pH. The ionization of the cationic lipid affects the surface charge of the lipid nanoparticle under different pH conditions. This charge state can influence plasma protein absorption, blood clearance and tissue distribution (Semple, S. C., et al., Adv. Drug Deliv Rev 32:3-17 (1998)) as well as the ability to form endosomolytic non-bilayer structures (Hafez, I. M., et al., Gene Ther 8:1188-1196 (2001)) critical to the intracellular delivery of nucleic acids.

The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-DMG) and the like.

The term "neutral lipid" refers to any of a number of lipid species that exist either in an uncharged or neutral zwitterionic form at a selected pH. At physiological pH, such lipids include, but are not limited to, phosphotidylcholines such as 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), phosphatidylethanolamines such as 1,2-Dioleoyl-sn-glycero-3-phosphoethanolamine (DOPE), sphingomyelins (SM), ceramides, steroids such as sterols and their derivatives. Neutral lipids may be synthetic or naturally derived.

The term "charged lipid" refers to any of a number of lipid species that exist in either a positively charged or negatively charged form independent of the pH within a useful physiological range e.g. pH~3 to pH~9. Charged lipids may be synthetic or naturally derived. Examples of charged lipids include phosphatidylserines, phosphatidic acids, phosphatidylglycerols, phosphatidylinositols, sterol hemisuccinates, dialkyl trimethylammonium-propanes, (e.g. DOTAP, DOTMA), dialkyl dimethylaminopropanes, ethyl phosphocholines, dimethylaminoethane carbamoyl sterols (e.g. DC-Chol).

The term "lipid nanoparticle" refers to particles having at least one dimension on the order of nanometers (e.g., 1-1,000 nm) which include one or more of the compounds of structure (I) or other specified cationic lipids. In some embodiments, lipid nanoparticles are included in a formulation that can be used to deliver an active agent or therapeutic agent, such as a nucleic acid (e.g., mRNA) to a target site of interest (e.g., cell, tissue, organ, tumor, and the like). In some embodiments, the lipid nanoparticles of the invention comprise a nucleic acid. Such lipid nanoparticles typically comprise a compound of structure (I) and one or more excipient selected from neutral lipids, charged lipids, steroids and polymer conjugated lipids. In some embodiments, the active agent or therapeutic agent, such as a nucleic acid, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, nucleic acids, when present in the lipid nanoparticles, are resistant in aqueous solution to degradation with a nuclease. Lipid nanoparticles comprising nucleic acids and their method of preparation are disclosed in, e.g., U.S. Patent Publication Nos. 2004/0142025, 2007/0042031 and PCT Pub. Nos. WO 2017/004143, WO 2015/199952, WO 2013/016058 and WO 2013/086373, the full disclosures of which are herein incorporated by reference in their entirety for all purposes.

As used herein, "lipid encapsulated" refers to a lipid nanoparticle that provides an active agent or therapeutic agent, such as a nucleic acid (e.g., mRNA), with full encapsulation, partial encapsulation, or both. In an embodiment, the nucleic acid (e.g., mRNA) is fully encapsulated in the lipid nanoparticle.

As used herein, the term "aqueous solution" refers to a composition comprising water.

"Serum-stable" in relation to nucleic acid-lipid nanoparticles means that the nucleotide is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of a therapeutic product that can result in a broad exposure of an active agent within an organism. Some techniques of administration can lead to the systemic delivery of certain agents, but not others. Systemic delivery means that a useful, preferably therapeutic, amount of an agent is exposed to most parts of the body. Systemic delivery of lipid nanoparticles can be by any means known in the art including, for example, intravenous, intraarterial, subcutaneous, and intraperitoneal delivery. In some embodiments, systemic delivery of lipid nanoparticles is by intravenous delivery.

"Local delivery," as used herein, refers to delivery of an active agent directly to a target site within an organism. For example, an agent can be locally delivered by direct injection into a disease site such as a tumor, other target site such as a site of inflammation, or a target organ such as the liver, heart, pancreas, kidney, and the like. Local delivery can also include topical applications or localized injection techniques such as intramuscular, subcutaneous or intradermal injection. Local delivery does not preclude a systemic pharmacological effect.

"Alkyl" refers to a straight or branched hydrocarbon chain radical consisting solely of carbon and hydrogen atoms, which is saturated, having, for example, from one to twenty-four carbon atoms ($C_1$-$C_{24}$ alkyl), four to twenty carbon atoms ($C_4$-$C_{20}$ alkyl), six to sixteen carbon atoms ($C_6$-$C_{16}$ alkyl), six to nine carbon atoms ($C_6$-$C_9$ alkyl), one to fifteen carbon atoms ($C_1$-$C_{15}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond, e.g., methyl, ethyl, n-propyl, 1 methylethyl (iso propyl), n-butyl, n-pentyl, 1,1-dimethylethyl (t butyl), 3-methylhexyl, 2-methylhexyl, and the like. Unless stated otherwise specifically in the specification, an alkyl group is optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group is optionally substituted.

"Alkylaminyl" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylaminyl group is optionally substituted.

"Alkenyl" refers to a straight or branched hydrocarbon chain radical consisting solely of carbon and hydrogen atoms, which contains one or more carbon-carbon double bonds, and having, for example, from two to twenty-four carbon atoms ($C_2$-$C_{24}$ alkenyl), four to twenty carbon atoms ($C_4$-$C_{20}$ alkenyl), six to sixteen carbon atoms ($C_6$-$C_{16}$ alkenyl), six to nine carbon atoms ($C_6$-$C_9$ alkenyl), two to fifteen carbon atoms ($C_2$-$C_{15}$ alkenyl), two to twelve carbon atoms ($C_2$-$C_{12}$ alkenyl), two to eight carbon atoms ($C_2$-$C_8$ alkenyl) or two to six carbon atoms ($C_2$-$C_6$ alkenyl) and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group is optionally substituted.

"Alkylene" or "alkylene chain" refers to a straight or branched divalent hydrocarbon chain linking the rest of the molecule to a radical group, consisting solely of carbon and hydrogen, which is saturated, and having, for example, from one to twenty-four carbon atoms ($C_1$-$C_{24}$ alkylene), two to twenty-four carbon atoms ($C_2$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene), e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted.

"Alkenylene" or "alkenylene chain" refers to a straight or branched divalent hydrocarbon chain linking the rest of the molecule to a radical group, consisting solely of carbon and hydrogen, which contains one or more carbon-carbon double bonds, and having, for example, from two to twenty-four carbon atoms ($C_2$-$C_{24}$ alkenylene), two to fifteen carbon atoms ($C_2$-$C_{15}$ alkenylene), two to twelve carbon atoms ($C_2$-$C_{12}$ alkenylene), two to eight carbon atoms ($C_2$-$C_8$ alkenylene), two to six carbon atoms ($C_2$-$C_6$ alkenylene) or two to four carbon atoms ($C_2$-$C_4$ alkenylene), e.g., ethenylene, propenylene, n-butenylene, and the like. The alkenylene chain is attached to the rest of the molecule through a single or double bond and to the radical group through a single or double bond. The points of attachment of the alkenylene chain to the rest of the molecule and to the radical group can be through one carbon or any two carbons within the chain. Unless stated otherwise specifically in the specification, an alkenylene chain may be optionally substituted.

"Aryl" refers to a carbocyclic ring system radical comprising hydrogen, 6 to 18 carbon atoms and at least one aromatic ring. For purposes of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene or alkenylene as defined above and $R_c$ is one or more aryl radicals as defined above, for example, benzyl, diphenylmethyl and the like. Unless stated otherwise specifically in the specification, an aralkyl group is optionally substituted.

"Heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"Heteroaryl" refers to a 5- to 14-membered ring system radical comprising hydrogen atoms, one to thirteen ring carbon atoms, one to six ring heteroatoms selected from the group consisting of nitrogen, oxygen and sulfur, and at least one aromatic ring comprising a heteroatom. For purposes of embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

The term "substituted" used herein means any of the above groups (e.g. alkyl, alkenyl, alkylene, alkenylene, aryl and aralkyl) wherein at least one hydrogen atom is replaced by a bond to a non-hydrogen atom such as, but not limited to: a halogen atom such as F, Cl, Br, or I; oxo groups (=O); hydroxyl groups (—OH); $C_1$-$C_{12}$ alkyl groups; cycloalkyl groups; —(C=O)OR'; —O(C=O)R'; —C(=O)R'; —OR'; —S(O), —OR'; —S—SR';
- —C(=O)SR'; —SC(=O)R'; —NR'R'; —NR'C(=O)R'; —C(=O)NR'R'; —NR'C(=O)NR'R';
- —OC(=O)NR'R'; —NR'C(=O)OR'; —NR'S(O)$_x$NR'R'; —NR'S(O), —OR'; and —S(O)$_x$NR'R', wherein: R' is, at each occurrence, independently H, $C_1$-$C_{15}$ alkyl or cycloalkyl, and x is 0, 1 or 2. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is an oxo (=O) group. In other embodiments, the substituent is a hydroxyl group. In other embodiments, the substituent is an alkoxy group (—OR'). In other embodiments, the substituent is a carboxyl group. In other embodiments, the substituent is an amine group (—NR'R').

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Prodrug" is meant to indicate a compound that may be converted under physiological conditions or by solvolysis to a biologically active compound of structure (I). Thus, the term "prodrug" refers to a metabolic precursor of a compound of structure (I) that is pharmaceutically acceptable. A prodrug may be inactive when administered to a subject in need thereof, but is converted in vivo to an active compound of structure (I). Prodrugs are typically rapidly transformed in vivo to yield the parent compound of structure (I), for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of structure (I) in vivo when such prodrug is administered to a mammalian subject. Prodrugs of a compound of structure (I) may be prepared by modifying functional groups present in the compound of structure (I) in such a way that the modifications are cleaved, either in routine manipulation or in vivo, to the parent compound of structure (I). Prodrugs include compounds of structure (I) wherein a hydroxy, amino or mercapto group is bonded to any group that, when the prodrug of the compound of structure (I) is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of structure (I) and the like.

Embodiments of the invention disclosed herein are also meant to encompass all pharmaceutically acceptable compounds of the compound of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}P$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labelled compounds of structure (I) or (II), for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Embodiments of the invention disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments of the invention include compounds produced by a process comprising administering a compound of this invention to a mammal for a period of time sufficient to yield a metabolic product thereof. Such products are typically identified by administering a radiolabeled compound of structure (I) in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethane-sulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, decanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of structure (I). As used herein, the term "solvate" refers to an aggregate that comprises one or more molecules of a compound of structure (I) with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some embodiments, the compound of structure (I) may exist as a true solvate, while in other cases, the compound of structure (I) may merely retain adventitious water or be a mixture of water plus some adventitious solvent.

A "pharmaceutical composition" refers to a formulation of a compound of structure (I) and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of structure (I) which, when administered to a mammal, preferably a human, is sufficient to effect treatment in the mammal, preferably a human. The amount of a lipid nanoparticle of embodiments the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of structure (I), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.
Compounds In an aspect, the invention provides novel lipid compounds which are capable of combining with other lipid components such as neutral lipids, charged lipids, steroids and/or polymer conjugated-lipids to form lipid nanoparticles with oligonucleotides. Without wishing to be bound by theory, it is thought that these lipid nanoparticles shield oligonucleotides from degradation in the serum and provide for effective delivery of oligonucleotides to cells in vitro and in vivo.

In one embodiment, the compounds have the following structure (I):

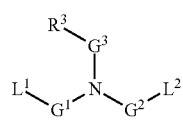

(I)

or a pharmaceutically acceptable salt, prodrug or stereoisomer thereof, wherein:
 $L^1$ is —NR$^a$C(=O)R$^1$ or —C(=O)NR$^b$R$^c$;
 $L^2$ is —NR$^d$C(=O)R$^2$ or —C(=O)NR$^e$R$^f$;
 $G^1$ and $G^2$ are each independently $C_2$-$C_{12}$ alkylene, or $C_2$-$C_{12}$ alkenylene;
 $G^3$ is $C_1$-$C_{24}$ alkylene, or $C_2$-$C_{24}$ alkenylene;
 $R^a$, $R^b$, $R^d$ and $R^e$ are each independently H, $C_1$-$C_{16}$ alkyl or $C_2$-$C_{16}$ alkenyl;
 $R^c$ and $R^f$ are each independently $C_1$-$C_{16}$ alkyl or $C_2$-$C_{16}$ alkenyl;
 $R^1$ and $R^2$ are each independently $C_6$-$C_{24}$ alkyl or $C_6$-$C_{24}$ alkenyl;
 $R^3$ is H, —OH, CN, —N(R$^4$)R$^5$; —C(=O)N(R$^4$)R$^5$; —N(R$^4$)C(=O)R$^5$; —N(R$^4$)C(=O)OR$^5$; —C(=O)OR$^6$, —OC(=O)R$^6$, —OR$^7$, heteroaryl or aryl;
 $R^4$ and $R^5$ are each independently is H, $C_1$-$C_{12}$ alkyl, $C_3$-$C_6$ cycloalkyl or $C_3$-$C_6$ cycloalkenyl, or $R^4$ and $R^5$, together with the nitrogen or carbon atom to which they are bound, form a 5 to 7-membered heterocyclic ring;
 $R^6$ is H, $C_1$-$C_{12}$ alkyl, $C_2$-$C_{12}$ alkenyl or aralkyl;
 $R^7$ is $C_1$-$C_{12}$ alkyl optionally substituted with hydroxyl or alkoxy; and
 wherein each alkyl, alkenyl, alkylene, alkenylene, aryl and aralkyl is independently substituted or unsubstituted unless otherwise specified. In certain embodiments, at least one alkyl, alkenyl, alkylene, alkenylene, $C_3$-$C_6$ cycloalkyl or $C_3$-$C_6$ cycloalkenyl, aryl or aralkyl is substituted with one or more fluorine and/or one or more oxo and/or one or more NH$_2$ and/or one or more alkylaminyl.

In one embodiment, the compounds have the following structure (I):

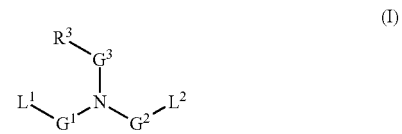

(I)

or a pharmaceutically acceptable salt, prodrug or stereoisomer thereof, wherein:
 $L^1$ is —NR$^a$C(=O)R$^1$ or —C(=O)NR$^b$R$^c$;
 $L^2$ is —NR$^d$C(=O)R$^2$ or —C(=O)NR$^e$R$^f$;
 $G^1$ and $G^2$ are each independently $C_1$-$C_{12}$ alkylene, or $C_2$-$C_{12}$ alkenylene;
 $G^3$ is $C_1$-$C_{24}$ alkylene, or $C_2$-$C_{24}$ alkenylene;
 $R^a$, $R^b$, $R^d$ and $R^e$ are each independently H, $C_1$-$C_{16}$ alkyl or $C_2$-$C_{16}$ alkenyl;
 $R^c$ and $R^f$ are each independently $C_1$-$C_{16}$ alkyl or $C_2$-$C_{16}$ alkenyl;
 $R^1$ and $R^2$ are each independently $C_6$-$C_{24}$ alkyl or $C_6$-$C_{24}$ alkenyl;
 $R^3$ is H, —OH, CN, —N(R$^4$)R$^5$; —C(=O)N(R$^4$)R$^5$; —N(R$^4$)C(=O)R$^5$; —C(=O)OR$^6$, —OC(=O)R$^6$, or aryl;
 $R^4$ and $R^5$ are each independently is H, $C_1$-$C_{12}$ alkyl, or $R^4$ and $R^5$, together with the nitrogen or carbon atom to which they are bound, form a 5 to 7-membered heterocyclic ring;
 $R^6$ is H, $C_1$-$C_{12}$ alkyl, $C_2$-$C_{12}$ alkenyl or aralkyl; and
 wherein each alkyl, alkenyl, alkylene, alkenylene, $C_3$-$C_6$ cycloalkyl or $C_3$-$C_6$ cycloalkenyl, aryl and aralkyl is independently substituted or unsubstituted unless otherwise specified. In certain embodiments, at least one alkyl, alkenyl, alkylene, alkenylene, $C_3$-$C_6$ cycloalkyl or $C_3$-$C_6$ cycloalkenyl, aryl or aralkyl is substituted with one or more fluorine and/or one or more oxo and/or one or more NH$_2$ and/or one or more alkylaminyl.

In certain embodiments, $G^3$ is unsubstituted. In some embodiments, $G^3$ is substituted with one or more fluorine atoms. In more specific embodiments $G^3$ is $C_1$-$C_{12}$ alkylene, for example. In some embodiments, $G^3$ is $C_1$, $C_2$, $C_3$, $C_4$, $C_5$, $C_6$, $C_7$, or $C_8$ alkylene. For example, in some embodiments $G^3$ is methyl, ethyl, n-propyl, n-butyl, n-pentyl, n-hexyl, n-heptyl, or n-octyl.

In certain embodiments, $G^1$ and/or $G^2$ is unsubstituted. In some embodiments, $G^1$ and/or $G^2$ is substituted with one or more fluorine atoms. In more specific embodiments $G^1$ and/or $G^2$ is $C_1$-$C_{12}$ alkylene, for example. In some embodiments, $G^1$ and/or $G^2$ is $C_1$, $C_2$, $C_3$, $C_4$, $C_5$, $C_6$, $C_7$, or $C_8$ alkylene.

In some of the foregoing embodiments, the compound has the following structure (IA):

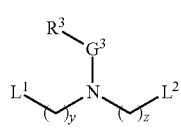
(IA)

wherein y and z are each independently integers ranging from 2 to 12, for example an integer from 2 to 6, for example 4 or 5. In some certain embodiments, y and z are each integers of 5. In some certain embodiments, y and z are each integers of 6. In some certain embodiments, y and z are each integers of 7. In some certain embodiments, y and z are each integers of 9.

In some of the foregoing embodiments, $L^1$ is —C(=O)NR$^b$R$^c$, and $L^2$ is —C(=O)NR$^e$R$^f$. In some of the foregoing embodiments, $L^1$ is —NR$^a$C(=O)R$^1$ and $L^2$ is —NR$^d$C(=O)R$^2$.

In other embodiments of the foregoing, the compound having one of the following structures (IB) or (IC):

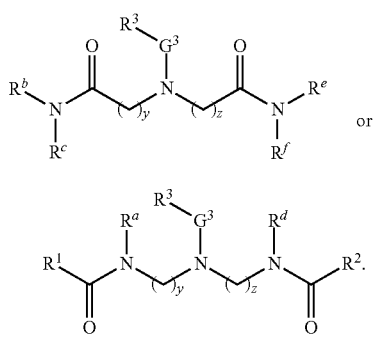

In some of the foregoing embodiments, y and z are each independently an integer ranging from 2 to 10, 2 to 8, from 4 to 10 or from 4 to 7. For example, in some embodiments, y is 4, 5, 6, 7, 8, 9, 10, 11 or 12. In some embodiments, z is 4, 5, 6, 7, 8, 9, 10, 11 or 12. In some certain embodiments, y and z are each integers of 5. In some certain embodiments, y and z are each integers of 6. In some certain embodiments, y and z are each integers of 7. In some certain embodiments, y and z are each integers of 9. In some embodiments, y and z are the same, while in other embodiments y and z are different.

In some of the foregoing embodiments, $R^1$ or $R^2$, or both is branched $C_6$-$C_{24}$ alkyl. For example, in some embodiments, $R^1$ and $R^2$ each, independently have the following structure:

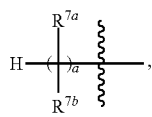

wherein:

$R^{7a}$ and $R^{7b}$ are, at each occurrence, independently either: (a) H or $C_1$-$C_{12}$ alkyl, or (b) $R^{7a}$ is H or $C_1$-$C_{12}$ alkyl, and $R^{7b}$ together with the carbon atom to which it is bound is taken together with an adjacent $R^{7b}$ and the carbon atom to which it is bound to form a carbon-carbon double bond; and a is an integer from 2 to 12, wherein $R^{7a}$, $R^{7b}$ and a are each selected such that $R^1$ and $R^2$ are each independently linear or branched and independently comprise from 6 to 20 carbon atoms. For example, in some embodiments a is an integer ranging from 5 to 9 or from 8 to 12.

In some of the foregoing embodiments, at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments, $R^1$ or $R^2$, or both, has one of the following structures:

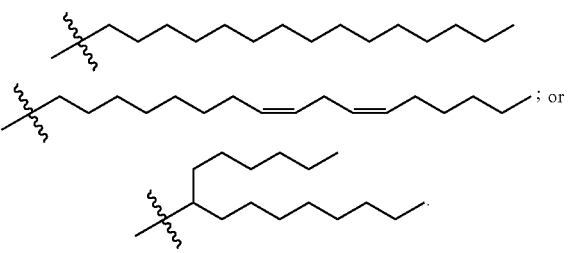

In different embodiments, $R^1$ or $R^2$, or both, has one of the following structures:

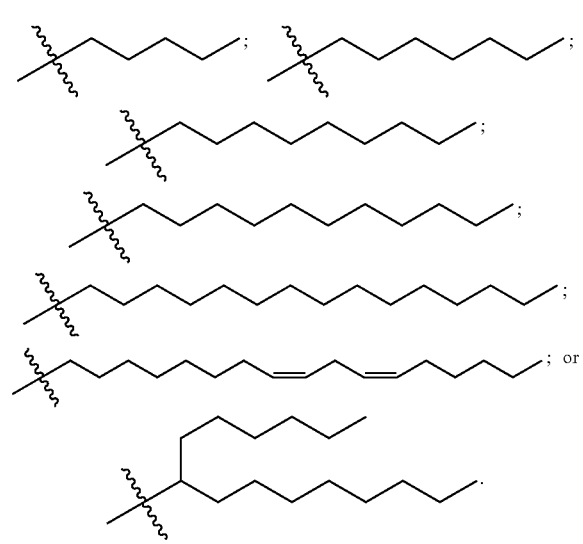

In some of the foregoing embodiments, $R^b$, $R^c$, $R^e$ and $R^f$ are each independently $C_3$-$C_{12}$ alkyl or $C_3$-$C_{16}$ alkyl. For example, in some embodiments $R^b$, $R^c$, $R^e$ and $R^f$ are selected from n-hexyl (—(CH$_2$)$_5$CH$_3$), n-octyl (—(CH$_2$)$_7$CH$_3$), are n-decanyl (—(CH$_2$)$_9$CH$_3$), n-dodecyl (—(CH$_2$)$_{11}$CH$_3$), (—(CH$_2$)$_{14}$CH$_3$), (—(CH$_2$)$_{15}$CH$_3$). For example, in some embodiments $R^b$, $R^c$, $R^e$ and $R^f$ are n-hexyl (—(CH$_2$)$_5$CH$_3$) and in other embodiments $R^b$, $R^c$, $R^e$ and $R^f$ are n-octyl (—(CH$_2$)$_7$CH$_3$). In another example in some embodiments $R^b$, $R^c$, $R^e$ and $R^f$ are n-decanyl (—(CH$_2$)$_9$CH$_3$). In other embodiments, $R^b$, $R^c$, $R^e$ and $R^f$ are n-dodecyl (—(CH$_2$)$_{11}$CH$_3$).

In some embodiments, $R^a$ and $R^d$ are each independently $C_1$-$C_{12}$ alkyl or $C_2$-$C_{12}$ alkenyl and $R^1$ and $R^2$ are each independently $C_6$-$C_{18}$ alkyl or $C_6$-$C_{18}$ alkenyl. For example in some embodiments $R^a$ and $R^d$ are n-hexyl (—$(CH_2)_5CH_3$) and $R^1$ and $R^2$ are dodecapentyl (—$(CH_2)_{14}CH_3$). In another example in some embodiments $R^a$ and $R^d$ are n-hexyl and $R^1$ and $R^2$ are (6Z,9Z)-heptadeca-6,9-diene (—$(CH_2)_7CHCHCH_2CHCH(CH_2)_4CH_3$). In yet another example in some embodiments $R^a$ and $R^d$ are n-hexyl and $R^1$ and $R^2$ are 7-pentadecane (—$CH((CH_2)_5CH_3)((CH_2)_7CH_3)$).

In some embodiment, $R^3$ is H.

In other embodiments, $R^3$ is —OH.

In some different embodiments, $R^3$ is —C(=O)O$R^6$, for example in some of these embodiments $R^6$ is $C_1$-$C_{18}$ alkyl. In another example in some embodiments, $R^6$ is $C_1$-$C_{12}$ branched alkyl. In yet another example in some embodiments, $R^6$ is $C_1$-$C_6$ alkyl. In another example in some embodiments, $R^6$ is $C_1$-$C_2$ alkyl. In some certain embodiments, $R^6$ is an ethyl. In some certain embodiments, $R^6$ is 5-methyl dodecyl.

In other embodiments, $R^3$ is —N($R^4$)$R^5$, for example in some of these embodiments $R^4$ and $R^5$ are each independently $C_1$-$C_{12}$ alkyl, optionally substituted with hydroxyl. In another example in some embodiments $R^4$ and $R^5$ are each independently $C_1$-$C_6$ alkyl, optionally substituted with hydroxyl. In yet another example in some embodiments $R^4$ and $R^5$ are each independently $C_1$-$C_2$ alkyl, optionally substituted with hydroxyl. In some certain embodiments, $R^4$ and $R^5$ are each methyl. In some certain embodiments, $R^4$ and $R^5$ are each n-hexyl.

In other embodiments, $R^3$ is —C(=O)N($R^4$)$R^5$ or $R^3$ is —N($R^4$)C(=O)$R^5$. In some of these embodiments, one of $R^4$ or $R^5$ is H and the other one of $R^4$ or $R^5$ is $C_1$-$C_{12}$ alkyl. In some embodiments, one of $R^4$ or $R^5$ is H and the other one of $R^4$ or $R^5$ is $C_1$-$C_{12}$ alkyl substituted with hydroxyl. In other embodiments, both $R^4$ and $R^5$ are $C_1$-$C_{12}$ alkyl or $C_1$-$C_6$ alkyl. In some embodiments, both $R^4$ and $R^5$ are $C_1$-$C_{12}$ alkyl or $C_1$-$C_6$ alkyl substituted with hydroxyl. In some certain embodiments, one of $R^4$ or $R^5$ is H and the other one of $R^4$ or $R^5$ is n-decyl. In some certain embodiments, one of $R^4$ or $R^5$ is H and the other one of $R^4$ or $R^5$ is n-tridecyl.

In some embodiments, $R^3$ is aryl. In some embodiments, $R^3$ is substituted aryl. In some certain embodiments, $R^3$ is a phenyl.

In other embodiments, $R^3$ is —N($R^4$)$R^5$, and one of $R^4$ and $R^5$ is $C_3$-$C_6$ cycloalkyl or $C_3$-$C_6$ cycloalkenyl. For example, in some embodiments $R^3$ is —N($R^4$)$R^5$, $R^4$ is H and $R^5$ is $C_3$-$C_6$ cycloalkenyl.

In different embodiments, $R^3$ is —O$R^7$ and $R^7$ is $C_1$-$C_6$ alkyl substituted with OH or $OCH_3$.

In other embodiments, $R^3$ is —N($R^4$)C(=O)O$R^5$, wherein $R^4$ is H and $R^5$ is $C_1$-$C_6$ alkyl.

In still more embodiments, $R^3$ is heteroaryl, for example imidazolyl.

In some more specific embodiments, $R^3$ has one of the following structures:

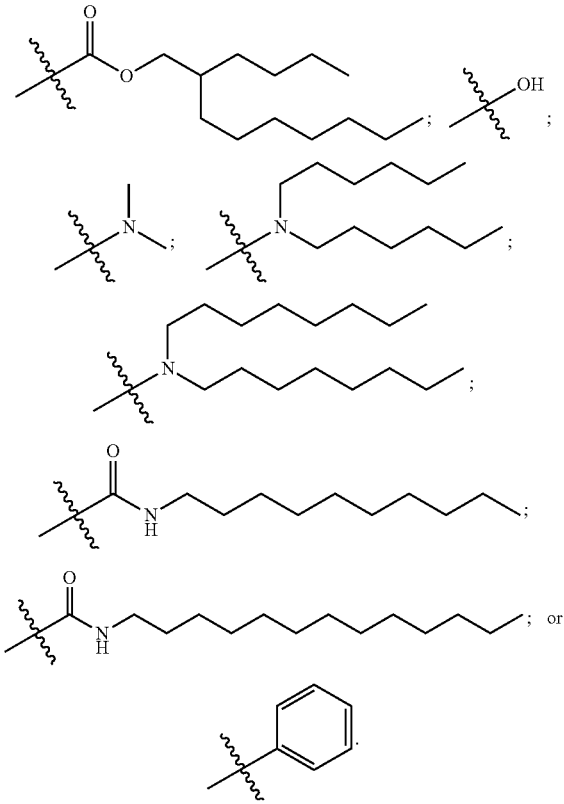

In some more specific embodiments, $R^3$ is H or has one of the following structures:

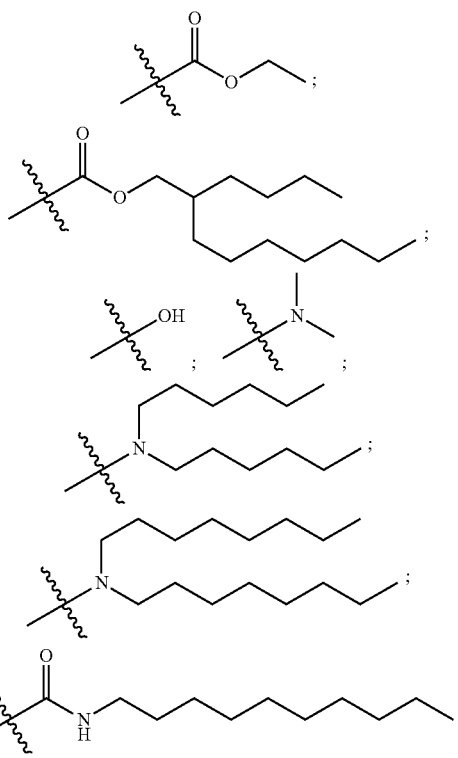

25
-continued
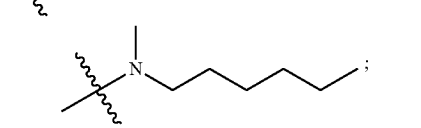
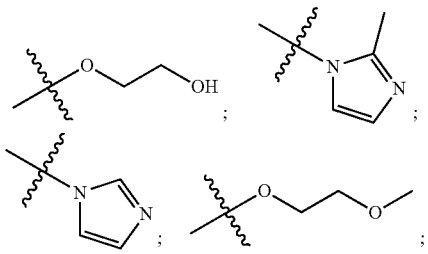
26
-continued
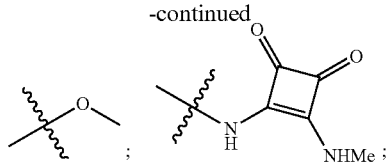
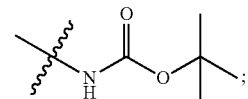
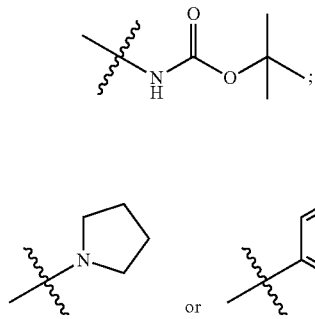
or
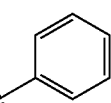
In various different embodiments, the compound has one of the structures set forth in Table 1 below.
TABLE 1
| Representative Compounds | |
|---|---|
| No. | Structure |
| I-1 | |
| I-2 | |

TABLE 1-continued
Representative Compounds
| No. | Structure |
|---|---|
| I-3 | 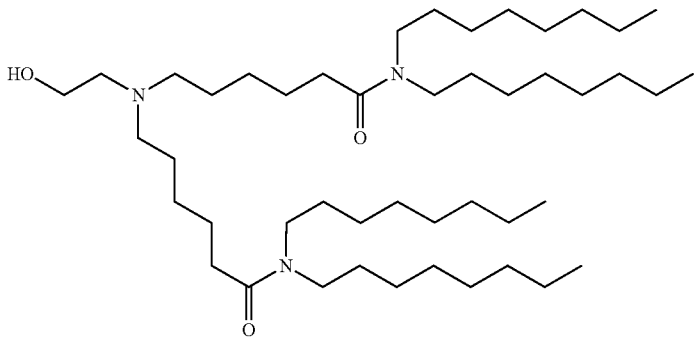 [SMILES: CCCCCCCCN(CCCCCCCC)C(=O)CCCCCN(CCO)CCCCCC(=O)N(CCCCCCCC)CCCCCCCC] |
| I-4 | 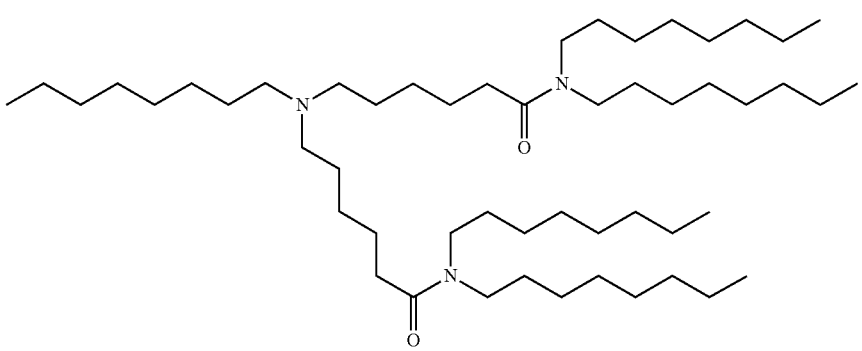 [SMILES: CCCCCCCCN(CCCCCC(=O)N(CCCCCCCC)CCCCCCCC)CCCCCC(=O)N(CCCCCCCC)CCCCCCCC] |
| I-5 | 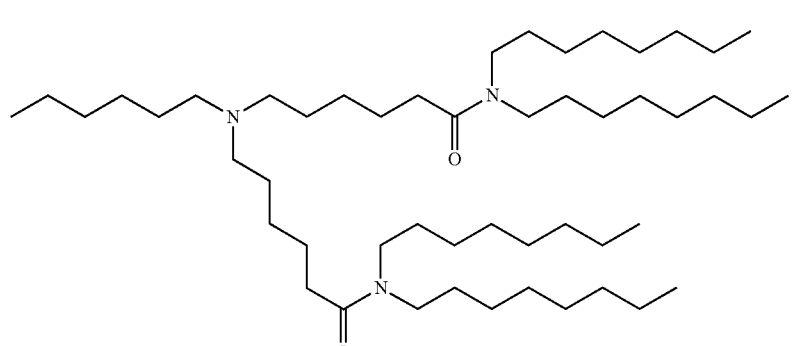 |
| I-6 | 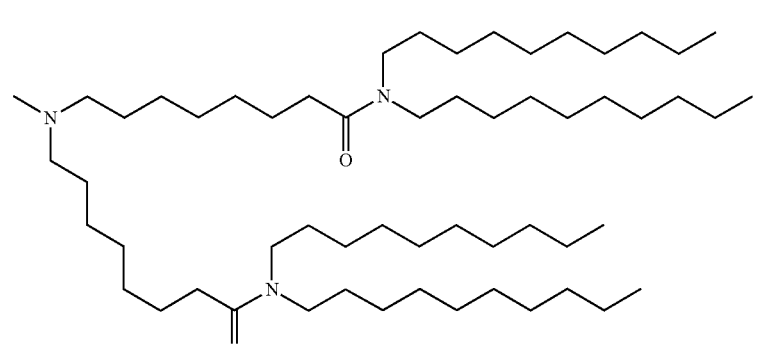 |

TABLE 1-continued

Representative Compounds

| No. | Structure |
|---|---|
| I-7 | 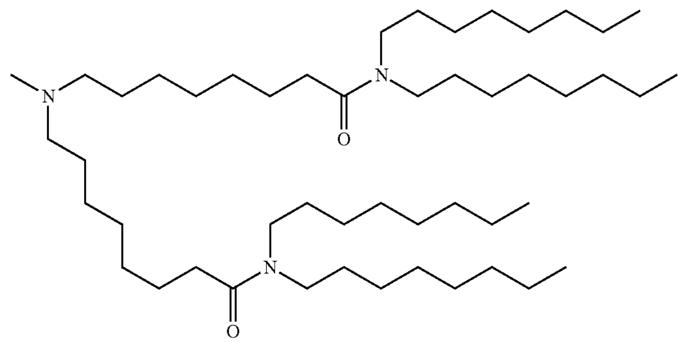 [SMILES: CCCCCCCCN(CCCCCCCC)C(=O)CCCCCCCN(C)CCCCCCCC(=O)N(CCCCCCCC)CCCCCCCC] |
| I-8 | 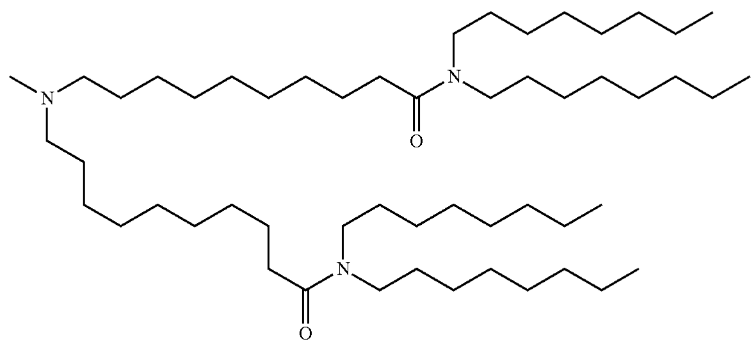 [SMILES: CCCCCCCCN(CCCCCCCC)C(=O)CCCCCCCCCN(C)CCCCCCCCCC(=O)N(CCCCCCCC)CCCCCCCC] |
| I-9 | 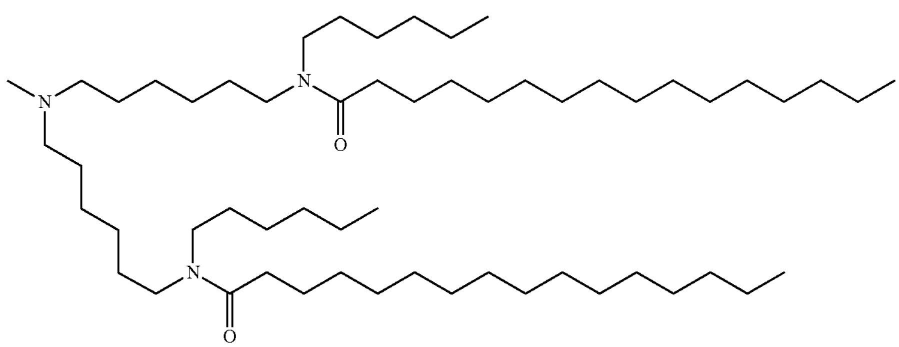 [SMILES: CCCCCCCCCCCCCCCC(=O)N(CCCCCC)CCCCCCN(C)CCCCCCN(CCCCCC)C(=O)CCCCCCCCCCCCCCC] |
| I-10 | 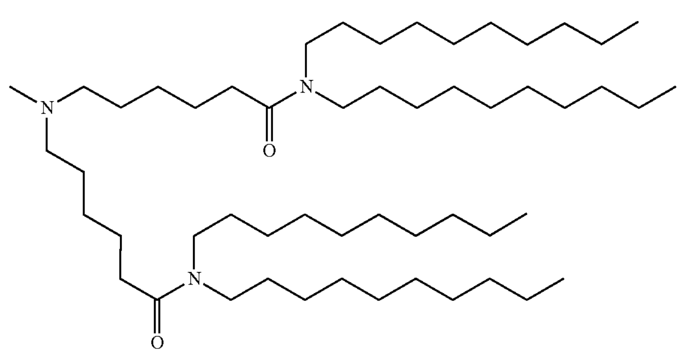 [SMILES: CCCCCCCCCCN(CCCCCCCCCC)C(=O)CCCCCN(C)CCCCCC(=O)N(CCCCCCCCCC)CCCCCCCCCC] |

TABLE 1-continued

Representative Compounds

| No. | Structure |
|---|---|
| I-11 | 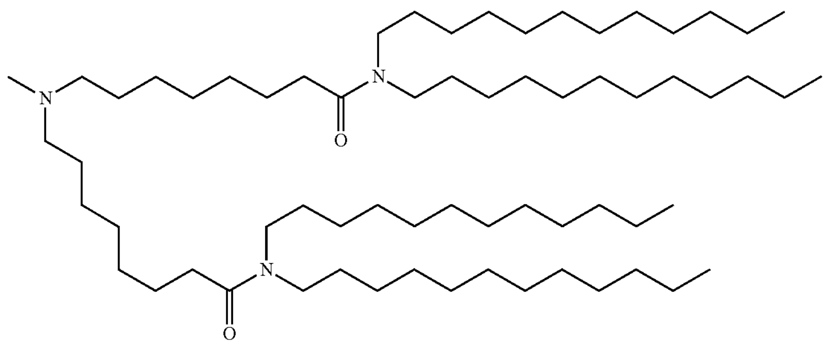 [SMILES: CCCCCCCCCCCCN(CCCCCCCCCCCC)C(=O)CCCCCCCN(C)CCCCCCCC(=O)N(CCCCCCCCCCCC)CCCCCCCCCCCC] |
| I-12 | 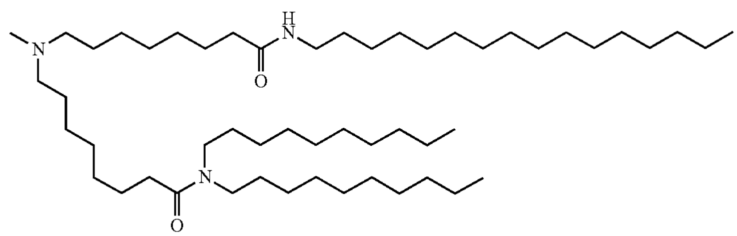 [SMILES: CCCCCCCCCCCCCCCCNC(=O)CCCCCCCN(C)CCCCCCCC(=O)N(CCCCCCCCCC)CCCCCCCCCC] |
| I-13 | 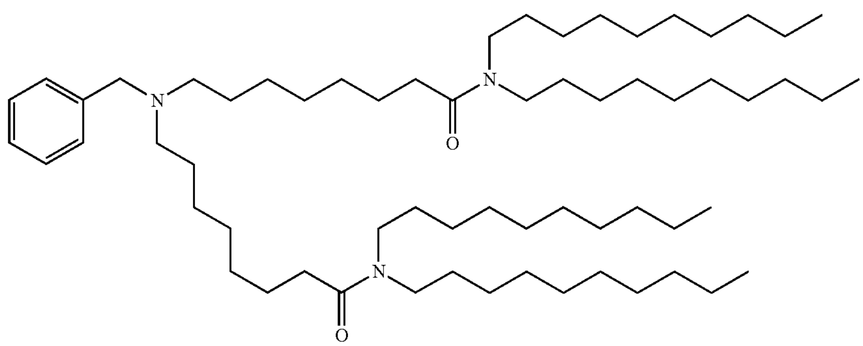 [SMILES: CCCCCCCCCCN(CCCCCCCCCC)C(=O)CCCCCCCN(CCCCCCCC(=O)N(CCCCCCCCCC)CCCCCCCCCC)Cc1ccccc1] |
| I-14 | 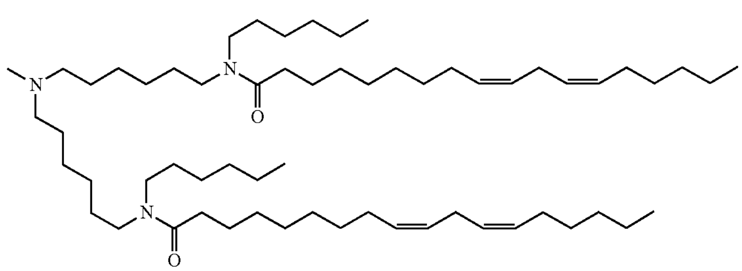 [SMILES: CCCCC/C=C\C/C=C\CCCCCCCC(=O)N(CCCCCC)CCCCCCN(C)CCCCCCN(CCCCCC)C(=O)CCCCCCC/C=C\C/C=C\CCCCC] |
| I-15 | 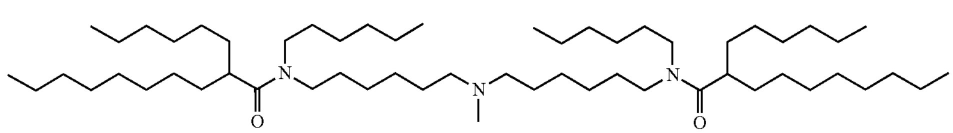 [SMILES: CCCCCCCCC(CCCCCC)C(=O)N(CCCCCC)CCCCCCN(C)CCCCCCN(CCCCCC)C(=O)C(CCCCCC)CCCCCCCC] |

TABLE 1-continued

Representative Compounds

| No. | Structure |
|---|---|
| I-16 | 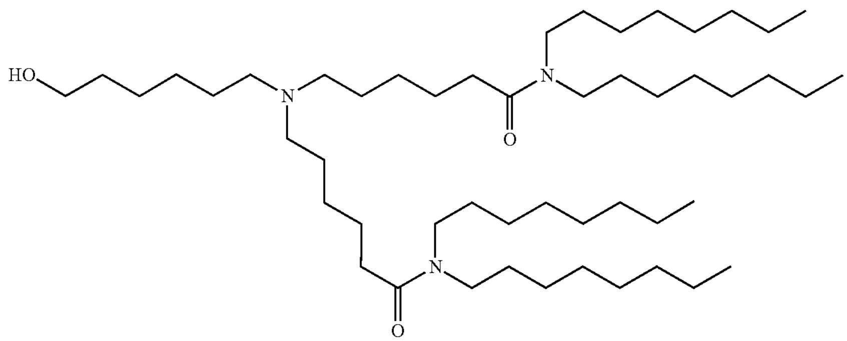 [SMILES: CCCCCCCCN(CCCCCCCC)C(=O)CCCCCN(CCCCCCO)CCCCCC(=O)N(CCCCCCCC)CCCCCCCC] |
| I-17 | 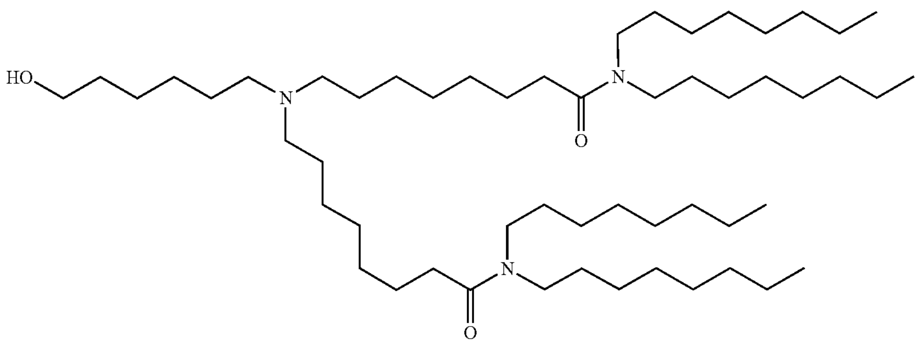 [SMILES: CCCCCCCCN(CCCCCCCC)C(=O)CCCCCCCN(CCCCCCO)CCCCCCCC(=O)N(CCCCCCCC)CCCCCCCC] |
| I-18 | 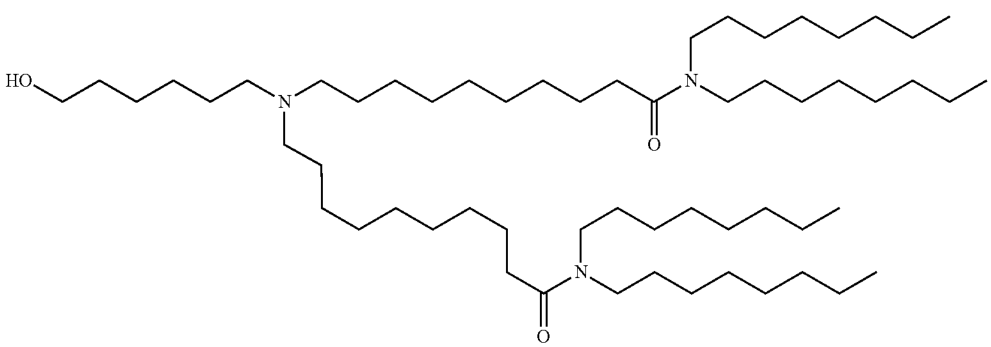 [SMILES: CCCCCCCCN(CCCCCCCC)C(=O)CCCCCCCCCN(CCCCCCO)CCCCCCCCCC(=O)N(CCCCCCCC)CCCCCCCC] |
| I-19 | 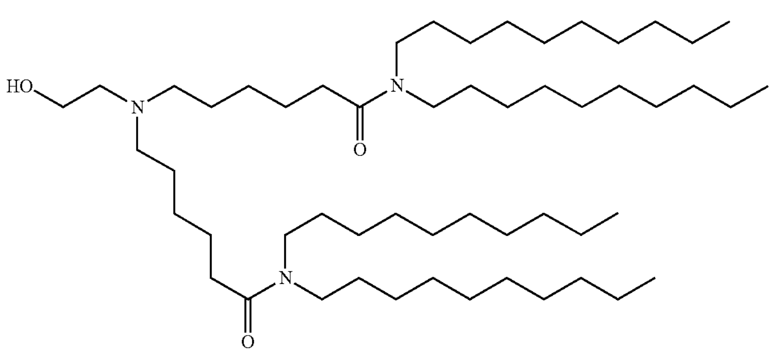 [SMILES: CCCCCCCCCCN(CCCCCCCCCC)C(=O)CCCCCN(CCO)CCCCCC(=O)N(CCCCCCCCCC)CCCCCCCCCC] |

TABLE 1-continued
Representative Compounds
| No. | Structure |
|---|---|
| I-20 | 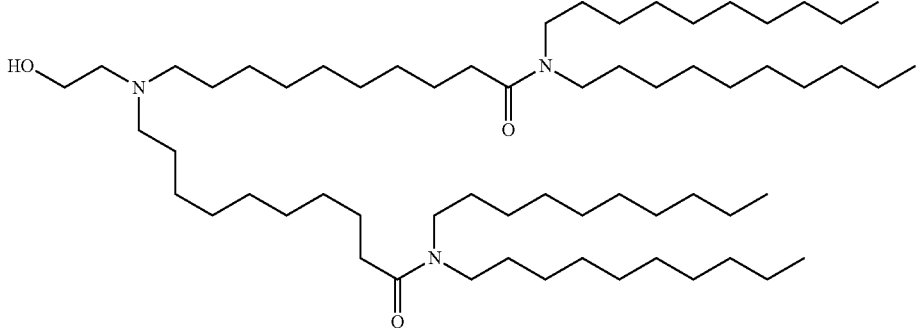 [SMILES: CCCCCCCCCCN(CCCCCCCCCC)C(=O)CCCCCCCCCN(CCO)CCCCCCCCCC(=O)N(CCCCCCCCCC)CCCCCCCCCC] |
| I-21 | 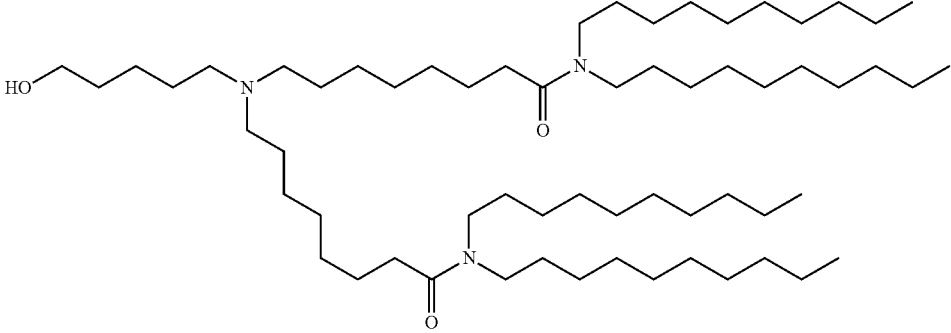 [SMILES: CCCCCCCCCCN(CCCCCCCCCC)C(=O)CCCCCCCN(CCCCCO)CCCCCCCC(=O)N(CCCCCCCCCC)CCCCCCCCCC] |
| I-22 | 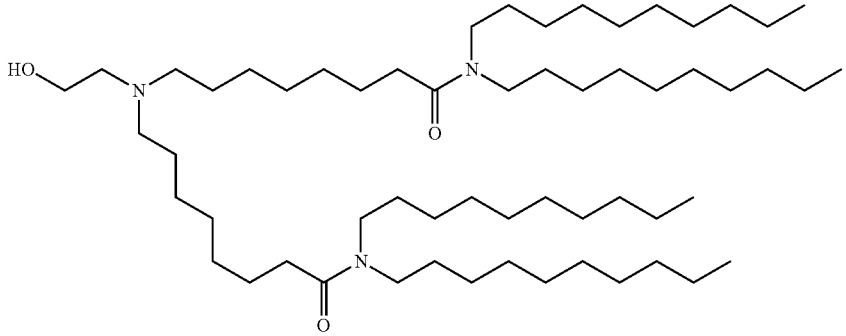 [SMILES: CCCCCCCCCCN(CCCCCCCCCC)C(=O)CCCCCCCN(CCO)CCCCCCCC(=O)N(CCCCCCCCCC)CCCCCCCCCC] |
| I-23 | 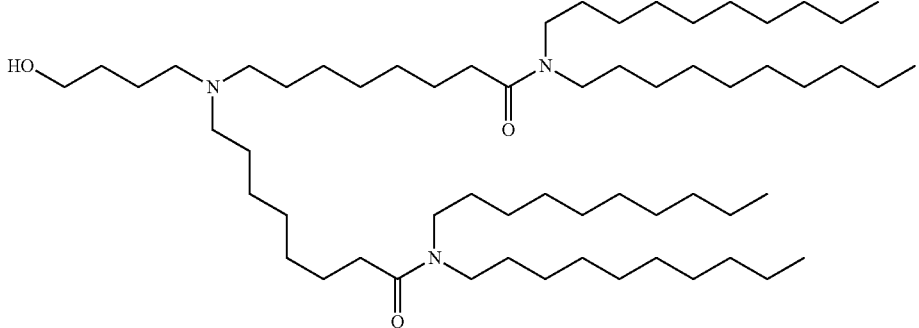 [SMILES: CCCCCCCCCCN(CCCCCCCCCC)C(=O)CCCCCCCN(CCCCO)CCCCCCCC(=O)N(CCCCCCCCCC)CCCCCCCCCC] |

TABLE 1-continued
Representative Compounds
| No. | Structure |
| --- | --- |
| I-24 | 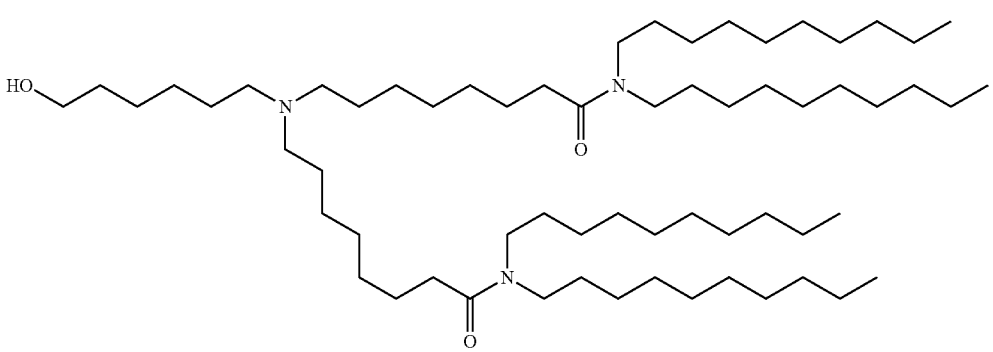 [SMILES: CCCCCCCCCCN(CCCCCCCCCC)C(=O)CCCCCCCN(CCCCCCO)CCCCCCCC(=O)N(CCCCCCCCCC)CCCCCCCCCC] |
| I-25 | 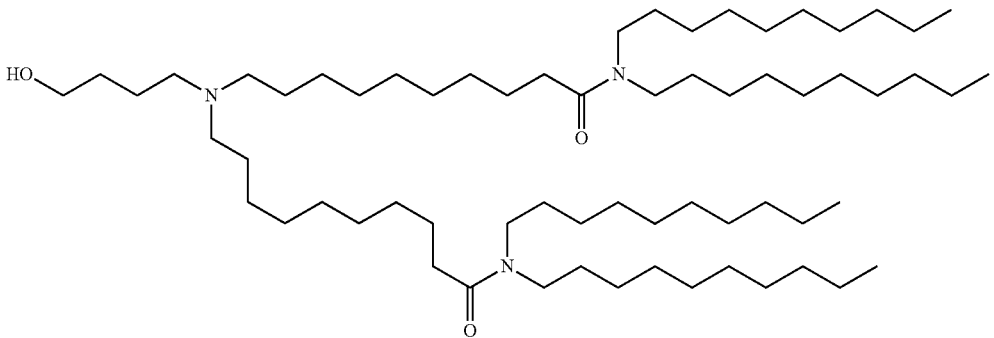 [SMILES: CCCCCCCCCCN(CCCCCCCCCC)C(=O)CCCCCCCCCN(CCCCO)CCCCCCCCCC(=O)N(CCCCCCCCCC)CCCCCCCCCC] |
| I-26 | 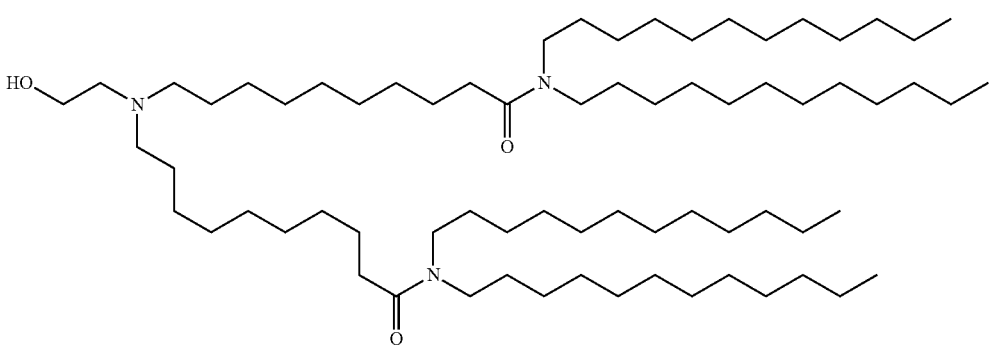 [SMILES: CCCCCCCCCCCCN(CCCCCCCCCCCC)C(=O)CCCCCCCCCN(CCO)CCCCCCCCCC(=O)N(CCCCCCCCCCCC)CCCCCCCCCCCC] |

TABLE 1-continued

Representative Compounds

| No. | Structure |
|---|---|
| I-27 | 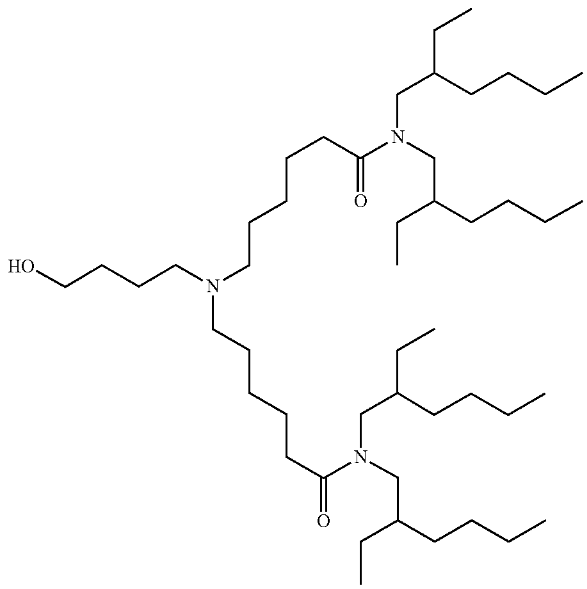 [SMILES: CCCCC(CC)CN(CC(CC)CCCC)C(=O)CCCCCN(CCCCO)CCCCCC(=O)N(CC(CC)CCCC)CC(CC)CCCC] |
| I-28 | 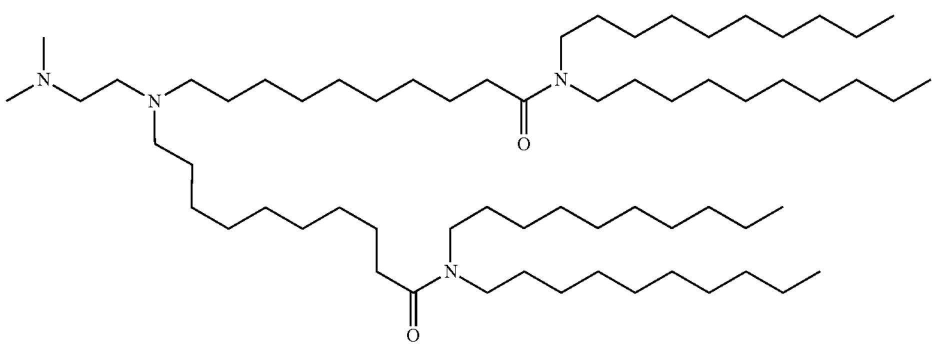 [SMILES: CCCCCCCCCCN(CCCCCCCCCC)C(=O)CCCCCCCCCN(CCCCCCCCCC(=O)N(CCCCCCCCCC)CCCCCCCCCC)CCN(C)C] |
| I-29 | 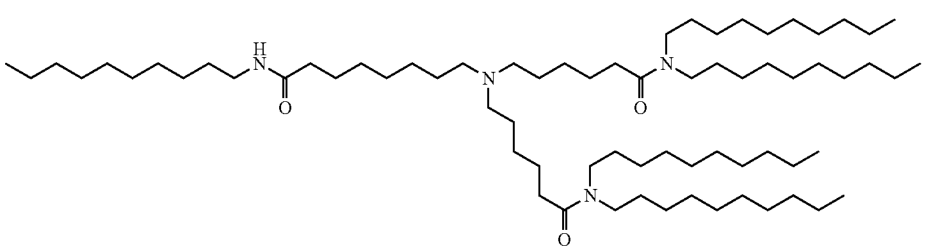 [SMILES: CCCCCCCCCCNC(=O)CCCCCCCN(CCCCCC(=O)N(CCCCCCCCCC)CCCCCCCCCC)CCCCCC(=O)N(CCCCCCCCCC)CCCCCCCCCC] |
| I-30 | 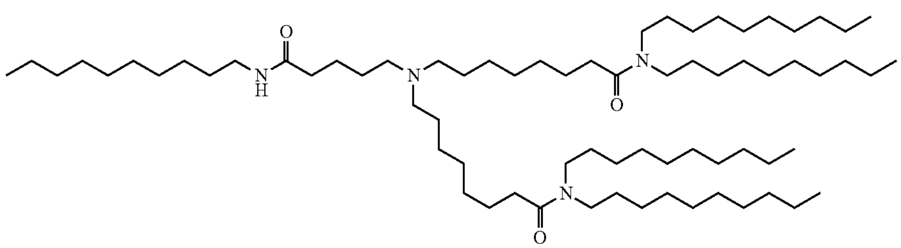 [SMILES: CCCCCCCCCCNC(=O)CCCCN(CCCCCCCC(=O)N(CCCCCCCCCC)CCCCCCCCCC)CCCCCCCC(=O)N(CCCCCCCCCC)CCCCCCCCCC] |

TABLE 1-continued

Representative Compounds

| No. | Structure |
|---|---|
| I-31 | 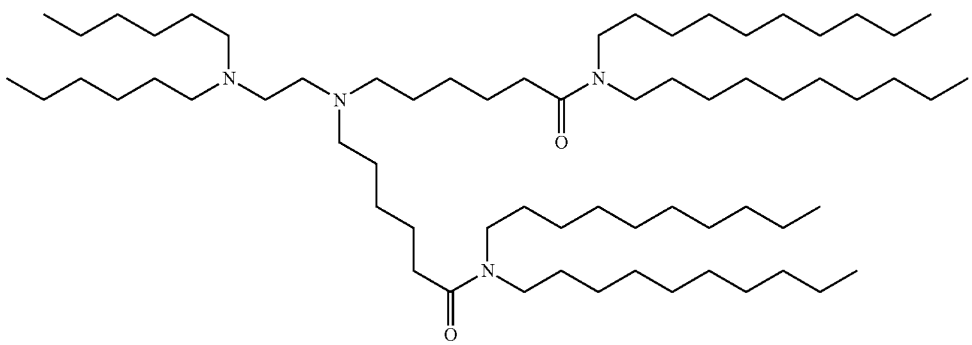 [SMILES: CCCCCCCCCCN(CCCCCCCCCC)C(=O)CCCCCN(CCCCCC(=O)N(CCCCCCCCCC)CCCCCCCCCC)CCN(CCCCCC)CCCCCC] |
| I-32 | 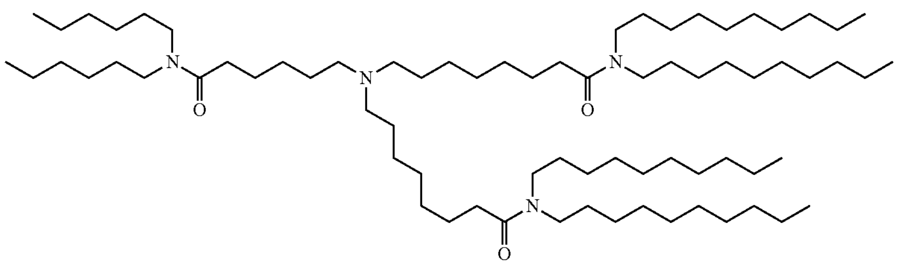 [SMILES: CCCCCCCCCCN(CCCCCCCCCC)C(=O)CCCCCCCN(CCCCCCCC(=O)N(CCCCCCCCCC)CCCCCCCCCC)CCCCCC(=O)N(CCCCCC)CCCCCC] |
| I-33 | 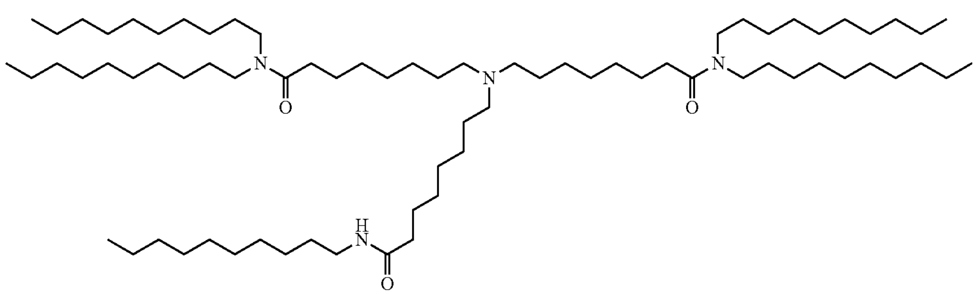 [SMILES: CCCCCCCCCCNC(=O)CCCCCCCN(CCCCCCCC(=O)N(CCCCCCCCCC)CCCCCCCCCC)CCCCCCCC(=O)N(CCCCCCCCCC)CCCCCCCCCC] |
| I-34 | 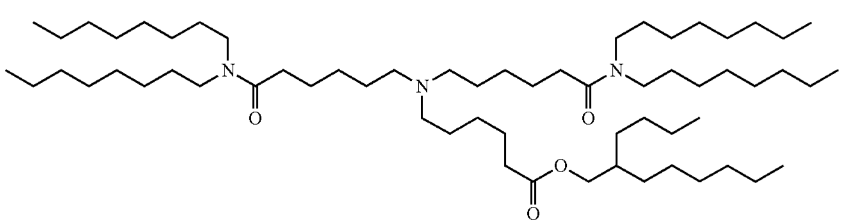 [SMILES: CCCCCCCCN(CCCCCCCC)C(=O)CCCCCN(CCCCCC(=O)OCC(CCCC)CCCCCC)CCCCCC(=O)N(CCCCCCCC)CCCCCCCC] |
| I-35 | 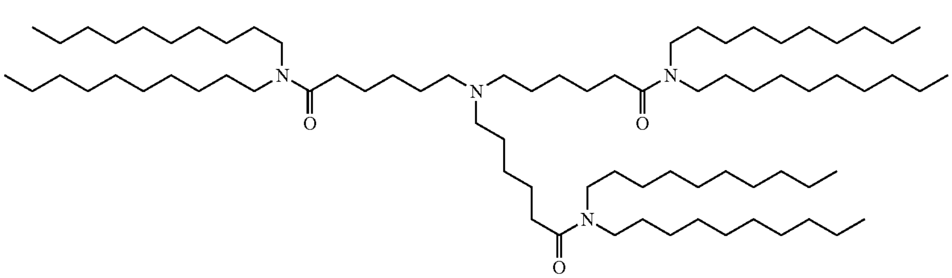 [SMILES: CCCCCCCCCCN(CCCCCCCCCC)C(=O)CCCCCN(CCCCCC(=O)N(CCCCCCCCCC)CCCCCCCCCC)CCCCCC(=O)N(CCCCCCCCCC)CCCCCCCCCC] |

TABLE 1-continued
Representative Compounds
| No. | Structure |
|---|---|
| I-36 | 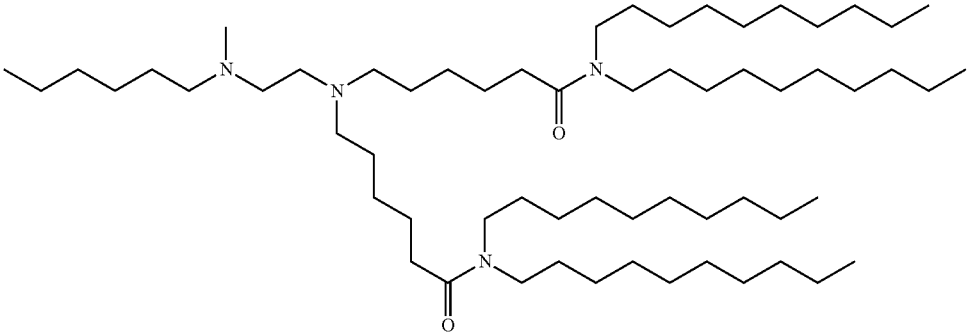 [SMILES: CCCCCCCCCCN(CCCCCCCCCC)C(=O)CCCCCN(CCCCCC(=O)N(CCCCCCCCCC)CCCCCCCCCC)CCN(C)CCCCCC] |
| I-37 | 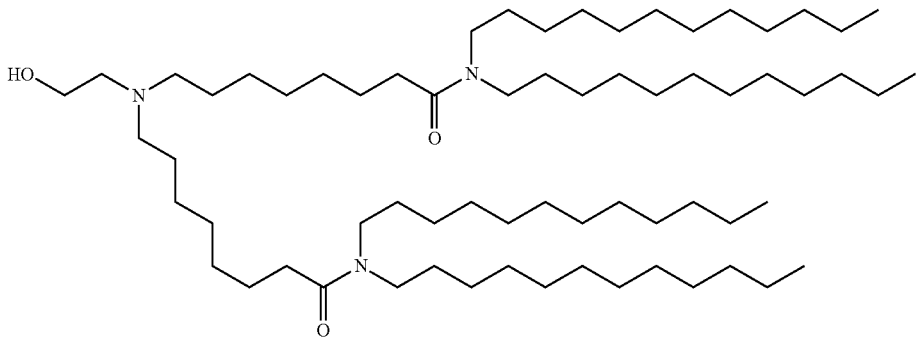 [SMILES: CCCCCCCCCCCCN(CCCCCCCCCCCC)C(=O)CCCCCCCN(CCO)CCCCCCCC(=O)N(CCCCCCCCCCCC)CCCCCCCCCCCC] |
| I-38 | 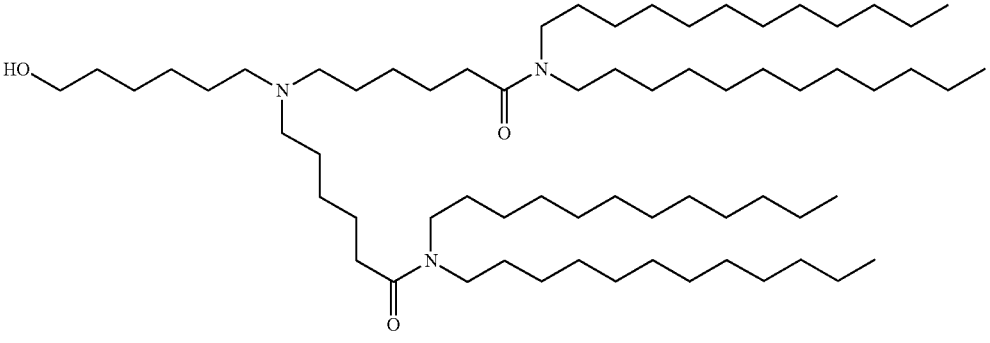 [SMILES: CCCCCCCCCCCCN(CCCCCCCCCCCC)C(=O)CCCCCN(CCCCCCO)CCCCCC(=O)N(CCCCCCCCCCCC)CCCCCCCCCCCC] |
| I-39 | 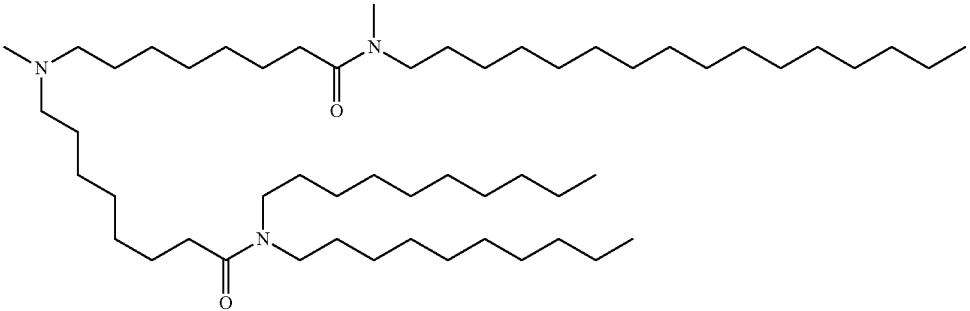 [SMILES: CCCCCCCCCCCCCCCCN(C)C(=O)CCCCCCCN(C)CCCCCCCC(=O)N(CCCCCCCCCC)CCCCCCCCCC] |

TABLE 1-continued
Representative Compounds
| No. | Structure |
|---|---|
| I-40 | 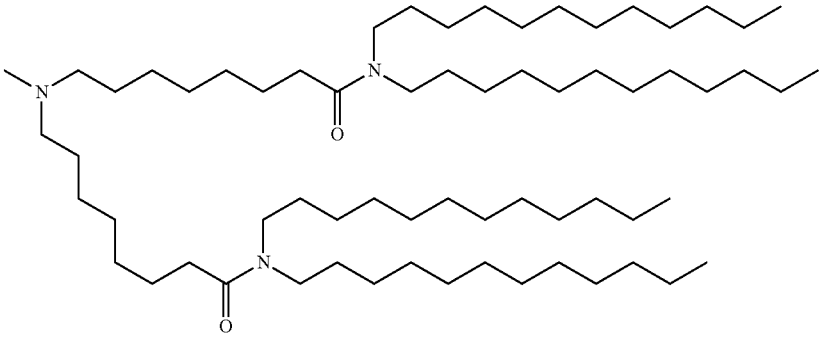 [SMILES: CCCCCCCCCCCCN(CCCCCCCCCCCC)C(=O)CCCCCCCN(C)CCCCCCCC(=O)N(CCCCCCCCCCCC)CCCCCCCCCCCC] |
| I-41 | 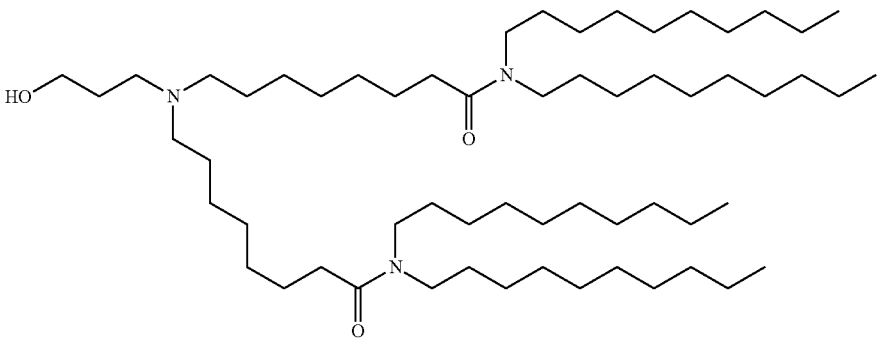 [SMILES: CCCCCCCCCCN(CCCCCCCCCC)C(=O)CCCCCCCN(CCCO)CCCCCCCC(=O)N(CCCCCCCCCC)CCCCCCCCCC] |
| I-42 | 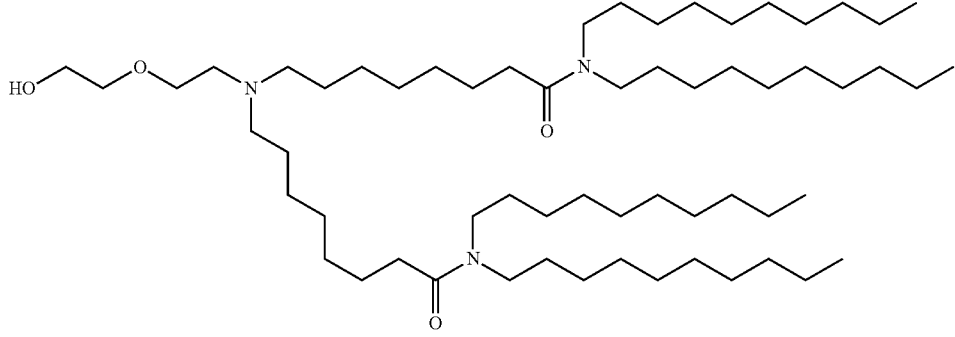 [SMILES: CCCCCCCCCCN(CCCCCCCCCC)C(=O)CCCCCCCN(CCCCCCCC(=O)N(CCCCCCCCCC)CCCCCCCCCC)CCOCCO] |
| I-43 | 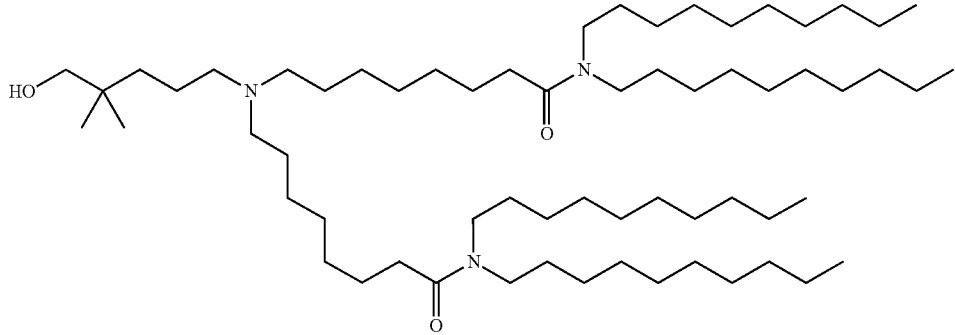 [SMILES: CCCCCCCCCCN(CCCCCCCCCC)C(=O)CCCCCCCN(CCCCCCCC(=O)N(CCCCCCCCCC)CCCCCCCCCC)CCCC(C)(C)CO] |

TABLE 1-continued
Representative Compounds
| No. | Structure |
|---|---|
| I-44 | 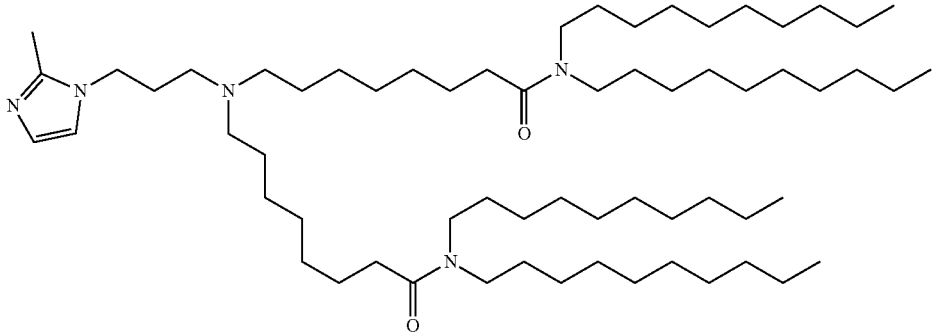 [SMILES: CCCCCCCCCCN(CCCCCCCCCC)C(=O)CCCCCCCN(CCCCCCCC(=O)N(CCCCCCCCCC)CCCCCCCCCC)CCCn1ccnc1C] |
| I-45 | 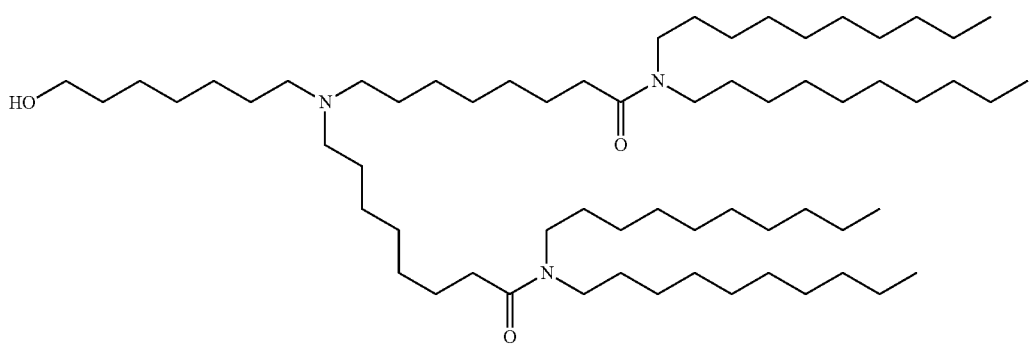 [SMILES: CCCCCCCCCCN(CCCCCCCCCC)C(=O)CCCCCCCN(CCCCCCCO)CCCCCCCC(=O)N(CCCCCCCCCC)CCCCCCCCCC] |
| I-46 | 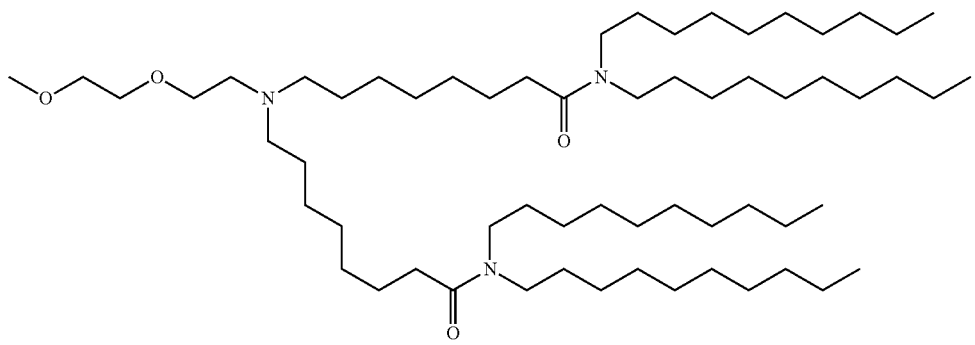 [SMILES: CCCCCCCCCCN(CCCCCCCCCC)C(=O)CCCCCCCN(CCCCCCCC(=O)N(CCCCCCCCCC)CCCCCCCCCC)CCOCCOC] |
| I-47 | 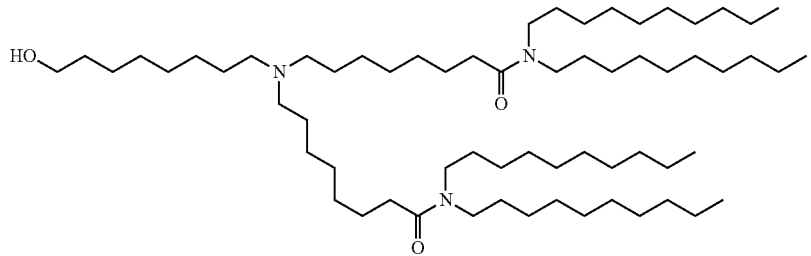 [SMILES: CCCCCCCCCCN(CCCCCCCCCC)C(=O)CCCCCCCN(CCCCCCCCO)CCCCCCCC(=O)N(CCCCCCCCCC)CCCCCCCCCC] |

TABLE 1-continued
Representative Compounds
| No. | Structure |
|---|---|
| I-48 | 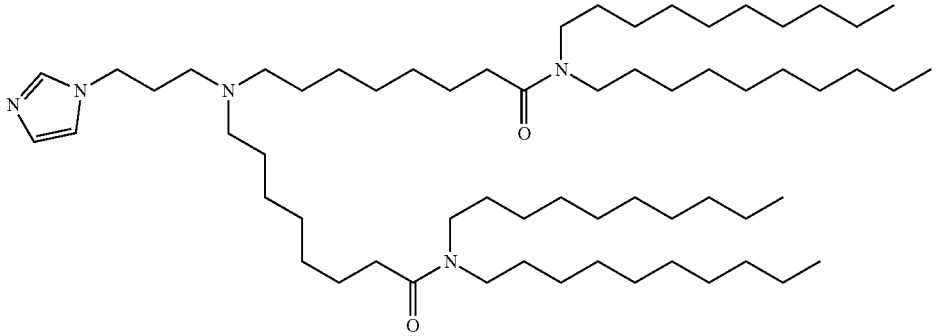 [SMILES: CCCCCCCCCCN(CCCCCCCCCC)C(=O)CCCCCCCN(CCCCCCCC(=O)N(CCCCCCCCCC)CCCCCCCCCC)CCCn1ccnc1] |
| I-49 | 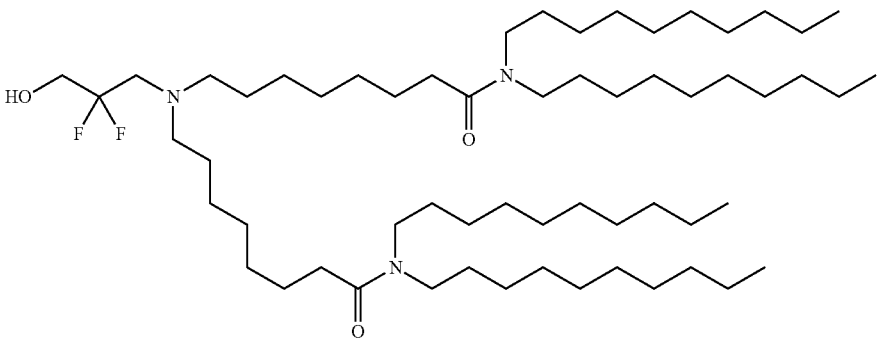 [SMILES: CCCCCCCCCCN(CCCCCCCCCC)C(=O)CCCCCCCN(CCCCCCCC(=O)N(CCCCCCCCCC)CCCCCCCCCC)CC(F)(F)CO] |
| I-50 | 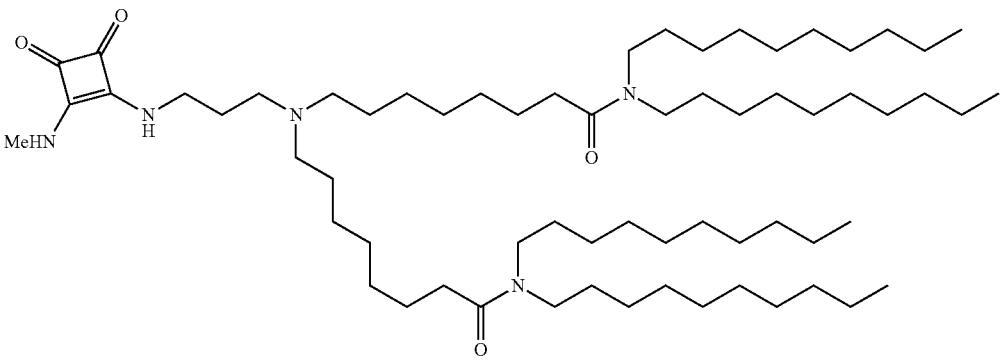 [SMILES: CCCCCCCCCCN(CCCCCCCCCC)C(=O)CCCCCCCN(CCCCCCCC(=O)N(CCCCCCCCCC)CCCCCCCCCC)CCCNc1c(NC)c(=O)c1=O] |
| I-51 | 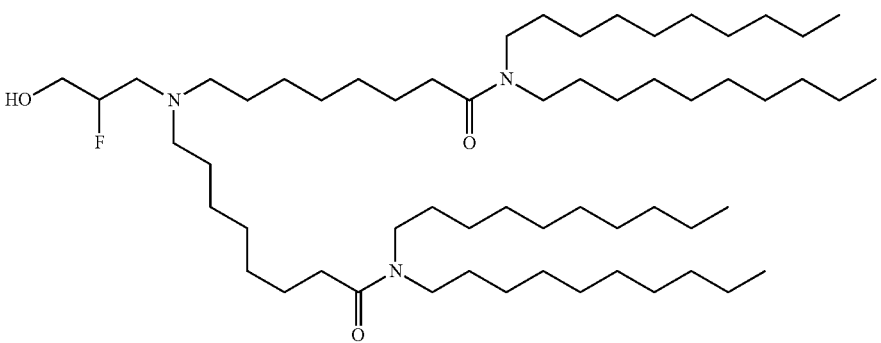 [SMILES: CCCCCCCCCCN(CCCCCCCCCC)C(=O)CCCCCCCN(CCCCCCCC(=O)N(CCCCCCCCCC)CCCCCCCCCC)CC(F)CO] |

TABLE 1-continued

Representative Compounds

| No. | Structure |
|---|---|
| I-52 | 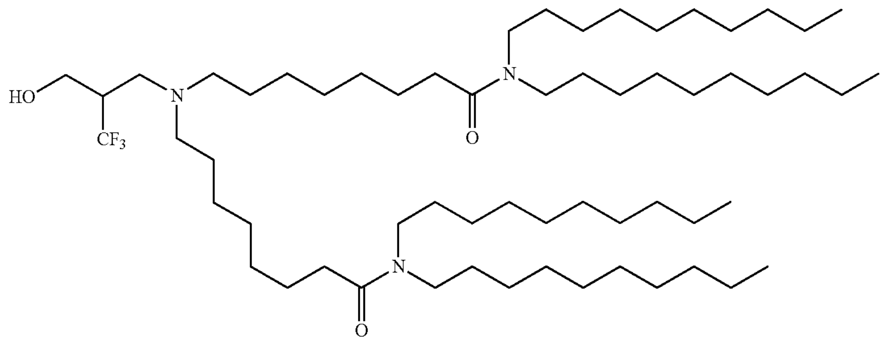 [SMILES: CCCCCCCCCCN(CCCCCCCCCC)C(=O)CCCCCCCN(CCCCCCCC(=O)N(CCCCCCCCCC)CCCCCCCCCC)CC(CO)C(F)(F)F] |
| I-53 | 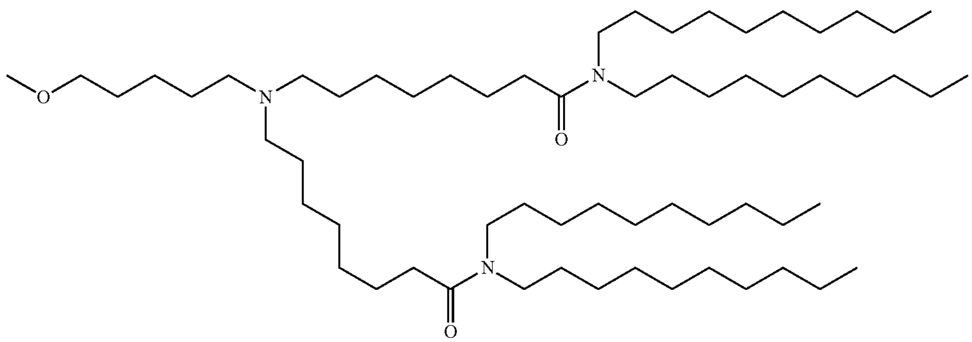 [SMILES: CCCCCCCCCCN(CCCCCCCCCC)C(=O)CCCCCCCN(CCCCCCCC(=O)N(CCCCCCCCCC)CCCCCCCCCC)CCCCCOC] |
| I-54 | 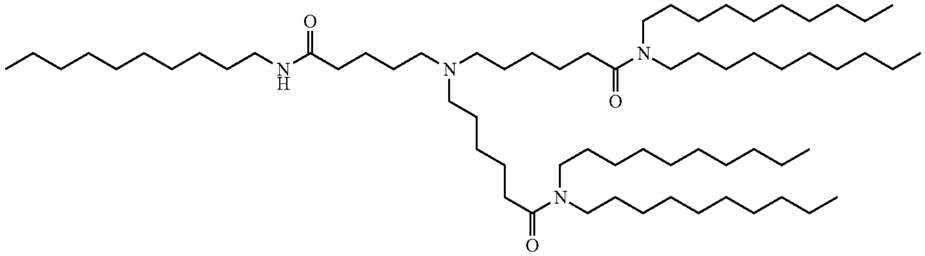 [SMILES: CCCCCCCCCCNC(=O)CCCCN(CCCCCC(=O)N(CCCCCCCCCC)CCCCCCCCCC)CCCCCC(=O)N(CCCCCCCCCC)CCCCCCCCCC] |
| I-55 | 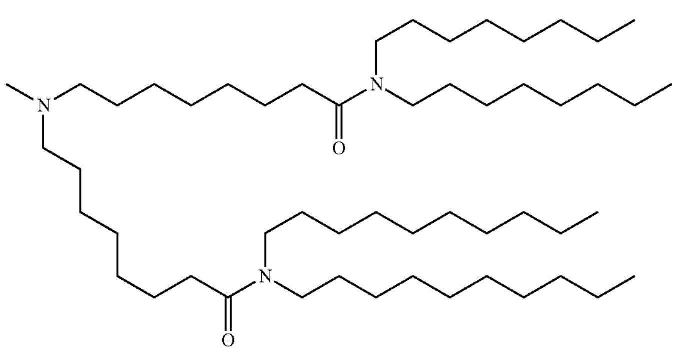 [SMILES: CCCCCCCCCCN(CCCCCCCCCC)C(=O)CCCCCCCN(C)CCCCCCCC(=O)N(CCCCCCCC)CCCCCCCC] |
| I-56 | 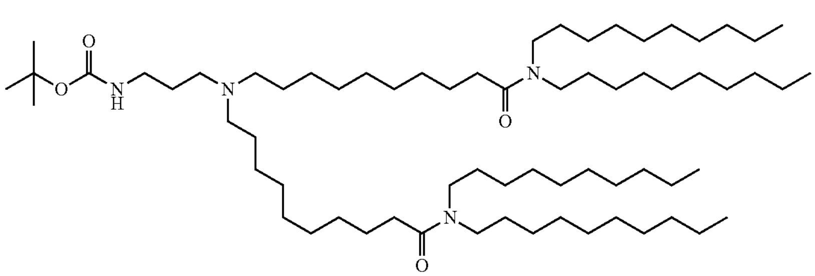 [SMILES: CCCCCCCCCCN(CCCCCCCCCC)C(=O)CCCCCCCCCN(CCCCCCCCCC(=O)N(CCCCCCCCCC)CCCCCCCCCC)CCCNC(=O)OC(C)(C)C] |

TABLE 1-continued

Representative Compounds

| No. | Structure |
|---|---|
| I-57 | 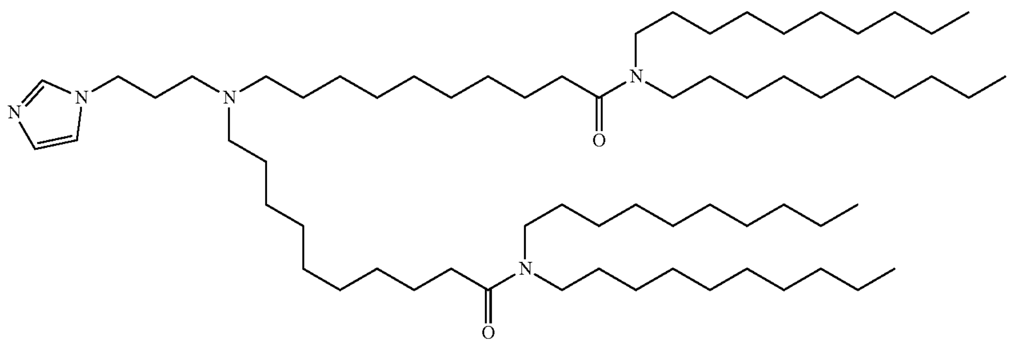 [SMILES: CCCCCCCCCCN(CCCCCCCCCC)C(=O)CCCCCCCCCN(CCCCCCCCCC(=O)N(CCCCCCCCCC)CCCCCCCCCC)CCCn1ccnc1] |
| I-58 | 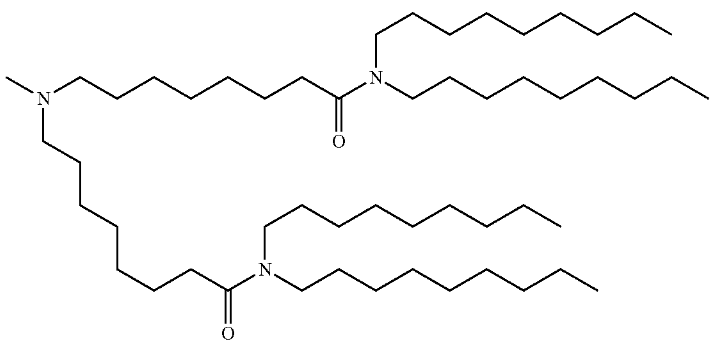 [SMILES: CCCCCCCCCN(CCCCCCCCC)C(=O)CCCCCCCN(C)CCCCCCCC(=O)N(CCCCCCCCC)CCCCCCCCC] |
| I-59 | 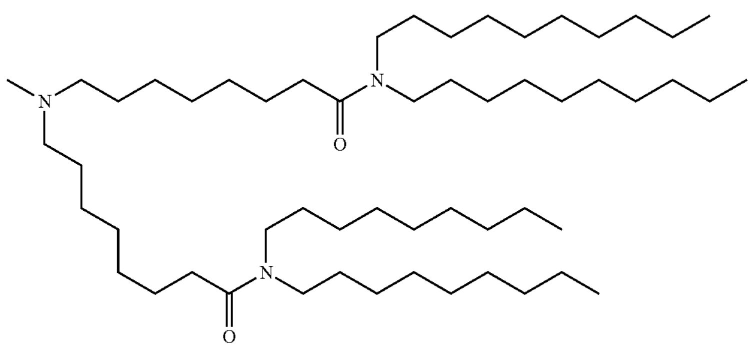 [SMILES: CCCCCCCCCCN(CCCCCCCCCC)C(=O)CCCCCCCN(C)CCCCCCCC(=O)N(CCCCCCCCC)CCCCCCCCC] |
| I-60 | 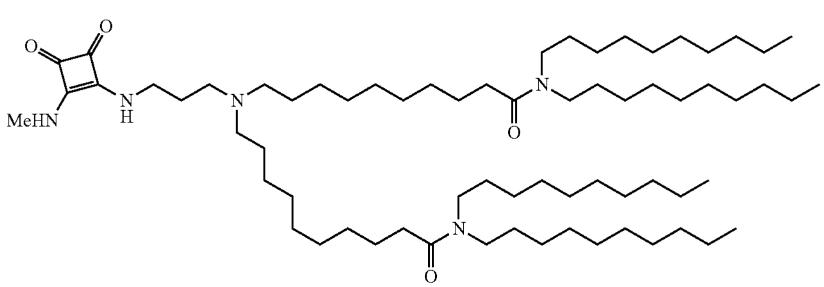 [SMILES: CCCCCCCCCCN(CCCCCCCCCC)C(=O)CCCCCCCCCN(CCCCCCCCCC(=O)N(CCCCCCCCCC)CCCCCCCCCC)CCCNc1c(NC)c(=O)c1=O] |

TABLE 1-continued

Representative Compounds

| No. | Structure |
|---|---|
| I-61 | 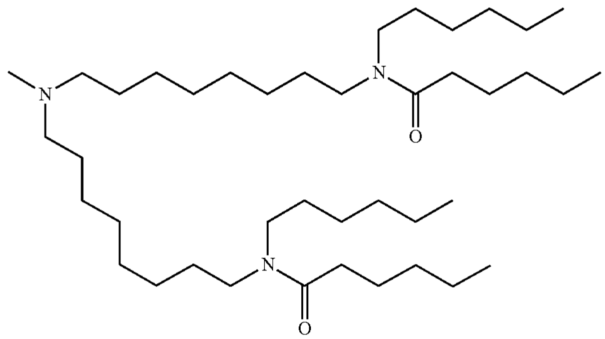 [SMILES: CCCCCCN(CCCCCCCCN(C)CCCCCCCCN(CCCCCC)C(=O)CCCCC)C(=O)CCCCC] |
| I-62 | 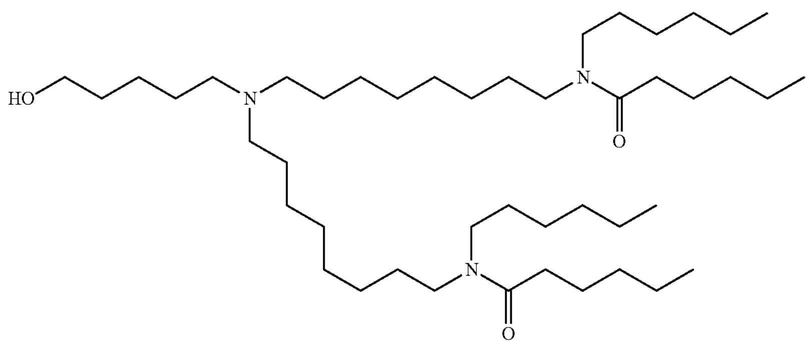 [SMILES: CCCCCCN(CCCCCCCCN(CCCCCO)CCCCCCCCN(CCCCCC)C(=O)CCCCC)C(=O)CCCCC] |
| I-63 | 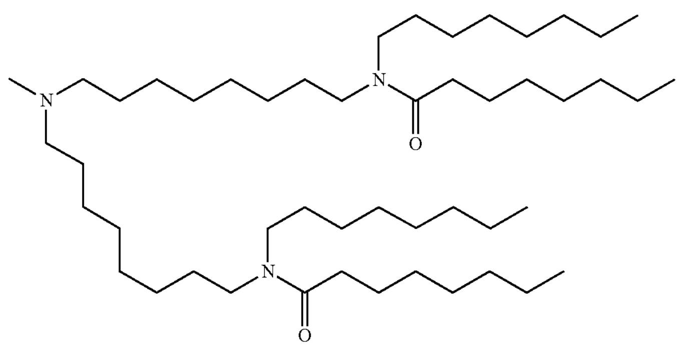 [SMILES: CCCCCCCCN(CCCCCCCCN(C)CCCCCCCCN(CCCCCCCC)C(=O)CCCCCCC)C(=O)CCCCCCC] |
| I-64 | 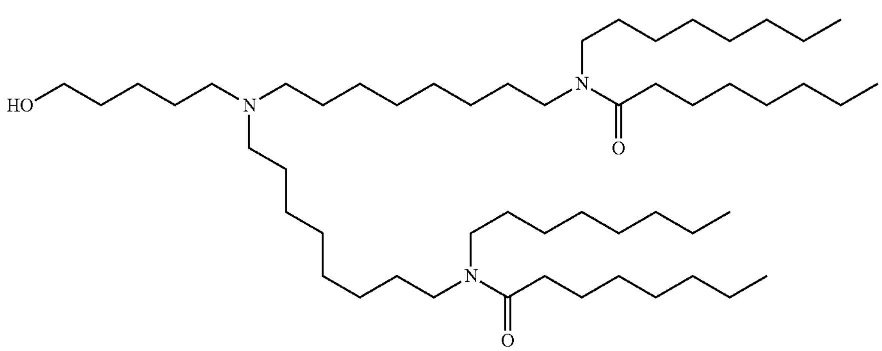 [SMILES: CCCCCCCCN(CCCCCCCCN(CCCCCO)CCCCCCCCN(CCCCCCCC)C(=O)CCCCCCC)C(=O)CCCCCCC] |

TABLE 1-continued
Representative Compounds
| No. | Structure |
|---|---|
| I-65 | 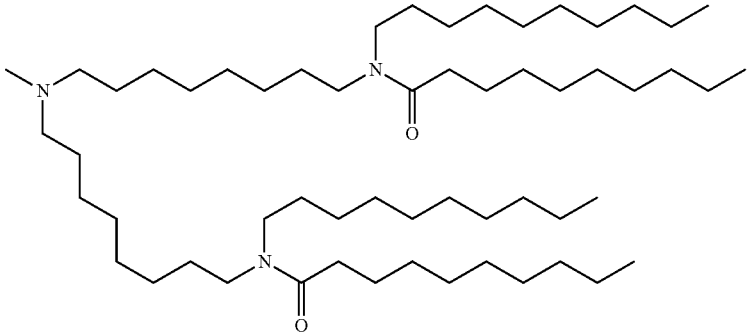 [SMILES: CCCCCCCCCCN(CCCCCCCCN(C)CCCCCCCCN(CCCCCCCCCC)C(=O)CCCCCCCCC)C(=O)CCCCCCCCC] |
| I-66 | 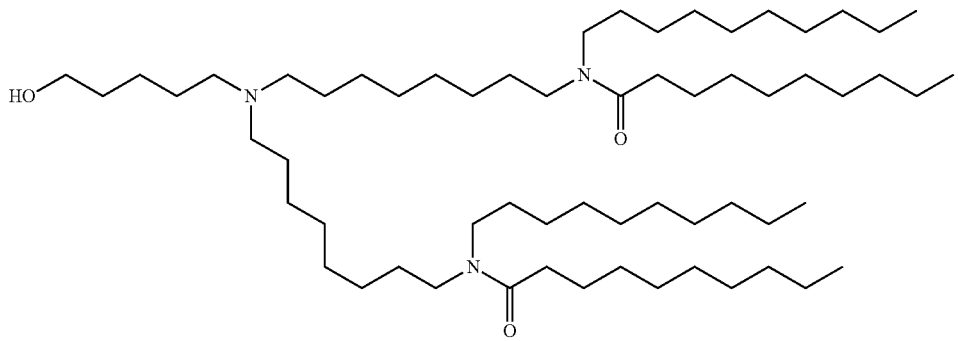 [SMILES: CCCCCCCCCCN(CCCCCCCCN(CCCCCO)CCCCCCCCN(CCCCCCCCCC)C(=O)CCCCCCCCC)C(=O)CCCCCCCCC] |
| I-67 | 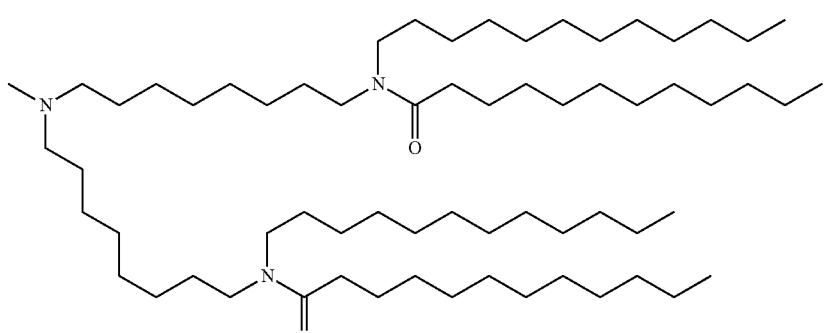 |
| I-68 | 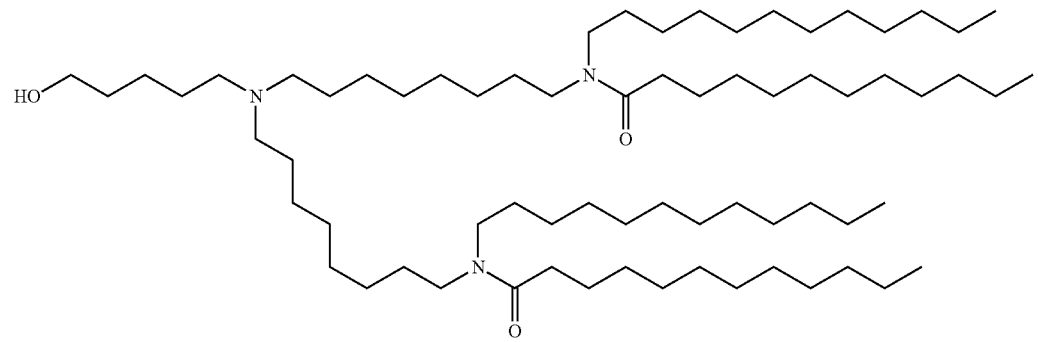 [SMILES: CCCCCCCCCCCCN(CCCCCCCCN(CCCCCO)CCCCCCCCN(CCCCCCCCCCCC)C(=O)CCCCCCCCCCC)C(=O)CCCCCCCCCCC] |

TABLE 1-continued
Representative Compounds
| No. | Structure |
|---|---|
| I-69 | 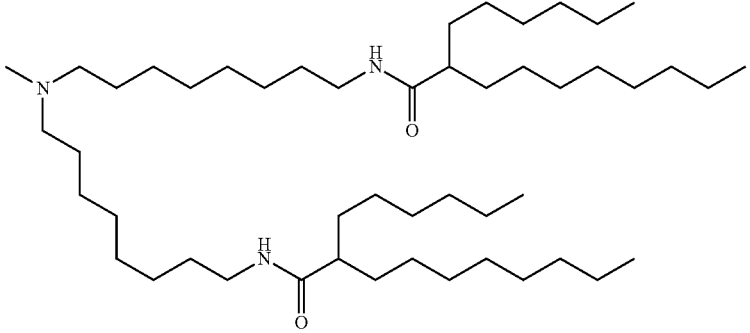 [SMILES: CCCCCCCCC(CCCCCC)C(=O)NCCCCCCCCN(C)CCCCCCCCNC(=O)C(CCCCCC)CCCCCCCC] |
| I-70 | 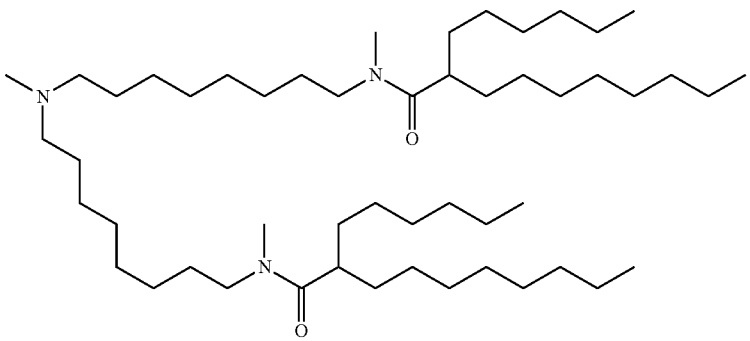 [SMILES: CCCCCCCCC(CCCCCC)C(=O)N(C)CCCCCCCCN(C)CCCCCCCCN(C)C(=O)C(CCCCCC)CCCCCCCC] |
| I-71 | 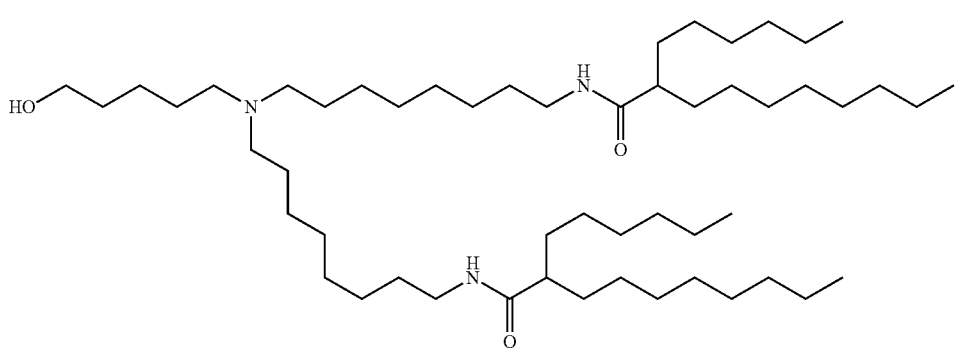 [SMILES: CCCCCCCCC(CCCCCC)C(=O)NCCCCCCCCN(CCCCCO)CCCCCCCCNC(=O)C(CCCCCC)CCCCCCCC] |
| I-72 | 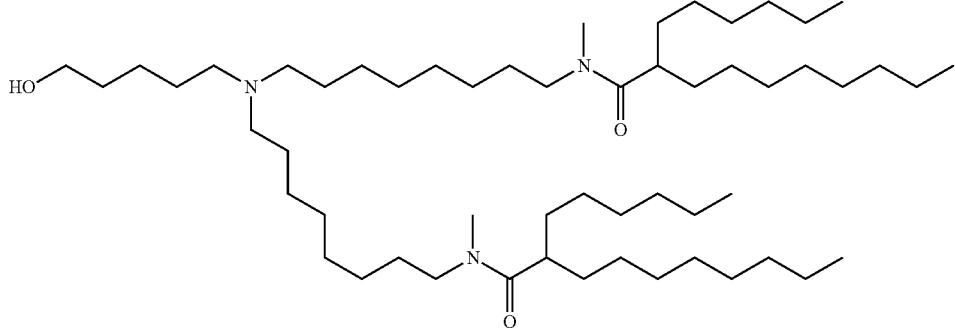 [SMILES: CCCCCCCCC(CCCCCC)C(=O)N(C)CCCCCCCCN(CCCCCO)CCCCCCCCN(C)C(=O)C(CCCCCC)CCCCCCCC] |

TABLE 1-continued
Representative Compounds
| No. | Structure |
|---|---|
| I-73 | 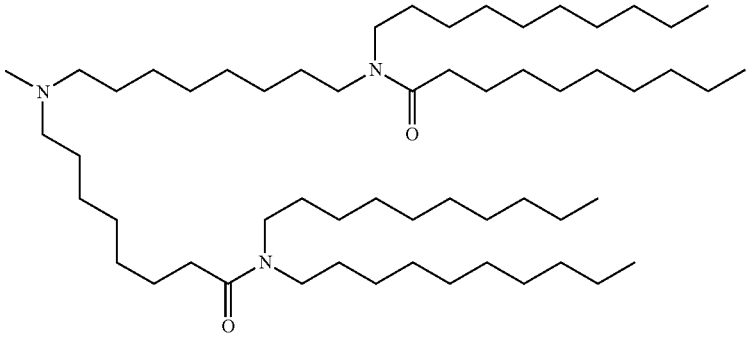 [SMILES: CCCCCCCCCCN(CCCCCCCCN(C)CCCCCCCC(=O)N(CCCCCCCCCC)CCCCCCCCCC)C(=O)CCCCCCCCC] |
| I-74 | 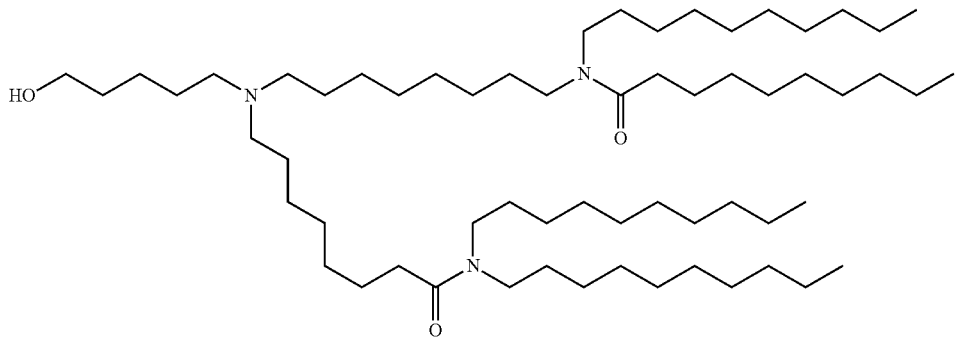 [SMILES: CCCCCCCCCCN(CCCCCCCCN(CCCCCO)CCCCCCCC(=O)N(CCCCCCCCCC)CCCCCCCCCC)C(=O)CCCCCCCCC] |
| I-75 | 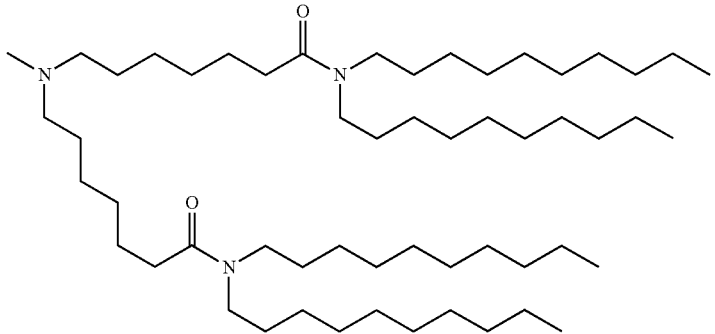 [SMILES: CCCCCCCCCCN(CCCCCCCCCC)C(=O)CCCCCCN(C)CCCCCCC(=O)N(CCCCCCCCCC)CCCCCCCCCC] |
| I-76 | 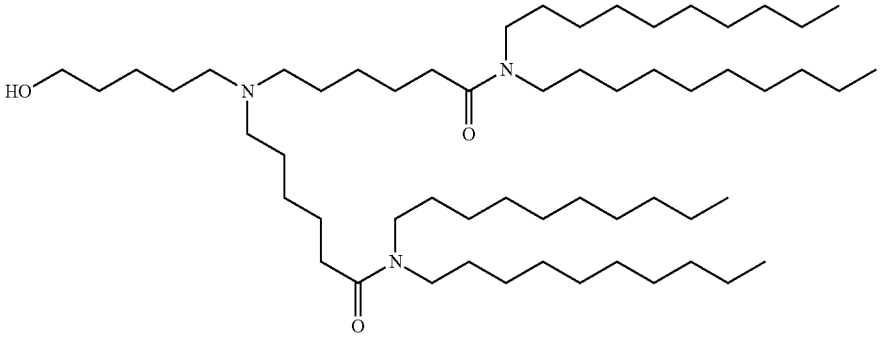 [SMILES: CCCCCCCCCCN(CCCCCCCCCC)C(=O)CCCCCN(CCCCCO)CCCCCC(=O)N(CCCCCCCCCC)CCCCCCCCCC] |

TABLE 1-continued

Representative Compounds

| No. | Structure |
|---|---|
| I-77 | 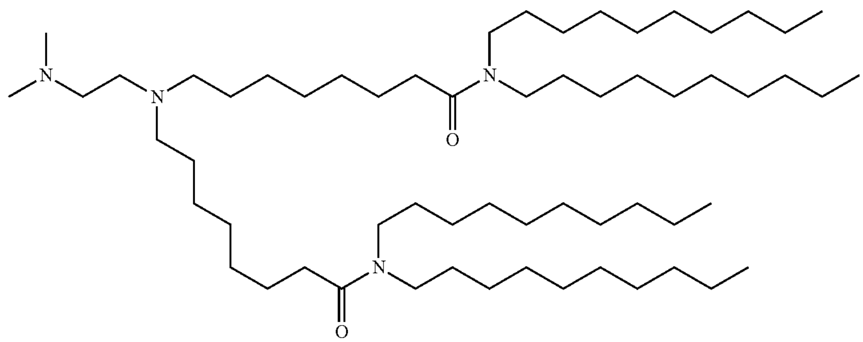 [SMILES: CCCCCCCCCCN(CCCCCCCCCC)C(=O)CCCCCCCN(CCCCCCCC(=O)N(CCCCCCCCCC)CCCCCCCCCC)CCN(C)C] |
| I-78 | 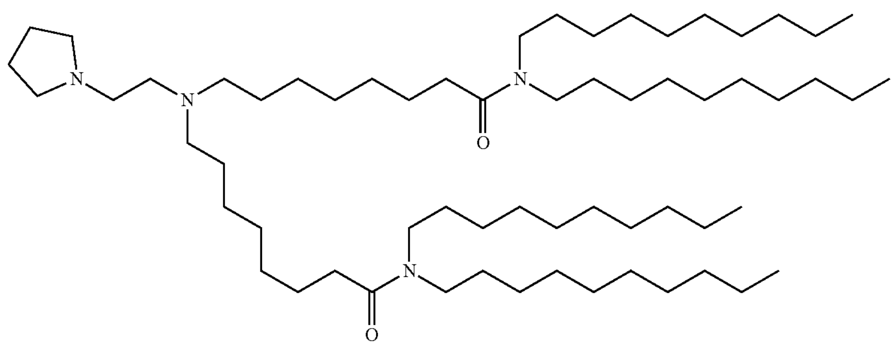 [SMILES: CCCCCCCCCCN(CCCCCCCCCC)C(=O)CCCCCCCN(CCCCCCCC(=O)N(CCCCCCCCCC)CCCCCCCCCC)CCN1CCCC1] |
| I-79 | 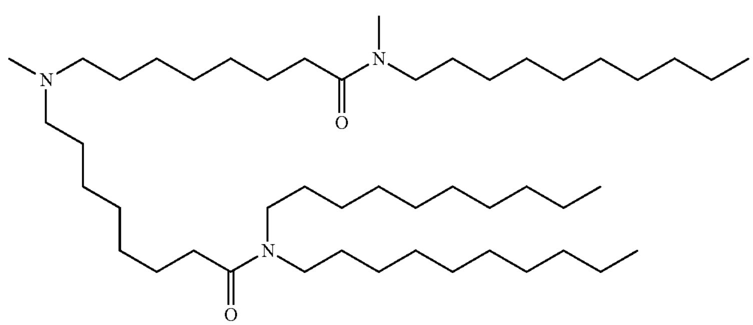 [SMILES: CCCCCCCCCCN(C)C(=O)CCCCCCCN(C)CCCCCCCC(=O)N(CCCCCCCCCC)CCCCCCCCCC] |
| I-80 | 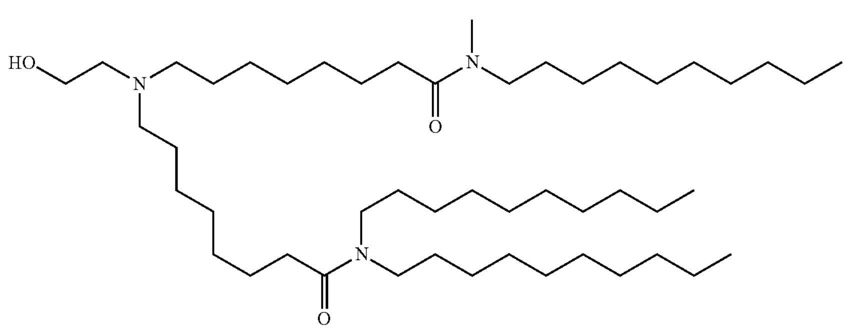 [SMILES: CCCCCCCCCCN(C)C(=O)CCCCCCCN(CCO)CCCCCCCC(=O)N(CCCCCCCCCC)CCCCCCCCCC] |

TABLE 1-continued
Representative Compounds
| No. | Structure |
|---|---|
| I-81 | 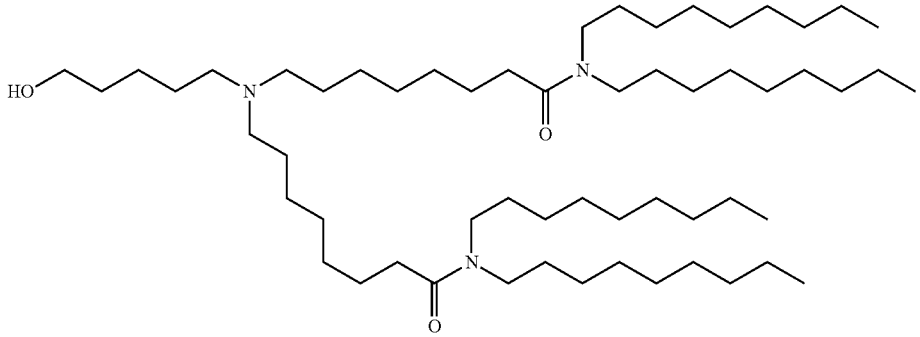 [SMILES: CCCCCCCCCN(CCCCCCCCC)C(=O)CCCCCCCN(CCCCCO)CCCCCCCC(=O)N(CCCCCCCCC)CCCCCCCCC] |
| I-82 | 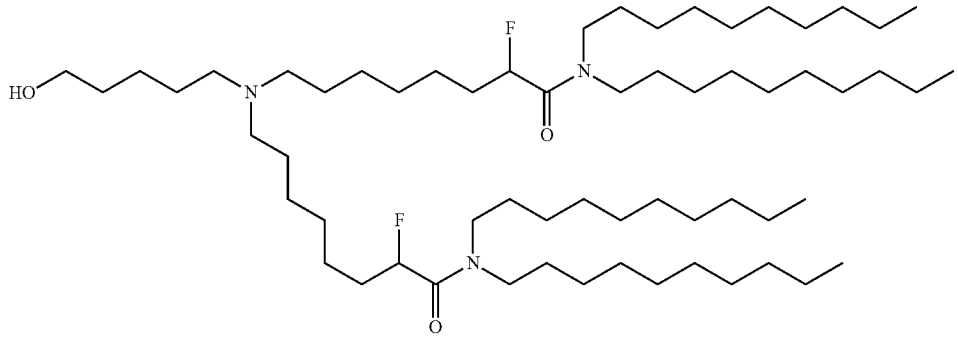 [SMILES: CCCCCCCCCCN(CCCCCCCCCC)C(=O)C(F)CCCCCCN(CCCCCO)CCCCCCC(F)C(=O)N(CCCCCCCCCC)CCCCCCCCCC] |
| I-83 | 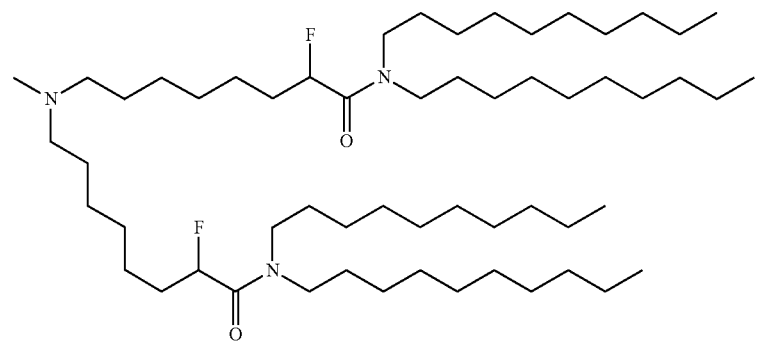 [SMILES: CCCCCCCCCCN(CCCCCCCCCC)C(=O)C(F)CCCCCCN(C)CCCCCCC(F)C(=O)N(CCCCCCCCCC)CCCCCCCCCC] |
| I-84 | 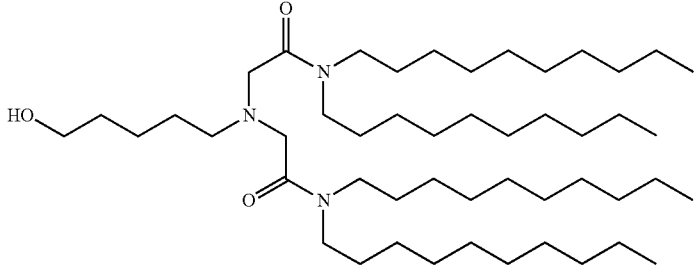 [SMILES: CCCCCCCCCCN(CCCCCCCCCC)C(=O)CN(CCCCCO)CC(=O)N(CCCCCCCCCC)CCCCCCCCCC] |

TABLE 1-continued

Representative Compounds

| No. | Structure |
|---|---|
| I-85 | (structure shown) |

The compounds in Table 1 were prepared and tested according to methods known in the art, for example those general methods described herein below.

It is understood that any embodiment of the compounds of structure (I), as set forth above, and any specific substituent and/or variable in the compound structure (I), as set forth above, may be independently combined with other embodiments and/or substituents and/or variables of compounds of structure (I) to form embodiments of the inventions not specifically set forth above. In addition, in the event that a list of substituents and/or variables is listed for any particular R group, L group, G group, or variables a, x, y, or z in a particular embodiment and/or claim, it is understood that each individual substituent and/or variable may be deleted from the particular embodiment and/or claim and that the remaining list of substituents and/or variables will be considered to be within the scope of embodiments of the invention.

It is understood that in the present description, combinations of substituents and/or variables of the depicted formulae are permissible only if such contributions result in stable compounds.

In some embodiments, compositions comprising a compound of structure (I) are provided. In some embodiments, the compositions comprise lipid nanoparticles comprising a compound of structure (I) are provided. The lipid nanoparticles optionally include excipients selected from a neutral lipid, a steroid and a polymer conjugated lipid.

In some embodiments, lipid nanoparticles comprising any one or more of the compounds of structure (I) and a therapeutic agent are provided. For example, in some embodiments, the lipid nanoparticles comprise any of the compounds of structure (I) and a therapeutic agent and one or more excipient selected from neutral lipids, steroids and polymer conjugated lipids. Other pharmaceutically acceptable excipients and/or carriers are also included in various embodiments of the lipid nanoparticles.

In some embodiments, the neutral lipid is selected from DSPC, DPPC, DMPC, DOPC, POPC, DOPE and SM. In some embodiments, the neutral lipid is DSPC. In various embodiments, the molar ratio of the compound to the neutral lipid ranges from about 2:1 to about 8:1.

In various embodiments, the lipid nanoparticles s further comprise a steroid or steroid analogue. In certain embodiments, the steroid or steroid analogue is cholesterol. In some of these embodiments, the molar ratio of the compound to cholesterol ranges from about 5:1 to 1:1 or about 2:1 to 1:1.

In various embodiments, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanolamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropyl-carbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate. In various embodiments, the molar ratio of the compound to the pegylated lipid ranges from about 100:1 to about 20:1 or about 100:1 to 10:1.

In some embodiments, the composition comprises a pegylated lipid having the following structure (II):

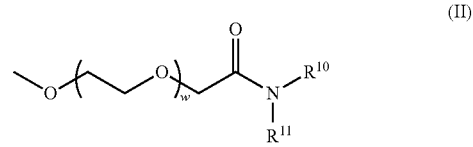

(II)

or a pharmaceutically acceptable salt, tautomer or stereoisomer thereof, wherein:

$R^{10}$ and $R^{11}$ are each independently a straight or branched, alkyl, alkenyl or alkynyl containing from 10 to 30 carbon atoms, wherein the alkyl, alkenyl or alkynyl is optionally interrupted by one or more ester bonds; and w has a mean value ranging from 30 to 60.

In some embodiments, $R^{10}$ and $R^{11}$ are each independently straight alkyl containing from 10 to 30 carbon atoms. In some embodiments, $R^{10}$ and $R^{11}$ are each independently straight alkyl containing 12 to 16 carbon atoms. In some embodiments, w has a mean value ranging from 30 to 60. In some embodiments, w has a mean value ranging 43 to 53. In other embodiments, the average w is about 45. In other different embodiments, the average w is about 49.

Preparation methods for the above lipids, lipid nanoparticles and compositions are described herein below and/or known in the art, for example, in PCT Pub. No. WO 2015/199952, WO 2017/004143 and WO 2017/075531, each of which is incorporated herein by reference in their entireties.

In some embodiments of the foregoing composition, the therapeutic agent comprises a nucleic acid. For example, in some embodiments, the nucleic acid is selected from antisense and messenger RNA.

In other different embodiments, the invention is directed to a method for administering a therapeutic agent to a patient in need thereof, the method comprising preparing or providing any of the foregoing compositions and administering the composition to the patient For the purposes of administration, the compounds of structure (I) (typically in the form of lipid nanoparticles in combination with a therapeutic agent) may be administered as a raw chemical or may be formulated as pharmaceutical compositions. Pharmaceutical compositions of embodiments of the present invention comprise a compound of structure (I) (e.g., as a component in an LNP) and one or more pharmaceutically acceptable carrier, diluent or excipient. The compound of structure (I) is present in the composition in an amount which is effective to form a lipid nanoparticle and deliver the therapeutic agent, e.g., for treating a particular disease or condition of interest. Appropriate concentrations and dosages can be readily determined by one skilled in the art.

Administration of the compositions and/or LNPs of embodiments of the invention can be carried out via any of the accepted modes of administration of agents for serving similar utilities. The pharmaceutical compositions of embodiments of the invention may be formulated into preparations in solid, semi-solid, liquid or gaseous forms, such as tablets, capsules, powders, granules, ointments, solutions, suspensions, suppositories, injections, inhalants, gels, microspheres, and aerosols. Typical routes of administering such pharmaceutical compositions include, without limitation, oral, topical, transdermal, inhalation, peritoneal, sublingual, buccal, rectal, vaginal, and intranasal. The term peritoneal as used herein includes subcutaneous injections, intravenous, intramuscular, intradermal, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of structure (I) in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of structure (I), or a pharmaceutically acceptable salt thereof, for treatment of a disease or condition of interest in accordance with the teachings of embodiments of this invention.

A pharmaceutical composition of embodiments of the invention may be in the form of a solid or liquid. In one aspect, the carrier(s) are particulate, so that the compositions are, for example, in tablet or powder form. The carrier(s) may be liquid, with the compositions being, for example, oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds or LNPs, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of embodiments of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose; agents to act as cryoprotectants such as sucrose or trehalose. The peritoneal preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of embodiments of the invention intended for either peritoneal or oral administration should contain an amount of a compound of structure (I) such that a suitable LNP will be obtained.

The pharmaceutical composition of embodiments of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of embodiments of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of embodiments of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of embodiments of the invention in solid or liquid form may include an agent that binds to the compound of structure (I) and thereby assists in the delivery of the compound. Suitable agents that may act in this capacity include a monoclonal or polyclonal antibody, or a protein.

The pharmaceutical composition of embodiments of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of structure (I) may be delivered in single phase, bi-phasic, or tri-phasic systems in order to deliver the active ingredient(s). Delivery of the aerosol includes the necessary container, activators, valves, sub-containers, and the like, which together may form a kit. One skilled in the art, without undue experimentation may determine preferred aerosols.

The pharmaceutical compositions of embodiments of the invention may be prepared by methodology well known in the pharmaceutical art. For example, a pharmaceutical composition intended to be administered by injection can be prepared by combining the lipid nanoparticles of the invention with sterile, distilled water or other carrier so as to form a solution. A surfactant may be added to facilitate the formation of a homogeneous solution or suspension. Surfactants are compounds that non-covalently interact with the compound of structure (I) so as to facilitate dissolution or homogeneous suspension of the compound in the aqueous delivery system.

The compositions of embodiments of the invention, or their pharmaceutically acceptable salts, are administered in a therapeutically effective amount, which will vary depending upon a variety of factors including the activity of the specific therapeutic agent employed; the metabolic stability and length of action of the therapeutic agent; the age, body weight, general health, sex, and diet of the patient; the mode and time of administration; the rate of excretion; the drug combination; the severity of the particular disorder or condition; and the subject undergoing therapy.

Compositions of embodiments of the invention may also be administered simultaneously with, prior to, or after administration of one or more other therapeutic agents. Such combination therapy includes administration of a single pharmaceutical dosage formulation of a composition of embodiments of the invention and one or more additional active agents, as well as administration of the composition of the invention and each active agent in its own separate pharmaceutical dosage formulation. For example, a composition of embodiments of the invention and the other active agent can be administered to the patient together in a single oral dosage composition such as a tablet or capsule, or each agent administered in separate oral dosage formulations. Where separate dosage formulations are used, the compounds of structure (I) and one or more additional active agents can be administered at essentially the same time, i.e., concurrently, or at separately staggered times, i.e., sequentially; combination therapy is understood to include all these regimens.

Preparation methods for the above compounds and compositions are described herein below and/or known in the art.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of structure (I) which are pharmacologically active. Such derivatives may therefore be described as "prodrugs". All prodrugs of compounds of structure (I) are included within the scope of embodiments of the invention.

Furthermore, all compounds of structure (I) which exist in free base or acid form can be converted to their pharmaceutically acceptable salts by treatment with the appropriate inorganic or organic base or acid by methods known to one skilled in the art. Salts of the compounds of structure (I) can be converted to their free base or acid form by standard techniques.

The compounds of structure (I), and lipid nanoparticles comprising the same, can be prepared according to methods known or derivable by one of ordinary skill in the art, for example those methods disclosed in PCT Pub. No. WO 2015/199952, WO 2017/004143 and WO 2017/075531, each of which is incorporated herein by reference in their entireties.

The following General Reaction Schemes illustrate exemplary methods to make compounds of structure (I):

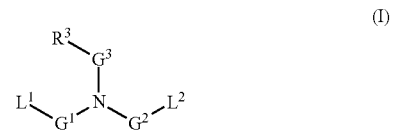

or a pharmaceutically acceptable salt, tautomer or stereoisomer thereof, wherein $R^3$, $L^1$, $L^2$, $G^1$, $G^2$, and $G^3$ are as defined herein. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

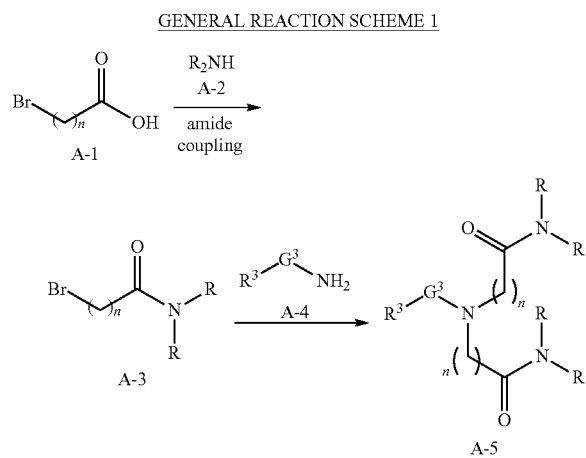

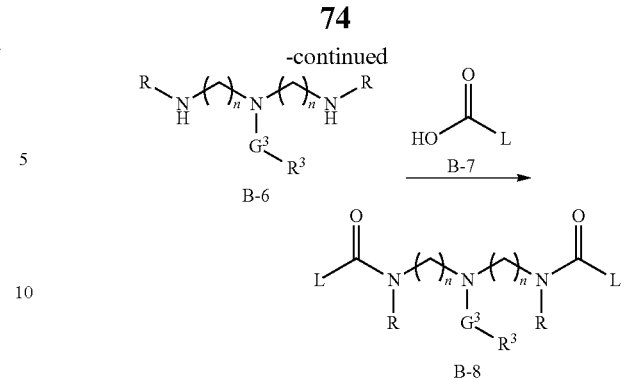

Embodiments of the compound of structure (I) (e.g., compound A-5) can be prepared according to General Reaction Scheme 1 ("Method A"), wherein R, at each occurrence, independently represents $R^b$, $R^c$, $R^e$ or $R^f$, and each n is independently an integer from 2 to 12. Referring to General Reaction Scheme 1, compounds of structure A-1 can be purchased from commercial sources or prepared according to methods familiar to one of ordinary skill in the art. A mixture of A-1, A-2 and DMAP is treated with DCC to give the bromide A-3. A mixture of the bromide A-3, a base (e.g., N,N-diisopropylethylamine) and the N,N-dimethyldiamine A-4 is heated at a temperature and time sufficient to produce A-5 after any necessary workup and or purification step.

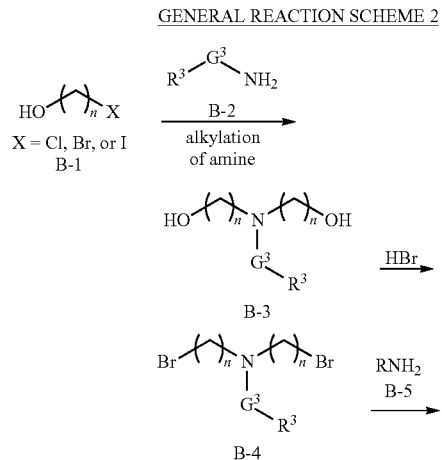

Embodiments of the compound of structure (I) (e.g., compound B-8) can be prepared according to General Reaction Scheme 2 ("Method B"), wherein R, at each occurrence, independently represents $R^a$ or $R^d$, L, at each occurrence, independently represents $R^1$ or $R^2$, and each n is independently an integer from 2 to 12. Referring to General Reaction Scheme 2, compounds of structure B-1 can be purchased from commercial sources or prepared according to methods familiar to one of ordinary skill in the art. A nitrogen of B-2 is alkylated with B-1 to afford a diol product B-3, which is then converted into the bromide B-4 with a slow addition of HBr solution followed by a reflux. The resulting bromide B-4 in presence of alkylamine B-5, N,N-diisopropylethylamine, and sodium iodide in a solvent is heated at a temperature and time sufficient to produce B-6 after any necessary workup and or purification step. Into a solution of a carboxylic acid B-7, oxalyl chloride is added dropwise. Then, the solution of B-6 is added to the mixture and stirred, which results in B-8 after any necessary workup and or purification step.

It should be noted that various alternative strategies for preparation of compounds of structure (I) are available to those of ordinary skill in the art. For example, the $R^3$ moiety may include a substituent, such as hydroxyl, and appropriate protecting groups may be required to mask the substituent, or the substituent may be added after $R^5$ is added to the remainder of the molecule. The use of protecting groups as needed and other modification to the above General Reaction Scheme 1 will be readily apparent to one of ordinary skill in the art. The following examples are provided for purpose of illustration and not limitation.

Example 1

Luciferase mRNA In Vivo Evaluation Using Lipid Nanoparticle Compositions

A lipid of structure (I), DSPC, cholesterol and PEG-lipid are solubilized in ethanol at a molar ratio of 50:10:38.5:1.5 or 47.5:10:40.7:1.8. Lipid nanoparticles (LNP) are prepared at a total lipid to mRNA weight ratio of approximately 10:1 to 40:1. Briefly, the mRNA is diluted to 0.2 mg/mL in 10 to 50 mM citrate buffer, pH 4 or 10 to 25 mM acetate buffer, pH 4. Syringe pumps are used to mix the ethanolic lipid solution with the mRNA aqueous solution at a ratio of about 1:5 to 1:3 (vol/vol) with total flow rates above 15 mL/min. The ethanol is then removed and the external buffer replaced with PBS by dialysis. Finally, the lipid nanoparticles are filtered through a 0.2 m pore sterile filter.

Studies are performed in 6-8 week old female $C_{57}BL/6$ mice (Charles River) 8-10 week old CD-1 (Harlan) mice (Charles River) according to guidelines established by an institutional animal care committee (ACC) and the Canadian Council on Animal Care (CCAC). Varying doses of mRNA-lipid nanoparticle are systemically administered by tail vein injection and animals euthanized at a specific time point (e.g., 4 hours) post-administration. Liver and spleen are collected in pre-weighed tubes, weights determined, immediately snap frozen in liquid nitrogen and stored at −80° C. until processing for analysis.

For liver, approximately 50 mg is dissected for analyses in a 2 mL FastPrep tubes (MP Biomedicals, Solon OH). ¼" ceramic sphere (MP Biomedicals) is added to each tube and 500 µL of Glo Lysis Buffer—GLB (Promega, Madison WI) equilibrated to room temperature is added to liver tissue. Liver tissues are homogenized with the FastPrep24 instrument (MP Biomedicals) at 2×6.0 m/s for 15 seconds. Homogenate is incubated at room temperature for 5 minutes prior to a 1:4 dilution in GLB and assessed using SteadyGlo Luciferase assay system (Promega). Specifically, 50 µL of diluted tissue homogenate is reacted with 50 µL of Steady-Glo substrate, shaken for 10 seconds followed by 5 minute incubation and then quantitated using a CentroXS$^3$ LB 960 luminometer (Berthold Technologies, Germany). The amount of protein assayed is determined by using the BCA protein assay kit (Pierce, Rockford, IL). Relative luminescence units (RLU) are then normalized to total µg protein assayed. To convert RLU to ng luciferase a standard curve is generated with QuantiLum Recombinant Luciferase (Promega).

The FLuc mRNA (L-6107) from Trilink Biotechnologies will express a luciferase protein, originally isolated from the firefly, *Photinus pyralis*. FLuc is commonly used in mammalian cell culture to measure both gene expression and cell viability. It emits bioluminescence in the presence of the substrate, luciferin. This capped and polyadenylated mRNA is fully substituted with 5-methylcytidine and pseudouridine.

Example 2

Immunoglobulin G (Igg) mRNA In Vivo Evaluation Using Lipid Nanoparticle Compositions A lipid of structure (I), DSPC, cholesterol and PEG-lipid are solubilized in ethanol at a molar ratio of 50:10:38.5:1.5 or 47.5:10:40.7:1.8. Lipid nanoparticles (LNP) are prepared at a total lipid to mRNA weight ratio of approximately 10:1 to 40:1. Briefly, the mRNA is diluted to 0.2 mg/mL in 10 to 50 mM citrate buffer, pH 4 or 10 to 25 mM acetate buffer, pH 4. Syringe pumps are used to mix the ethanolic lipid solution with the mRNA aqueous solution at a ratio of about 1:5 to 1:3 (vol/vol) with total flow rates above 15 mL/min. The ethanol is then removed and the external buffer replaced with PBS by dialysis. Finally, the lipid nanoparticles are filtered through a 0.2 m pore sterile filter.

Studies are performed in 6-8 week old CD-1/ICR mice (Envigo) according to guidelines established by an institutional animal care committee (ACC) and the Canadian Council on Animal Care (CCAC). Varying doses of mRNA-lipid nanoparticle are systemically administered by tail vein injection and animals euthanized at a specific time point (e.g., 24 hours) post-administration. The whole blood is collected, and the serum subsequentially separated by centrifuging the tubes of the whole blood at 2000×g for 10 minutes at 4° C. and stored at −80° C. until use for analysis.

For immunoglobulin G (IgG) ELISA (Life Diagnostics Human IgG ELISA kit), the serum samples are diluted at 100 to 15000 folds with 1×diluent solution. 100 µL of diluted serum is dispensed into anti-human IgG coated 96-well plate in duplicate alongside human IgG standards and incubated in a plate shaker at 150 rpm at 25° C. for 45 minutes. The wells are washed 5 times with 1× wash solution using a plate washer (400 µL/well). 100 µL of HRP conjugate is added into each well and incubated in a plate shaker at the same condition above. The wells are washed 5 times again with 1× wash solution using a plate washer (400 µL/well). 100 µL of TMB reagent is added into each well and incubated in a plate shaker at the same condition above. The reaction is stopped by adding 100 µL of Stop solution to each well. The absorbance is read at 450 nm (A450) with a microplate reader. The amount of human IgG in mouse serum is determined by plotting A450 values for the assay standard against human IgG concentration.

Example 3

Determination of Pk$_A$ of Formulated Lipids

As described elsewhere, the pKa of formulated lipids is correlated with the effectiveness of LNPs for delivery of nucleic acids (see Jayaraman et al, Angewandte Chemie, International Edition (2012), 51(34), 8529-8533; Semple et al, Nature Biotechnology 28, 172-176 (2010)). In some embodiments, the preferred range of pKa is ~5 to ~7. The pK$_a$ of each lipid is determined in lipid nanoparticles using an assay based on fluorescence of 2-(p-toluidino)-6-napthalene sulfonic acid (TNS). Lipid nanoparticles comprising compound of structure (I)/DSPC/cholesterol/PEG-lipid (50/10/38.5/1.5 or 47.5:10:40.7:1.8 mol %) in PBS at a concentration of 0.4 mM total lipid are prepared using the in-line process as described in Example 1. TNS is prepared as a 100 µM stock solution in distilled water. Vesicles are diluted to 24 µM lipid in 2 mL of buffered solutions containing 10 mM HEPES, 10 mM MES, 10 mM ammonium acetate, and 130 mM NaCl, where the pH ranged from 2.5 to 11. An aliquot of the TNS solution is added to give a final concentration of 1 µM and following vortex mixing fluorescence intensity is measured at room temperature in a SLM Aminco Series 2 Luminescence Spectrophotometer using excitation and emission wavelengths of 321 nm and 445 nm. A sigmoidal best fit analysis is applied to the fluorescence data and the pK$_a$ is measured as the pH giving rise to half-maximal fluorescence intensity.

Example 4

Determination of Efficacy of Lipid Nanoparticle Formulations Containing Various Cationic Lipids Using an In Vivo Luciferase/IgG mRNA Expression Rodent Model Representative compounds of the disclosure shown in Table 2 were formulated using the following molar ratio: 50% cationic lipid/10% distearoylphosphatidylcholine (DSPC)/38.5% Cholesterol/1.5% PEG lipid 2-[2-(ω-methoxy(polyethyleneglycol$_{2000}$)ethoxy]-N,N-ditetradecyl acetamide) or 47.5% cationic lipid/10% DSPC/40.7% Cholesterol/1.8% PEG lipid. Relative activity was determined by measuring luciferase expression in the liver 4 hours following administration via tail vein injection as described in Example 1 or by measuring the amount of human IgG in mouse serum as described in example 2. The activity was compared at a dose of 1.0 or 0.5 or 0.3 mg mRNA/kg and expressed as ng luciferase/g liver measured 4 hours after administration, as described in Example 1 or as µg IgG/mL serum measured 24 hours after administration, as described in Example 2. Compound numbers in Table 2 refer to the compound numbers of Table 1.

TABLE 2

Novel Cationic Lipids and Associated Activity

| Cmp. No. | pKa | Liver Luc @ 0.3 mg/kg (ng/g) | Liver Luc @ 1.0 mg/kg (ng/g) | Serum IgG @ 0.3 mg/kg (ug/mL) | Serum IgG @ 1.0 mg/kg (ug/mL) |
|---|---|---|---|---|---|
| I-3 | 6.87 | 227 ± 138* *Determined at 0.5 mg/kg | — | — | — |
| I-6 | 6.19 | 20084 ± 5967 | 78367 ± 15904 | — | — |
| I-7 | 6.43 | 16595 ± 836 | 81021 ± 24105 | — | — |
| I-8 | 6.02 | 8743 ± 2153 | 37220 ± 15377 | — | — |
| I-9 | 6.83 | 4337 ± 1394 | 21023 ± 12693 | — | — |
| I-10 | 6.77 | 10779 ± 2473 | 22622 ± 8189 | — | — |
| I-11 | 6.67 | — | — | 8.22 ± 0.84 | 47.68 ± 5.26 |
| I-14 | 6.59 | 2738 ± 728 | 5735 ± 2364 | — | — |
| I-18 | 6.02 | 7115 ± 2087 | 14879 ± 1595 | — | — |
| I-20 | 6.27 | 879 ± 365* *Determined at 0.5 mg/kg | — | — | — |
| I-21 | 6.54 | 29492 ± 4887 | 43216 ± 25636 | 48.78 ± 6.88 | 220.38 ± 62.57 |
| I-22 | 6.47 | 12829 ± 3326 | 38933 ± 23162 | 31.00 ± 9.33 | 99.12 ± 18.03 |
| I-23 | 6.48 | 15876 ± 7588 | 34202 ± 19178 | 43.34 ± 7.70 | 103.91 ± 31.29 |
| I-24 | 6.24 | 9106 ± 1760 | 38913 ± 14318 | 27.46 ± 9.22 | 112.31 ± 14.51 |
| I-25 | 6.28 | 20276 ± 3044 | 64656 ± 24090 | — | — |
| I-27 | 6.56 | 21 ± 6* *Determined at 0.5 mg/kg | — | — | — |
| I-28 | 6.22 | 6602 ± 2609 | 13298 ± 4040 | — | — |
| I-30 | 6.16 | 6567 ± 1534 | 19625 ± 2173 | — | — |
| I-37 | 6.39 | — | — | 1.75 ± 0.58 | 10.05 ± 2.32 |
| I-38 | 6.48 | — | — | 4.71 ± 0.46 | 45.87 ± 2.33 |
| I-40 | 6.17 | — | — | 16.72 ± 5.38 | 101.96 ± 4.12 |
| I-41 | 6.60 | — | — | 4.78 ± 1.65 | — |
| I-42 | 6.66 | — | — | 3.13 ± 0.27 | 12.42 ± 3.81 |
| I-43 | 6.02 | — | — | 2.45 ± 0.66 | 9.97 ± 1.17 |
| I-44 | 6.69 | — | — | 0.59 ± 0.11 | 1.86 ± 0.27 |
| I-45 | 5.96 | — | — | 3.03 ± 0.66 | 13.00 ± 2.05 |
| I-46 | 5.91 | 10201 ± 2440 | 52937 ± 8101 | — | — |
| I-48 | 6.63 | — | — | 1.02 ± 0.20 | 3.40 ± 0.87 |
| I-50 | 6.73 | — | — | 1.32 ± 0.28 | 11.05 ± 2.19 |
| I-55 | 6.22 | 8244 ± 1599 | 30106 ± 13756 | — | — |
| I-57 | 6.24 | 476 ± 134 | 1456 ± 518 | — | — |
| I-58 | 6.19 | 18664 ± 5438 | 73794 ± 14083 | — | — |
| I-59 | 6.27 | 10786 ± 1924 | 43489 ± 5698 | — | — |
| I-60 | 6.38 | 2176 ± 162 | 9178 ± 2483 | — | — |
| I-65 | 6.33 | 3172 ± 658 | 24740 ± 6297 | — | — |
| I-66 | 6.49 | — | — | 32.06 ± 5.07 | 253.37 ± 52.48 |
| I-67 | 6.18 | — | — | 7.19 ± 1.41 | 62.94 ± 13.88 |
| I-68 | 6.41 | — | — | 12.30 ± 2.41 | 121.93 ± 34.85 |
| I-70 | 6.17 | 7516 ± 1487 | 33238 ± 9902 | — | — |
| I-73 | 6.32 | — | — | 27.72 ± 6.23 | 213.39 ± 18.85 |
| I-74 | 6.53 | — | — | 50.16 ± 6.58 | 292.44 ± 40.55 |
| I-75 | 6.48 | — | — | 84.87 ± 12.19 | 343.06 ± 42.39 |
| I-77 | 6.71 | — | — | 17.45 ± 2.05 | — |
| I-82 | 6.47 | — | — | 24.36 ± 4.39 | 239.26 ± 39.80 |
| I-83 | 6.12 | — | — | 12.94 ± 2.03 | 142.26 ± 26.31 |
| I-85 | 6.81 | — | — | 10.74 ± 2.79 | — |

Example 5

6,6'-(methylazanediyl)bis(N,N-dioctylhexanamide) (Compound I-1)

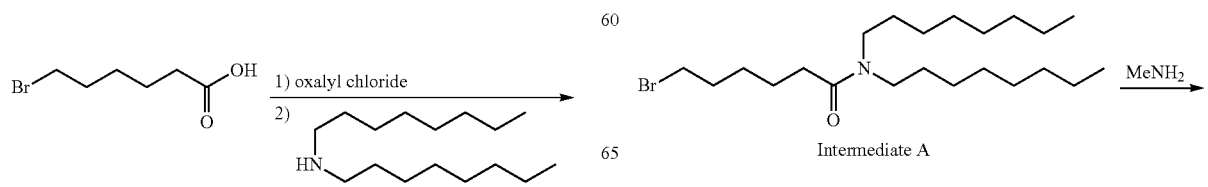

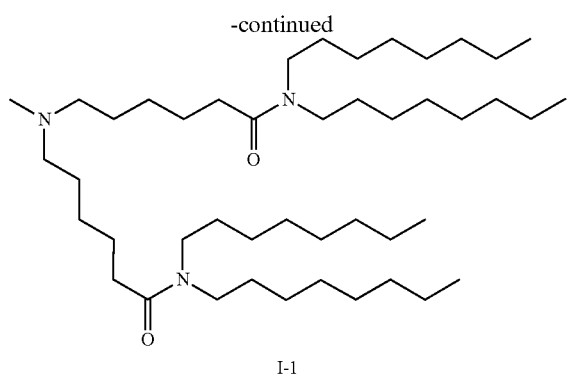

I-1

Synthesis of 6-bromo-N,N-dioctylhexanamide (Intermediate A)

To a solution of 6-bromohexanoic acid (2.93 g, 15 mmol) in DCM (25 mL) and DMF (0.1 mL) was added oxalyl chloride (45 mmol, 5.7 g, 3.93 mL) at RT under Ar. The resulting mixture was stirred at RT overnight. Next day the mixture was concentrated. The residue was dissolved in 20 mL of DCM and added slowly to a solution of dioctylamine (1.1 eq, 16.5 mmol, 3.98 g, 4.98 mL) and triethylamine (90 mmol, 9.09 g, 12.5 mL) and DMAP (10 mg) in DCM (20 mL) at RT. When the addition was complete, the mixture stirred at for 2.5 h and then concentrated. The residue was taken up in diluted HCl and filtered. The filtrate was extracted with DCM three times. Evaporation of the extracts after washing with brine and dried over NaSO4 gave a yellow oil. The oil was purified by chromatography (hexane and ethyl acetate (1:0 to 4:1). The desired product was obtained as slightly yellow oil, 5.09 g, 12.2 mmol, 81%.

Synthesis of I-1

To a mixture of 6-bromo-N,N-dioctylhexanamide (1.19 mmol, 500 mg), anhydrous acetonitrile (15 mL) and N,N-diisopropylethylamine (1.89 mmol, 244 mg, 0.33 mL) was added methylamine (0.32 mL, 0.63 mmol, 2 M in THF). The mixture was heated at 80° C. for 16 h in a sealed pressure flask. The reaction mixture was concentrated. The crude product was purified by flash dry column chromatography on silica gel (hexane/EtOAc/Et$_3$N, 95:5:0 to 80:20:1). The desired product was obtained as a colorless oil (183 mg, 0.26 mmol, 44%). $^1$HNMR (400 MHz, CDCl$_3$ at 7.27 ppm) δ: 3.32-3.25 (m, 4H), 3.23-3.16 (m, 4H), 2.34-2.26 (m, 8H), 2.20 (s, 3H), 1.66 (quintet, 7.6 Hz, 4H), 1.57-1.44 (m, 12H), 1.38-1.19 (m, 44H), 0.92-0.86 (m, 12H). ESI-MS: MW for C$_{45}$H$_{91}$N$_3$O$_2$ [M+H]+ Calc. 706.7; Found 706.8.

Example 6

6,6'-(octylazanediyl)bis(N,N-dioctylhexanamide) (Compound I-4)

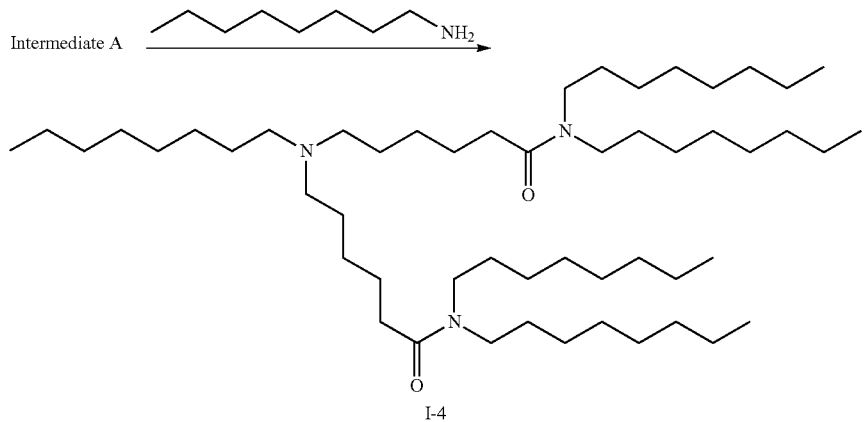

I-4

Synthesis of I-4

To a mixture of 6-bromo-N,N-dioctylhexanamide (1.6 eq, 1.19 mmol, 500 mg), anhydrous acetonitrile (15 mL) and N,N-diisopropylethylamine (1.89 mmol, 244 mg, 0.33 mL) was added octylamine (0.123 mL, 0.74 mmol). The mixture was heated at 80° C. for 16 h in a sealed pressure flask. The reaction mixture was concentrated. The crude product was purified by flash dry column chromatography on silica gel (hexane/EtOAc/Et$_3$N, 95:5:0 to 80:20:1) and further purified using 0 to 5% MeOH in chloroform as elution solvent mixture. The desired product was obtained as a colorless oil (173 mg, 0.22 mmol, 36%). $^1$HNMR (400 MHz, CDCl3) δ: 3.33-3.25 (m, 4H), 3.23-3.16 (m, 4H), 3.08-2.86 (br. 3H), 2.5-2.32 (br, 3H), 2.29 (t, 7.6 Hz, 4H), 1.85-1.70 (br, 2H), 1.67 (quintet, 7 Hz, 4H), 1.57-1.38 (m, 12H), 1.38-1.17 (m, 54H), 0.92-0.86 (m, 15H). ESI-MS: MW for $C_{52}H_{105}N_3O_2$ [M+H]$^+$ Calc. 804.8; Found 805.0.

Example 7

6,6'-(hexylazanediyl)bis(N,N-dioctylhexanamide) (Compound I-5)

Compound I-5 was prepared according to the general procedures of example 6 to yield the desired product as a colorless oil (155 mg, 0.20 mmol, 34%). $^1$HNMR (400 MHz, CDCl$_3$ at 7.27 ppm) δ: 3.33-3.25 (m, 4H), 3.24-3.15 (m, 4H), 3.10-2.80 (br. 2H), 2.58-2.32 (br, 4H), 2.29 (t, 7.4 Hz, 4H), 1.88-1.69 (br, 2H), 1.66 (quintet, 7.4 Hz, 4H), 1.57-1.39 (m, 12H), 1.39-1.17 (m, 50H), 0.92-0.86 (m, 15H).

Example 8

8,8'-(methylazanediyl)bis(N,N-dioctyloctanamide) (Compound I-7)

Compound I-7 was prepared according to the general procedures of example 5 to yield the desired product as a slightly yellow oil (230 mg, 0.30 mmol, 59%). $^1$HNMR (400 MHz, CDCl$_3$ at 7.27 ppm) δ: 3.32-3.25 (m, 4H), 3.23-3.15 (m, 4H), 2.31-2.25 (m, 8H), 2.20 (s, 3H), 1.64 (quintet, 7.3 Hz, 4H), 1.57-1.41 (m, 12H), 1.38-1.19 (m, 52H), 0.92-0.86 (m, 12H). ESI-MS: MW for $C_{49}H_{99}N_3O_2$ [M+H]$^+$ Calc. 762.8; Found 762.9.

Example 9

10,10'-(methylazanediyl)bis(N,N-dioctyldecanamide) (Compound I-8)

Compound I-8 was prepared according to the general procedures of example 5 to yield the desired product as a colorless oil (205 mg, 0.25 mmol, 64%). $^1$HNMR (400 MHz, CDCl$_3$ at 7.27 ppm) δ: 3.33-3.25 (m, 4H), 3.23-3.16 (m, 4H), 2.31-2.25 (q-like, 8H), 2.20 (s, 3H), 1.63 (quintet, 7.3 Hz, 4H), 1.57-1.41 (m, 12H), 1.38-1.19 (m, 60H), 0.92-0.86 (m, 12H). ESI-MS: MW for $C_{53}H_{107}N_3O_2$ [M+H]$^+$ Calc. 818.8; Found 819.0.

Example 10

8,8'-(methylazanediyl)bis(N,N-didecyloctanamide) (Compound I-6)

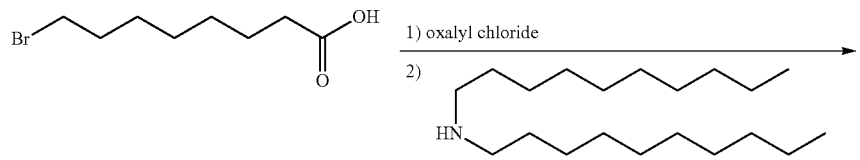

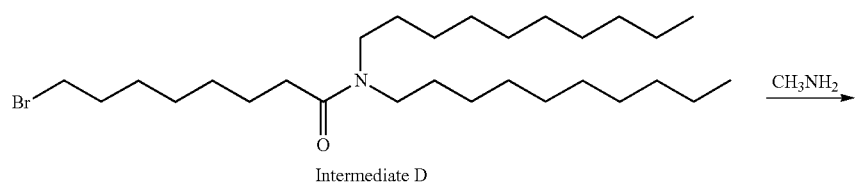

Intermediate D

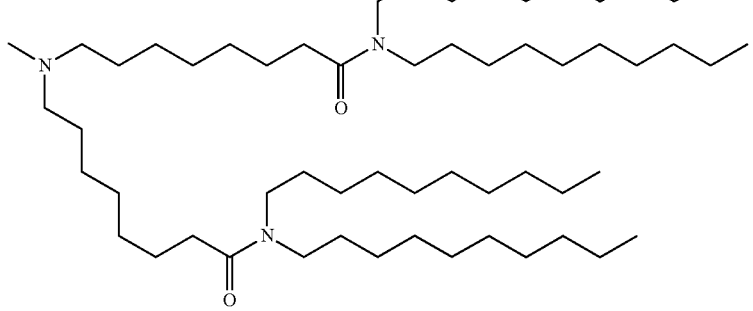

I-6

Synthesis of 8-bromo-N,N-didecyloctanamide (Intermediate D)

To a solution of 8-bromooctanoic acid (1 eq. 10.78 mmol, 2.41 g) in DCM (20 mL) and DMF (d 0.944; 0.1 mL) was added oxalyl chloride (2.5 eq, 27 mmol, 3.42 g, 2.35 mL) at RT under Ar. The resulting mixture was stirred at RT overnight. Next, the mixture was concentrated under reduced pressure. The residue was dissolved in 15 mL of DCM and added slowly to a solution of didecylamine (1.1 eq, 3.53 g, 11.86 mmol) and triethylamine (53.9 mmol, 7.5 mL) and DMAP (10 mg) in DCM (20 mL) at RT. When the addition was complete, the mixture stirred at RT overnight and then concentrated. The residue was taken up in hexane (100 mL) and was loaded on a silica gel column under reduced pressure. Then column was washed with a mixture of hexane and ethyl acetate (100:0 to 90:10) under reduced pressure. The desired product was obtained as yellow oil, 4.81 g, 9.6 mmol, 89%.

Synthesis of I-6

A mixture of 8-bromo-N,N-didecyloctanamide (0.8 mmol, 400 mg), CH$_3$CN (15 mL) and DIPEA (0.26 mL) and methylamine (33 wt % in EtOH, 0.062 mL, ca 0.5 mmol) was sealed in a pressure flask and heated at 74° C. overnight. The reaction mixture was concentrated. The crude product was purified by flash dry column chromatography on silica gel (hexane/EtOAc/Et$_3$N, 95:5:0 to 80:20:1) and further purified using 0 to 5% MeOH in chloroform with a trace of Et$_3$N as elution solvent mixture. The desired product was obtained as a colorless oil (167 mg, 0.19 mmol, 48%). $^1$HNMR (400 MHz, CDCl$_3$ at 7.26 ppm) δ: 3.32-3.24 (m, 4H), 3.23-3.15 (m, 4H), 2.30-2.24 (m, 8H), 2.18 (s, 3H), 1.63 (quintet, 7.1 Hz, 4H), 1.57-1.38 (m, 12H), 1.38-1.19 (m, 68H), 0.92-0.86 (m, 12H). ESI-MS: MW for C$_{57}$H$_{115}$N$_3$O$_2$ [M+H]$^+$ Calc. 874.9; Found 875.1.

Example 11

6,6'-(methylazanediyl)bis(N,N-didecylhexanamide) (Compound I-10)

Compound I-10 was prepared according to the general procedures of example 5 to yield the desired product as a colorless oil (249 mg, 0.30 mmol, 58%). $^1$HNMR (400 MHz, CDCl$_3$ at 7.26 ppm) δ: 3.32-3.24 (m, 4H), 3.22-3.15 (m, 4H), 2.33-2.25 (m, 8H), 2.19 (s, 3H), 1.65 (quintet, 7.6 Hz, 4H), 1.57-1.41 (m, 12H), 1.38-1.08 (m, 60H), 0.91-0.85 (m, 12H). ESI-MS: MW for C$_{53}$H$_{107}$N$_3$O$_2$ [M+H]$^+$ Calc. 818.8; Found 819.0.

Example 12

6,6'-(methylazanediyl)bis(N,N-didodecylhexanamide) (Compound I-11)

Compound I-11 was prepared according to the general procedures of example 5 to yield the desired product as a colorless oil (313 mg, 0.34 mmol, 68%). $^1$HNMR (400 MHz, CDCl$_3$) δ: 3.32-3.24 (m, 4H), 3.22-3.15 (m, 4H), 2.33-2.25 (m, 8H), 2.19 (s, 3H), 1.65 (quintet, 7.6 Hz, 4H), 1.57-1.43 (m, 12H), 1.37-1.10 (m, 76H), 0.91-0.85 (m, 12H). ESI-MS: MW for C$_{61}$H$_{123}$N$_3$O$_2$ [M+H]$^+$ Calc. 931.0; Found 931.2.

Example 13

6,6'-((2-hydroxyethyl)azanediyl)bis(N,N-dioctylhexanamide) (Compound I-3)

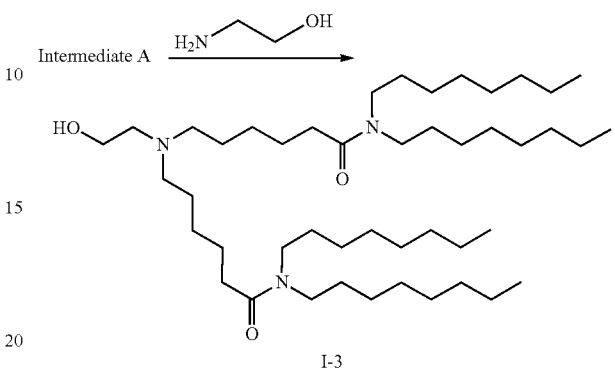

Synthesis of I-3

A mixture of 2-aminoethanol (1.25 mmol, 77 mg) in 15 ml of anhydrous THF, 6-bromo-N,N-dioctylhexanamide (Intermediate A, 1.9 eq, 1 g, 2.39 mmol), potassium carbonate (1.9 eq, 330 mg, 2.39 mmol), cesium carbonate (0.3 eq, 234 mg, 0.72 mmol) and sodium iodide (3 mg) in a pressure flask was heated for 6 days at 77° C. (oil bath). The reaction mixture was concentrated. The crude product was purified by flash dry column chromatography on silica gel (hexane/EtOAc/Et$_3$N, 95:5:0 to 80:20:1). The desired product was obtained as a colorless oil (233 mg, 0.31 mmol, 26%). $^1$HNMR (400 MHz, CDCl$_3$) δ: 3.52 (t, 5.3 Hz, 2H), 3.23-3.25 (m, 4H), 3.24-3.15 (m, 4H), 3.10-2.96 (br. 1H), 2.57 (t, 5.3 Hz, 2H), 2.50-2.41 (m, 4H), 2.28 (t, 7.5 Hz, 4H), 1.65 (quintet, 7.6 Hz, 4H), 1.60-1.42 (m, 12H, overlap with water), 1.38-1.19 (m, 44H), 0.92-0.86 (m, 12H). ESI-MS: MW for C$_{46}$H$_{93}$N$_3$O$_3$ [M+H]$^+$ Calc. 736.7; Found 736.8.

Example 14

6,6'-((6-hydroxyhexyl)azanediyl)bis(N,N-dioctylhexanamide) (Compound I-16)

Compound I-16 was prepared according to the general procedures of example 13 to yield the desired product as a colorless oil (63 mg). $^1$HNMR (400 MHz, CDCl$_3$) δ: 3.68-3.62 (m, 2H), 3.32-3.24 (m, 4H), 3.23-3.15 (m, 4H), 3.07-2.91 (br, 6H), 2.31 (t, 7.5 Hz, 4H), 1.93-1.73 (br., 6H), 1.68 (quintet, 7.6 Hz, 4H), 1.63-1.46 (m, 10H, overlap with water), 1.46-1.35 (m, 8H), 1.35-1.10 (m, 40H), 0.92-0.86 (m, 12H). The product exists partially in its HCl salt form. ESI-MS: MW for C$_{50}$H$_{101}$N$_3$O$_3$[M+H]$^+$ Calc. 792.8; Found 792.9.

Example 15

6,6'-((2-hydroxyethyl)azanediyl)bis(N,N-didecylhexanamide) (Compound I-19)

Compound I-19 was prepared according to the general procedures of example 13 to yield the desired product as a slightly yellow oil (154 mg, 0.18 mmol, 35%). $^1$HNMR (400 MHz, CDCl$_3$) δ: 3.51 (t, 5.2, 2H), 3.32-3.24 (m, 4H), 3.23-3.15 (m, 4H), 3.08-2.92 (br, 1H), 2.56 (t, 5.3 Hz, 2H), 2.45 (t, 7.4 Hz, 4H), 2.27 (t, 7.5 Hz, 4H), 1.64 (quintet, 7.5 Hz, 4H), 1.59-1.40 (m, 12H, overlapped with water peak), 1.36-1.10 (m, 60H), 0.91-0.86 (m, 12H). ESI-MS: MW for $C_{54}H_{109}N_3O_3$ $[M+H]^+$ Calc. 848.9; Found 849.0.

Example 16

8,8'-((6-hydroxyhexyl)azanediyl)bis(N,N-dioctyloctanamide) (Compound I-17)

Compound I-17 was prepared according to the general procedures of example 13 to yield the desired product as a slightly yellow oil (546 mg, 0.64 mmol, 54%). $^1$HNMR (400 MHz, $CDCl_3$) δ: 3.65 (t, 6.4 Hz, 2H), 3.33-3.25 m, 4H), 3.23-3.15 (m, 4H), 2.40-2.34 (m, 6H), 2.28 (t, 7.5 Hz, 4H), 1.75-1.59 (m, 6H), 1.58-1.46 (m, 8H), 1.46-1.36 (m, 8H), 1.36-1.10 (m, 54H), 0.92-0.86 (m, 12H). ESI-MS: MW for $C_{54}H_{109}N_3O_3$ $[M+H]^+$ Calc. 848.9; Found 849.0.

Example 17

10,10'-((6-hydroxyhexyl)azanediyl)bis(N,N-dioctyldecanamide) (Compound I-18)

Compound I-18 was prepared according to the general procedures of example 13 to yield the desired product as a slightly yellow oil (251 mg, 0.28 mmol, 52%). $^1$HNMR (400 MHz, $CDCl_3$) δ: 3.67-3.63 (m, 2H), 3.33-3.25 m, 4H), 3.24-3.16 (m, 4H), 2.41-2.35 (m, 6H), 2.28 (t, 7.5 Hz, 4H), 1.68-1.59 (m, 6H), 1.59-1.47 (m, 8H, overlapped with water peak), 1.47-1.37 (m, 8H), 1.37-1.10 (m, 62H), 0.92-0.86 (m, 12H).

Example 18

10,10'-((2-hydroxyethyl)azanediyl)bis(N,N-didecyldecanamide) (Compound I-20)

Compound I-20 was prepared according to the general procedures of example 13 to yield the desired product as a colorless oil (248 mg, 0.26 mmol, 49%). $^1$HNMR (400 MHz, $CDCl_3$) δ: 3.51 (t, 5.4, 2H), 3.32-3.24 (m, 4H), 3.22-3.15 (m, 4H), 3.08-2.92 (br, 1H), 2.56 (t, 5.4 Hz, 2H), 2.43 (t, 7.4 Hz, 4H), 2.27 (t, 7.5 Hz, 4H), 1.64 (quintet, 7.5 Hz, 4H), 1.59-1.36 (m, 12H, overlapped with water peak), 1.36-1.10 (m, 76H), 0.91-0.86 (m, 12H). ESI-MS: MW for $C_{62}H_{125}N_3O_3$ $[M+H]^+$ Calc. 961.0; Found 961.1.

Example 19

8,8'-((5-hydroxypentyl)azanediyl)bis(N,N-didecyloctanamide) (Compound I-21)

Compound I-21 was prepared according to the general procedures of example 13 to yield the desired product as a colorless oil (166 mg, 0.18 mmol, 35%). $^1$HNMR (400 MHz, $CDCl_3$ at 7.26 ppm) δ: 3.64 (t, 6.5 Hz, 2H), 3.32-3.24 (m, 4H), 3.22-3.15 (m, 4H), 2.41-2.34 (m, 6H), 2.27 (t, 7.5 Hz, 4H), 2.05 (br. s, 1H), 1.67-1.57 (m, 6H), 1.54-1.36 (m, 16H), 1.36-1.10 (m, 68H), 0.90-0.85 (m, 12H). ESI-MS: MW for $C_{61}H_{123}N_3O_3$ $[M+H]^+$ Calc. 947.0; Found 947.2.

Example 20

8,8'-((4-hydroxybutyl)azanediyl)bis(N,N-didecyloctanamide) (Compound I-23)

Compound I-23 was prepared according to the general procedures of example 13 to yield the desired product as a colorless oil (209 mg, 0.22 mmol, 45%). $^1$HNMR (400 MHz, $CDCl_3$ at 7.26 ppm) δ: 6.64 (br. s, 1H), 3.57-3.50 (m, 2H), 3.32-3.24 (m, 4H), 3.23-3.15 (m, 4H), 2.44-2.39 (m, 6H), 2.26 (t, 7.5 Hz, 4H), 1.67-1.57 (m, 8H), 1.54-1.37 (m, 12H), 1.36-1.10 (m, 68H), 0.90-0.85 (m, 12H). ESI-MS: MW for $C_{60}H_{121}N_3O_3$ $[M+H]^+$ Calc. 932.9; Found 933.1.

Example 21

8,8'-((6-hydroxyhexyl)azanediyl)bis(N,N-didecyloctanamide) (Compound I-24)

Compound I-24 was prepared according to the general procedures of example 13 to yield the desired product as a colorless oil (229 mg, 0.24 mmol, 48%). $^1$HNMR (400 MHz, $CDCl_3$, at 7.26 ppm) δ: 3.67-3.59 (m, 2H), 3.32-3.24 (m, 4H), 3.23-3.15 (m, 4H), 2.39-2.33 (m, 6H), 2.26 (t, 7.5 Hz, 4H), 1.73-1.68 (br. 1H), 1.68-1.38 (m, est. 20H), 1.38-1.10 (m, 72H), 0.90-0.85 (m, 12H). ESI-MS: MW for $C_{62}H_{125}N_3O_3$ $[M+H]^+$ Calc. 961.0; Found 961.1.

Example 22

8,8'-((2-hydroxyethyl)azanediyl)bis(N,N-didecyloctanamide) (Compound I-22)

Compound I-22 was prepared according to the general procedures of example 13 to yield the desired product as a colorless oil (165 mg, 0.18 mmol, 35%). $^1$HNMR (400 MHz, $CDCl_3$) δ: 3.51 (t, 5.4, 2H), 3.32-3.24 (m, 4H), 3.23-3.15 (m, 4H), 3.07-2.98 (br, 1H), 2.56 (t, 5.4 Hz, 2H), 2.42 (t, 7.4 Hz, 4H), 2.27 (t, 7.5 Hz, 4H), 1.68-1.59 (m, 4H), 1.59-1.36 (m, 12H, overlapped with water peak), 1.36-1.10 (m, 68H), 0.91-0.86 (m, 12H). ESI-MS: MW for $C_{58}H_{117}N_3O_3$ $[M+H]^+$ Calc. 904.9; Found 905.1.

Example 23

10,10'-((4-hydroxybutyl)azanediyl)bis(N,N-didecyldecanamide) (Compound I-25)

Compound I-25 was prepared according to the general procedures of example 13 to yield the desired product as a colorless oil (202 mg, 0.21 mmol, 42%). $^1$HNMR (400 MHz, $CDCl_3$, at 7.26 ppm) δ: 6.66 (br. s, 1H), 3.58-3.50 (m, 2H), 3.32-3.24 (m, 4H), 3.23-3.15 (m, 4H), 2.44-2.39 (m, 6H), 2.26 (t, 7.5 Hz, 4H), 1.70-1.58 (m, 8H), 1.55-1.38 (m, 12H), 1.37-1.14 (m, 76H), 0.90-0.85 (m, 12H). ESI-MS: MW for $C_{64}H_{129}N_3O_3$ $[M+H]^+$ Calc. 989.0; Found 989.1.

Example 24

N,N'-((methylazanediyl)bis(hexane-6,1-diyl))bis(N,2-dihexyldecanamide) (Compound I-15)

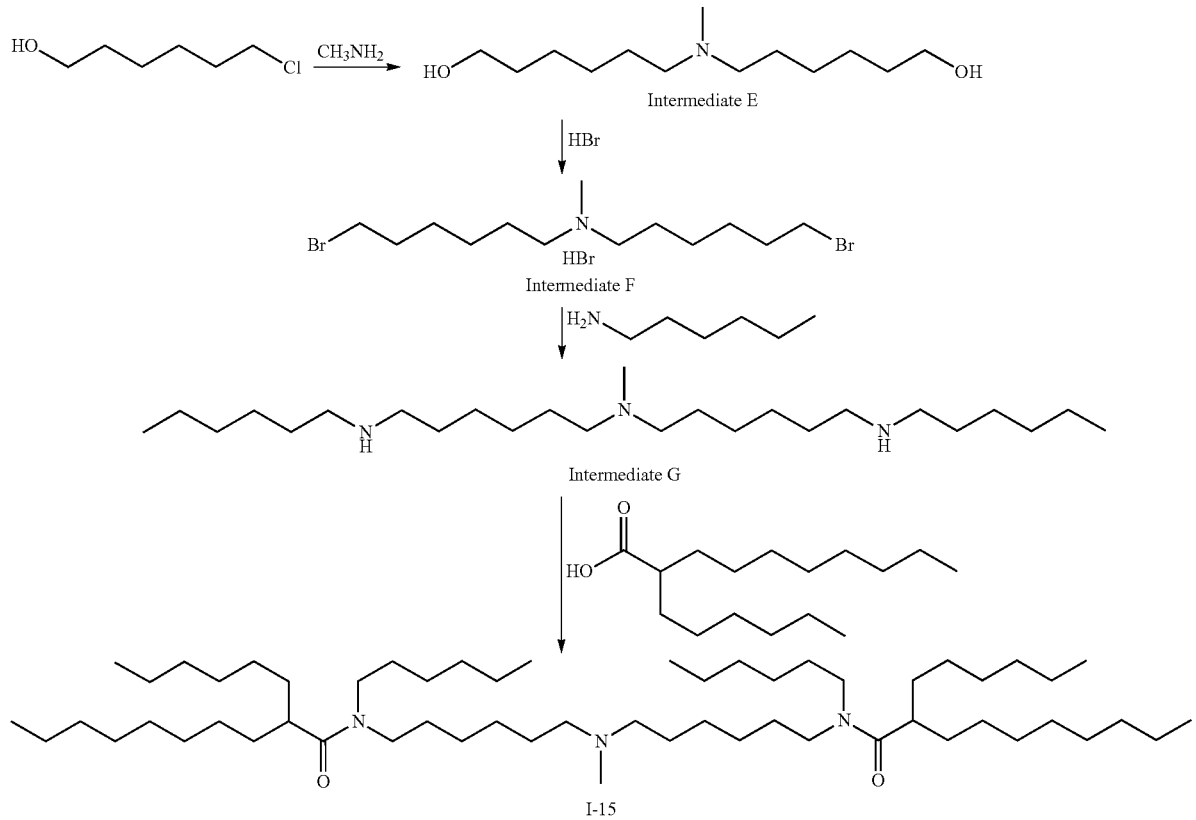

Synthesis of 6,6'-(methylazanediyl)bis(hexan-1-ol) (Intermediate E)

To a mixture of 6-chloro-1-hexanol (22.8 mmol, 3.11 g, 3.04 mL), absolute ethanol (60 mL), potassium carbonate (2 eq, 24 mmol, 3.32 g), cesium carbonate (eq, 500 mg) and sodium iodide (40 mg) was added methylamine (2 mmol, 1.49 ml, 33 wt. % in absolute ethanol). The mixture was heated for 16 h in a sealed pressure flask (oil bath: 68° C.). The reaction was monitored by TLC. More methylamine (0.1 mL), NaI (300 mg) and potassium carbonate (1 g) were added to the reaction mixture. Heating was resumed and after an additional 4 days, then more 6-chloro-1-hexanol (1.5 mL) and NaI (220 mg) were added. Heating was continued at 76° C. for an additional 3 days. Finally, the mixture was cooled and filtered. The filtrate was concentrated, and the residue was taken up DCM and filtered. The filtrate was concentrated to dryness under reduced pressure. This gave 4.86 g brown viscous oil. The oil was taken up in DCM (100 mL) and loaded on a short column of silica gel under reduced pressure. The column was eluted with a mixture of DCM, methanol and conc. ammonia solution (100:0:0 to 85:15:1). Fractions containing the desired product were combined and concentrated. The residue was taken up in DCM and filtered. The filtrated was concentrated to dryness to give the desired product as brown viscous oil (1.40 g, 6.05 mmol, 50%). The product was used for the next step without further purification.

Synthesis $N^1$-hexyl-$N^6$-(6-(hexylamino)hexyl)-$N^6$-methylhexane-1,6-diamine (Intermediate G)

Hydrobromic acid (6 mL, 48 wt. % solution in water) was added slowly to Intermediate E (1.40 g, 6.05 mmol) with stirring over 5 minutes. The reaction mixture was then heated at 105° C. (oil bath) for 2 hrs. The reaction mixture was cooled a little bit and then toluene (50 mL) was slowly added. The reaction was heated to reflux, and water was removed azeotropically. The reaction mixture was cooled to RT and then transferred to a pressure flask and concentrated to dryness under reduced pressure (brown oil 2.62 g, 5.97 mmol, 98%). TLC (CHCl$_3$/MeOH=9:1) showed a major spot of 6-bromo-N-(6-bromohexyl)-N-methylhexan-1-amine (Intermediate F). The product was used for the next step without further purification.

A mixture of 6-bromo-N-(6-bromohexyl)-N-methylhexan-1-amine (Intermediate F, 2.62 g, 5.97 mmol), hexylamine (10 eq. 120 mmol, 12.14 g), N,N-diisopropylethylamine (6.0 mmol, 1.04 mL), and sodium iodide (20 mg) in acetonitrile (30 mL) was sealed and heated at 76° C. (oil bath) for 24 h. The mixture was then concentrated at about 75° C. (ca 9 mmHg) to remove solvent and the excess hexylamine. the residue (yellow oil/solid) was taken up in DCM and filtered. TLC showed that hexylamine was not removed completely. The filtrate was concentrated under reduced pressure, giving a yellow foam 4.33 g. The residue was taken up in NaOH solution (1.44 g of sodium hydroxide in 10 mL of water) and then concentrated at 75° C. for 1.5 hrs under reduced pressure. The residue was taken up DCM and filtered. The filtrate was concentrated under reduced pressure to dryness, giving a pale paste (2.671 g, >100%). The product was used for the next step without further purification.

Synthesis of I-15

To a solution of 2-hexyldecanoic acid (4 mmol, 1.03 g) in DCM (15 mL) and DMF (3 drops from a middle size needle) was added dropwise oxalyl chloride (1.5 eq, 6 mmol, 762 mg, 0.524 mL) at RT. The resulting mixture was then stirred at RT overnight. Next, the mixture was concentrated under reduced pressure at RT. The residue (light yellow paste) was dissolved in 8 mL of DCM and added to a solution of crude Intermediate G (0.67 g) and triethylamine (3 eq, 3.1 mmol, 308 mg, 0.42 mL) and DMAP (5 mg) in DCM (5 mL) at RT in ca 5 min. After addition, the resulting mixture was stirred at RT for 2 h and then concentrated. The residue was taken up in a mixture of hexane, ethyl acetate and Et3N (80:20:1) and was filtered through a pad of silica gel. The pad was washed with the same solvent mixture. Concentration of the filtrate and washings gave a brownish oil (ca 543 mg). The crude product was purified by flash dry column chromatography on silica gel (0 to 6% MeOH in chloroform with a trace of $Et_3N$). The desired product was obtained as a colorless oil (426 mg, 0.49 mmol, 33%). $^1$HNMR (400 MHz, $CDCl_3$) δ: 3.34-3.27 (m, 4H), 3.26-3.18 (m, 4H), 2.53-2.45 (m, 2H), 2.34-2.25 (m, 4H), 2.18 (t, 4.7 Hz, 3H), 1.65-1.36 (m, 20H), 1.36-1.10 (m, 60H), 0.92-0.84 (m, 18H). ESI-MS: MW for $C_{57}H_{115}N_3O_2$ [M+H]$^+$ Calc. 874.9; Found 875.3.

Example 25

N,N'-((methylazanediyl)bis(hexane-6,1-diyl))bis(N-hexylpalmitamide) (Compound I-9)

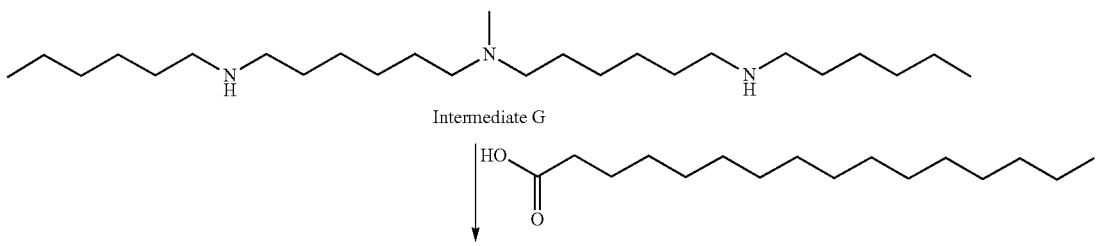

Intermediate G

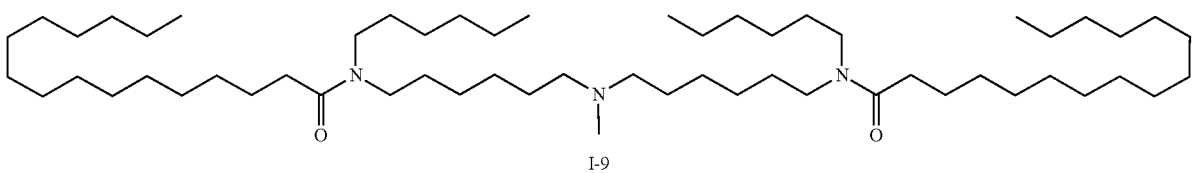

I-9

Synthesis of I-9

To a solution of palmitic acid (2.5 mmol, 0.64 g) in DCM (15 mL) and DMF (2 drops from a small size needle) was added dropwise oxalyl chloride (1.5 eq, 3.75 mmol, 484 mg, 0.33 mL) at RT. The resulting mixture was then stirred at RT overnight. Next, the mixture was concentrated under reduced pressure at RT. The residue (light yellow paste) was dissolved in 8 mL of DCM and added to a solution of crude Intermediate G (300 mg) and triethylamine (0.4 mL) and DMAP (5 mg) in DCM (5 mL) at RT in ca 5 min. After addition, the resulting mixture was stirred at RT for 2 h and then concentrated. The residue was taken up in a mixture of hexane, ethyl acetate and Et3N (80:20:1) and was filtered through a pad of silica gel and the pad was washed with the same solvent mixture. Concentration of the filtrate and washings gave a yellow oil/solid which was taken up in a mixture of hexane, ethyl acetate and Et3N (80:20:1) and was filtered again through a pad of silica gel and the pad was washed with the same solvent mixture. Concentration of the filtrate and washings gave a yellow oil (ca 244 mg). The crude product was purified by flash dry column chromatography on silica gel (0 to 5% MeOH in chloroform with a trace of Et$_3$N). The desired product was obtained as a colorless oil (200 mg, 0.22 mmol, 34%). $^1$HNMR (400 MHz, CDCl3 at 7.26 ppm) δ: 3.32-3.25 (m, 4H), 3.23-3.15 (m, 4H), 2.33-2.24 (m, 8H), 2.18 (t, 4.2 Hz, 3H), 1.67-1.56 (m, 4H), 1.56-1.36 (m, 12H), 1.36-1.10 (m, 68H), 0.92-0.85 (m, 12H). ESI-MS: MW for $C_{57}H_{115}N_3O_2$ [M+H]$^+$ Calc. 874.9; Found 875.1.

Example 26

(9Z,9'Z,12Z,12'Z)—N,N'-((methylazanediyl)bis(hexane-6,1-diyl))bis(N-hexyloctadeca-9,12-dienamide) (Compound I-14)

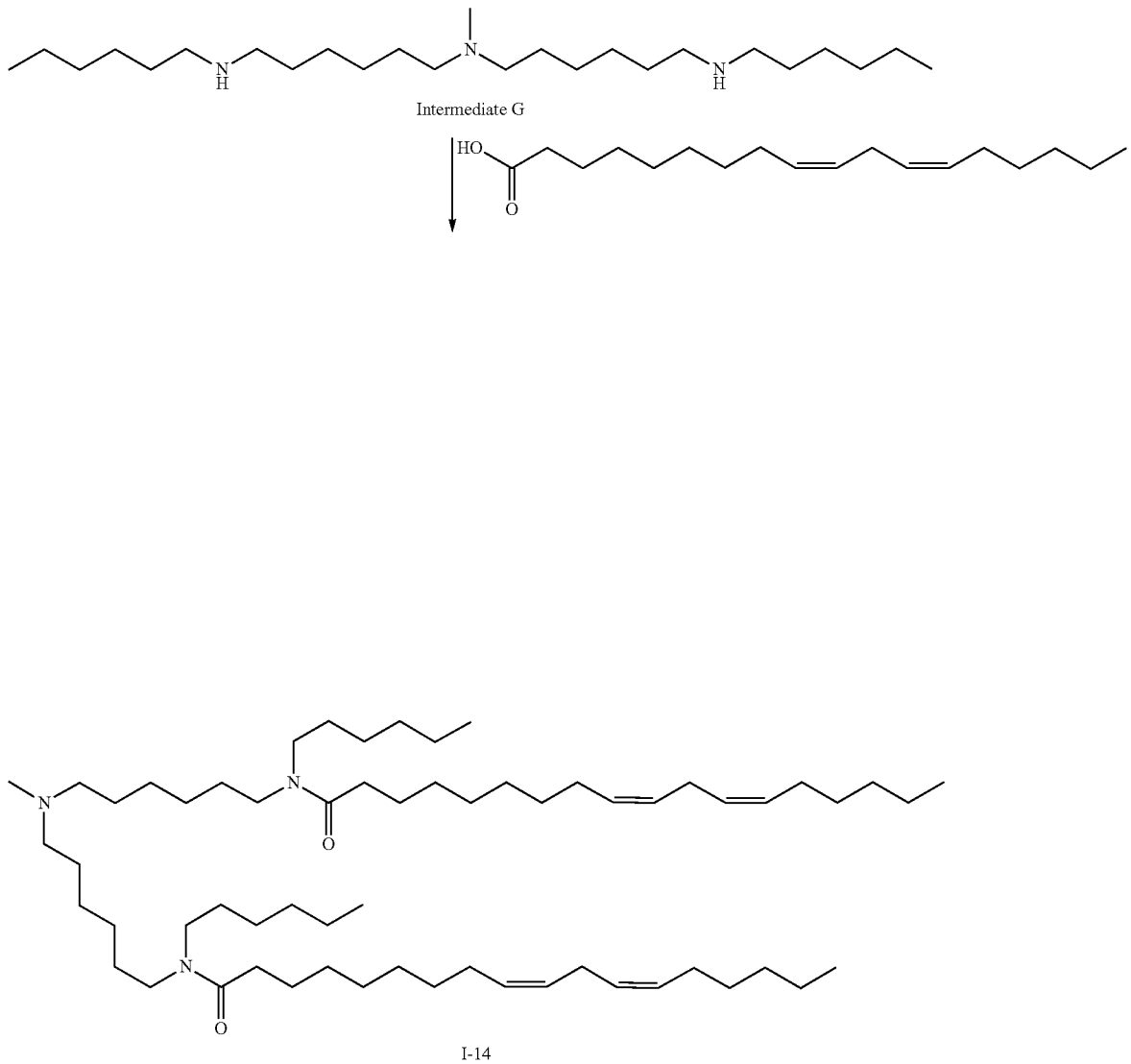

Intermediate G

I-14

Synthesis of I-14

To a solution of linoleic acid (2.5 mmol, 0.70 g) in DCM (12 mL) and DMF (2 drops from a small size needle) was added dropwise oxalyl chloride (1.5 eq, 3.75 mmol, 484 mg, 0.33 mL) at RT. The resulting mixture was then stirred at RT overnight. Next, the mixture was concentrated under reduced pressure at RT. The residue (light yellow paste) was dissolved in 8 mL of DCM and added to a solution of crude Intermediate G (300 mg) and triethylamine (0.4 mL) and DMAP (5 mg) in DCM (5 mL) at RT in ca 5 min. After addition, the resulting mixture was stirred at RT for 2 h and then concentrated. The residue was taken up in a mixture of hexane, ethyl acetate and Et$_3$N (80:20:1) and was filtered through a pad of silica gel and the pad was washed with the same solvent mixture. Concentration of the filtrate and washings gave a yellow oil/solid) which was taken up in hexane and filtered again to remove the solid. The crude product was purified by flash dry column chromatography on silica gel (0 to 5% MeOH in chloroform with a trace of Et$_3$N). The desired product was obtained as a colorless oil (160 mg, 0.17 mmol, 25%). $^1$HNMR (400 MHz, CDCl$_3$) δ: 5.42-5.29 (m, 8H), 3.32-3.24 (m, 4H), 3.22-3.15 (m, 4H), 2.77 (t, 6.4 Hz, 4H), 2.33-2.24 (m, 8H), 2.19 (t, 4.0 Hz, 3H), 2.05 (q, 6.8 Hz, 8H), 1.67-1.56 (m, 4H), 1.56-1.40 (m, 12H), 1.40-1.10 (m, 46H), 0.92-0.85 (m, 12H). ESI-MS: MW for C$_{61}$H$_{115}$N$_3$O$_2$ [M+H]$^+$ Calc. 922.9; Found 923.1.

Example 27

N,N-didecyl-8-((8-(hexadecylamino)-8-oxooctyl)(methyl)amino)octanamide (Compound I-12)

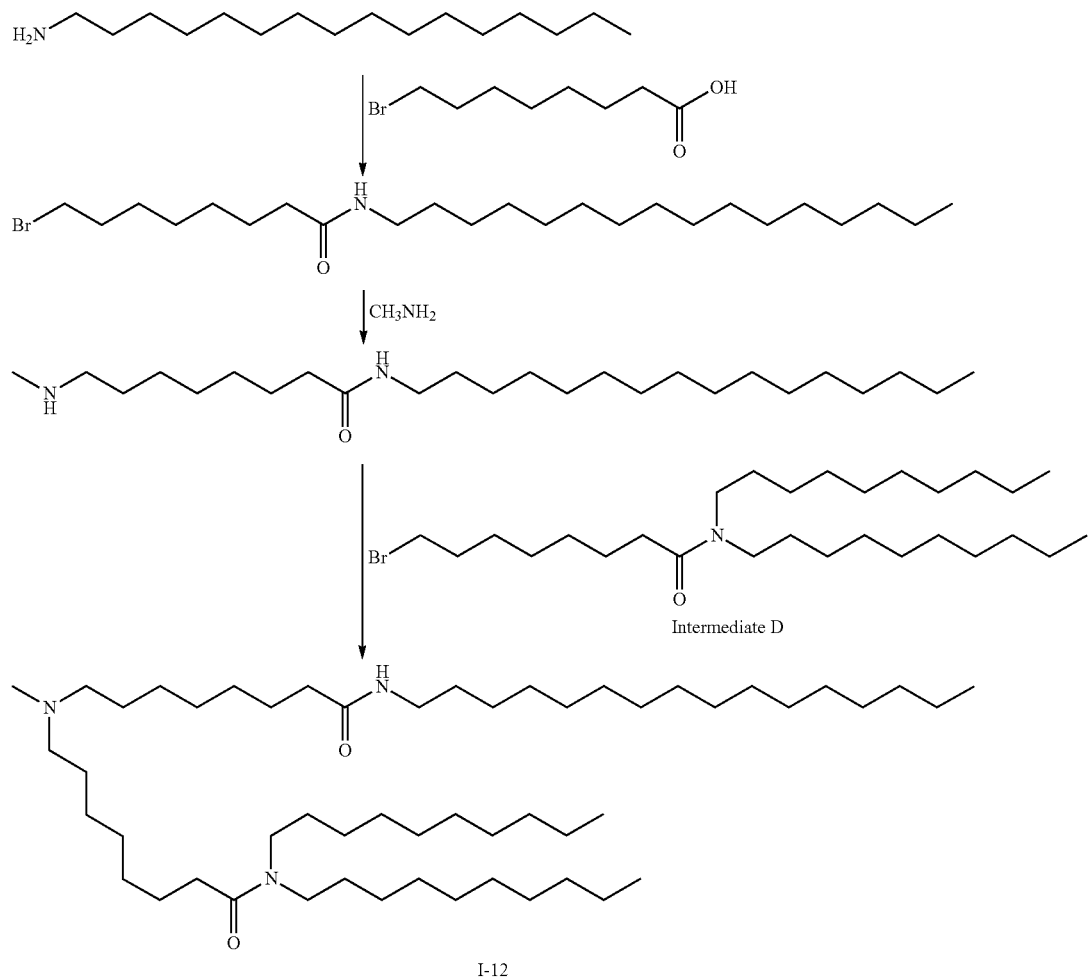

I-12

Synthesis of 8-bromo-N-hexadecyloctanamide

To a mixture of 8-bromohexanoic acid (1.0 equiv, 2.53 g, 11.36 mmol), and 4-dimethylaminopyridine (0.3 eq., 3.41 mmol, 416 mg) and N-hydroxysuccinimide (1.0 equiv, 11.36 mmol, 1.31 g) in 20 mL of DCM was added DCC (1.05 equiv, 11.93 mmol, 2.46 g) and the mixture stirred at room temperature for 2.5 h. The reaction mixture was filtered into a flask containing hexadecylamine (1 equiv, 11.36 mmol, 2.743 g) and washed with DCM (ca 20 mL). The resulting mixture was stirred at RT overnight. After concentration of the reaction mixture, a white solid was obtained. The solid was taken up in DCM (100 mL) and ultrasonicated to get a slightly cloudy solution. The cloudy solution was loaded on a short silica gel column under reduced pressure. The column was eluted with a mixture of DCM and MeOH (100:0 to 98.75:1.25) under reduced pressure. The desired product was obtained as a white solid (4.50 g, 10.1 mmol, 89%).

Synthesis of N-hexadecyl-8-(methylamino)octanamide

A mixture of methylamine (1 mL, 8 mmol, 33 wt. % in absolute ethanol), 8-bromo-N-hexadecyloctanamide (1 eq. 288 mg, 0.61 mml) and $K_2CO_3$ (1 mmol, 138 mg) in 10 mL of EtOH was sealed in a pressure bottle and heated at 85° C. (oil bath) overnight. After concentration of the mixture, the residue was taken up in a mixture of DCM, MeOH and Et3N (90:10:0.5) and filtered. Concentration of the filtrate and washings gave a white solid (228 mg, 0.57 mmol, 89%) which was used for the next step without further purification.

Synthesis of I-12

A mixture of crude N-hexadecyl-8-(methylamino)octanamide (228 mg), anhydrous acetonitrile (15 mL), N,N-diisopropylethylamine (0.33 mL) and Intermediate D (327 mg, 0.65 mmol) was heated at 74° C. (oil bath) for 16 h in a pressure flask. Then the reaction mixture was concentrated. The residue was taken up in a mixture of hexane, ethyl acetate and $Et_3N$ (80:20:1) and was filtered through a pad of silica gel. The pad was washed with the same solvent mixture. Concentration of the filtrate and washings gave a colorless oil. The crude product was further purified flash dry column chromatography on silica gel using 0 to 5% MeOH in chloroform with a trace of $Et_3N$ as elution solvent mixture. The desired product was obtained as a colorless oil (192 mg, 0.23 mmol, 40%). $^1$HNMR (400 MHz, $CDCl_3$, at 7.26 ppm) δ: 5.45 (s, 1H), 3.30-3.16 (m, 6H), 2.30-2.24 (m, 6H), 2.18 (s, 3H), 2.14 (t, 7.6 Hz, 2H), 1.67-1.57 (m, 4H), 1.54-1.37 (m, 10H), 1.37-1.16 (m, 66H), 0.91-0.86 (m, 9H). ESI-MS: MW for $C_{53}H_{107}N_3O_2$ $[M+H]^+$ Calc. 818.8; Found 819.0.

Example 28

8,8'-((8-(decylamino)-8-oxooctyl)azanediyl)bis(N,N-didecyloctanamide) (Compound I-33)

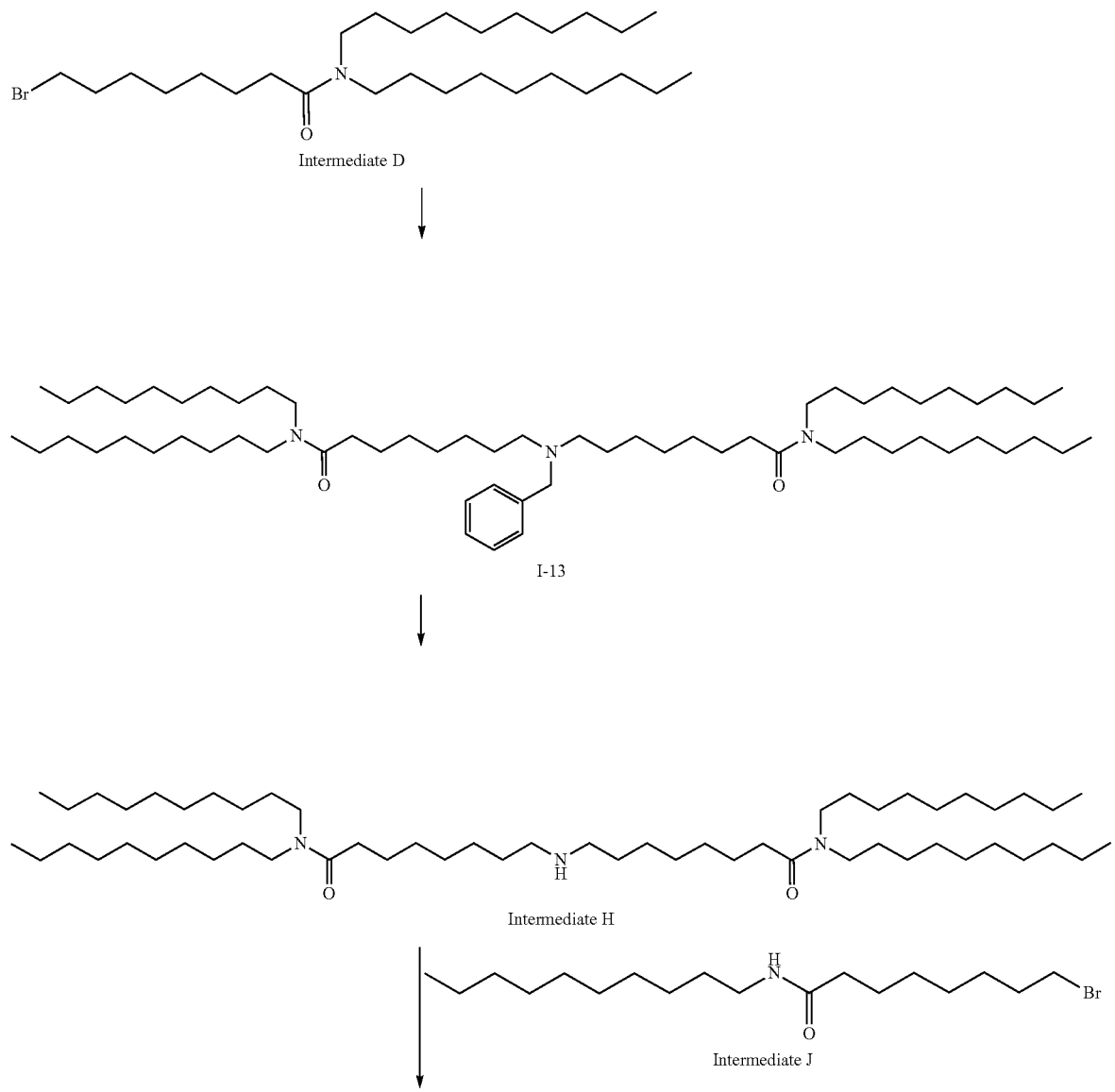

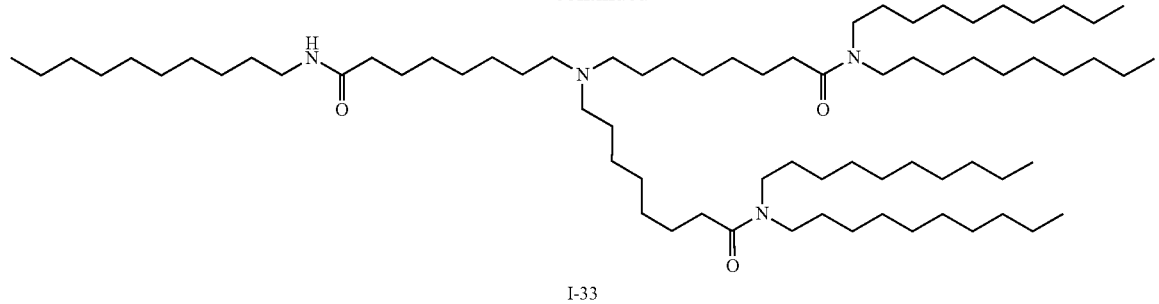

I-33

To a mixture of Intermediate D (1.9 eq, 2.0 g, 3.98 mmol), anhydrous acetonitrile (25 mL) and N,N-diisopropylethylamine (2.08 mL) in a pressure flask was added benzylamine (2.09 mmol, 224 mg, 0.23 mL). the resulting mixture was heated at 75° C. (oil bath) overnight. Then the reaction mixture was concentrated. The crude product was purified by flash dry column chromatography on silica gel (hexane/EtOAc/Et₃N, 90:10:0 to 80:20:1). Concentration of the fractions containing the desired product gave a brown oil (1.43 g) which was pure enough to use for the next step without further purification. A small amount of the product was further purified by flash dry column chromatography on silica gel using 0 to 5% MeOH in chloroform with a trace of Et₃N as elution solvent mixture for analysis and testing. $^1$HNMR (400 MHz, CDCl$_3$, at 7.26 pp) δ: 7.33-7.18 (m, 5H), 3.52 (s, 2H), 3.31-3.24 (m, 4H), 3.22-3.14 (m, 4H), 2.41-2.33 (m, 4H), 2.29-2.21 (m, s4H), 1.61 (quintet, 7.3 Hz, 4H), 1.56-1.38 (m, 12H), 1.38-1.10 (m, 68H), 0.90-0.85 (m, 12H).

Synthesis of 8,8'-azanediylbis(N,N-didecyloctanamide) (Intermediate H)

A mixture of I-13 (1.18 g, 1.24 mmol), 10% Pd/C (39 mg) in methanol (15 mL) was stirred under hydrogen for 3 days at RT. The reaction mixture was filtered through a pad of Celite© and washed with MeOH. The filtrate was concentrated (1.092 g colorless oil/solid) which was used for the next step without further purification.

Synthesis of 8-bromo-N-decyloctanamide (Intermediate J)

To a mixture of 8-bromohexanoic acid (1.0 equiv, 2.53 g 11.36 mmol), and 4-dimethylaminopyridine (0.3 eq., 3.41 mmol, 416 mg) in 20 mL of DCM was added N-hydroxysuccinimide (1.0 equiv, 11.36 mmol, 1.31 g), followed by addition of DCC (1.05 equiv, 11.93 mmol, 2.46 g). After the resulting mixture was stirred at room temperature for 2.5 h, the mixture was filtered into a flask containing decylamine (1 equiv, 11.36 mmol, 1.79 g, 2.27 mL) and the solid was washed with more DCM (3 mL×2). The resulting mixture of the filtrate and decylamine was stirred at RT overnight. The next day the mixture was concentrated. The residue was taken up in DCM and loaded onto a silica gel column. The column was eluted with a mixture of DCM and MeOH (100:0 to 97.5:2.5). The desired product was obtained as white solid (3.447 g, 9.51 mmol, 84%).

Synthesis of I-33

A mixture of 8,8'-azanediylbis(N,N-didecyloctanamide) (Intermediate H, 300 mg, 0.35 mmol), 8-bromo-N-decyloctanamide (Intermediate J, 1 eq, 0.35 mmol, 127 mg), anhydrous acetonitrile (15 mL), N,N-diisopropylethylamine (0.12 mL), and NaI (44 mg) in a pressure flask was heated at 73° C. (oil bath) overnight. Then the reaction mixture was concentrated. The residue was taken up in a mixture of hexane, ethyl acetate and Et₃N (80:20:1) and was filtered through a pad of silica gel. The pad was washed with the same solvent mixture. Concentration of the filtrate and washings gave a yellow oil. The crude product was further purified by flash dry column chromatography on silica gel using 0 to 5% MeOH in chloroform with a trace of Et₃N as elution solvent mixture. The desired product was obtained as a colorless oil (212 mg, 0.19 mmol, 53%). $^1$HNMR (400 MHz, CDCl$_3$, at 7.26 pp) δ: 5.62 (br. t, 5 Hz, 1H), 3.31-3.24 (m, 4H), 3.24-3.16 (m, 6H), 2.40-2.31 (m, 6H), 2.30-2.23 (m, 4H), 2.15 (t, 7.6 Hz, 2H), 1.67-1.57 (m, 6H), 1.55-1.36 (m, 16H), 1.36-1.10 (m, 88H), 0.90-0.85 (m, 15H). ESI-MS: MW for C$_{74}$H$_{148}$N$_4$O$_3$ [M+H]$^+$ Calc. 1142.2; Found 1142.2.

Example 29

8,8'-((6-(dihexylamino)-6-oxohexyl)azanediyl)bis(N,N-didecyloctanamide) (Compound I-32)

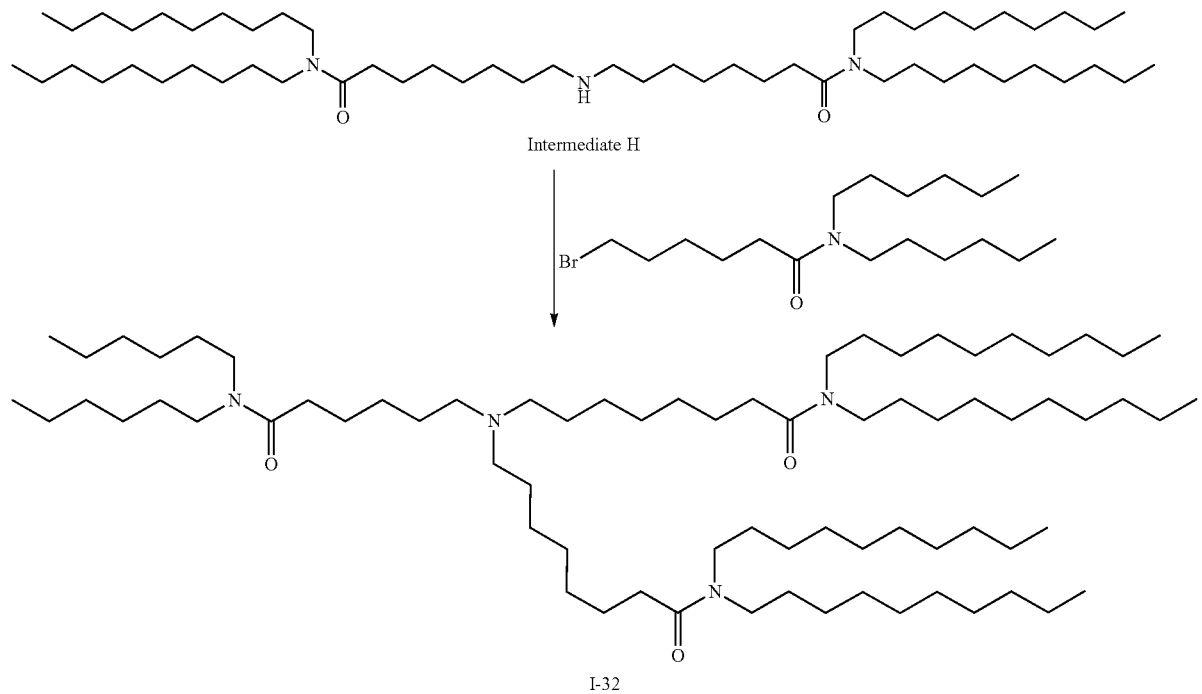

Synthesis of I-32

A mixture of 6-bromo-N,N-dihexylhexanamide (1 eq, 0.35 mmol, 127 mg; made from 6-bromohexanoic acid and dihexylamine in a similar way to Intermediate D), anhydrous acetonitrile (15 mL), N,N-diisopropylethylamine (0.12 mL), 8,8'-azanediylbis(N,N-didecyloctanamide) (Intermediate H, 300 mg, 0.35 mmol) and NaI (44 mg) in a pressure flask was heated at 80° C. (oil bath) overnight. Then the reaction mixture was concentrated. The residue was taken up in a mixture of hexane, ethyl acetate and Et$_3$N (80:20:1) and was filtered through a pad of silica gel. The pad was washed with the same solvent mixture. Concentration of the filtrate and washings gave a yellow oil. The crude product was further purified by flash dry column chromatography on silica gel using 0 to 5% MeOH in chloroform with a trace of Et$_3$N as elution solvent mixture. The desired product was obtained as a slightly yellow oil (228 mg, 0.20 mmol, 57%). $^1$HNMR (400 MHz, CDCl$_3$ at 7.26 ppm) δ: 3.31-3.24 (m, 6H), 3.22-3.15 (m, 6H), 2.40-2.33 (m, 6H), 2.30-2.24 (m, 6H), 1.69-1.58 (m, 6H), 1.54-1.36 (m, 18H), 1.36-1.10 (m, 82H), 0.92-0.85 (m, 18H). ESI-MS: MW for C$_{74}$H$_{148}$N$_4$O$_3$ [M+H]$^+$ Calc. 1142.2; Found 1142.2.

Example 30

8,8'-((5-(decylamino)-5-oxopentyl)azanediyl)bis(N,N-didecyloctanamide) (Compound I-30)

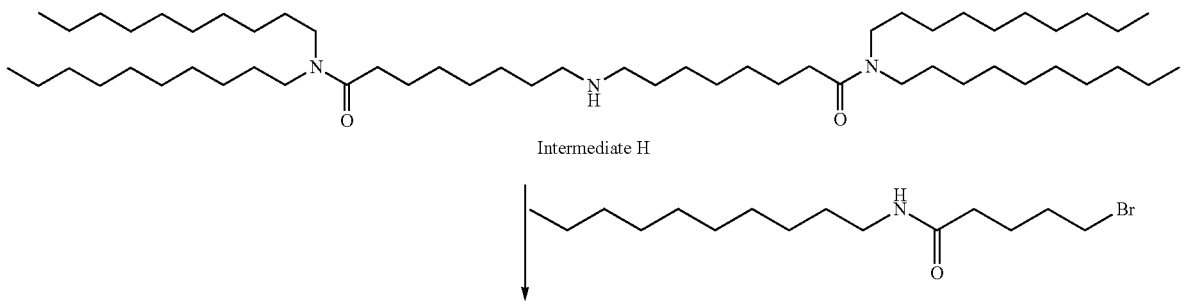

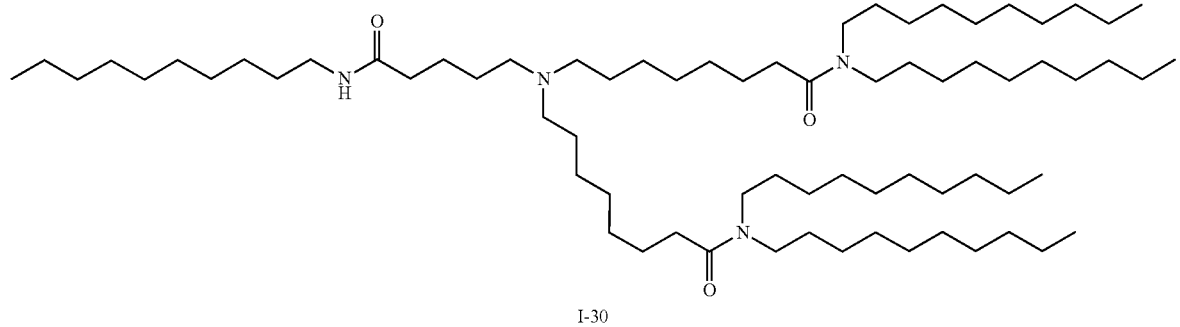

I-30

Synthesis of 5-bromo-N-decylpentanamide

To a mixture of 5-bromovaleric acid (1.0 equiv, 2.06 g 11.36 mmol), and 4-dimethylaminopyridine (0.3 eq., 3.41 mmol, 416 mg) in 20 mL of DCM was added N-hydroxysuccinimide (1.0 equiv, 11.36 mmol, 1.31 g), followed by addition of DCC (1.05 equiv, 11.93 mmol, 2.46 g). After the resulting mixture was stirred at room temperature for 2.5 h, the mixture was filtered into a flask containing decylamine (1 equiv, 11.36 mmol, 1.79 g, 2.27 mL) and the solid was washed with more DCM (3 mL×2). The resulting mixture of the filtrate and decylamine was stirred at RT overnight. The next day the mixture was concentrated. The residue was taken up in DCM and loaded onto a silica gel column. The column was eluted with a mixture of DCM and MeOH (100:0 to 98:2). The desired product was obtained as white solid (2.758 g, 8.62 mmol, 76%).

Synthesis of I-30

A mixture of 8,8'-azanediylbis(N,N-didecyloctanamide) (Intermediate H, 246 mg, 0.27 mmol), 5-bromo-N-decylpentanamide (130 mg), anhydrous acetonitrile (12 mL), N,N-diisopropylethylamine (0.10 mL) and NaI (40 mg) in a pressure flask was heated at 73° C. (oil bath) overnight. After the reaction mixture was concentrated, the residue was taken up in a mixture of hexane, ethyl acetate, MeOH and Et$_3$N (80:20:2:1) and was filtered through a pad of silica gel. The pad was washed with the same solvent mixture. Concentration of the filtrate and washings gave a yellow oil. The crude product was further purified by flash dry column chromatography on silica gel using 0 to 5% MeOH in chloroform with a trace of Et$_3$N as elution solvent mixture. The desired product was obtained as a colorless oil (60 mg). $^1$HNMR (400 MHz, CDCl$_3$ at 7.26 ppm) δ: 5.75 (br. t, 5 Hz, 1H), 3.33-3.13 (m, 10H), 2.41-2.32 (m, 6H), 2.27 (t, 7.6 Hz, 4H), 2.17 (t, 7.6 Hz, 2H), 1.67-1.57 (m, 6H), 1.55-1.35 (m, 16H), 1.35-1.16 (m, 82H), 0.90-0.85 (m, 15H).

Example 31

6,6'-((8-(decylamino)-8-oxooctyl)azanediyl)bis(N,N-didecylhexanamide) (Compound I-29)

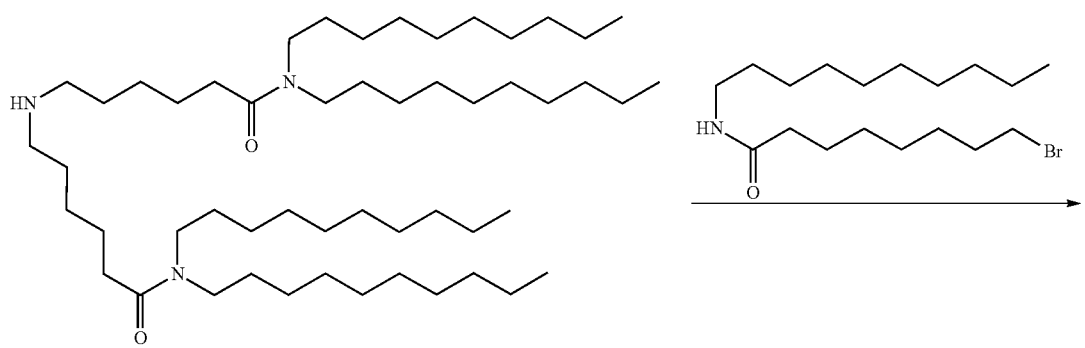

-continued

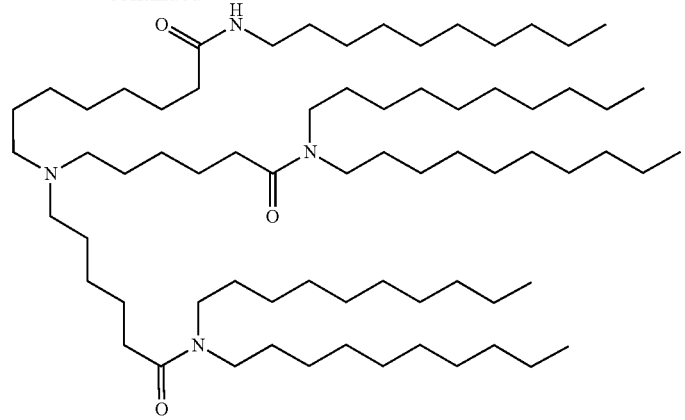

I-29

Synthesis of I-29

A mixture of 6,6'-azanediylbis(N,N-didecylhexanamide) (300 mg, 0.37 mmol; made in a similar way to Intermediate H), 8-bromo-N-decyloctanamide (1 eq, 0.37 mmol, 135 mg), anhydrous acetonitrile (15 mL), N,N-diisopropylethylamine (0.12 mL), and NaI (70 mg) in a pressure flask was heated at 73° C. (oil bath) overnight. After the reaction mixture was concentrated, the residue was taken up in a mixture of hexane, ethyl acetate, MeOH and Et$_3$N (80:20: 2:1) and was filtered through a pad of silica gel. The pad was washed with the same solvent mixture. Concentration of the filtrate and washings gave a yellow oil. The crude product was further purified flash dry column chromatography on silica gel using 0 to 5% MeOH in chloroform with a trace of Et$_3$N as elution solvent mixture. The desired product was obtained as a colorless oil (254 mg, brownish oil, 0.23 mmol, 63%). $^1$HNMR (400 MHz, CDCl$_3$ at 7.26 ppm) δ: 5.62 (br. t, 5 Hz, 1H), 3.34-3.16 (m, 10H), 2.40-2.33 (m, 6H), 2.27 (t, 7.6 Hz, 4H), 2.15 (t, 7.6 Hz, 2H), 1.68-1.57 (m, 6H), 1.56-1.36 (m, 16H), 1.36-1.10 (m, 80H), 0.90-0.85 (m, 15H). ESI-MS: MW for C$_{70}$H$_{140}$N$_4$O$_3$ [M+H]$^+$ Calc. 1086.1; Found 1086.3.

Example 32

6,6'-((2-(dihexylamino)ethyl)azanediyl)bis(N,N-didecylhexanamide) (Compound I-31)

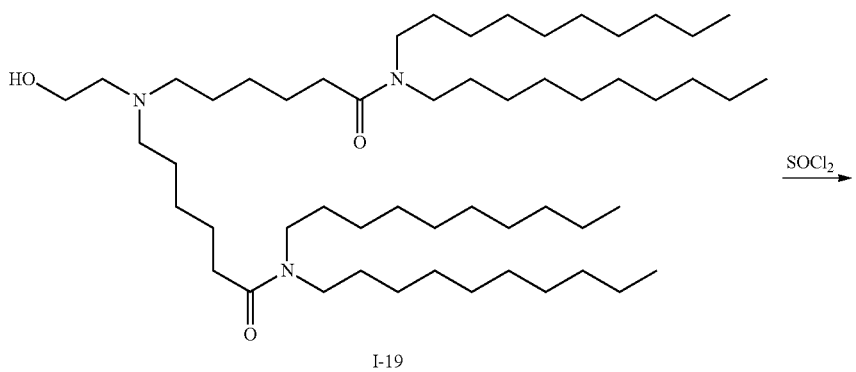

I-19

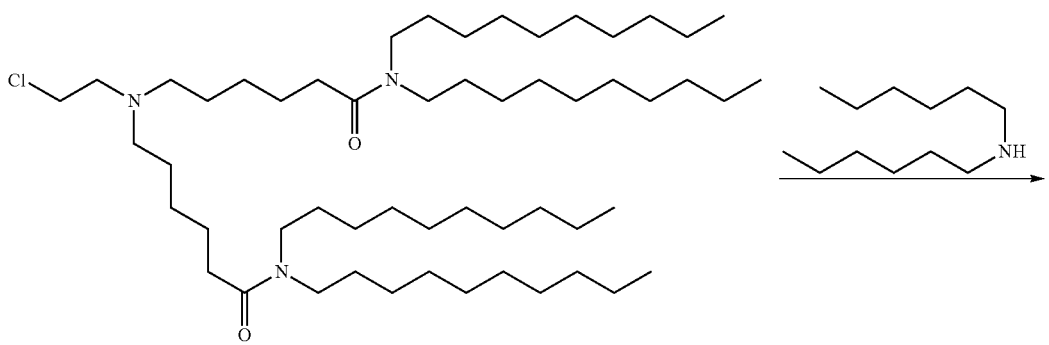

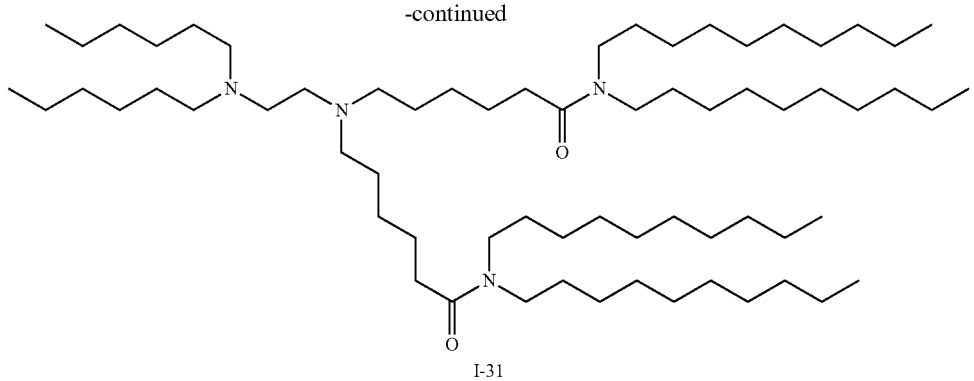

I-31

Synthesis of 6,6'-((2-chloroethyl)azanediyl)bis(N,N-didecylhexanamide)

To an ice-cooled solution of I-19 (333 mg, 0.39 mmol) of in 2 mL of $CHCl_3$, was added dropwise a solution of thionyl chloride (200 mg) in 10 mL of chloroform under Ar. After the completion of addition of $SOCl_2$ (10 min), the ice bath was removed and the reaction mixture was stirred for 16 h at room temperature. The next day removal of $CHCl_3$ and $SOCl_2$ under reduced pressure gave brown oil. The residual oil was taken up in a mixture of hexane, ethyl acetate and $Et_3N$, (ca (80:20:1) and was filtered through a pad of silica gel. The pad was washed with the same solvent mixture. Concentration of the filtrate and washings gave a yellow oil (282 mg, 0.325 mmol, 83%). The product was used for the next step without further purification.

Synthesis of I-31

A mixture of 6,6'-((2-chloroethyl)azanediyl)bis(N,N-didecylhexanamide) (282 mg, 0.33 mmol), dihexylamine (5 eq. 1.6 mmol, 1.066 g), N,N-diisopropylethylamine (2 equiv., 0.66 mmol, 85 mg, 0.11 mL; MW129.25, d 0.742), and sodium iodide (60 mg) in acetonitrile (10 mL) was sealed and heated at 76° C. for 24 h. After the reaction mixture was concentrated, the residue was taken up in a mixture of hexane, ethyl acetate, MeOH and $Et_3N$ (80:20:1:1) and was filtered through a pad of silica gel. The pad was washed with the same solvent mixture. Concentration of the filtrate and washings gave a yellow oil. The yellow oil was treated with a solution of acetyl chloride and $Et_3N$ in DCM at RT to transfer the unreacted dihexylamine to an amide. After removal of DCM, the crude product was purified by flash dry column chromatography on silica gel (hexane/ethyl acetate/$Et_3N$, 9:1 to 80:20:1; 0 to 5% MeOH in chloroform with a trace of Et3N). The desired product was obtained as a colorless oil (256 mg, colorless oil, 0.25 mmol, 76%). $^1$HNMR (400 MHz, $CDCl_3$ at 7.26 ppm) δ: 3.31-3.24 (m, 4H), 3.23-3.15 (m, 4H), 2.50 (s, 4H), 2.45-2.36 (m, 8H), 2.27 (t, 7.6 Hz, 4H), 1.64 (quintet, 7.6 Hz, 4H), 1.59-1.36 (m, 16H), 1.36-1.10 (m, 72H), 0.92-0.84 (m, 18H). ESI-MS: MW for $C_{66}H_{134}N_4O_2$ [M+H]$^+$ Calc. 1016.1; Found 1016.2.

Example 33

10,10'-((2-(dimethylamino)ethyl)azanediyl)bis(N,N-didecyldecanamide) (Compound I-28)

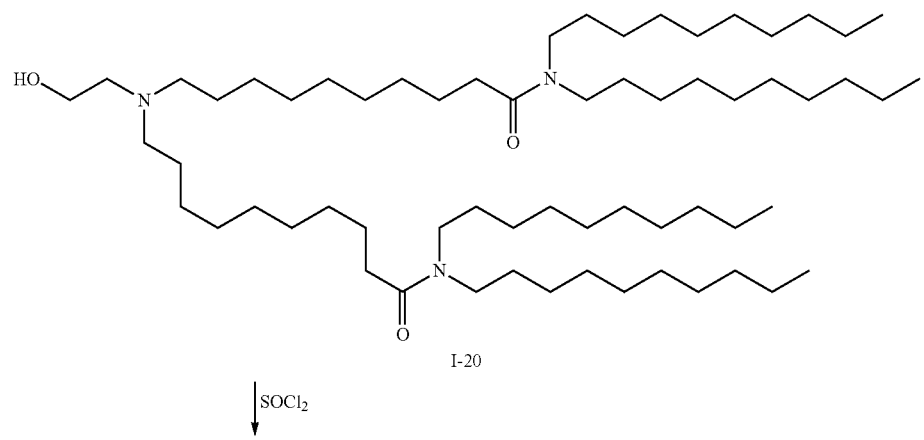

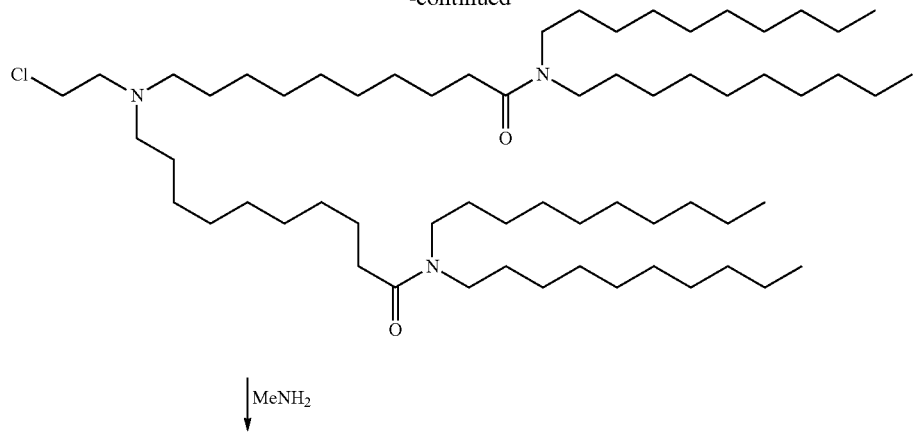

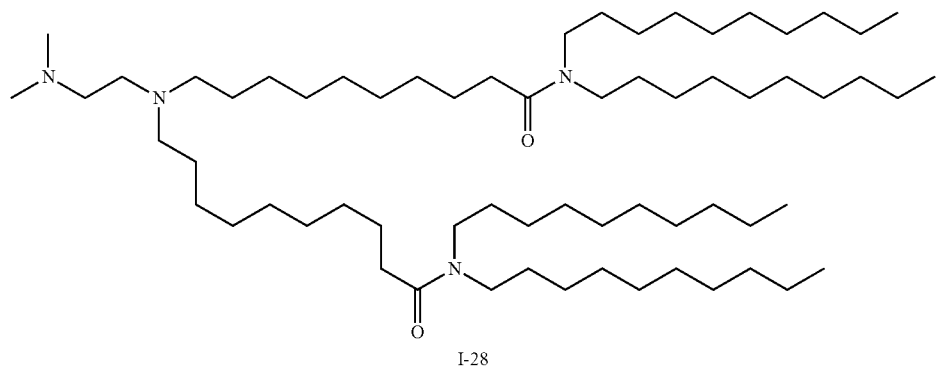

I-28

Synthesis of 10,10'-((2-chloroethyl)azanediyl)bis(N, N-didecyldecanamide)

To an ice-cooled solution of I-20 (293 mg, 0.30 mmol) of in 2 mL of CHCl$_3$, was added dropwise a solution of thionyl chloride (1.17 mmol, 139 mg, 0.085 mL) in 10 mL of chloroform. After the completion of addition of SOCl$_2$ (10 min), the ice bath was removed and the reaction mixture was stirred for 16 h at room temperature. The next day removal of CHCl3, and SOCl2 under reduced pressure gave brown oil. The residual oil was taken up in a mixture of hexane, ethyl acetate and Et$_3$N, (ca (80:20:1) and was filtered through a pad of silica gel. The pad was washed with the same solvent mixture. Concentration of the filtrate and washings gave a yellow oil (278 mg, 0.28 mmol, 95%). The product was used for the next step without further purification.

Synthesis of I-28

A mixture of 10,10'-((2-chloroethyl)azanediyl)bis(N,N-didecyldecanamide) (278 mg, 0.28 mmol), dimethylamine (2 M in THF, 10 mL) and N,N-diisopropylethylamine (0.66 mmol) in a pressure flask was sealed and heated at 75° C. for 24 h. After the reaction mixture was concentrated, the residue was taken up in a mixture of hexane, ethyl acetate, MeOH and Et$_3$N (80:20:1:1) and was filtered through a pad of silica gel. The pad was washed with the same solvent mixture. Concentration of the filtrate and washings gave a yellow oil. The crude product was purified by flash dry column chromatography on silica gel (0 to 5% MeOH in chloroform with a trace of Et$_3$N). The desired product was obtained as a colorless oil (244 mg, slightly yellow oil, 0.25 mmol, 76%). $^1$HNMR (400 MHz, CDCl$_3$ at 7.26 ppm) δ: 3.31-3.25 (m, 4H), 3.22-3.15 m, 4H), 2.56-2.551 (m, 2H), 2.43-2.33 (m, 6H), 2.26 (t, 7.6 Hz, 4H), 2.23 (s, 6H), 1.67-1.59 (m, 4H), 1.56-1.45 (m, 8H), 1.45-1.36 (m, 4H), 1.36-1.15 (m, 76H), 0.90-0.85 (m, 12H). ESI-MS: MW for C$_{64}$H$_{130}$N$_4$O$_2$[M+H]$^+$ Calc. 988.0; Found 988.1.

Example 34

2-butyloctyl 6-(bis(6-(dioctylamino)-6-oxohexyl)amino)hexanoate (Compound I-34)

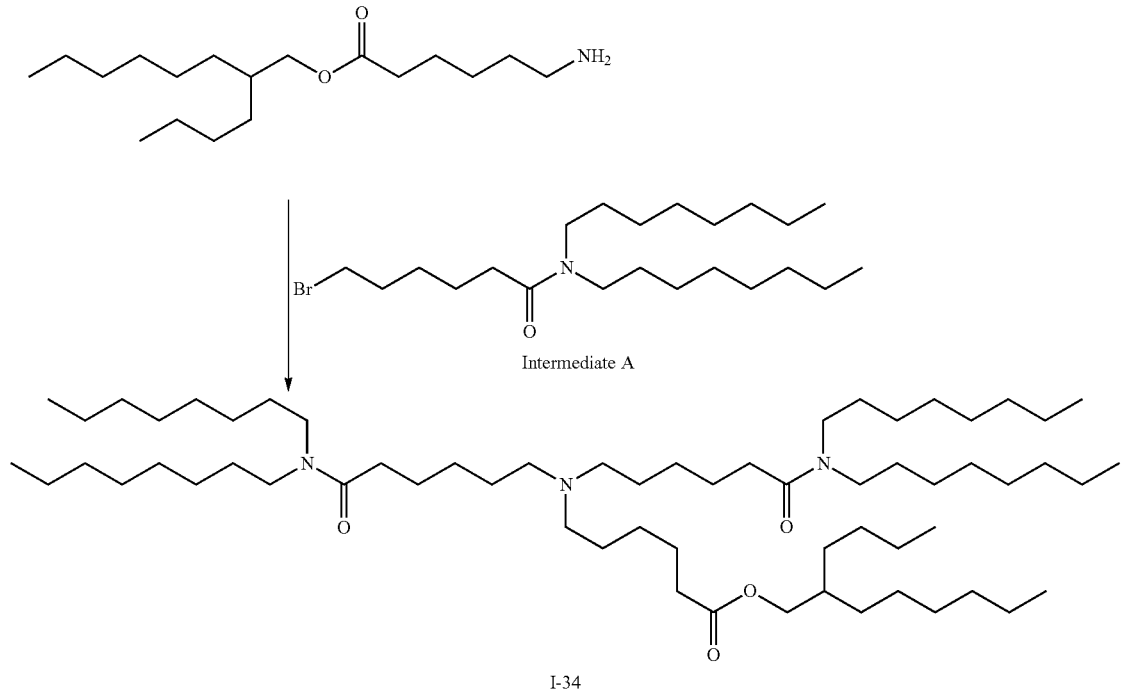

A mixture of 2-butyloctyl-6-aminohexanoate (0.76 mmol, 228 mg; made from 2-butyl-1-octanol and 6-aminocaproic acid; the purity is less than 80%), 6-bromo-N,N-dioctyl-hexanamide (Intermediate A, 1.44 mmol, 603 mg), anhydrous acetonitrile (15 mL) and N,N-diisopropylethylamine (0.4 mL) in a pressure flask was sealed and heated at 80° C. for 16 h. After the reaction mixture was concentrated, the residue was taken up in a mixture of hexane, ethyl acetate, and Et₃N (80:20:1) and was filtered through a pad of silica gel. The pad was washed with the same solvent mixture. Concentration of the filtrate and washings gave a yellow oil. The crude product was purified by flash dry column chromatography on silica gel (0 to 5% MeOH in chloroform with a trace of Et3N). The desired product was obtained as a colorless oil (172 mg, colorless oil, 0.18 mmol, 25%). $^1$HNMR (400 MHz, CDCl₃ at 7.26 ppm) δ: 3.97 (d, 5.8 Hz, 2H), 3.33-3.24 (m, 4H), 3.24-3.15 (m, 4H), 3.02-2.91 (br., 1H), 2.42 (m, 5H), 2.33-2.25 (m, 6H), 1.86-1.74 (br. 1H), 1.70-1.36 (m, 20H), 1.36-1.16 (m, 62H), 0.91-0.85 (m, 18H).

Example 35

6,6'-((4-hydroxybutyl)azanediyl)bis(N,N-bis(2-ethylhexyl)hexanamide) (Compound I-27)

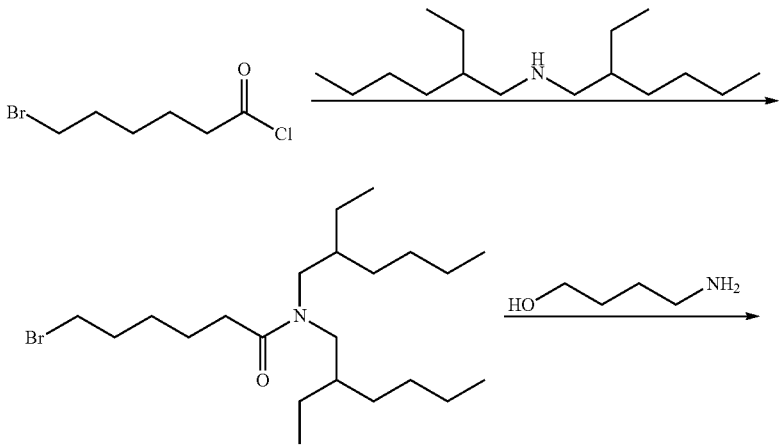

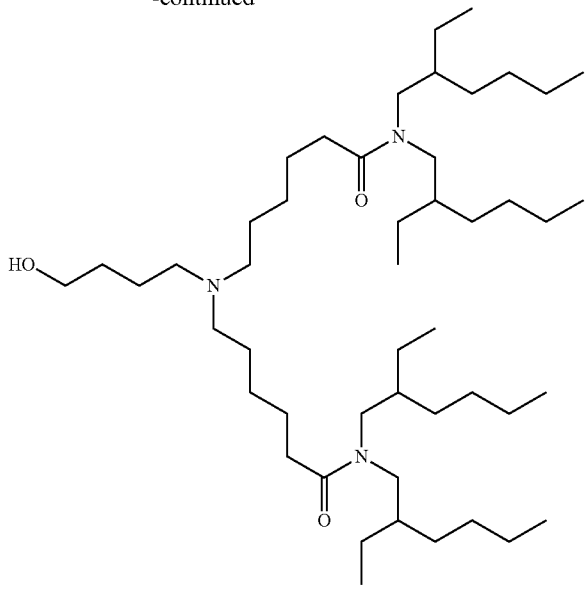

I-27

Synthesis of I-27

A solution of bis-(2-ethylhexyl)amine (7.5 g) and 6-bromohexanoyl chloride (6.1 g) in dichloromethane (60 mL) was treated with triethylamine (6 mL) and stirred for two hours. The solution was washed with dilute hydrochloric acid. The organic fractions were dried over anhydrous magnesium sulphate, filtered and the solvent removed. The crude product was passed down a silica gel column using dichloromethane to remove polar impurities. A solution of the resultant product (3 g) in THF was treated with 4-aminobutan-1-ol (0.22 g) and N,N-diisopropylethylamine (1 mL). The reaction was refluxed for three days, then partitioned between dilute hydrochloric acid and dichloromethane. The solvent was removed from the organic fraction and the residue passed down a silica gel (55 g) column using a methanol/dichloromethane gradient, yielding I-27 (1.6 g). $^1$H NMR (400 MHz, CDCl$_3$ at 7.26 ppm): 3.57-4.49 (m, 2H), 3.33-3.18 (m, 4H) 3.12 (d, 7.4 Hz, 4H), 2.47-2.26 (m, 10H), 1.74-1.12 (m, 52H), 0.93-0.81 (m, 24H). ESI-MS: MW for C$_{48}$H$_{97}$N$_3$O$_3$ [M+H]$^+$ Calc. 764.8; Found 764.8.

Example 36

8,8'-((2-hydroxyethyl)azanediyl)bis(N,N-didodecyloctanamide) (Compound I-37)

Compound I-37 was prepared according to the general procedures of example 13 to yield the desired product as a colorless oil (148 mg, 0.15 mmol, 32%). $^1$HNMR (400 MHz, CDCl$_3$ at 7.26 ppm) δ: 3.51 (t, 5.0 Hz, 2H), 3.30-3.25 (m, 4H), 3.22-3.16 (m, 4H), 2.56 (t, 5.3 Hz, 2H), 2.42 (t, 7.4 Hz, 4H), 2.27 (t, 7.6 Hz, 4H), 1.68-1.38 (m, 16H), 1.36-1.15 (84H), 0.90-0.86 (m, 12H). ESI-MS: MW for C$_{66}$H$_{133}$N$_3$O$_3$ [M+H]$^+$ Calc. 1017.0; Found 1017.1.

Example 37

6,6'-((6-hydroxyhexyl)azanediyl)bis(N,N-didodecylhexanamide) (Compound I-38)

Compound I-38 was prepared according to the general procedures of example 13 to yield the desired product as a colorless oil (259 mg, 0.25 mmol, 51%). $^1$HNMR (400 MHz, CDCl$_3$ at 7.26 ppm) δ: 3.67-3.61 (m, 2H), 3.28 (t, 7.6 Hz, 4H), 3.19 (t, 7.7 Hz, 4H), 2.41-2.35 (m, 6H), 2.27 (t, 7.5 Hz, 4H), 1.64 (quintet, 7.6 Hz, 4H), 1.60-1.40 (m, 16H), 1.40-1.10 (m, 80H), 0.90-0.85 (m, 12H). ESI-MS: MW for C$_{66}$H$_{133}$N$_3$O$_3$ [M+H]$^+$ Calc. 1017.0; Found 1017.4.

Example 38

N,N-didecyl-8-((8-(hexadecyl(methyl)amino)-8-oxooctyl)(methyl)amino)octanamide (Compound I-39)

Compound I-39 was prepared according to the general procedures of example 27 to yield the desired product as a colorless oil (152 mg, 0.18 mmol, 46%). $^1$HNMR (400 MHz, CDCl$_3$ at 7.26 ppm) δ: 3.36-3.16 (m, 6H), 2.96, 2.90 (2 sets of singlet, 3H), 2.31-2.24 (m, 8H), 2.18 (s, 3H), 1.68-1.58 (m, 4H), 1.56-1.38 (m, 10H), 1.38-1.18 (m, 66H), 0.91-0.86 (m, 9H). ESI-MS: MW for C$_{54}$H$_{109}$N$_3$O$_3$ [M+H]$^+$ Calc. 832.8; Found 832.8.

Example 39

8,8'-(methylazanediyl)bis(N,N-didodecyloctanamide) (Compound I-40)

Compound I-40 was prepared according to the general procedures of example 10 to yield the desired product as a colorless oil (235 mg, 0.24 mmol, 53%). $^1$HNMR (400 MHz, CDCl$_3$ at 7.26 ppm) δ: 3.28 (t, 7.6 Hz, 4H), 3.19 (t, 7.7 Hz, 4H), 2.30-2.24 (m, 8H), 2.18 (s, 3H), 1.63 (quintet, 7.6 Hz, 4H), 1.57-1.43 (m, 12H), 1.37-1.10 (m, 84H), 0.90-0.86 (m, 12H). ESI-MS: MW for C$_{65}$H$_{131}$N$_3$O$_2$ [M+H]$^+$ Calc. 987.0; Found 987.4.

Example 40

8,8'-((3-hydroxypropyl)azanediyl)bis(N,N-didecyloctanamide) (Compound I-41)

Compound I-41 was prepared according to the general procedures of example 13 to yield the desired product (100 mg, 22%). ¹HNMR (400 MHz, CDCl₃ at 7.26 ppm) δ: 3.78 (t, J=5.1 Hz, 2H), 3.32-3.23 (m, 4H), 3.23-3.15 (m, 4H), 2.64 (t, J=5.6 Hz, 2H), 2.44-2.36 (m, 4H), 2.31-2.22 (m, 4H), 1.65 (dp, J=22.1, 6.3 Hz, 6H), 1.58-1.40 (m, 12H), 1.38-1.18 (m, 70H), 0.88 (td, J=6.8, 3.0 Hz, 12H). ESI-MS: MW for $C_{59}H_{119}N_3O_3$ [M+H]⁺ Calc. 918.9; Found 919.3.

Example 41

8,8'-((2-(2-hydroxyethoxy)ethyl)azanediyl)bis(N,N-didecyloctanamide) (Compound I-42)

Intermediate D 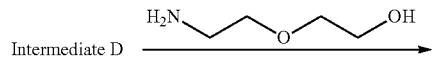 →

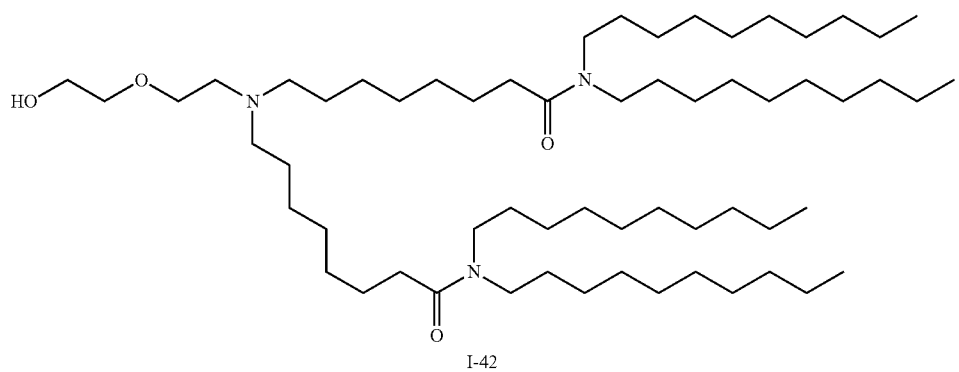

I-42

Synthesis of I-42

A mixture of Intermediate D (1.2 mmol, 600 mg), 2-(2-aminoethoxy)ethan-1-ol (0.74 mmol, 78 mg), and DIEA (3.0 mmol, 0.52 mL) in ACN (7 mL) was heated at 72° C. for 48 h. The reaction mixture was concentrated and the crude material was purified via automated flash chromatography (5% to 60% EtOAc in hexanes with 1% Et₃N) to give compound I-42 (200 mg, 35%). ¹H NMR (400 MHz, CDCl₃) δ 3.68 (m, 3.0 Hz, 2H), 3.63-3.57 (m, 4H), 3.32-3.23 (m, 4H), 3.23-3.14 (m, 4H), 2.62 (t, J=5.4 Hz, 2H), 2.49-2.41 (m, 4H), 2.30-2.22 (m, 4H), 1.61 (m, 4H), 1.48 (m, 12H), 1.38-1.23 (m, 68H), 0.88 (m, 12H). ESI-MS: MW for $C_{60}H_{121}N_3O_4$ [M+H]⁺ Calc. 948.9; Found 949.4.

Example 42

8,8'-((5-hydroxy-4,4-dimethylpentyl)azanediyl)bis(N,N-didecyloctanamide) (Compound I-43)

Intermediate D 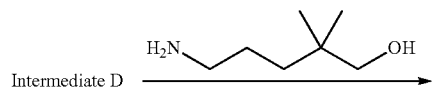 →

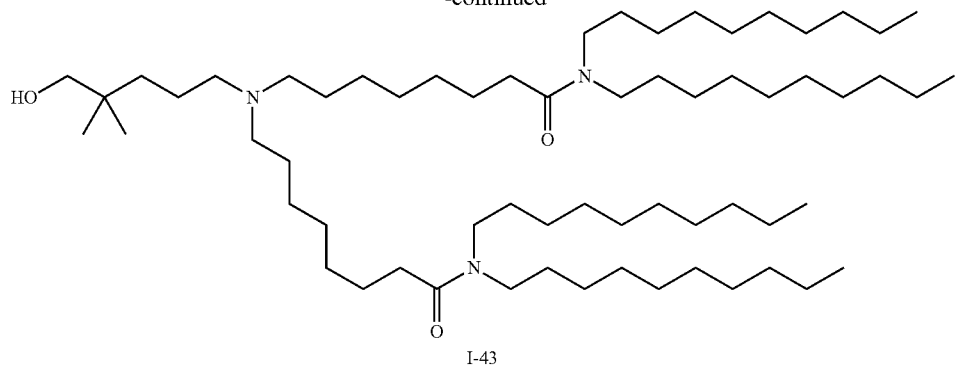

I-43

Synthesis of I-43

A mixture of Intermediate D (1.2 mmol, 600 mg), 5-amino-4,4-dimethylpentan-1-ol (0.74 mmol, 97 mg), and DIEA (3.0 mmol, 0.52 mL) in ACN (7 mL) was heated at 72° C. for 48 h. The reaction mixture was concentrated and the crude material was purified via automated flash chromatography (5% to 60% EtOAc in hexanes with 1% Et$_3$N) to give compound I-43 (280 mg, 48%). $^1$H NMR (400 MHz, CDCl$_3$) δ 3.31-3.23 (m, 6H), 3.22-3.12 (m, 4H), 2.41-2.30 (m, 6H), 2.30-2.22 (m, 4H), 1.71-1.58 (m, 4H), 1.56-1.46 (m, 5H), 1.44-1.36 (m, 3H), 1.36-1.17 (t, 74H), 0.98-0.81 (m, 18H). ESI-MS: MW for C$_{63}$H$_{127}$N$_3$O$_3$ [M+H]$^+$ Calc. 975.0; Found 975.4.

Example 43

8,8'-((3-(2-methyl-1H-imidazol-1-yl)propyl)azanediyl)bis(N,N-didecyloctanamide) (Compound I-44)

Intermediate D 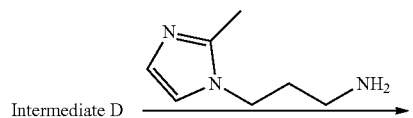

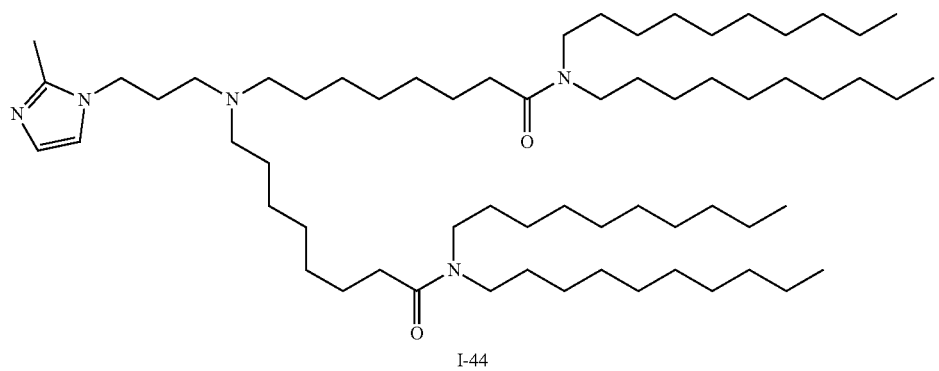

I-44

Synthesis of I-44

A mixture of Intermediate D (1.2 mmol, 600 mg), 3-(2-methyl-1H-imidazol-1-yl)propan-1-amine (0.74 mmol, 103 mg), and DIEA (3.0 mmol, 0.52 mL) in ACN (7 mL) was heated at 72° C. for 48 h. The reaction mixture was concentrated and the crude material was purified via automated flash chromatography (5% to 100% EtOAc in hexanes with 1% Et$_3$N). A second purification via automated flash chromatography (c18 column, 50% to 100% MeOH in water with 1% TFA) gave pure compound I-44 (60 mg, 10%). $^1$H NMR (400 MHz, CDCl$_3$) δ 6.90 (s, 1H), 6.82 (s, 1H), 3.87 (t, J=7.2 Hz, 2H), 3.34-3.24 (m, 4H), 3.23-3.11 (m, 4H), 2.43-2.34 (m, 8H), 2.31-2.23 (m, 4H), 1.89-1.77 (m, 3H), 1.67-1.59 (m, 4H), 1.58-1.45 (m, 8H), 1.45-1.18 (m, 72H), 0.94-0.83 (m, 12H). ESI-MS: MW for C$_{63}$H$_{123}$N$_5$O$_2$ [M+H]$^+$ Calc. 983.0; Found 983.4.

Example 44

8,8'-((7-hydroxyheptyl)azanediyl)bis(N,N-didecyloctanamide) (Compound I-45)

Compound I-45 was prepared according to the general procedures of example 13 to yield the desired product (320 mg, 55%). $^1$HNMR (400 MHz, CDCl$_3$ at 7.26 ppm) δ: 6.90 (s, 1H), 6.82 (s, 1H), 3.87 (t, J=7.2 Hz, 2H), 3.33-3.22 (m, 4H), 3.23-3.13 (m, 4H), 2.42-2.34 (m, 8H), 2.33-2.20 (m, 4H), 1.90-1.76 (m, 2H), 1.66-1.59 (m, 4H), 1.57-1.45 (m, 8H), 1.45-1.13 (m, 71H), 0.88 (m, 12H). ESI-MS: MW for C$_{63}$H$_{127}$N$_3$O$_3$ [M+H]$^+$ Calc. 975.0; Found 975.4.

Example 45

8,8'-((2-(2-methoxyethoxy)ethyl)azanediyl)bis(N,N-didecyloctanamide) (Compound I-46)

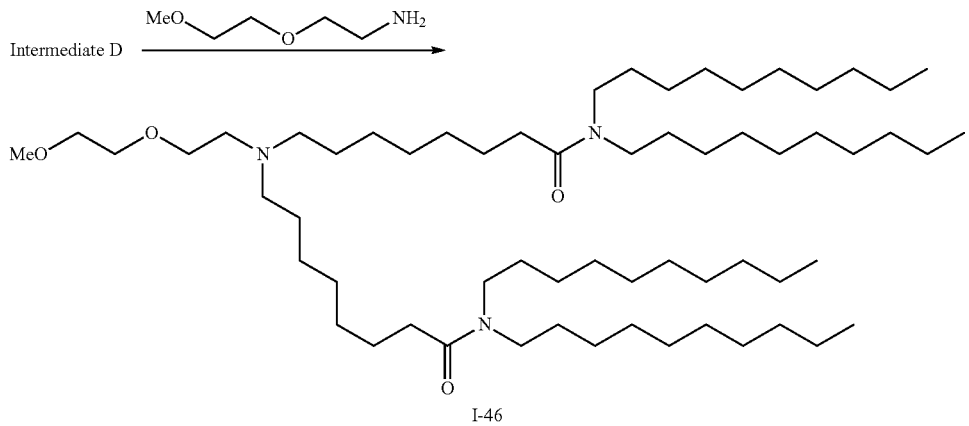

I-46

Synthesis of I-46

A mixture of Intermediate D (1.2 mmol, 600 mg), 2-(2-methoxyethoxy)ethan-1-amine (0.74 mmol, 89 mg), and DIEA (3.0 mmol, 0.52 mL) in ACN (7 mL) was heated at 72° C. for 48 h. The reaction mixture was concentrated and the crude material was purified via automated flash chromatography (5% to 60% EtOAc in hexanes with 1% Et$_3$N) to give compound I-46 (333 mg, 58%). $^1$H NMR (400 MHz, CDCl$_3$) δ 3.65-3.60 (m, 2H), 3.59-3.51 (m, 4H), 3.40 (s, 3H), 3.33-3.26 (m, 4H), 3.25-3.18 (m, 4H), 2.67 (t, J=6.7 Hz, 2H), 2.48-2.39 (m, 4H), 2.33-2.25 (m, 4H), 1.68-1.61 (m, 4H), 1.59-1.48 (m, 8H), 1.48-1.40 (m, 3H), 1.37-1.24 (m, 69H), 0.95-0.85 (m, 12H). ESI-MS: MW for C$_{61}$H$_{123}$N$_3$O$_4$ [M+H]$^+$ Calc. 963.0; Found 963.4.

Example 46

8,8'-((8-hydroxyoctyl)azanediyl)bis(N,N-didecyloctanamide) (Compound I-47)

Compound I-47 was prepared according to the general procedures of example 13 to yield the desired product (320 mg, 54%). $^1$HNMR (600 MHz, CDCl$_3$ at 7.26 ppm) δ: 3.65 (t, J=6.7 Hz, 2H), 3.32-3.27 (m, 4H), 3.23-3.18 (m, 4H), 2.41-2.34 (m, 6H), 2.32-2.25 (m, 4H), 1.68-1.62 (m, 4H), 1.60-1.48 (m, 10H), 1.47-1.39 (m, 6H), 1.38-1.23 (m, 76H), 0.96-0.84 (m, 12H). ESI-MS: MW for C$_{64}$H$_{129}$N$_3$O$_3$ [M+H]$^+$ Calc. 989.0; Found 989.5.

Example 47

8,8'-((3-(1H-imidazol-1-yl)propyl)azanediyl)bis(N,N-didecyloctanamide) (Compound I-48)

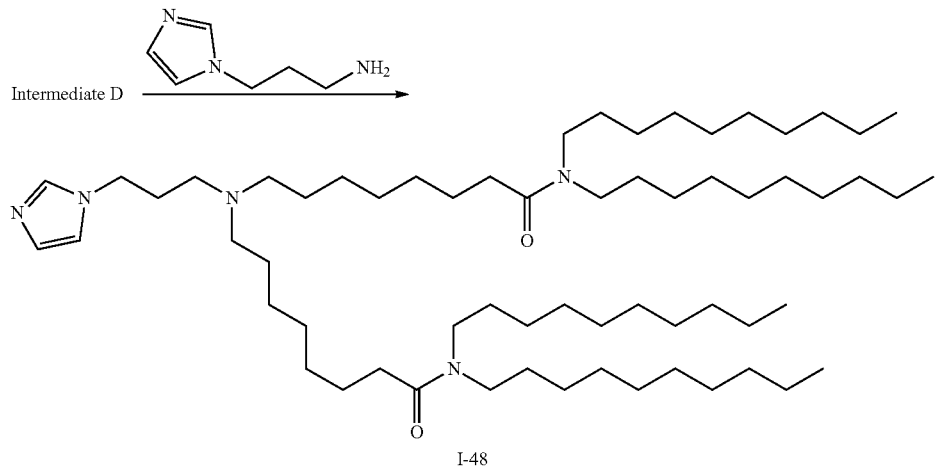

Synthesis of I-48

A mixture of Intermediate D (1.2 mmol, 600 mg), 3-(1H-imidazol-1-yl)propan-1-amine (0.74 mmol, 93 mg), and DIEA (3.0 mmol, 0.52 mL) in ACN (7 mL) was heated at 72° C. for 48 h. The reaction mixture was concentrated and the crude material was purified via automated flash chromatography (5% to 100% EtOAc in hexanes with 1% Et$_3$N) to give compound I-48 (82 mg, 14%). $^1$H NMR (600 MHz, CDCl$_3$) δ 7.48 (s, 1H), 7.07 (s, 1H), 6.93 (s, 1H), 4.00 (t, J=7.0 Hz, 2H), 3.30 (t, J=7.7 Hz, 4H), 3.21 (t, J=7.8 Hz, 4H), 2.41-2.34 (m, 6H), 2.29 (t, J=7.6 Hz, 4H), 1.92-1.87 (m, 2H), 1.69-1.61 (m, 4H), 1.59-1.47 (m, 8H), 1.41-1.22 (m, 74H), 0.93-0.87 (m, 12H). ESI-MS: MW for C$_{62}$H$_{121}$N$_5$O$_2$ [M+H]$^+$ Calc. 969.0; Found 969.1.

Example 48

8,8'-((2,2-difluoro-3-hydroxypropyl)azanediyl)bis(N,N-didecyloctanamide) (Compound I-49)

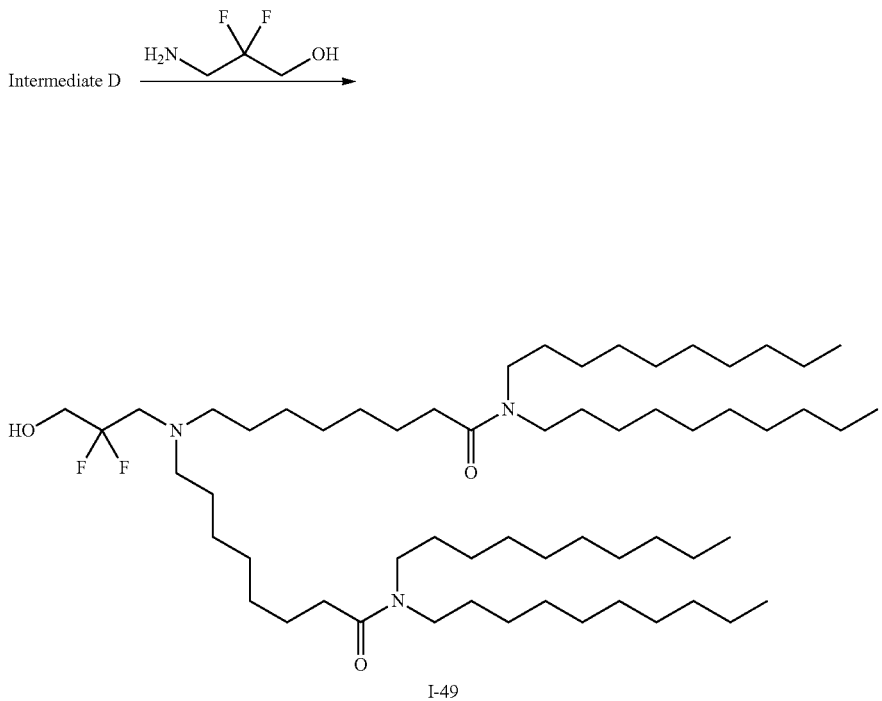

Synthesis of I-49

A mixture of Intermediate D (1.0 mmol, 500 mg), 3-amino-2,2-difluoropropan-1-ol (0.62 mmol, 69 mg), and DIEA (3.0 mmol, 0.43 mL) in ACN (6 mL) was heated at 72° C. for 48 h. The reaction mixture was concentrated and the crude material was purified via automated flash chromatography (5% to 60% EtOAc in hexanes with 1% Et$_3$N) to give compound I-49 (55 mg, 12%). $^1$H NMR (600 MHz, CDCl$_3$) δ 4.87 (s, 1H), 3.88 (t, J=12.1 Hz, 2H), 3.33-3.27 (m, 4H), 3.24-3.18 (m, 4H), 2.96 (t, J=12.7 Hz, 2H), 2.56-2.51 (m, 4H), 2.32-2.26 (m, 4H), 1.68-1.61 (m, 6H), 1.59-1.42 (m, 12H), 1.39-1.23 (m, 70H), 0.93-0.87 (m, 12H). ESI-MS: MW for C$_{59}$H$_{117}$F$_2$N$_3$O$_3$[M+H]$^+$ Calc. 954.9; Found 955.1.

Example 49

8,8'-((3-((2-(methylamino)-3,4-dioxocyclobut-1-en-1-yl)amino)propyl)azanediyl)bis(N,N-didecyloctanamide) (Compound I-50)

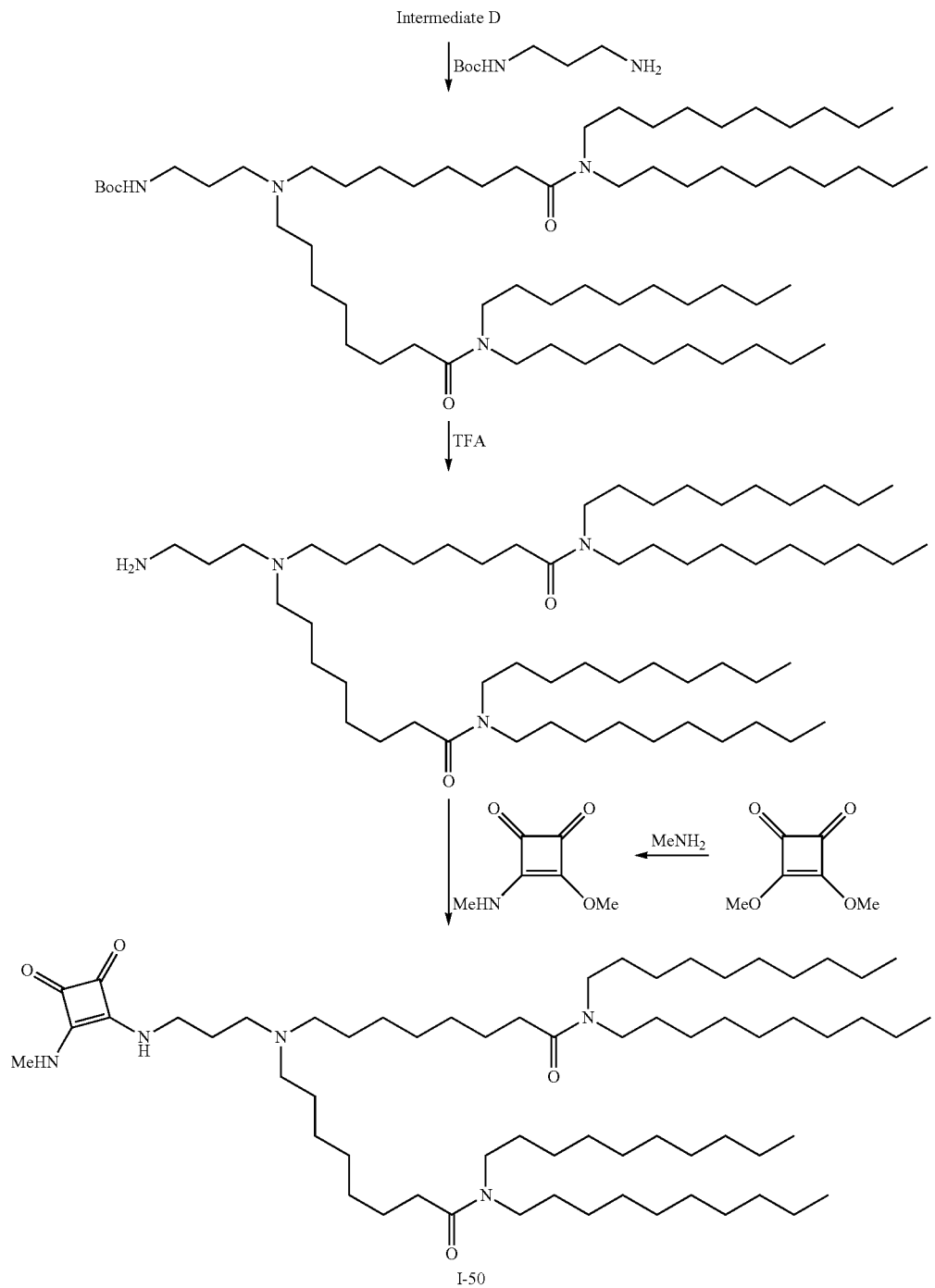

Synthesis of tert-butyl (3-(bis(8-(didecylamino)-8-oxooctyl)amino)propyl)carbamate A mixture of Intermediate D (1.60 mmol, 800 mg), tert-butyl (3-aminopropyl)carbamate (0.99 mmol, 173 mg), and DIEA (4.0 mmol, 0.7 mL) in ACN (10 mL) was heated at 72° C. for 48 h. The reaction mixture was concentrated and the crude material was purified via automated flash chromatography (5% to 60% EtOAc in hexanes with 1% $Et_3N$) to give compound tert-butyl (3-(bis(8-(didecylamino)-8-oxooctyl)amino)propyl)carbamate (388 mg, 48%).

Synthesis of 8,8'-((3-aminopropyl)azanediyl)bis(N,N-didecyloctanamide)

A mixture of tert-butyl (3-(bis(8-(didecylamino)-8-oxooctyl)amino)propyl)carbamate (0.38 mmol, 385 mg) and TFA (1.0 mL) in DCM (2.0 mL) was stirred at room temperature for 90 min. The reaction mixture was concentrated and the crude material was partitioned between EtOAc and sat. $NaHCO_3$ to give compound 8,8'-((3-aminopropyl)azanediyl)bis(N,N-didecyloctanamide) (385 mg, quantitative) which was used in the next step without further purification.

Synthesis of 3-methoxy-4-(methylamino)cyclobut-3-ene-1,2-dione

A mixture of 3,4-dimethoxycyclobut-3-ene-1,2-dione (7.0 mmol, 1 g) and 2 M methylamine in THF (7.7 mmol, 3.9 mL) in diethyl ether (100 mL) was stirred at room temperature for 19 h. The solids were filtered and washed with diethyl ether. The crude solids were triturated in hot EtOAc, cooled to 5° C., then filtered and washed with cold EtOAc to give 3-methoxy-4-(methylamino)cyclobut-3-ene-1,2-dione (700 mg, 71%).

Synthesis of I-50

A mixture of 8,8'-((3-aminopropyl)azanediyl)bis(N,N-didecyloctanamide) (0.11 mmol, 100 mg) and 3-methoxy-4-(methylamino)cyclobut-3-ene-1,2-dione (0.11 mmol, 15 mg) in ethanol (5 mL) was stirred at room temperature for 19 h then heated at 50° C. for 19 h. The reaction mixture was concentrated and the crude material was purified via automated flash chromatography (5% to 100% EtOAc in hexanes with 1% $Et_3N$, then 2% MeOH in DCM). A second purification via automated flash chromatography (1% to 10% MeOH in DCM) was performed to give I-50 (32 mg, 28%). $^1H$ NMR (400 MHz, $CDCl_3$) δ 8.22 (bs, 0.5H), 7.60 (bs, 0.5H), 3.70 (bs, 2H), 3.33-3.23 (m, 7H), 3.23-3.14 (m, 4H), 2.96 (bs, 2H), 2.80 (bs, 4H), 2.28 (t, J=7.4 Hz, 4H), 1.98 (bs, 2H), 1.66-1.45 (m, 16H), 1.40-1.20 (m, 67H), 0.92-0.83 (m, 12H). ESI-MS: MW for $C_{64}H_{123}N_5O_4$ $[M+H]^+$ Calc. 1027.0; Found 1027.1.

Example 50

8,8'-((2-fluoro-3-hydroxypropyl)azanediyl)bis(N,N-didecyloctanamide) (Compound I-51)

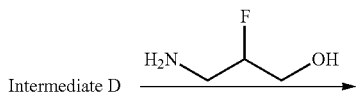

Intermediate D

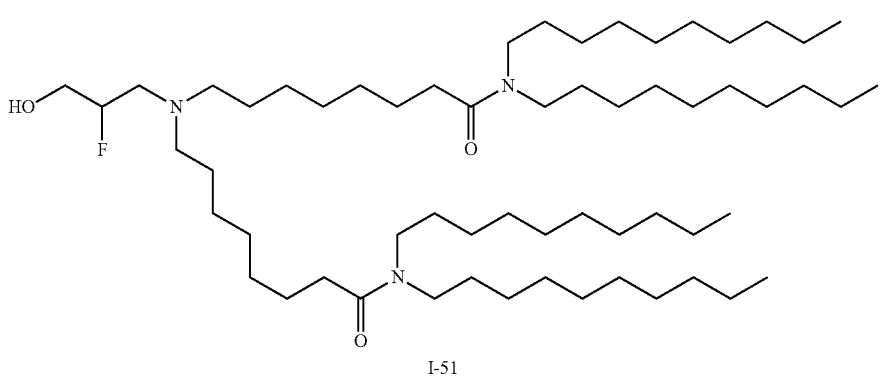

I-51

Synthesis of I-51

A mixture of Intermediate D (1.0 mmol, 500 mg), 3-amino-2-fluoropropan-1-ol hydrochloride (0.62 mmol, 80 mg), and DIEA (3.1 mmol, 0.54 mL) in ACN (6 mL) was heated at 72° C. for 24 h, then at 55° C. for 72 h. The reaction mixture was concentrated and the crude material was purified via automated flash chromatography (5% to 60% EtOAc in hexanes with 1% Et$_3$N) to give compound I-51 (45 mg, 10%). $^1$H NMR (400 MHz, CDCl$_3$) δ 4.60 (dt, J=46.8, 4.8 Hz, 1H), 3.92-3.80 (m, 2H), 3.35-3.24 (m, 4H), 3.24-3.12 (m, 4H), 2.85-2.72 (m, 2H), 2.53-2.37 (m, 4H), 2.31-2.23 (m, 4H), 1.67-1.40 (m, 20H), 1.38-1.19 (m, 66H), 0.94-0.82 (m, 12H). ESI-MS: MW for C$_{59}$H$_{118}$FN$_3$O$_3$[M+H]$^+$ Calc. 936.9; Found 937.0.

Example 51

8,8'-((3,3,3-trifluoro-2-(hydroxymethyl)propyl)azanediyl)bis(N,N-didecyloctanamide) (Compound I-52)

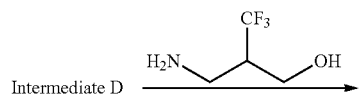

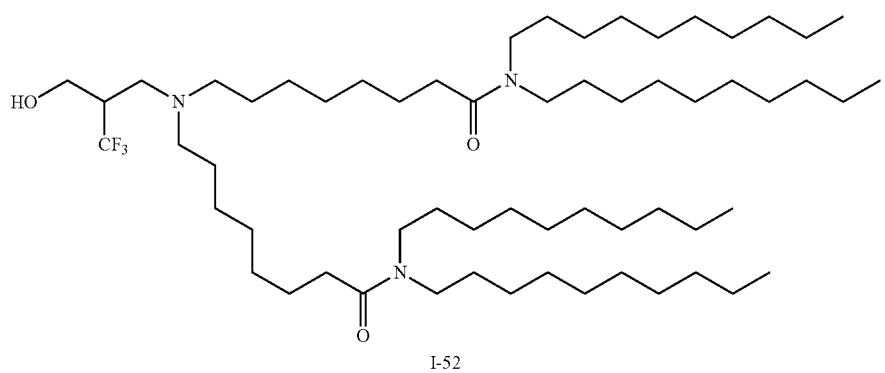

I-52

Synthesis of I-52

A mixture of Intermediate D (1.0 mmol, 500 mg), 2-(aminomethyl)-3,3,3-trifluoropropan-1-ol (0.62 mmol, 111 mg), and DIEA (2.4 mmol, 0.43 mL) in ACN (6 mL) was heated at 72° C. for 24 h, then at 55° C. for 72 h. The reaction mixture was concentrated and the crude material was purified via automated flash chromatography (5% to 60% EtOAc in hexanes with 1% Et$_3$N) to give compound I-52 (100 mg, 20%). $^1$H NMR (400 MHz, CDCl$_3$) δ 5.88 (s, 1H), 4.01-3.92 (m, 1H), 3.89-3.78 (m, 1H), 3.33-3.24 (m, 4H), 3.23-3.15 (m, 4H), 2.91-2.73 (m, 2H), 2.69-2.50 (m, 3H), 2.34-2.21 (m, 6H), 1.69-1.39 (m, 20H), 1.38-1.21 (m, 68H), 0.95-0.84 (m, 12H). ESI-MS: MW for C$_{60}$H$_{118}$F$_3$N$_3$O$_3$ [M+H]$^+$ Calc. 986.9; Found 987.0.

Example 52

8,8'-((5-methoxypentyl)azanediyl)bis(N,N-didecyloctanamide) (Compound I-53)

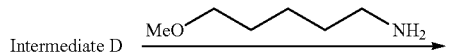

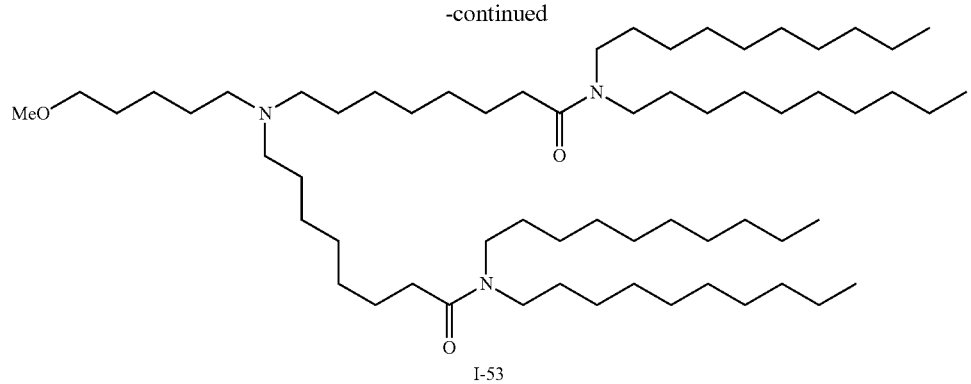

I-53

Synthesis of I-53

A mixture of Intermediate D (0.80 mmol, 400 mg), 5-methoxypentan-1-amine (0.50 mmol, 58 mg), and DIEA (2.0 mmol, 0.35 mL) in ACN (6 mL) was heated at 72° C. for 24 h, then at 55° C. for 72 h. The reaction mixture was concentrated and the crude material was purified via automated flash chromatography (5% to 60% EtOAc in hexanes with 1% Et$_3$N) to give compound I-53 (210 mg, 55%). $^1$H NMR (400 MHz, CDCl$_3$) δ 3.36 (t, J=6.6 Hz, 2H), 3.32 (s, 3H), 3.30-3.25 (m, 4H), 3.22-3.16 (m, 4H), 2.41-2.32 (m, 6H), 2.31-2.22 (m, 4H), 1.67-1.37 (m, 23H), 1.36-1.19 (m, 69H), 0.91-0.85 (m, 12H). ESI-MS: MW for C$_{62}$H$_{125}$N$_3$O$_3$ [M+H]$^+$ Calc. 961.0; Found 961.1.

Example 53

N,N-didecyl-8-((8-(dioctylamino)-8-oxooctyl)(methyl)amino)octanamide (Compound I-55)

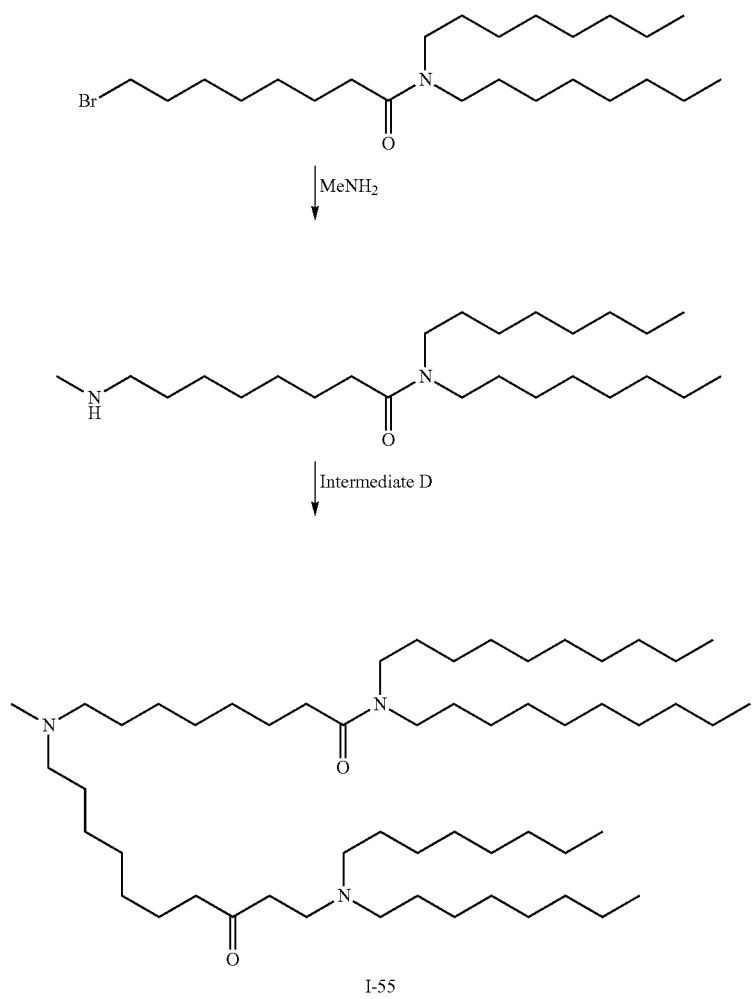

I-55

Synthesis of
8-(methylamino)-N,N-dioctyloctanamide

A mixture of 8-bromo-N,N-dioctyloctanamide (5.8 mmol, 2.6 g) and 8 M methylamine in EtOH (30 mL) in ACN (12 mL) was heated at 70° C. for 19 h. The reaction mixture was concentrated and the crude material was purified via automated flash chromatography (5% to 100% EtOAc in hexanes, then 1% to 10% MeOH in DCM) to give compound 8-(methylamino)-N,N-dioctyloctanamide (1.91 g, 83%).

Synthesis of I-55

A mixture of 8-(methylamino)-N,N-dioctyloctanamide (3.4 mmol, 1.3 g), Intermediate D (3.4 mmol, 1.7 g), and DIEA (13.8 mmol, 2.4 mL) in ACN (120 mL) was heated at 70° C. for 19 h. The reaction mixture was concentrated and the crude material was purified via automated flash chromatography (5% to 60% EtOAc in hexanes with 1% Et$_3$N) to give compound I-55 (1.38 g, 50%). $^1$H NMR (400 MHz, CDCl$_3$) δ 3.34-3.26 (m, 4H), 3.25-3.17 (m, 4H), 2.34-2.25 (m, 8H), 2.21 (s, 3H), 1.70-1.61 (m, 6H), 1.60-1.41 (m, 12H), 1.39-1.23 (m, 59H), 0.95-0.85 (m, 12H). ESI-MS: MW for C$_{53}$H$_{107}$N$_3$O$_2$ [M+H]$^+$ Calc. 818.8; Found 819.0.

Example 54 tert-butyl (3-(bis(10-(didecylamino)-10-oxodecyl)amino)propyl)carbamate (Compound I-56)

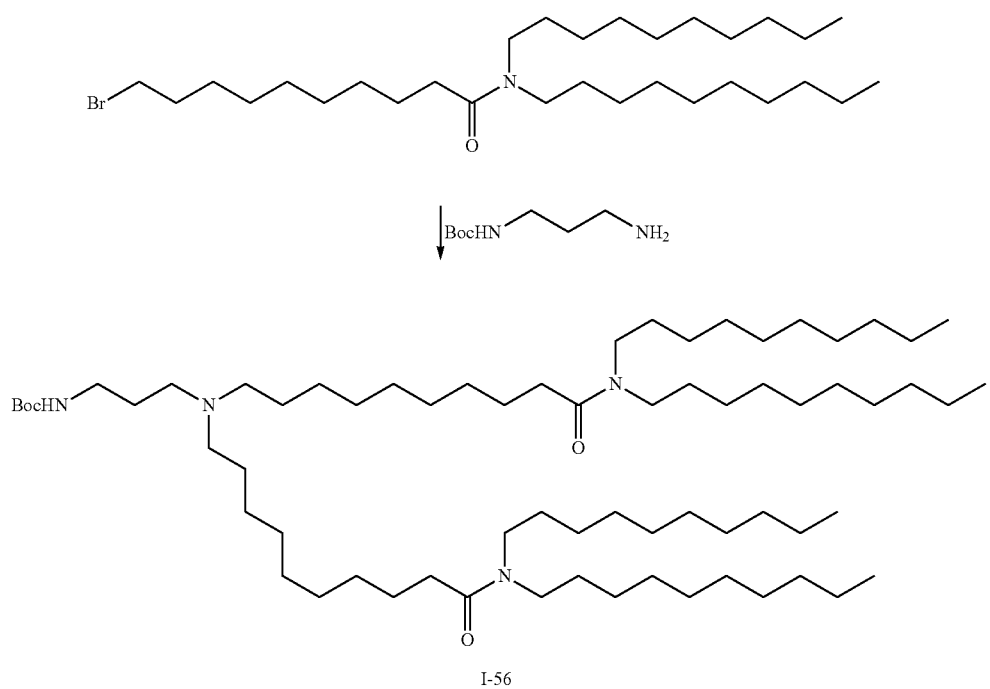

I-56

Synthesis of I-56

To mixture of 10-bromo-N,N-didecyldecanamide (was prepared according to the general procedures of example 5, 1.5 mmol, 800 mg), tert-butyl (3-aminopropyl)carbamate (0.93 mmol, 162 mg), and DIEA (4.5 mmol, 0.78 mL), in ACN (10 mL) was stirred at 70° C. for 48 h. The reaction mixture was concentrated and the crude material was purified via automated flash chromatography (5% to 65% EtOAc in hexanes with 1% Et$_3$N) to give I-56 (555 mg, 69%). $^1$H NMR (400 MHz, CDCl$_3$) δ 5.72 (bs, 1H), 3.32-3.24 (m, 4H), 3.23-3.14 (m, 6H), 2.44 (t, J=6.4 Hz, 2H), 2.31-2.23 (m, 4H), 2.31-2.23 (m, 4H), 1.67-1.58 (m, 9H), 1.57-1.47 (m, 3H), 1.47-1.37 (m, 12H), 1.35-1.19 (m, 77H), 0.92-0.83 (m, 12H). ESI-MS: MW for C$_{68}$H$_{136}$N$_4$O$_4$ [M+H]$^+$ Calc. 1074.1; Found 1074.2.

Example 55

10,10'-((3-(1H-imidazol-1-yl)propyl)azanediyl)bis(N,N-didecyldecanamide) (Compound I-57)

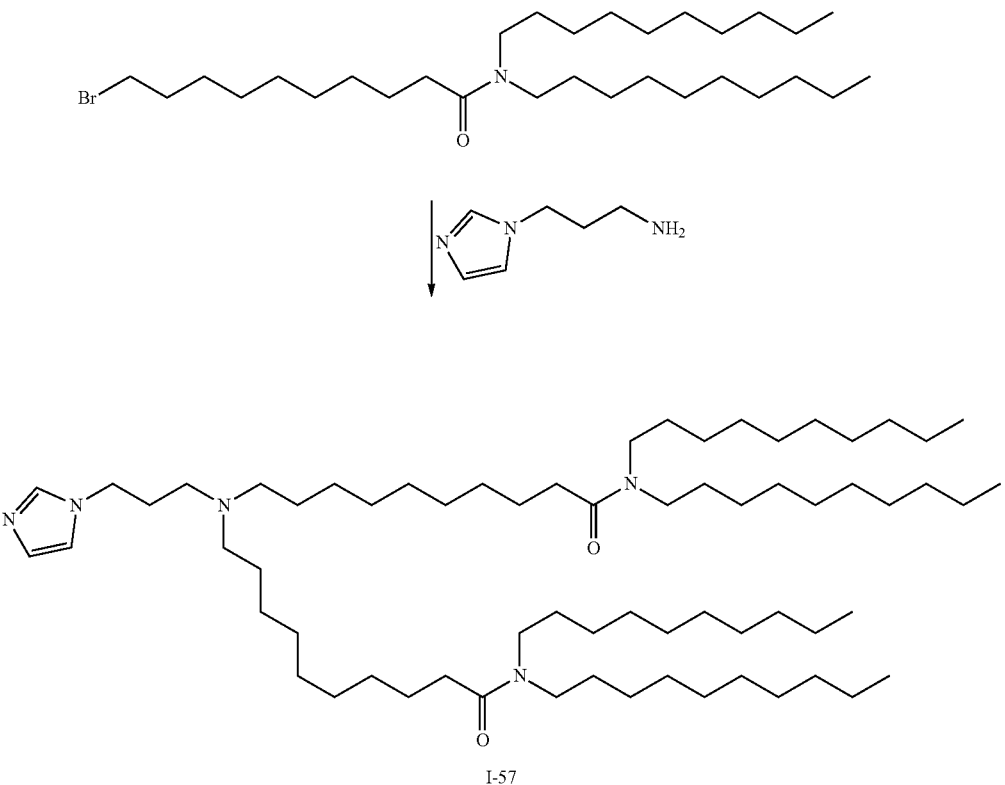

I-57

Synthesis of I-57

A mixture of 10-bromo-N,N-didecyldecanamide (was prepared according to the general procedures of example 5, 1.1 mmol, 600 mg), 3-(1H-imidazol-1-yl)propan-1-amine (0.68 mmol, 88 mg), and DIEA (3.3 mmol, 0.57 mL) in ACN (7 mL) was heated at 70° C. for 48 h. The reaction mixture was concentrated and the crude material was purified via automated flash chromatography (5% to 100% EtOAc in hexanes with 1% Et$_3$N). A second purification via reverse phase (C$_{18}$) automated flash chromatography (50% to 100% MeOH in water) gave compound I-57 (45 mg, 8%). $^1$H NMR (400 MHz, CDCl$_3$) δ 7.52 (bs, 1H), 7.06 (s, 1H), 6.92 (s, 1H), 4.00 (t, J=7.0 Hz, 2H), 3.32-3.24 (m, 4H), 3.22-3.15 (m, 4H), 2.38 (bs, 6H), 2.31-2.21 (m, 4H), 1.90 (bs, 2H), 1.73-1.57 (m, 8H), 1.57-1.45 (m, 8H), 1.43-1.16 (m, 81H), 0.95-0.81 (m, 12H). ESI-MS: MW for C$_{66}$H$_{129}$N$_5$O$_2$ [M+H]$^+$ Calc. 1025.0; Found 1025.1.

Example 56

8,8'-(methylazanediyl)bis(N,N-dinonyloctanamide) (Compound I-58)

Compound I-58 was prepared according to the general procedures of example 5 to yield the desired product (1.78 g, 59%). $^1$H NMR (600 MHz, CDCl$_3$) δ 3.33-3.27 (m, 4H), 3.24-3.18 (m, 4H), 2.33-2.26 (m, 8H), 2.21 (s, 3H), 1.69-1.61 (m, 7H), 1.59-1.42 (m, 12H), 1.39-1.21 (m, 61H), 0.94-0.86 (m, 12H). ESI-MS: MW for C$_{53}$H$_{107}$N$_3$O$_2$ [M+H]$^+$ Calc. 818.8; Found 819.0.

Example 57 tert-butyl (3-(bis(10-(didecylamino)-10-oxodecyl)amino)propyl)carbamate (Compound I-59)

Intermediate D

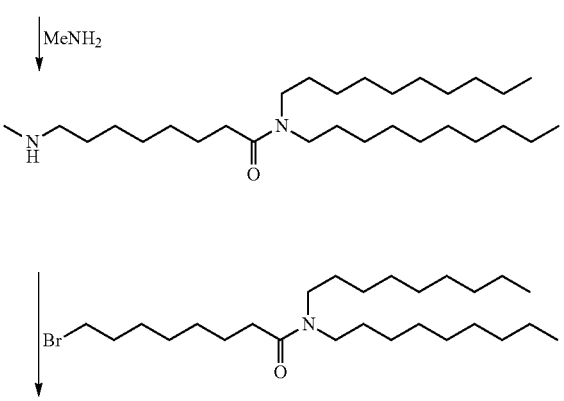

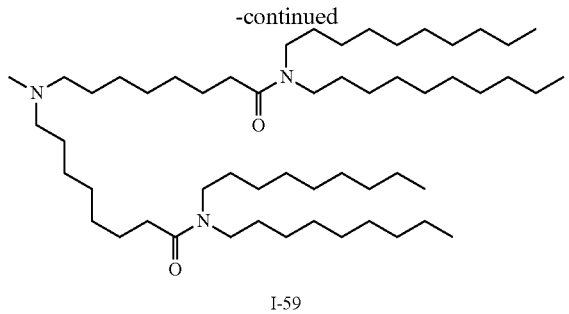

I-59

Synthesis of N,N-didecyl-8-(methylamino)octanamide

A mixture of Intermediate D (6.3 mmol, 2.8 g) and 8 M methylamine in EtOH (30 mL) in ACN (12 mL) was heated at 70° C. for 19 h. The reaction mixture was concentrated and the crude material was purified via automated flash chromatography (5% to 100% EtOAc in hexanes, then 1% to 10% MeOH in DCM) to give N,N-didecyl-8-(methylamino)octanamide (2.24 g, 79%).

Synthesis of I-59

A mixture of N,N-didecyl-8-(methylamino)octanamide (3.3 mmol, 1.5 g), 8-bromo-N,N-dinonyloctanamide (was prepared according to the general procedures of example 5, 3.3 mmol, 1.6 g), and DIEA (13.2 mmol, 2.3 mL) in ACN (10 mL) was heated at 70° C. for 19 h. The reaction mixture was concentrated and the crude material was purified via automated flash chromatography (5% to 60% EtOAc in hexanes with 1% Et$_3$N) to give compound I-59 (1.5 g, 53%). $^1$H NMR (400 MHz, CDCl$_3$) δ 3.34-3.26 (m, 4H), 3.25-3.17 (m, 4H), 2.34-2.24 (m, 8H), 2.21 (s, 3H), 1.75-1.59 (m, 4H), 1.61-1.41 (m, 12H), 1.38-1.23 (m, 66H), 0.95-0.86 (m, 12H). ESI-MS: MW for C$_{55}$H$_{111}$N$_3$O$_2$ [M+H]$^+$ Calc. 846.9; Found 847.1.

Example 58

10,10'-((3-((2-(methylamino)-3,4-dioxocyclobut-1-en-1-yl)amino)propyl)azanediyl)bis(N,N-didecyldecanamide) (Compound I-60)

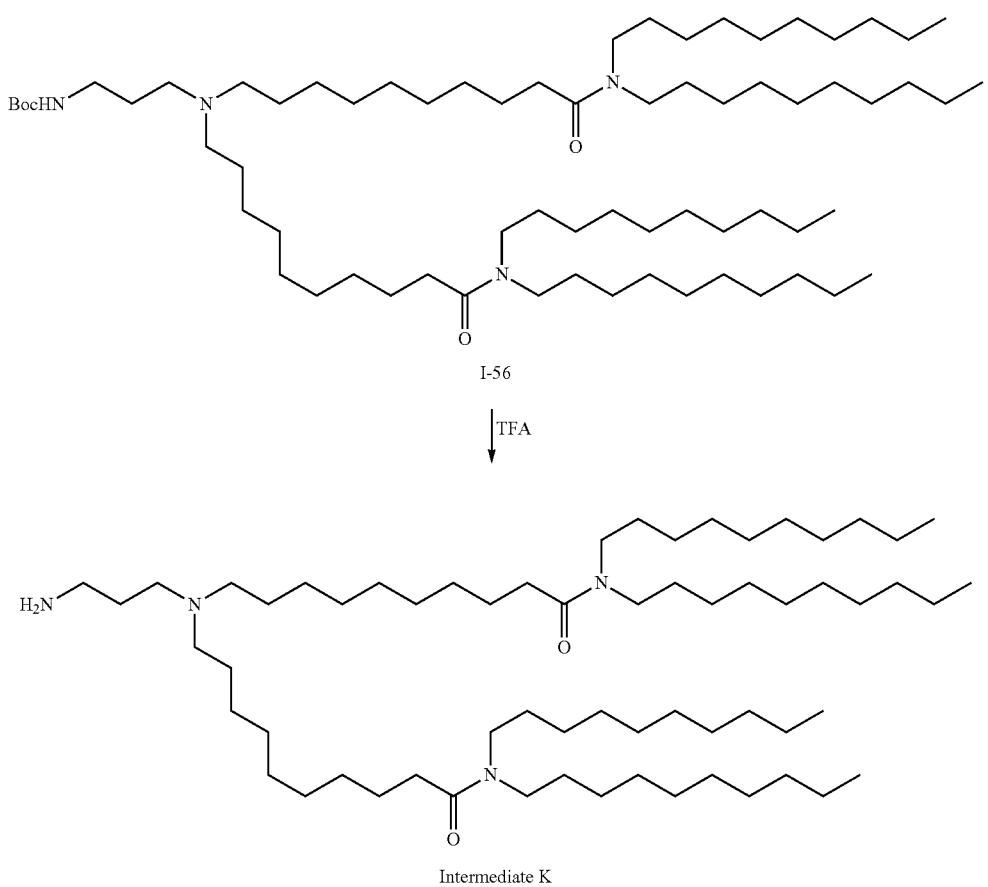

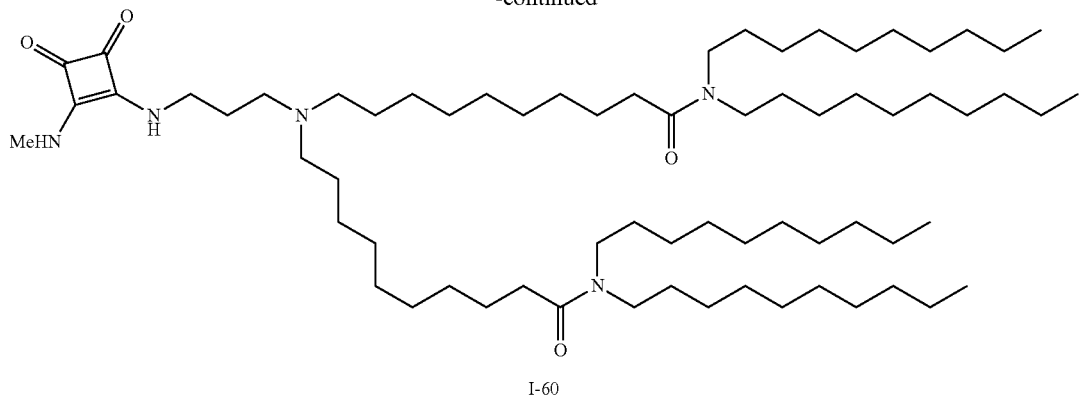

I-60

Synthesis of Intermediate K

A mixture of I-56 (0.42 mmol, 455 mg) and TFA (2.0 mL) in DCM (1.0 mL) was stirred at room temperature for 2 h. The reaction mixture was concentrated and the crude material was partitioned between EtOAc and sat. NaHCO$_3$ to give 10,10'-((3-aminopropyl)azanediyl)bis(N,N-didecyldecanamide) (Intermediate K, 369 mg, 90%) which was used in the next step without further purification.

Synthesis of I-60

A mixture of Intermediate K (0.1 mmol, 100 mg) and 3-methoxy-4-(methylamino)cyclobut-3-ene-1,2-dione (was prepared according to the general procedures of example 49, 0.5 mmol, 75 mg) in EtOH (1.0 mL) was heated at 80° C. for 5 h. The reaction mixture was concentrated and the crude material was purified via automated flash chromatography (50% to 100% EtOAc in hexanes with 1% Et$_3$N, then 2% to 10% MeOH in DCM) to give I-60 (27 mg, 25%). $^1$H NMR (400 MHz, CDCl$_3$) δ 7.15-6.86 (bs, 1H), 3.68 (bs, 2H), 3.33-3.18 (m, 11H), 2.58 (t, J=6.7 Hz, 2H), 2.46 (t, J=7.6 Hz, 4H), 2.30 (t, J=7.6 Hz, 4H), 2.05-1.73 (m, 6H), 1.71-1.41 (m, 18H), 1.38-1.20 (m, 79H), 0.96-0.83 (m, 12H). ESI-MS: MW for C$_{68}$H$_{131}$N$_5$O$_4$ [M+H]$^+$ Calc. 1083.0; Found 1083.1.

Example 59

Synthetic Pathway for Compounds I-61 to I-68

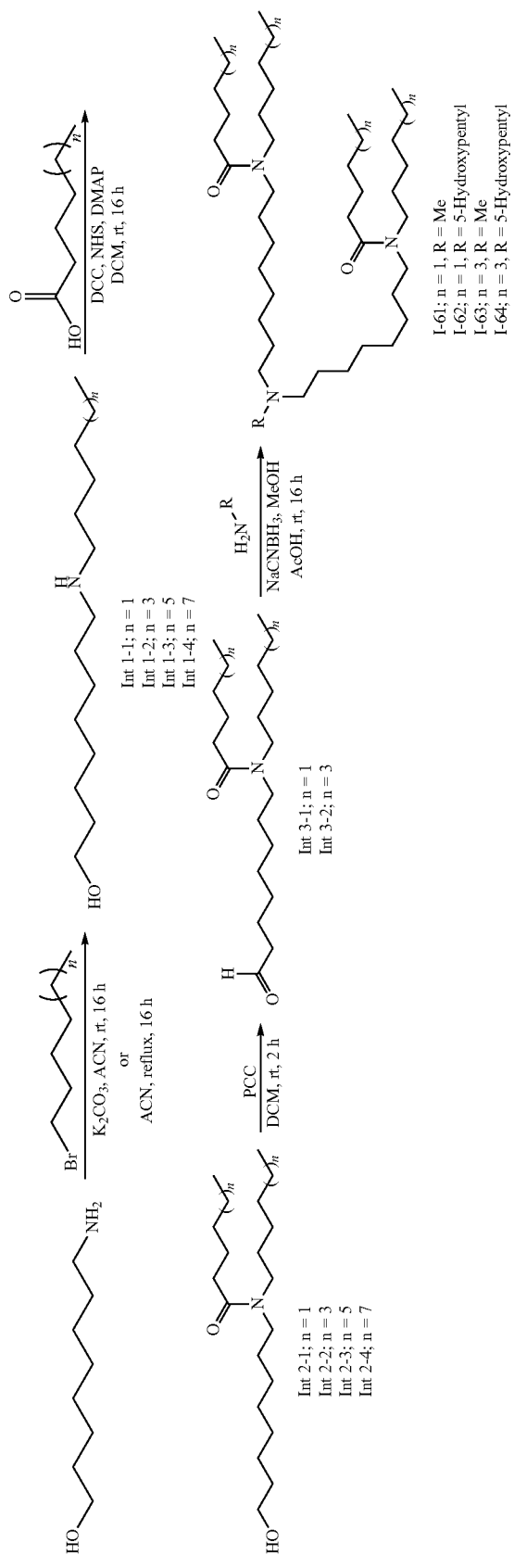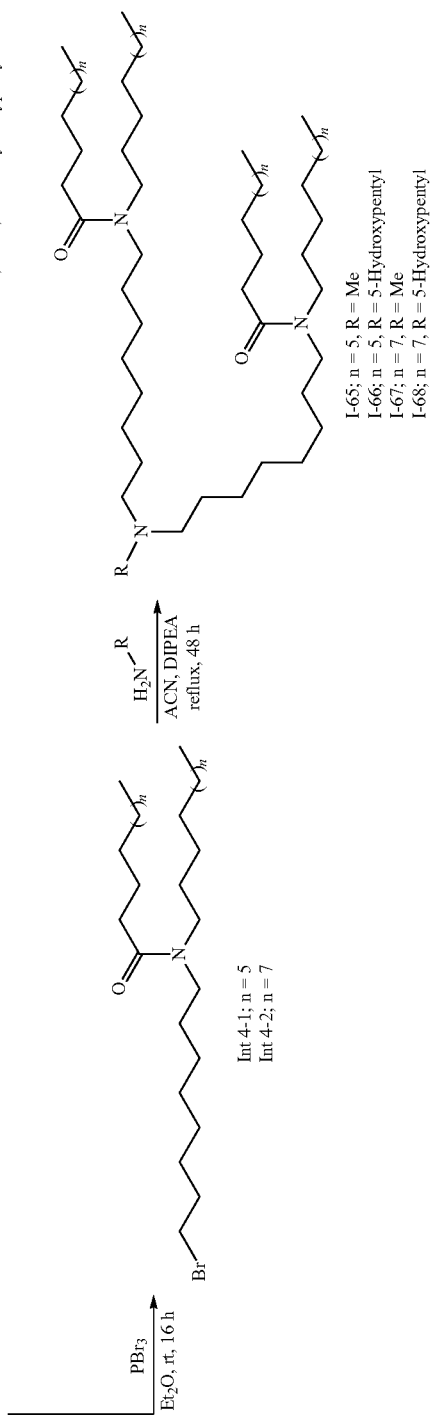

General Procedure for the Preparation of the Int 1-1 & Int 1-2

To a solution of $K_2CO_3$ (1.0 eq) in ACN (7 mL/mmol) was added 8-aminooctanol (1.0 eq) at RT under $N_2$, and the resulting suspension was stirred for 30 min at RT. Appropriate bromide (1.0 eq) was then added dropwise and the reaction mixture was stirred overnight at RT under $N_2$. Then, the suspension was filtered, and the remaining solution was concentrated. The solid crude product was purified by column chromatography (DCM/3% $NH_3$ in MeOH, 100:0 to 80:20).

General Procedure for the Preparation of the Int 1-3 & Int 1-4

To a solution of 8-aminooctanol (1.0 eq) in ACN (7 mL/mmol) was added appropriate bromide (1.0 eq) and the reaction mixture was refluxed overnight under $N_2$. Then, the reaction mixture was concentrated to afford the crude product. The solid crude product was purified by column chromatography (DCM/3% $NH_3$ in MeOH, 100:0 to 80:20).

General procedure or the preparation of the Int 2-1 to Int 2-4

To a solution of acid (0.9 eq) in DCM (2.5 mL/mmol) were added N-hydroxysuccinimide (0.9 eq), 4-dimethylaminopyridine (0.9 eq) and dicyclohexylcarbodiimide (0.9 eq) at RT under $N_2$. The resulting mixture was stirred at RT until complete conversion. The precipitate was filtered off, and the filtrate was added dropwise to a solution of the Int 1-1 or Int 1-2, Int 1-3, or Int 1-4 (1.0 eq) in DCM (2.3 mL/mmol) at RT. The reaction mixture was stirred overnight at RT under $N_2$. Then, the organic phase was washed with HCl (aq., 1 mol/L), $Na_2CO_3$ (aq.), and dried over $Na_2SO_4$. The organic phase was concentrated. The pale-yellow solid was purified by column chromatography (Hex/EtOAc, 100:0 to 0:100).

General Procedure for the Preparation of the Int 3-1 & Int 3-2

To a solution of the Int 2-1 or Int 2-2 (1.0 eq) in DCM (10-15 mL/mmol) was added PCC (5.0 eq) in small portions. The resulting suspension was stirred at RT for two hours, under $N_2$. Then, the mixture was concentrated under reduced pressure, and the obtained crude product was purified by chromatography (Hex/EtOAc, 100:0 to 80:20).

General Procedure for the Preparation of the Int 4-1 & Int 4-2

To a solution of Int 2-3 or Int 2-4 (1.0 eq) in diethyl ether (8.0 mL/mmol) was added $PBr_3$ (2-3 eq) dropwise at 0° C. under $N_2$. The reaction mixture was slowly warmed up to RT and stirred at RT under $N_2$ until the completion of the reaction. Then, ice-cooled water was added gradually until a clear solution was obtained. The aqueous phase was extracted with ethyl acetate three times, dried over $Na_2SO_4$, and concentrated under reduced pressure. The crude product was purified by column chromatography (Hex/EtOAc, 100:0 to 90:10).

General Procedure for the Preparation of the Compounds I-61, I-62, I-63 & I-64

To a solution of the Int 3-1 or Int 3-2 (1.0 eq) in MeOH (10 mL/mmol) was added the appropriate primary amine (0.35 eq). The resultant solution was stirred at RT for 30 min under $N_2$. Then, $Na(CNBH_3)$ (4.0 eq), and a drop of AcOH were added and the reaction mixture was stirred for 2-3 d at RT under $N_2$. After the complete reaction, it was diluted with DCM (100 mL/mmol) and $Na_2CO_3$ (aq.) (200 mL/mmol), stirred for 30 min at RT, separated and the organic phase dried over $Na_2SO_4$. The crude product was purified by chromatography (DCM/3% $NH_3$ in MeOH, 100:0 to 80:20).

General Procedure for the Preparation of the Compounds I-65, I-66, I-67 & I-68

To a solution of Int 4-1 or Int 4-2 (1.5 eq) in ACN (5.5 mL/mmol) were added DIPEA (3.8 eq.) and the desired alkylation reagent (1.0 eq). The reaction was carried out in a sealed tube at 80° C. for 24 h. Then, more Int 4-1 or Int 4-2 (0.5 eq) in ACN (2.0 mL/mmol) was added to the reaction mixture, and stirring continued for another 24 h at 80° C. The reaction mixture was then cooled to RT and concentrated under reduced pressure. The crude product was purified by column chromatography (Hex/1% $NEt_3$ in EtOAc, 95:5 to 0:100).

Synthesis of N,N'-((methylazanediyl)bis(octane-8,1-diyl))bis(N-hexylhexanamide) (I-61)

N,N'-((methylazanediyl)bis(octane-8,1-diyl))bis(N-hexylhexanamide) (I-61) was prepared according to the general procedure from Int 3-1 (500 mg, 1.5 mmol) and methylamine (2 M in MeOH, 0.26 mL, 0.52 mmol). The product was obtained as pale-yellow oil (250 mg, 0.38 mmol, 73%). $^1$H NMR (400 MHz, $CDCl_3$) δ 3.28 (dd, J=7.8, 7.4 Hz, 4H), 3.19 (dd, J=7.5 Hz, 4H), 2.34 (s, 3H), 2.30-2.17 (m, 7H), 1.63 (dt, J=14.8, 7.6 Hz, 6H), 1.52 (td, J=14.4, 7.4 Hz, 12H), 1.39-1.19 (m, 40H), 0.92-0.87 (m, 12H), ESI-MS: MW for $C_{41}H_{83}N_3O_2$ $[M+H]^+$ calc. 650.66, found 650.85.

Synthesis of N,N'-(((5-hydroxypentyl)azanediyl)bis(octane-8,1-diyl))bis(N-hexylhexanamide) (I-62)

N,N'-(((5-hydroxypentyl)azanediyl)bis(octane-8,1-diyl))bis(N-hexylhexanamide) (I-62) was prepared according to the general procedure from Int 3-1 (500 mg, 1.5 mmol) and 5-aminopentan-1-ol (54 mg, 0.52 mmol). The product was obtained as pale-yellow oil (242 mg, 0.34 mmol, 66%). $^1$H NMR (400 MHz, $CDCl_3$) δ 3.64 (t, J=6.5 Hz, 2H), 3.27 (dd, J=10.8, 4.4 Hz, 4H), 3.22-3.16 (m, 4H), 2.45 (s, 1H), 2.29-2.24 (m, 4H), 1.81 (s, 1H), 1.62 (dt, J=16.1, 7.7 Hz, 7H), 1.50 (dd, J=14.4, 7.2 Hz, 15H), 1.40-1.19 (m, 42H), 0.93-0.85 (m, 12H), ESI-MS: MW for $C_{45}H_{91}N_3O_3$ $[M+H]^+$ calc. 722.72, found 722.80.

Synthesis of N,N'-((methylazanediyl)bis(octane-8,1-diyl))bis(N-octyloctanamide) (I-63)

N,N'-((methylazanediyl)bis(octane-8,1-diyl))bis(N-octyloctanamide) (I-63) was prepared according to the general procedure from Int 3-2 (450 mg, 1.2 mmol) and methylamine (2 M in MeOH, 0.21 mL, 0.42 mmol). The product was obtained as pale-yellow oil (180 mg, 0.24 mmol, 65%). $^1$H NMR (400 MHz, $CDCl_3$) δ 3.30-3.24 (m, 4H), 3.22-3.14 (m, 4H), 2.63-2.59 (m, 3H), 2.47 (t, J=17.2 Hz, 3H), 2.30-2.23 (m, 4H), 1.75-1.57 (m, 8H), 1.57-1.42 (m, 9H), 1.29 (m, 52H), 0.91-0.84 (m, 12H), ESI-MS: MW for $C_{49}H_{99}N_3O_2$ $[M+H]^+$ calc. 762.78, found 762.81.

Synthesis of N,N'-(((5-hydroxypentyl)azanediyl)bis(octane-8,1-diyl))bis(N-octyloctanamide) (I-64)

N,N'-(((5-hydroxypentyl)azanediyl)bis(octane-8,1-diyl))bis(N-octyloctanamide) (I-64) was prepared according to the general procedure from Int 3-2 (450 mg, 1.2 mmol) and 5-aminopentan-1-ol (43.3 mg, 0.42 mmol). The product was obtained as pale-yellow oil (220 mg, 0.26 mmol, 66%). $^1$H NMR (600 MHz, $CDCl_3$) δ 3.64 (t, J=6.5 Hz, 2H), 3.27 (dd, J=10.9, 4.4 Hz, 4H), 3.21-3.17 (m, 4H), 2.41 (s, 1H), 2.28-2.25 (m, 4H), 1.67-1.57 (m, 10H), 1.57-1.46 (m, 11H), 1.46-1.35 (m, 6H), 1.35-1.21 (m, 55H), 0.91-0.85 (m, 12H), ESI-MS: MW for $C_{53}H_{107}N_3O_3$ [M+H]$^+$ calc. 834.84, found 834.70.

Synthesis of N,N'-((methylazanediyl)bis(octane-8,1-diyl))bis(N-octyloctanamide) (I-65)

N,N'-((methylazanediyl)bis(octane-8,1-diyl))bis(N-octyloctanamide) (I-65) was prepared according to the general procedure from Int 4-1 (493 mg, 1.1 mmol) and methylamine (2 M in MeOH, 0.19 mL, 0.385 mmol). The product was obtained as pale-yellow oil (232 mg, 0.27 mmol, 66%). $^1$H NMR (400 MHz, CDCl$_3$) δ 3.30-3.24 (m, 4H), 3.22-3.15 (m, 4H), 2.33-2.23 (m, 7H), 2.20 (s, 3H), 1.73-1.58 (m, 10H), 1.58-1.40 (m, 12H), 1.37-1.20 (m, 71H), 0.92-0.84 (m, 12H), ESI-MS: MW for $C_{57}H_{115}N_3O_2$[M+H]$^+$ calc. 874.91, found 875.60.

Synthesis of N,N'-(((5-hydroxypentyl)azanediyl)bis(octane-8,1-diyl))bis(N-decyldecanamide) (I-66)

N,N'-(((5-hydroxypentyl)azanediyl)bis(octane-8,1-diyl))bis(N-decyldecanamide) (I-66) was prepared according to the general procedure from Int 4-1 (493 mg, 1.1 mmol) and 5-aminopentan-1-ol (40 mg, 0.385 mmol). The product was obtained as pale-yellow oil (247 mg, 0.26 mmol, 65%). The product was obtained as an oil (76.8 mg, 0.08 mmol, 28%). $^1$H NMR (400 MHz, CDCl$_3$) δ 3.65 (t, J=6.4 Hz, 2H), 3.32-3.23 (m, 4H), 3.22-3.12 (m, 4H), 2.52 (s, 1H), 2.30-2.22 (m, 4H), 1.62 (dt, J=15.0, 7.5 Hz, 12H), 1.57-1.43 (m, 14H), 1.34-1.21 (m, 70H), 0.91-0.84 (m, 12H), ESI-MS: MW for $C_{61}H_{123}N_3O_3$ [M+H]$^+$ calc. 946.97, found 946.73.

Synthesis of N,N'-((methylazanediyl)bis(octane-8,1-diyl))bis(N-dodecyldodecanamide) (I-67)

N,N'-((methylazanediyl)bis(octane-8,1-diyl))bis(N-dodecyldodecanamide) (I-67) was prepared according to the general procedure from Int 4-2 (700 mg, 1.25 mmol) and methylamine (2 M in MeOH, 0.21 mL, 0.425 mmol). The product was obtained as pale-yellow oil (510 mg, 0.52 mmol, 84%). $^1$H NMR (600 MHz, CDCl$_3$) δ 3.29-3.25 (m, 4H), 3.21-3.16 (m, 4H), 2.28 (dt, J=15.4, 8.4 Hz, 8H), 2.19 (t, J=2.8 Hz, 3H), 1.67-1.58 (m, 15H), 1.57-1.40 (m, 12H), 1.35-1.20 (m, 87H), 0.88 (t, J=7.0 Hz, 12H), ESI-MS: MW for $C_{65}H_{131}N_3O_2$ [M+H]$^+$ calc. 987.03, found 986.87.

Synthesis of N,N'-(((5-hydroxypentyl)azanediyl)bis(octane-8,1-diyl))bis(N-dodecyldodecanamide) (I-68)

N,N'-(((5-hydroxypentyl)azanediyl)bis(octane-8,1-diyl))bis(N-dodecyldodecanamide) (I-68) was prepared according to the general procedure from Int 4-2 (700 mg, 1.25 mmol) and 5-aminopentan-1-ol (44 mg, 0.425 mmol). The product was obtained as pale-yellow oil (471 mg, 0.45 mmol, 72%). $^1$H NMR (600 MHz, CDCl$_3$) δ 3.63 (t, J=6.5 Hz, 2H), 3.27 (dd, J=10.7, 4.5 Hz, 4H), 3.22-3.15 (m, 4H), 2.43-2.33 (m, 6H), 2.29-2.23 (m, 4H), 1.69 (s, 4H), 1.65-1.34 (m, 24H), 1.34-1.19 (m, 88H), 0.91-0.84 (m, 12H), ESI-MS: MW for $C_{69}H_{139}N_3O_3$ [M+H]$^+$ calc. 1059.09, found 1058.89.

Example 60

Synthetic Pathway for Compounds I-69 & I-71

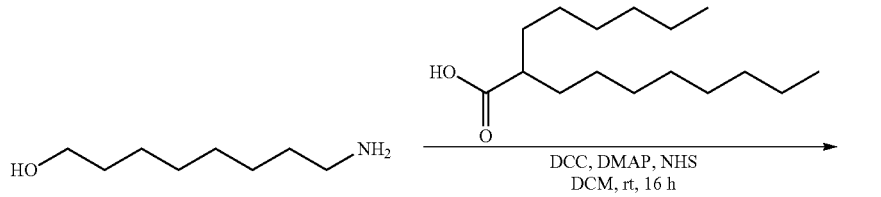

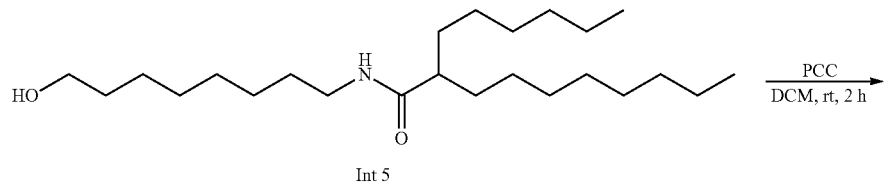

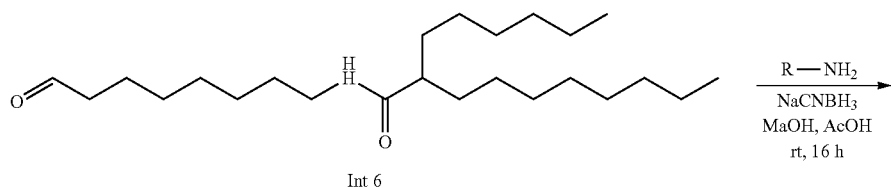

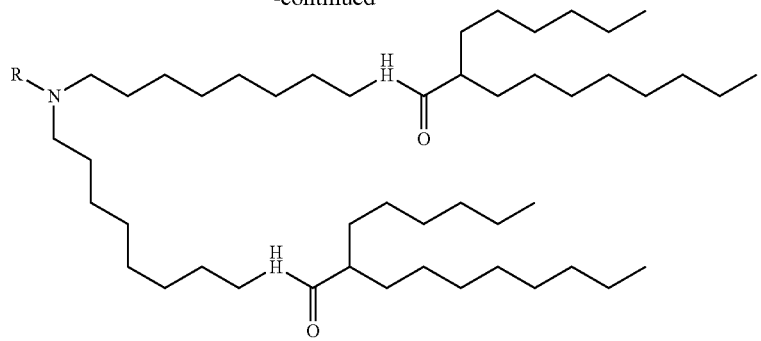

I-69; R = Me
I-71; R = 5-hydroxypentyl

Synthesis of N,N'-((methylazanediyl)bis(octane-8,1-diyl))bis(2-hexyldecanamide) (I-69)

N,N'-((methylazanediyl)bis(octane-8,1-diyl))bis(2-hexyldecanamide) (I-69) was prepared according to the general procedures of example 59 from Int 6 (0.408 g, 1.06 mmol) and methylamine (2 M in THF, 0.181 mL, 0.36 mmol). The product was obtained as pale-yellow oil (210 mg, 0.27 mmol, 26%). $^1$H NMR (400 MHz, CDCl$_3$) δ 3.32-3.23 (m, 4H), 3.23-3.14 (m, 4H), 2.75-2.37 (m, 7H), 2.26 (t, J=8.3 Hz, 4H), 1.71-1.58 (m, 8H), 1.50 (dq, J=14.4, 7.2, 6.8 Hz, 8H), 1.37-1.18 (m, 52H), 0.92-0.82 (m, 12H). ESI-MS: MW for C$_{49}$H$_{99}$N$_3$O$_2$ [M+H]$^+$ calc. 762.78, found 762.88.

Synthesis of N,N'-(((5-hydroxypentyl)azanediyl)bis(octane-8,1-diyl))bis(2-hexyldecanamide) (I-71)

N,N'-(((5-hydroxypentyl)azanediyl)bis(octane-8,1-diyl))bis(2-hexyldecanamide) (I-71) was prepared according to the general procedures of example 59 from Int 6 (458 mg, 1.20 mmol) and 5-Amino-1-pentanol (22 mg, 0.40 mmol). The product was obtained as pale-yellow oil (250 mg, 0.30 mmol, 25%). $^1$H NMR (400 MHz, CDCl$_3$-d) δ 5.52 (t, J=5.6 Hz, 2H), 3.66 (t, J=6.2 Hz, 2H), 3.24 (q, J=6.6 Hz, 4H), 3.02-2.94 (m, 2H), 2.77 (m, 5H), 2.04-1.89 (m, 4H), 1.67-1.13 (m, 86H), 0.94-0.78 (m, 13H). ESI-MS: MW for C$_{53}$H$_{107}$N$_3$O$_3$ [M+H]$^+$ calc. 834.84, found 834.98.

Example 61

Synthetic Pathway for Compounds I-70 & I-72

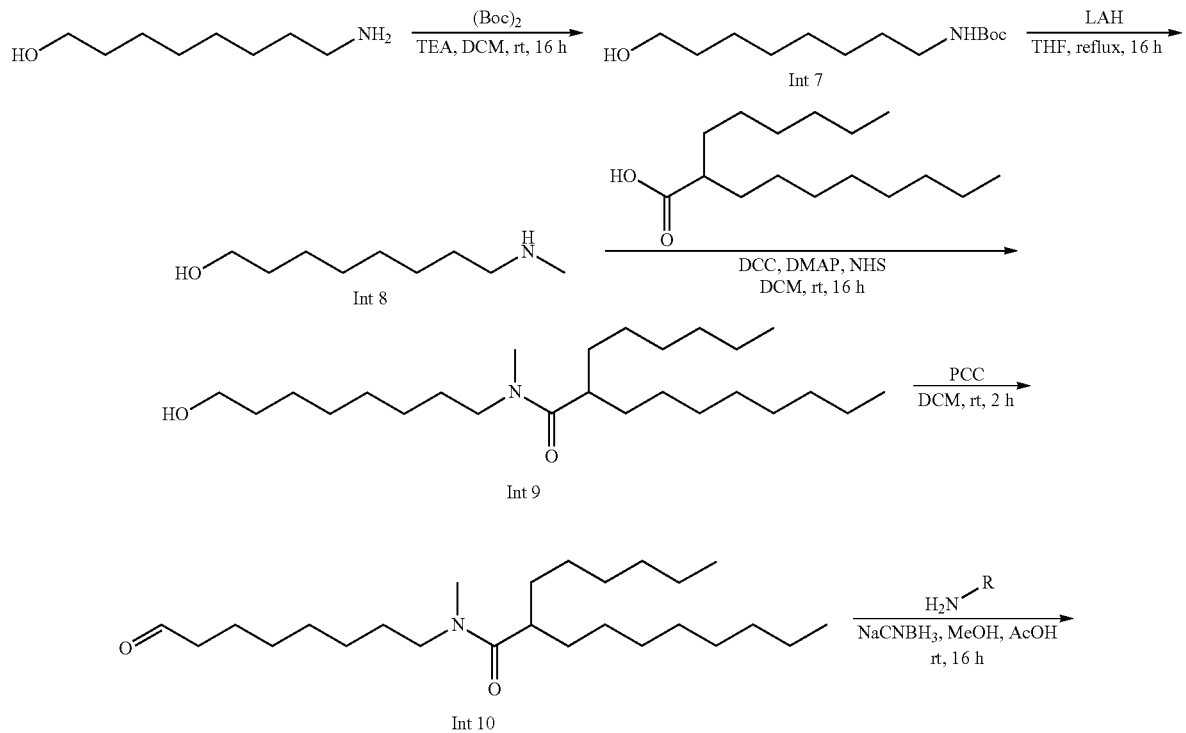

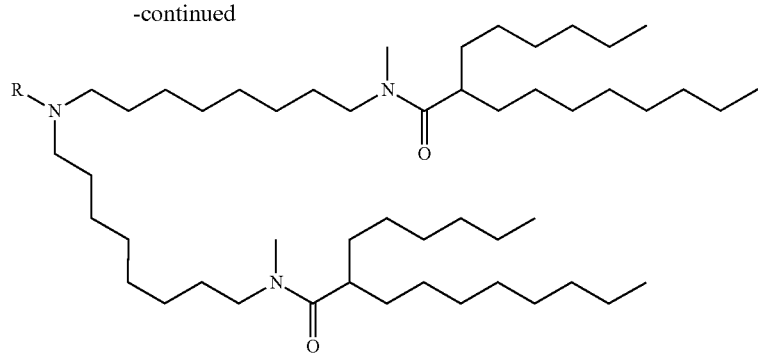

I-70; R = Me
I-71; R = 5-Hydroxypentyl

Synthesis of tert-butyl (8-hydroxyoctyl)carbamate (Int 7)

To a solution of 8-amino-1-octanol (10 g, 68.9 mmol) in DCM (100 mL) was added triethylamine (13.9 g, 137.74 mmol) at RT under $N_2$. Then, Boc-anhydride (16.5 g, 75.75 mmol) was added dropwise at 0° C. over 10 min. The resulting mixture was stirred at RT for 16 h. Water (200 mL) was then added to the reaction mixture and stirred for 20 min. The organic layer was separated, and the aqueous layer was extracted with DCM (100 mL×2). The combined organic layer was dried over $Na_2SO_4$, filtered, and concentrated under reduced pressure to yield the crude product. The obtained crude was purified by flash column chromatography (Hex/EtOAc 100:0 to 55:45) to yield Int 7 as solid (15.2 g, 61.94 mmol, 90%). ESI-MS: MW for $C_{13}H_{27}NO_3Na$ $[M+Na]^+$ calc. 268.35, found 268.31.

Synthesis of 8-(methylamino)octan-1-ol (Int 8)

To a stirred suspension of LAH (10.12 g, 266.80 mmol) in dry THF (100 mL) at 0° C. under $N_2$, was added a solution of Int 7 (15 g, 61.13 mmol) in dry THF (50 mL) dropwise over 30 min and the resulting suspension was refluxed for 16 h. The reaction mixture was then cooled to 0° C. and water (10 mL) was added dropwise. Subsequently, a solution of NaOH (15%, 10 mL) followed by water (10 mL) were added dropwise. To the resulting cake solution, $MgSO_4$ was added, and the mixture stirred at rt for 30 min. The precipitate was discarded by filtration and the filtrate was washed with brine and dried over $Na_2SO_4$. The organic layer was evaporated under reduced pressure to afford the crude 8-(methylamino)octan-1-ol (Int 8) (7.2 g, 45.20 mmol, 74%). ESI-MS: MW for $C_9H_{21}NO$ $[M+H]^+$ calc. 160.28; found 160.21.

Synthesis of 2-hexyl-N-(8-hydroxyoctyl)-N-methyldecanamide (Int 9)

Int 9 was prepared according to the general procedures of example 59 from Int 8 (2.6 g, 16.38 mmol) and 2-hexyldecanoic acid (3.78 g, 14.7 mmol). The product was obtained as colourless oil (2.2 g, 5.53 mmol, 34%). ESI-MS: MW for $C_{25}H_{51}NO_2$ $[M+H]^+$ calc. 398.70; found 398.41.

Synthesis of 2-hexyl-N-methyl-N-(8-oxooctyl)decanamide (Int 10)

According to the general procedures of example 59, Int 9 (2.05 g, 5.16 mmol) was converted into Int 10. The product was obtained as colourless oil (1.38 g, 3.49 mmol, 67.5%). ESI-MS: MW for $C_{25}H_{49}NO_2$ $[M+H]^+$ calc. 396.68; found 396.45.

Synthesis of N,N'-((methylazanediyl)bis(octane-8,1-diyl))bis(2-hexyl-N-methyldecanamide) (I-70)

N,N'-((methylazanediyl)bis(octane-8,1-diyl))bis(2-hexyl-N-methyldecanamide) (I-70) was prepared according to the general procedure of example 59 from Int 10 (500 mg, 1.26 mmol) and methylamine (2 M in MeOH, 13.4 mg, 0.225 mL, 0.43 mmol). The product was obtained as pale-yellow oil (200 mg, 0.25 mmol, 20%). $^1$H NMR (400 MHz, $CDCl_3$) δ 3.40-3.34 (m, 2H), 3.31-3.24 (m, 2H), 3.01 (s, 3H), 2.92 (s, 2H), 2.68-2.22 (m, 8H), 1.78-1.46 (m, 16H), 1.45-1.36 (m, 4H), 1.27 (m, 53H), 0.87 (t, J=6.8 Hz, 12H). ESI-MS: MW for $C_{51}H_{103}N_3O_2$ $[M+H]^+$ calc. 790.81; found 790.73.

Synthesis of N,N'-(((5-hydroxypentyl)azanediyl)bis(octane-8,1-diyl))bis(2-hexyl-N-methyldecanamide) (I-72)

N,N'-(((5-hydroxypentyl)azanediyl)bis(octane-8,1-diyl)) bis(2-hexyl-N-methyldecanamide) (I-72) was prepared according to the general procedure of example 59 from Int-10 (500 mg, 1.26 mmol) and 5-Amino-1-pentanol (44.4 mg, 0.43 mmol). The product was obtained as pale-yellow oil (235 mg, 0.27 mmol, 22%). $^1$H NMR (400 MHz, $CDCl_3$) δ 3.64 (t, J=6.5 Hz, 2H), 3.41-3.34 (m, 2H), 3.32-3.25 (m, 2H), 3.01 (s, 3H), 2.92 (s, 3H), 2.64-2.51 (m, 2H), 2.49-2.34 (m, 6H), 1.74 (bs, 6H), 1.65-1.53 (m, 8H), 1.43 (m, 14H), 1.26 (m, 56H), 0.87 (t, J=6.8 Hz, 12H). ESI-MS: MW for $C_{55}H_{111}N_3O_3$ $[M+H]^+$ calc. 862.87; found 862.69.

Example 62

Synthetic Pathway for Compounds I-75 to I-78

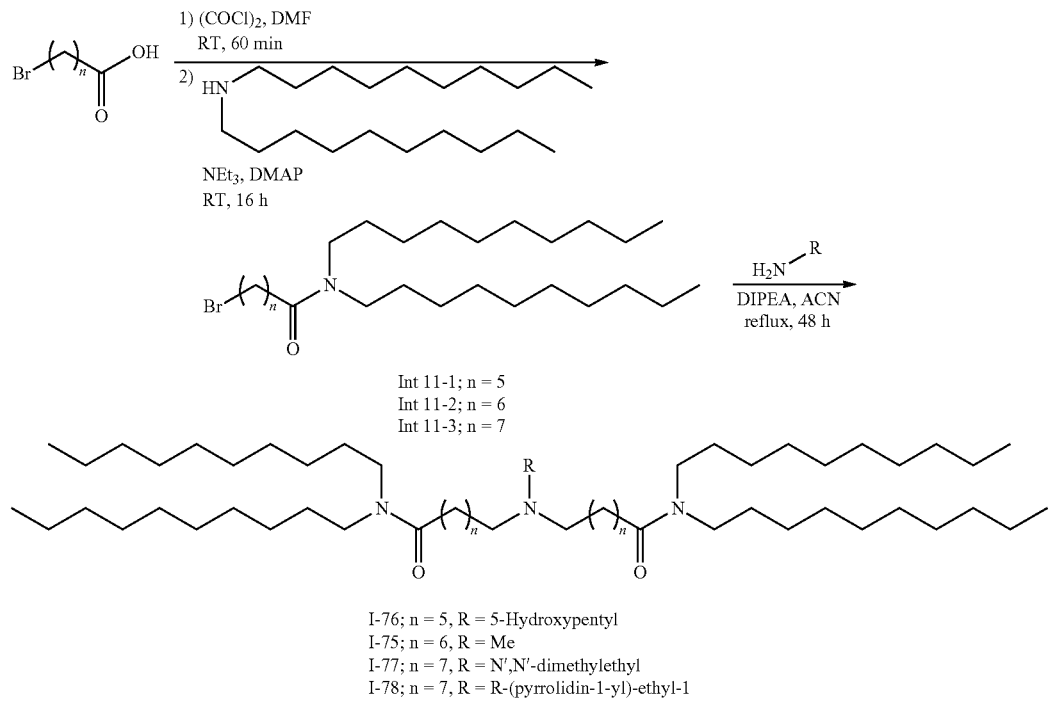

I-76; n = 5, R = 5-Hydroxypentyl
I-75; n = 6, R = Me
I-77; n = 7, R = N′,N′-dimethylethyl
I-78; n = 7, R = R-(pyrrolidin-1-yl)-ethyl-1

General Procedure for the Preparation of Int 11-1, Int 11-2, & Int 11-3

To a solution of the appropriate carboxylic acid (1.0 eq.) in DCM (2 mL/mmol) were added a catalytical amount of DMF and oxalyl chloride (3.0 eq). The reaction mixture was stirred at RT under $N_2$ until complete conversion. Excess oxalyl chloride and DCM were then evaporated under vacuum. A solution of this resulting acyl chloride in dry DCM (1 mL/mmol) was slowly added to a solution of didecylamine (1.1 eq), $NEt_3$ (6.0 eq), and DMAP (cat.) in dry DCM (3 mL/mmol). Then, the mixture was stirred for 16 h at RT under $N_2$. After concentrating under reduced pressure, the residue was partitioned between $H_2O$ (10 mL/mmol) and ethyl acetate (10 mL/mmol). The aqueous phase was extracted with ethyl acetate, and the combined organic phase was dried over $Na_2SO_4$, and concentrated under reduced pressure. The crude product was purified by column chromatography (hexane/ethyl acetate, 100:0 to 80:20).

General Procedure for the Preparation of Compounds I-77, I-78, I-75 & I-76

To a solution of Int 11-1, Int 11-2 or Int 11-3 (1.5 eq) in ACN (5.5 mL/mmol) were added DIPEA (3.8 eq.) and the desired alkylation reagent (1.0 eq). The reaction was carried out in a sealed tube at 80° C. for 24 h. More bromide (Int 11-1, Int 11-2 or Int 11-3) (0.5 eq, in ACN) (2.0 mL/mmol) was added to the reaction mixture, and it was stirred at 80° C. for another 24 h. The reaction mixture was then cooled to RT and concentrated under reduced pressure. The crude product was purified by column chromatography (Hex/1% $NEt_3$ in EtOAc, 95:5 to 0:100).

Synthesis of 6,6′-((5-hydroxypentyl)azanediyl)bis(N,N-didecylhexanamide) (I-77)

6,6′-((5-hydroxypentyl)azanediyl)bis(N,N-didecylhexanamide) (I-77) was prepared according to the general procedure from Int 11-1 (700 mg, 1.47 mmol) and 5-aminopentan-1-ol (0.053 g, 0.51 mmol). The product was obtained as pale-yellow oil (471 mg, (0.45 mmol, 72%). $^1H$ NMR (400 MHz, $CDCl_3$) δ 3.63 (t, J=6.5 Hz, 2H), 3.32-3.23 (m, 4H), 3.23-3.14 (m, 4H), 2.44-2.34 (m, 6H), 2.27 (t, J=7.5 Hz, 4H), 1.79-1.39 (m, 26H), 1.26 (m, 59H), 0.88 (td, J=6.8, 3.1 Hz, 12H). ESI-MS: MW for $C_{57}H_{115}N_3O_3$ $[M+H]^+$ calc. 890.90, found 890.81.

Synthesis of 7,7′-(methylazanediyl)bis(N,N-didecylheptanamide) (I-75)

7,7′-(methylazanediyl)bis(N,N-didecylheptanamide) (I-75) was prepared according to the general procedure from Int 11-2 (800 mg, 1.63 mmol) and methylamine (0.37 mL, 0.74 mmol, 2 M in MeOH). The product was obtained as pale-yellow oil (368 mg, 0.43 mmol, 43%). $^1H$ NMR (400 MHz, $CDCl_3$) δ 3.30-3.24 (m, 4H), 3.21-3.15 (m, 4H), 2.27 (dd, J=15.1, 7.5 Hz, 8H), 2.18 (s, 3H), 1.72-1.58 (m, 10H), 1.57-1.41 (m, 13H), 1.38-1.18 (m, 67H), 0.88 (td, J=6.8, 3.1 Hz, 12H), ESI-MS: MW for $C_{55}H_{111}N_3O_2$ $[M+H]^+$ calc. 846.88, found 846.51.

Synthesis of 8,8′-((2-(dimethylamino)ethyl)azanediyl)bis(N,N-didecyloctanamide) (I-77)

8,8′-((2-(dimethylamino)ethyl)azanediyl)bis(N,N-didecyloctanamide) (I-77) was prepared according to the general procedure from Int 11-3 (800 mg, 1.59 mmol) and N,N-dimethylethyldiamine (0.07 mL, 0.7 mmol). The product was obtained as pale-yellow oil (197 mg, 0.21 mmol, 30%). $^1$H NMR (400 MHz, CDCl$_3$) δ 3.31-3.23 (m, 4H), 3.23-3.13 (m, 4H), 2.63-2.51 (m, 2H), 2.49-2.35 (m, 6H), 2.31-2.20 (m, 10H), 1.84 (s, 3H), 1.67-1.58 (m, 4H), 1.57-1.39 (m, 12H), 1.28 (mi, 71H), 0.88 (td, J=6.8, 3.1 Hz, 12H), ESI-MS: MW for $C_{60}H_{122}N_4O_2$ [M+H]$^+$ calc. 931.97, found 931.98.

Synthesis of 8,8'-((2-(pyrrolidin-1-yl)ethyl)azanediyl)bis(N,N-didecyloctanamide) (I-78)

8,8'-((2-(pyrrolidin-1-yl)ethyl)azanediyl)bis(N,N-didecyloctanamide) (I-78) was prepared according to the general procedure from Int 11-3 (700 mg, 1.39 mmol) and 1-(2-aminoethyl)pyrrolidine (0.08 mL, 0.7 mmol). The product was obtained as pale-yellow oil (260 mg, 0.27 mmol, 39%). $^1$H NMR (400 MHz, CDCl$_3$) δ 3.32-3.23 (m, 4H), 3.22-3.12 (m, 4H), 2.64-2.47 (m, 7H), 2.45-2.36 (m, 4H), 2.30-2.23 (m, 4H), 1.84-1.68 (m, 9H), 1.67-1.58 (m, 4H), 1.57-1.37 (m, 12H), 1.26 (mi, 71H), 0.88 (td, J=6.7, 3.0 Hz, 12H), ESI-MS: MW for $C_{62}H_{124}N_4O_2$ [M+H]$^+$ calc. 957.98, found 957.92.

Example 63

Synthetic Pathway for Compounds I-73 & I-74 overnight. The reaction mixture was concentrated, and the crude material was purified by column chromatography (Hex/EtOAc 95:5 to 0:100 then DCM/3% NH$_3$ in MeOH 100:0 to 90:10).

General Procedure for the Preparation of I-73 & I-74

A mixture of Int 12-1 or Int 12-2 (1 eq), Int 4-1 (1.2 eq), and DIPEA (4 eq) in ACN (10 mL/mmol) was heated to reflux for overnight. The reaction mixture was then concentrated, and the crude material was purified via column chromatography (Hex/1% NEt$_3$ in EtOAc 100:0 to 35:65).

Synthesis of N-decyl-N-(8-((8-(didecylamino)-8-oxooctyl)(methyl)amino) octyl)decanamide (I-73)

N-decyl-N-(8-((8-(didecylamino)-8 oxooctyl)(methyl)amino) octyl)decanamide (I-73) was prepared according to the general procedure from Int 12-1 (0.4 g, 0.88 mmol) and Int 4-1 (0.53 g, 1.06 mmol). The product was obtained as pale-yellow oil (0.38 g, 0.43 mmol 49.3%). $^1$H NMR (400 MHz, CDCl$_3$) δ 3.34-3.23 (m, 4H), 3.22-3.11 (m, 4H), 2.34-2.22 (m, 8H), 2.18 (s, 3H), 1.67-1.58 (m, 4H), 1.50 (m, 12H), 1.37-1.18 (m, 68H), 0.87 (t, J=6.8 Hz, 12H). ESI-MS: MW for $C_{57}H_{115}N_3O_2$ [M+H]$^+$ calc. 874.91, found 874.56.

Synthesis of N-decyl-N-(8-((8-(didecylamino)-8-oxooctyl)(5-hydroxypentyl)amino)octyl)decanamide (I-74)

N-decyl-N-(8-((8-(didecylamino)-8-oxooctyl)(5-hydroxypentyl)amino)octyl)decanamide (I-74) was prepared

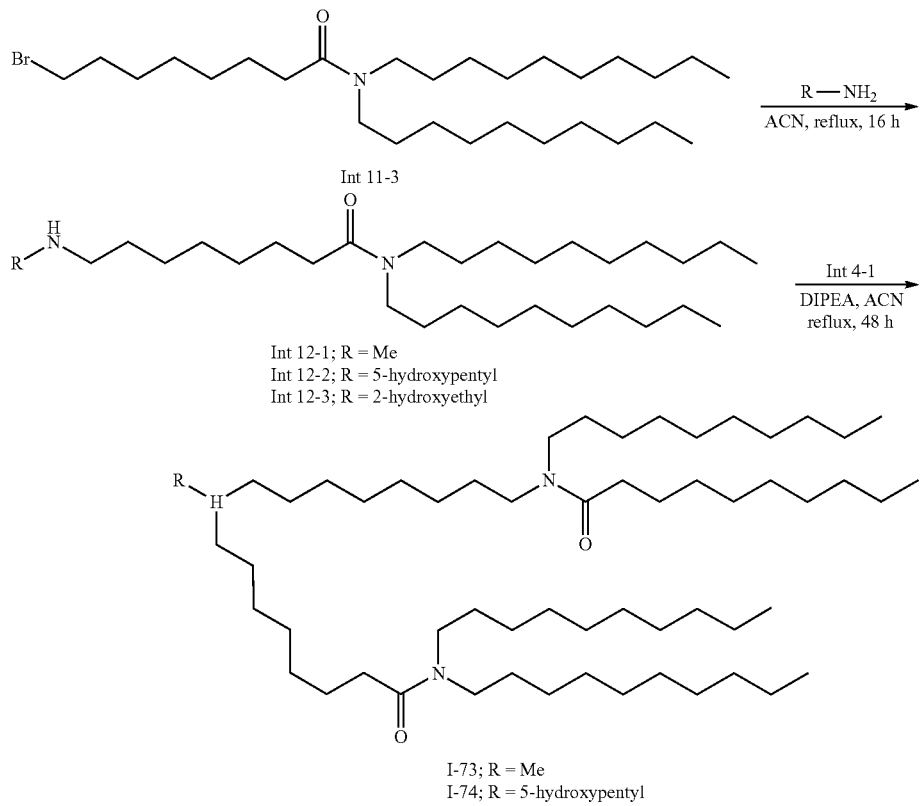

General Procedure for the Preparation of Int 12-1, Int 12-2, & Int 12-3

A solution of Int 11-3 (1 eq) and the appropriate amine (5 eq) in acetonitrile (10 mL/mmol) was heated to reflux for according to the general procedure from Int 12-2 (0.4 g, 0.76 mmol) and Int 4-1 (0.46 g, 0.91 mmol). The product was obtained as pale-yellow oil (0.4 g, 0.42 mmol 55.5%). $^1$H NMR (400 MHz, CDCl$_3$) δ 3.63 (t, J=6.5 Hz, 2H), 3.32-3.24

(m, 4H), 3.22-3.13 (m, 4H), 2.45-2.32 (m, 6H), 2.32-2.22 (m, 4H), 1.78-1.56 (m, 11H), 1.56-1.36 (m, 16H), 1.36-1.18 (m, 68H), 0.87 (t, J=6.8 Hz, 13H). ESI-MS: MW for $C_{61}H_{123}N_3O_3$ [M+H]$^+$ calc. 946.97, found 946.73.

Example 64

Synthetic Pathway for Compounds I-73 & I-74

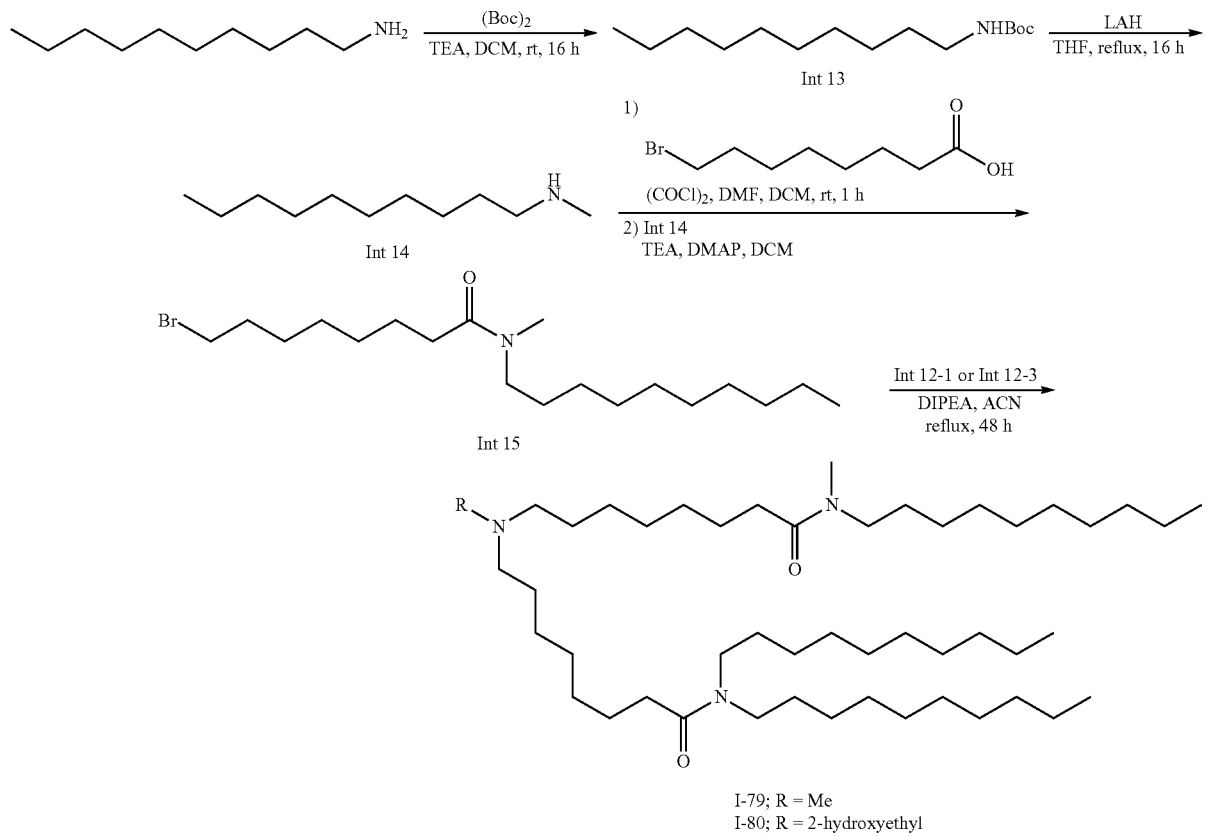

I-79; R = Me
I-80; R = 2-hydroxyethyl over 30 min. The resulted suspension was refluxed for 16 h, and then it was cooled to 0° C. and water (10 mL) was added dropwise. subsequently, a solution of NaOH (15%, 10 mL) followed by water (10 mL) were added dropwise. To the resulting cake solution, $MgSO_4$ was added, and the resulting mixture stirred at rt for 30 min. The precipitate was discarded by filtration, and filtrate was washed with brine and dried over $Na_2SO_4$. The organic layer was evaporated under Synthesis of tert-butyl decylcarbamate (Int 13)

To a solution of decan-1-amine (10 g, 63.57 mmol) in DCM (100 mL) was added triethylamine (12.9 g, 127.14 mmol), at RT under $N_2$. Then the Boc-anhydride (15.3 g, 69.93 mmol) was added dropwise at 0° C. over 10 min. The resulting mixture was stirred at RT for 16 h. Water (200 mL) was added to the reaction mixture and stirred for 20 min. The organic layer was separated, and the aqueous layer was extracted with DCM (100 mL×2). The combined organic layer was dried over $Na_2SO_4$, filtered, and concentrated under reduced pressure to yield the crude product. The obtained crude was purified by column chromatography (Hex/EtOAc 100:0 to 75:25). The product tert-butyl decylcarbamate Int 13 was obtained as solid (16 g, 62.15 mmol, 97%). ESI-MS: MW for $C_{15}H_{31}NO_2$ [M+Na]$^+$ calc. 280.22; found 280.26.

Synthesis of N-methyldecylamine (Int 14)

To a stirred suspension of LAH (5.9 g, 155.40 mmol) in dry THF (100 mL) at 0° C. under $N_2$, was added a solution of Int 13 (10 g, 38.85 mmol) in dry THF (50 mL) dropwise reduced pressure to afford the crude Int 14 (5.5 g 32.10 mmol, 82.6%). ESI-MS: MW for $C_{11}H_{25}N$ [M+H]$^+$ calc. 172.21; found 172.25.

Synthesis of 8-bromo-N-decyl-N-methyloctanamide (Int 15)

Step 1: To a solution of 1-bromooctanoic acid (3.5 g, 15.69 mmol) in DCM (50 mL) was added DMF (3 drops) followed by oxalyl chloride (4 mL, 47.06 mmol). The reaction mixture was stirred at RT for 1 h. The reaction mixture was then concentrated to give 8-bromooctanoyl chloride which was used in the next step without further purification.

Step 2: To a solution of N-methyldecylamine (3 g, 17.25 mmol), triethylamine (13.2 mL, 94.12 mmol) and DMAP (cat.) in DCM (50 mL) was added a solution of 8-bromooctanoyl chloride (~15.69 mmol) in DCM (20 mL). After stirring at RT overnight, the reaction mixture was concentrated and the remaining residue was partitioned between EtOAc and brine. The organic layer was separated, and the aqueous layer was extracted again with EtOAc. The combined organic layer was dried over $Na_2SO_4$, filtered, and concentrated. Purification via automated flash chromatography (5% to 35% EtOAc in hexanes) yielded Int 15 as pale-yellow oil (4.8 g, 12.75 mmol, 81%, 2 steps). ESI-MS: MW for $C_{19}H_{38}BrNO$ $[M+H]^+$ calc. 376.22; found 376.23.

General Procedure for the Preparation of I-79 & I-80

A mixture of Int 12-1 or Int 12-3 (1 eq), Int 15 (1.2 eq), and DIPEA (4 eq) in ACN (10 mL/mmol) was heated to reflux for overnight. The reaction mixture was then concentrated under reduced pressure, and the crude material was purified via automated flash chromatography (Hex/1% $NEt_3$ in EtOAc 95:5 to 35:65).

Synthesis of N,N-didecyl-8-((8-(decyl(methyl)amino)-8-oxooctyl)(methyl)amino)octanamide (I-79)

N,N-didecyl-8-((8-(decyl(methyl)amino)-8-oxooctyl)(methyl)amino)octanamide (I-79) was prepared according to the general procedure from Int 12-1 (0.5 g, 1.10 mmol), and Int 15 (0.5 g, 1.33 mmol). The product was obtained as pale-yellow oil (0.25 g, 0.33 mmol 30.3%). $^1$H NMR (400 MHz, $CDCl_3$) δ 3.38-3.14 (m, 6H), 2.92 (d, J=23.1 Hz, 3H), 2.33-2.22 (m, 8H), 2.18 (s, 3H), 1.67-1.59 (m, 4H), 1.57-1.40 (m, 10H), 1.37-1.21 (m, 55H), 0.87 (q, J=3.8 Hz, 9H). ESI-MS: MW for $C_{48}H_{97}N_3O_2$ $[M+H]^+$ calc. 748.77; found 748.68.

Synthesis of N,N-didecyl-8-((8-(decyl(methyl)amino)-8-oxooctyl)(2-hydroxyethyl)amino)octanamide (I-80)

N,N-didecyl-8-((8-(decyl(methyl)amino)-8-oxooctyl)(2-hydroxyethyl)amino)octanamide (I-80) was prepared according to the general procedure from Int12-3 (0.5 g, 1.03 mmol) and Int-15 (0.47 g, 1.24 mmol). The product was obtained as pale-yellow oil (0.260 g, 0.33 mmol 32.4%). $^1$H NMR (400 MHz, $CDCl_3$) δ 3.51 (t, J=5.4 Hz, 2H), 3.37-3.15 (m, 7H), 2.93 (d, J=23.4 Hz, 3H), 2.56 (t, J=5.3 Hz, 2H), 2.47-2.37 (m, 4H), 2.33-2.22 (m, 4H), 1.62 (s, 5H), 1.57-1.38 (m, 11H), 1.36-1.17 (m, 58H), 0.92-0.83 (m, 9H). ESI-MS: MW for $C_{49}H_{99}N_3O_3$ $[M+H]^+$ calc. 778.78; found 778.85.

Example 65

8,8'-((5-hydroxypentyl)azanediyl)bis(N,N-dinonyloctanamide) (Compound I-81)

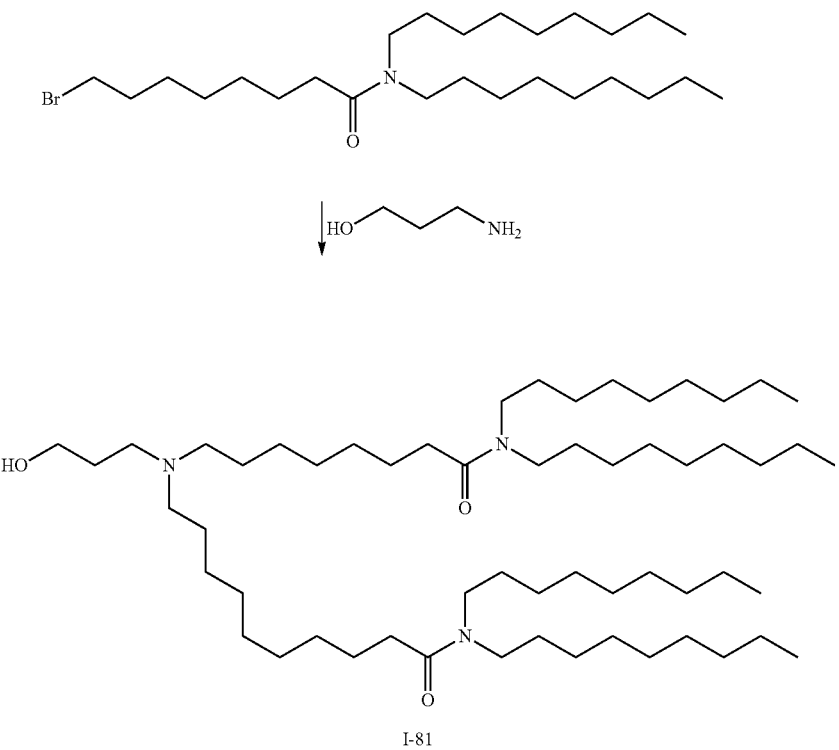

I-81

Synthesis of 8,8'-((5-hydroxypentyl)azanediyl)bis(N,N-dinonyloctanamide) (I-81)

A mixture of 8-bromo-N,N-dinonyloctanamide (was prepared according to the general procedures of example 5, 0.7 mmol, 330 mg), 5-aminopentan-1-ol (0.42 mmol, 43 mg), DIEA (1.3 mmol, 0.23 mL), and potassium iodide (0.7 mmol, 116 mg) in ACN (4 mL) was heated at 75° C. for 48 h. The reaction mixture was concentrated and the crude material was purified via automated flash chromatography (5% to 65% EtOAc in hexanes) to give compound I-81 (88 mg, 28%). $^1$H NMR (400 MHz, $CDCl_3$) δ 3.63 (t, J=6.5 Hz, 2H), 3.32-3.24 (m, 4H), 3.23-3.15 (m, 4H), 2.41-2.32 (m, 6H), 2.31-2.22 (m, 4H), 1.69-1.34 (m, 24H), 1.35-1.19 (m, 61H), 0.92-0.83 (m, 12H). ESI-MS: MW for $C_{57}H_{115}N_3O_3$ $[M+H]^+$ Calc. 890.9; Found 891.0.

Example 66

8,8'-((5-hydroxypentyl)azanediyl)bis(N,N-didecyl-2-fluorooctanamide) (Compound I-82)

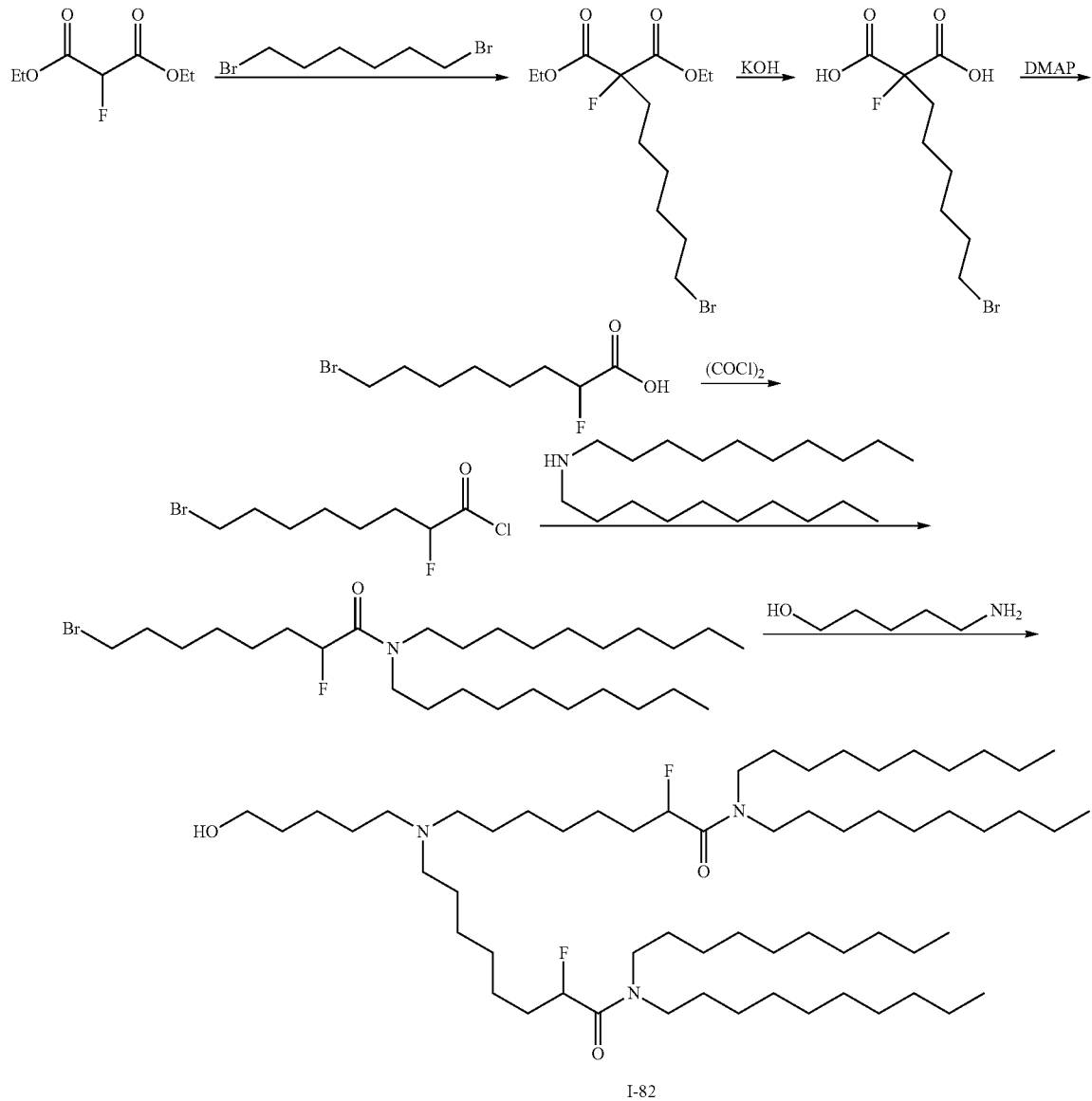

Synthesis of diethyl 2-(6-bromohexyl)-2-fluoromalonate

A mixture of diethyl 2-fluoromalonate (56.1 mmol, 10.0 g), 1,6-dibromohexane (168 mmol, 26 mL), and sodium methoxide (61.7 mmol, 3.3 g) in EtOH (110 mL) was stirred at room temperature for 24 h. The reaction mixture was concentrated and the crude material was partitioned between DCM and water. The organic layer was separated, dried over $Na_2SO_4$, filtered and concentrated. Purification via automated flash chromatography (0% to 25% EtOAc in hexanes) gave diethyl 2-(6-bromohexyl)-2-fluoromalonate (11.7 g, 61%).

Synthesis of 2-(6-bromohexyl)-2-fluoromalonic Acid

A mixture of diethyl 2-(6-bromohexyl)-2-fluoromalonate (5.9 mmol, 2.0 g) and KOH (11.8 mmol, 660 mg) in MeOH (20 mL), THF (2 mL), and water (4 mL) was stirred at room temperature for 3 h. The reaction mixture was concentrated and the crude material was diluted with 0.1 M NaOH (20 mL). The aqueous layer was washed with DCM (3×10 mL), acidified with 1 M HCl, then extracted with EtOAc (2×20 mL). The combined EtOAc layers were dried over $Na_2SO_4$, filtered and concentrated to give 2-(6-bromohexyl)-2-fluoromalonic acid (1.57 g, 94%) which was used in the next step without further purification.

Synthesis of 8-bromo-2-fluorooctanoic Acid

A mixture of 2-(6-bromohexyl)-2-fluoromalonic acid (4.1 mmol, 1.2 g) and DMAP (cat.) in DMF (3 mL), was heated at 180° C. for 12 min. The reaction mixture was partitioned between EtOAc and 1 M HCl. The organic layer was separated, dried over $Na_2SO_4$, filtered and concentrated to give 8-bromo-2-fluorooctanoic acid (960 mg, 98%) which was used in the next step without further purification.

Synthesis of 8-bromo-2-fluorooctanoyl Chloride

A mixture of 8-bromo-2-fluorooctanoic acid (4.0 mmol, 960 mg), oxalyl chloride (12 mmol, 1.0 mL), and DMF (cat.) in DCM (10 mL) was stirred at room temperature for 20 min. The reaction mixture was concentrated to give 8-bromo-2-fluorooctanoyl chloride which was used in the next step without further purification.

Synthesis of 8-bromo-N,N-didecyl-2-fluorooctanamide

To mixture of didecylamine (4.0 mmol, 1.2 g), triethylamine (24 mmol, 3.4 mL), and DMAP (cat.) in DCM (10 mL) was added a solution of crude 8-bromo-2-fluorooctanoyl chloride (4.0 mmol) in DCM (5 mL). The reaction mixture was stirred at room temperature for 1 h. The reaction was concentrated and purified via automated flash chromatography (5% to 25% EtOAc in hexanes) gave 8-bromo-N,N-didecyl-2-fluorooctanamide (1.2 g, 58% over 2 steps).

Synthesis of 8,8'-((5-hydroxypentyl)azanediyl)bis(N,N-didecyl-2-fluorooctanamide) (I-82)

A mixture of 8-bromo-N,N-didecyl-2-fluorooctanamide (0.56 mmol, 290 mg), 5-aminopentanol (0.34 mmol, 35 mg), and DIEA (1.0 mmol, 0.18 mL), potassium iodide (0.56 mmol, 93 mg) in ACN (4 mL) was heated at 75° C. for 19 h. The reaction mixture was concentrated and the crude material was purified via automated flash chromatography (5% to 100% EtOAc in hexanes) to give compound I-82 (158 mg, 57%). $^1$H NMR (400 MHz, $CDCl_3$) δ 5.03 (ddd, J=49.4, 8.5, 4.3 Hz, 2H), 3.64 (t, J=6.5 Hz, 2H), 3.37-3.25 (m, 6H), 3.25-3.12 (m, 2H), 2.43-2.33 (m, 6H), 1.97-1.68 (m, 6H), 1.64-1.34 (m, 26H), 1.33-1.22 (m, 62H), 0.93-0.83 (m, 12H). ESI-MS: MW for $C_{61}H_{121}F_2N_3O_3[M+H]^+$ Calc. 982.9; Found 983.0.

Example 67

8,8'-(methylazanediyl)bis(N,N-didecyl-2-fluorooctanamide) (Compound I-83)

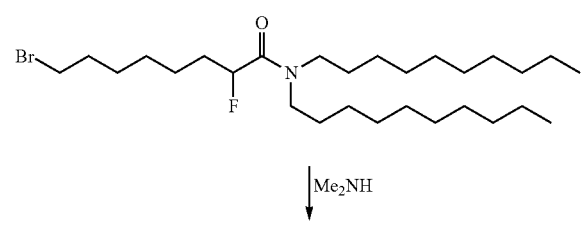

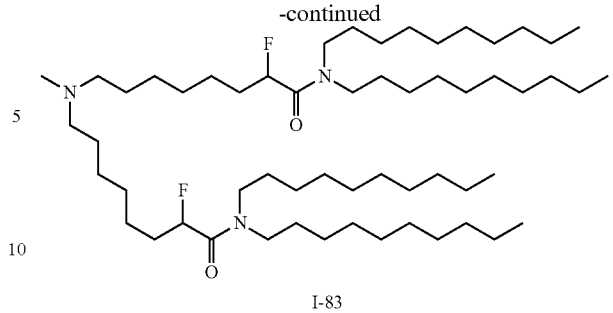

I-83

Synthesis of 8,8'-(methylazanediyl)bis(N,N-didecyl-2-fluorooctanamide) (I-83)

A mixture of 8-bromo-N,N-didecyl-2-fluorooctanamide (was prepared according to the general procedures of example 66, 0.58 mmol, 300 mg), 8 M methylamine in EtOH (0.36 mmol, 0.045 mL), and DIEA (1.1 mmol, 0.19 mL) in ACN (4 mL) was heated at 75° C. for 48 h. The reaction mixture was concentrated and the crude material was purified via automated flash chromatography (5% to 65% EtOAc in hexanes) to give compound I-83 (160 mg, 61%). $^1$H NMR (400 MHz, $CDCl_3$) δ 5.14-4.93 (m, 2H), 3.40-3.24 (m, 6H), 3.24-3.10 (m, 2H), 2.33-2.25 (m, 4H), 2.19 (s, 3H), 1.99-1.71 (m, 4H), 1.62-1.17 (m, 80H), 0.92-0.84 (m, 12H). ESI-MS: MW for $C_{57}H_{113}F_2N_3O_2[M+H]^+$ Calc. 910.9; Found 911.0.

Example 68

2,2'-((5-hydroxypentyl)azanediyl)bis(N,N-didecylacetamide) (Compound I-84)

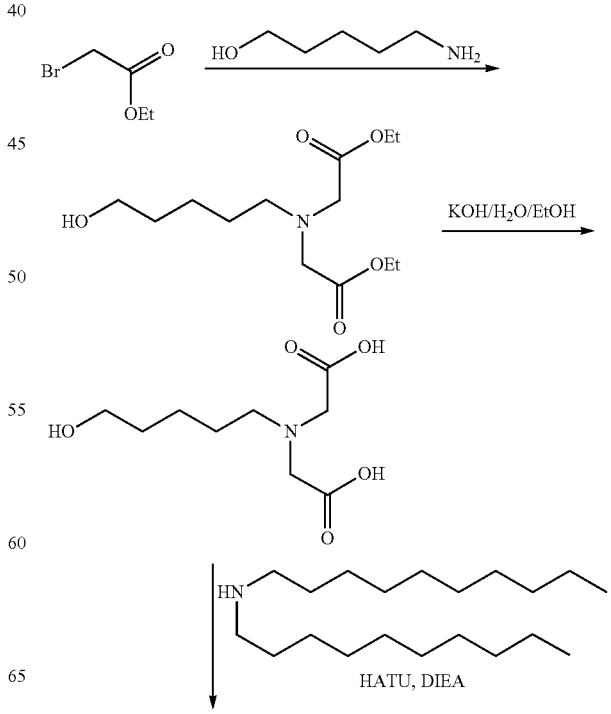

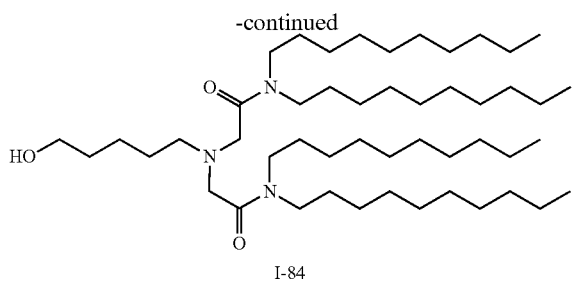

I-84

Synthesis of diethyl 2,2'-((5-hydroxypentyl)azanediyl)diacetate

A mixture of ethyl 2-bromoacetate (14.2 mmol, 2.38 g, 1.57 ml), 5-aminopentan-1-ol (7.3 mmol, 0.75 g) DIEA (26.0 mmol, 2.5 mL), in ACN (10 mL) was stirred at 90° C. for 1.5 h in a pressure flask. The reaction mixture was concentrated, residue partitioned between water and EtOAc. The crude product, obtained after removal of EtOAc under vacuum, was purified on $SiO_2$ column (gradient; from Hexanes:$Et_3N$=99:1 to EtOAc:$Et_3N$=99:1) to give 1.6 g of pure diethyl 2,2'-((5-hydroxypentyl)azanediyl)diacetate (yield: 82%).

Synthesis of 2,2'-((5-hydroxypentyl)azanediyl)diacetic Acid

To diethyl 2,2'-((5-hydroxypentyl)azanediyl)diacetate (1.6 g, 5.8 mmol), dissolved in 10 ml of EtOH, 15 ml of 1 M water solution of KOH were added. The reaction mixture was stirred for 1 h at room temperature. After that, EtOH was removed under vacuum and pH of the residue adjusted to 4. Water was removed under vacuum to give crude product that was used in the next step without any further purification.

Synthesis of 2,2'-((5-hydroxypentyl)azanediyl)bis (N,N-didecylacetamide) (I-84)

To crude 2,2'-((5-hydroxypentyl)azanediyl)diacetic acid, Int-PB2 (0.26 mmol), THF (20 ml), DMF (2 ml), didecylamine (0.42 g, 1.4 mmol), DIEA (0.25 ml, 2.6 mmol) and HATU (0.34 g, 0.68 mmol) were added in that order. Reaction mixture was stirred at room temperature for 30 min. The reaction mixture was concentrated, and the crude material was purified via automated flash chromatography (5% to 75% EtOAc in hexanes with 1% $Et_3N$) to give I-84 (85 mg, 42%). $^1$H NMR (400 MHz, $CDCl_3$) δ 3.62 (t, J=6.3 Hz, 2H), 3.50 (bs, 4H), 3.31-3.18 (m, 8H), 2.83-2.64 (m, 2H), 1.74-1.37 (m, 18H), 1.36-1.14 (m, 62H), 0.95-0.80 (m, 12H). ESI-MS: MW for $C_{49}H_{99}N_3O_3$ [M+H]$^+$ Calc. 778.8; Found 778.8.

Example 69

4,4'-((5-hydroxypentyl)azanediyl)bis(N,N-didecylbutanamide) (Compound I-85)

Compound I-85 was prepared according to the general procedures of example 68 to yield the desired product (445 mg, 76%). $^1$H NMR (400 MHz, $CDCl_3$) δ 3.67-3.60 (m, 2H), 3.33-3.24 (m, 4H), 3.24-3.14 (m, 4H), 2.52-2.25 (m, 10H), 1.86-1.69 (m, 4H), 1.69-1.35 (m, 10H), 1.35-1.18 (m, 60H), 0.93-0.83 (m, 12H). ESI-MS: MW for $C_{53}H_{107}N_3O_3$ [M+H]$^+$ Calc. 834.8; Found 834.9.

The invention claimed is:

1. A compound having the following structure (I):

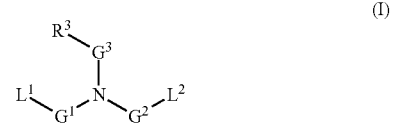

(I)

or a pharmaceutically acceptable salt or stereoisomer thereof, wherein:
  $L^1$ is —NR$^a$C(=O)R$^1$ or —C(=O)NR$^b$R$^c$;
  $L^2$ is —NR$^d$C(=O)R$^2$ or —C(=O)NR$^e$R$^f$;
  $G^1$ and $G^2$ are each independently $C_3$-$C_{12}$ alkylene or $C_3$-$C_{12}$ alkenylene;
  $G^3$ is $C_1$-$C_{24}$ alkylene or $C_2$-$C_{24}$ alkenylene;
  $R^a$, $R^b$, $R^d$ and $R^e$ are each independently H, $C_1$-$C_{16}$ alkyl or $C_2$-$C_{16}$ alkenyl;
  $R^c$ and $R^f$ are each independently $C_1$-$C_{16}$ alkyl or $C_2$-$C_{16}$ alkenyl;
  $R^1$ and $R^2$ are each independently $C_6$-$C_{24}$ alkyl or $C_6$-$C_{24}$ alkenyl;
  $R^3$ is H, —OH, CN, —C(=O)N(R$^4$)R$^5$; —N(R$^4$)C(=O) R$^5$; —N(R$^4$)C(=O)OR$^5$; —C(=O)OR$^6$, —OC(=O) R$^6$, —OR$^7$, heteroaryl or aryl;
  $R^4$ and $R^5$ are each independently is H, $C_1$-$C_{12}$ alkyl, $C_3$-$C_6$ cycloalkyl or $C_3$-$C_6$ cycloalkenyl, or $R^4$ and $R^5$, together with the nitrogen or carbon atom to which they are bound, form a 5 to 7-membered heterocyclic ring;
  $R^6$ is H, $C_1$-$C_{12}$ alkyl, $C_2$-$C_{12}$ alkenyl or aralkyl;
  $R^7$ is $C_1$-$C_{12}$ alkyl optionally substituted with hydroxyl or alkoxy; and
  wherein each alkyl, alkenyl, alkylene, alkenylene, $C_3$-$C_6$ cycloalkyl, $C_3$-$C_6$ cycloalkenyl, aryl and aralkyl is independently substituted or unsubstituted unless otherwise specified.

2. The compound of claim 1, wherein at least one alkyl, alkenyl, alkylene, alkenylene, $C_3$-$C_6$ cycloalkyl or $C_3$-$C_6$ cycloalkenyl, aryl or aralkyl is substituted with one or more fluorine and/or one or more oxo and/or one or more $NH_2$ and/or one or more alkylaminyl.

3. The compound of claim 1, wherein $G^3$ is $C_1$-$C_{12}$ alkylene.

4. The compound of claim 1, wherein $G^1$, $G^2$ and/or $G^3$ is substituted with one or more fluorine atoms.

5. The compound of claim 1, having the following structure (IA):

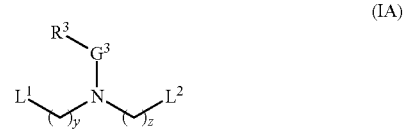

(IA)

wherein y and z are each independently integers ranging from 4 to 12.

6. The compound of claim 1, wherein:
  $L^1$ is —C(=O)NR$^b$R$^c$, and $L^2$ is —C(=O)NR$^e$R$^f$ or
  $L^1$ is —NR$^a$C(=O)R$^1$, and $L^2$ is —NR$^d$C(=O)R$^2$.

7. The compound of claim 6, having one of the following structures (IB) or (IC):

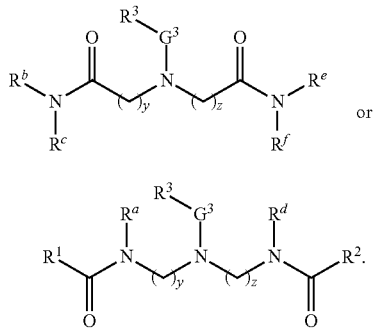

wherein y and z are each independently an integer ranging from 4 to 10.

8. The compound of claim 1, wherein $R^1$ and $R^2$ are each, independently, linear or branched $C_6$-$C_{24}$ alkyl.

9. The compound of claim 8, wherein $R^1$ and $R^2$ each, independently, have the following structure:

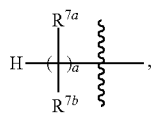

wherein:

$R^{7a}$ and $R^{7b}$ are, at each occurrence, independently either: (a) H or $C_1$-$C_{12}$ alkyl, or (b) $R^{7a}$ is H or $C_1$-$C_{12}$ alkyl, and $R^{7b}$ together with the carbon atom to which it is bound is taken together with an adjacent $R^{7b}$ and the carbon atom to which it is bound to form a carbon-carbon double bond; and a is an integer from 2 to 12, wherein $R^{7a}$, $R^{7b}$ and a are each selected such that $R^1$ and $R^2$ are each independently linear or branched and independently comprise from 6 to 20 carbon atoms.

10. The compound of claim 1, wherein $R^1$ or $R^2$, or both, independently has one of the following structures:

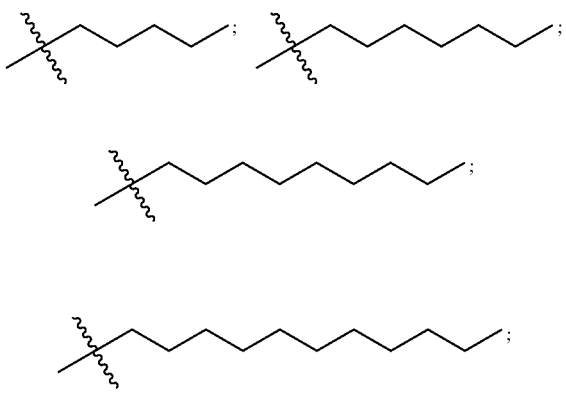

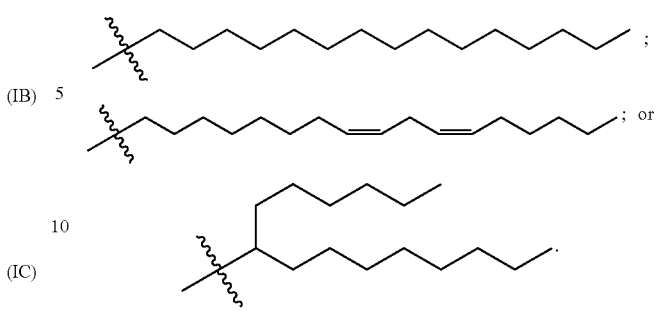

11. The compound of claim 1, wherein $R^b$, $R^c$, $R^e$ and $R^f$ are each independently $C_3$-$C_{12}$ alkyl.

12. The compound of claim 1, wherein $R^a$ and $R^d$ are each independently $C_1$-$C_{12}$ alkyl or $C_2$-$C_{12}$ alkenyl and $R^1$ and $R^2$ are each independently $C_6$-$C_{18}$ alkyl or $C_6$-$C_{18}$ alkenyl.

13. The compound of claim 1, wherein $R^3$ is H.

14. The compound of claim 1, wherein $R^3$ is —OH.

15. The compound of claim 1, wherein $R^3$ is —C(=O)$OR^6$.

16. The compound of claim 1, wherein $R^3$ is —C(=O)$N(R^4)R^5$.

17. The compound of claim 1, wherein $R^3$ is —N($R^4$)C(=O)$R^5$.

18. The compound of claim 1, wherein $R^3$ is aryl or heteroaryl.

19. The compound of claim 1, wherein $R^3$ has one of the following structures:

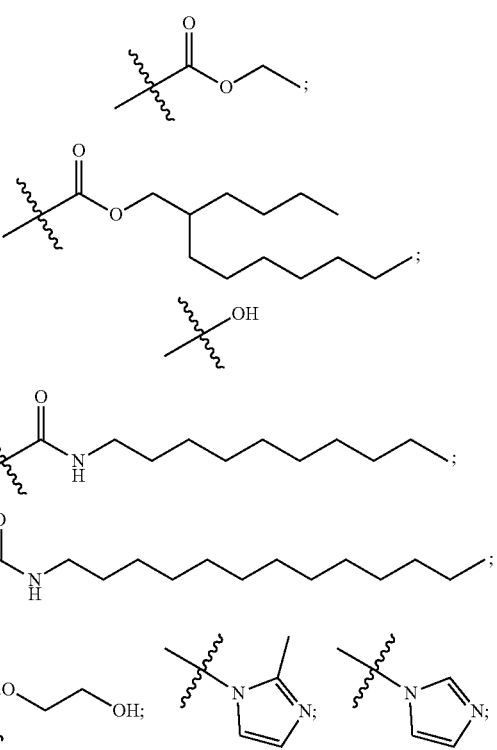

163
-continued
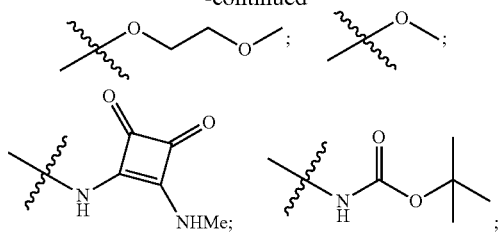
164
-continued
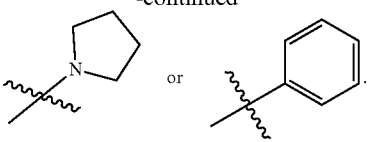
20. The compound of claim 1, having one of the following structures:
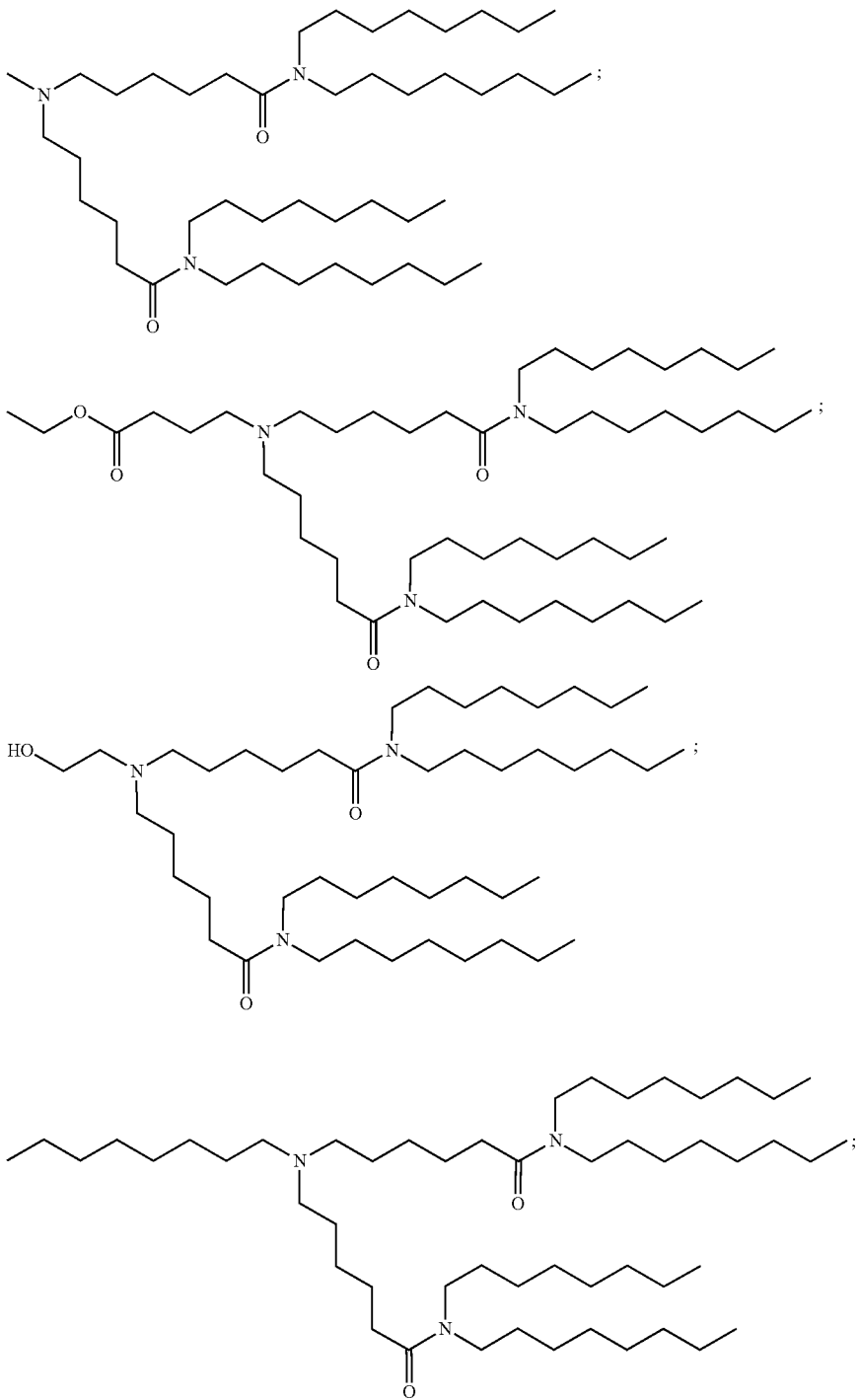

-continued
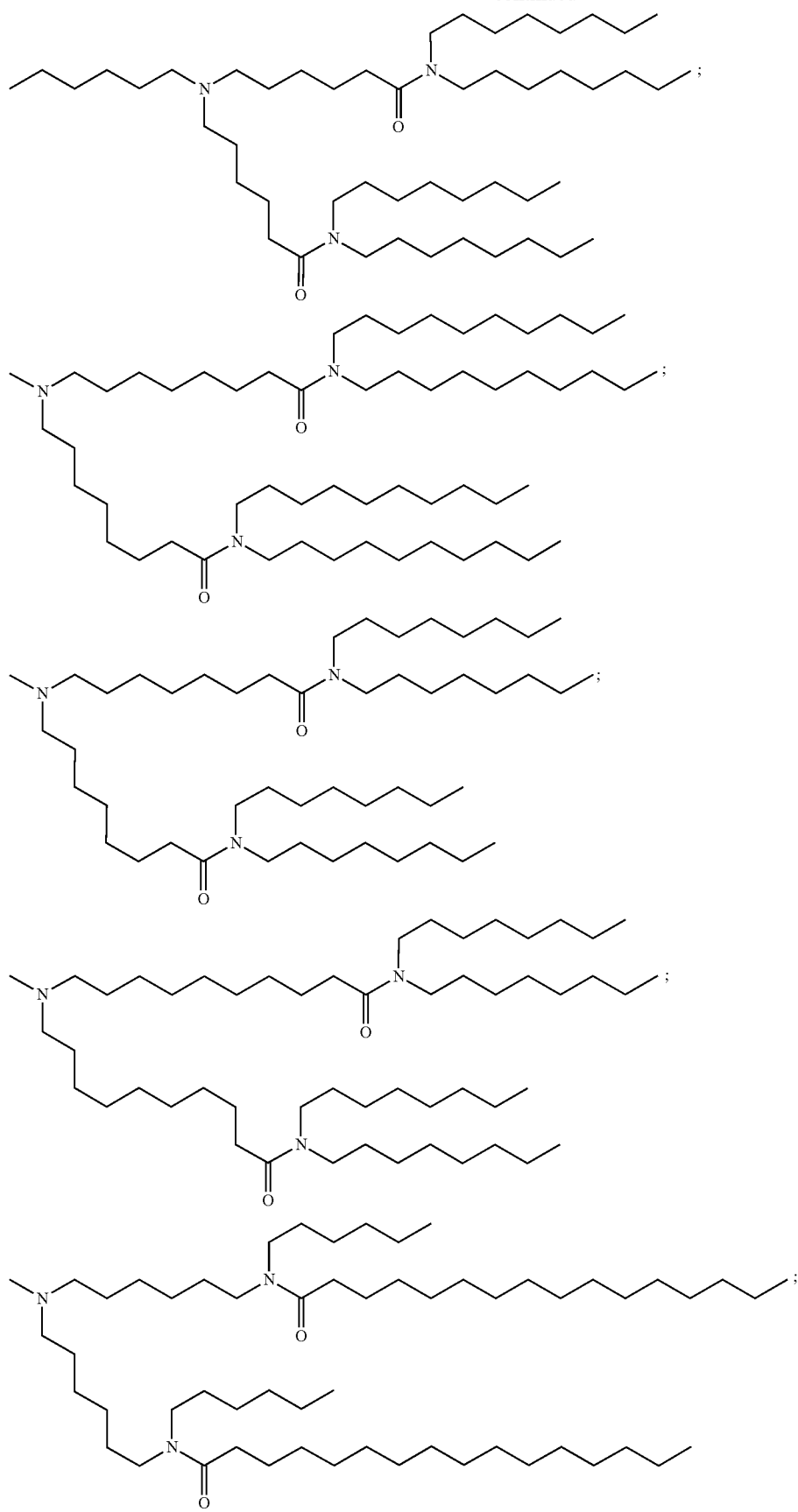

-continued
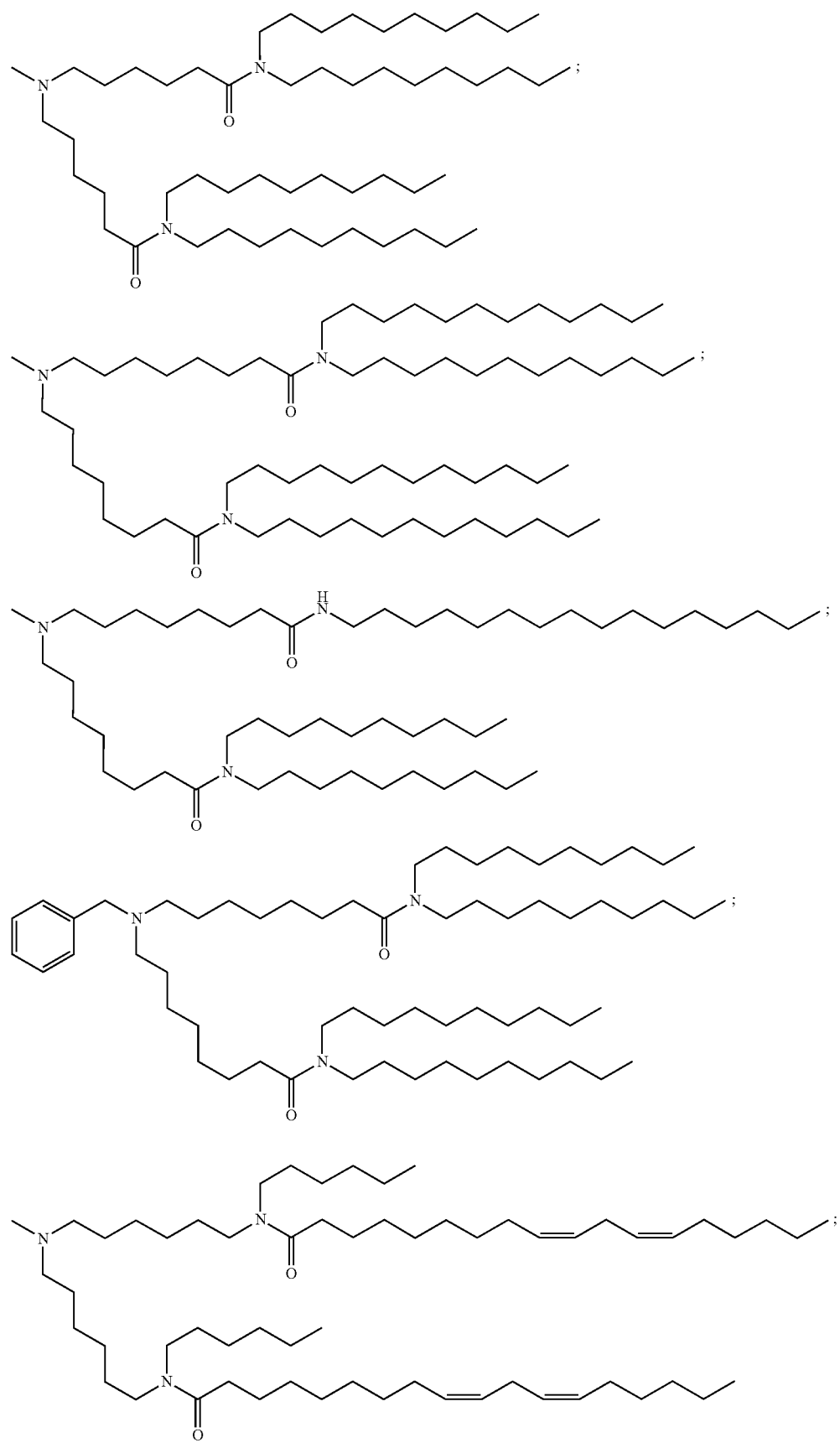

-continued
169 170
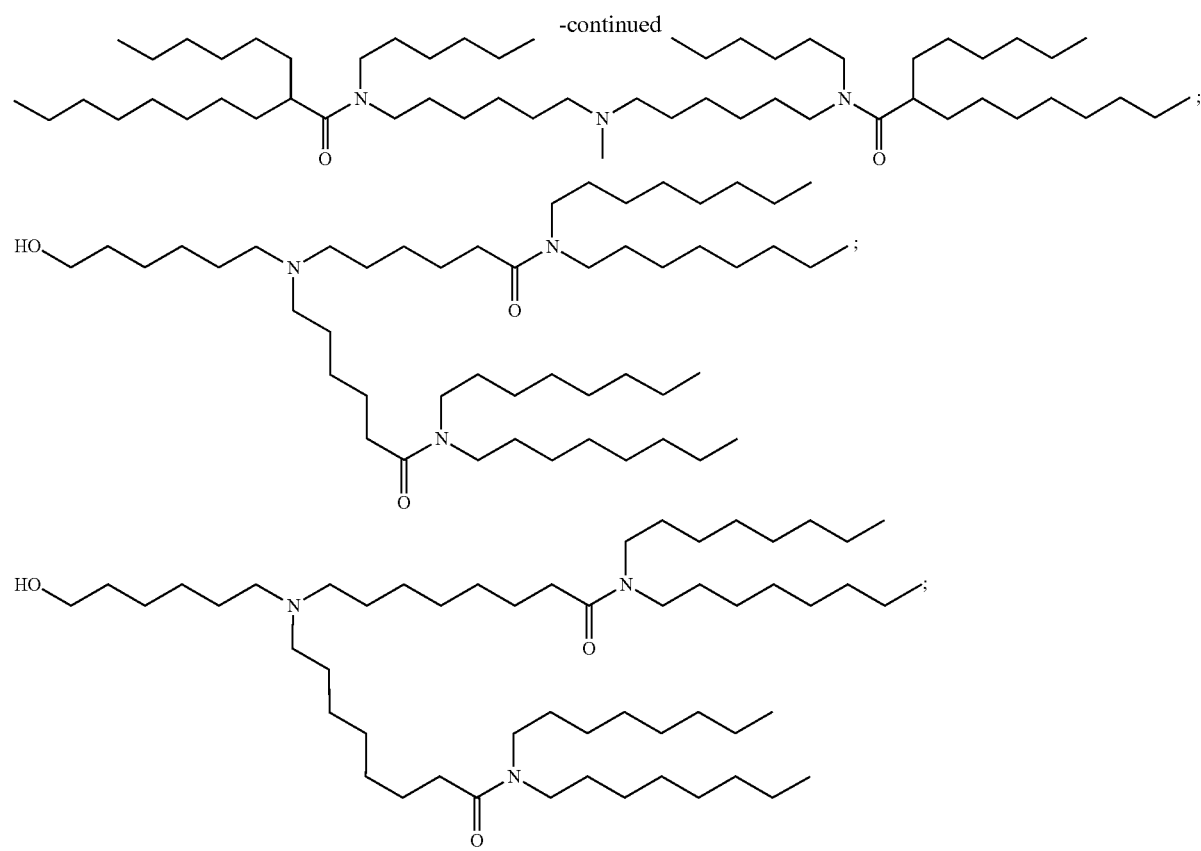
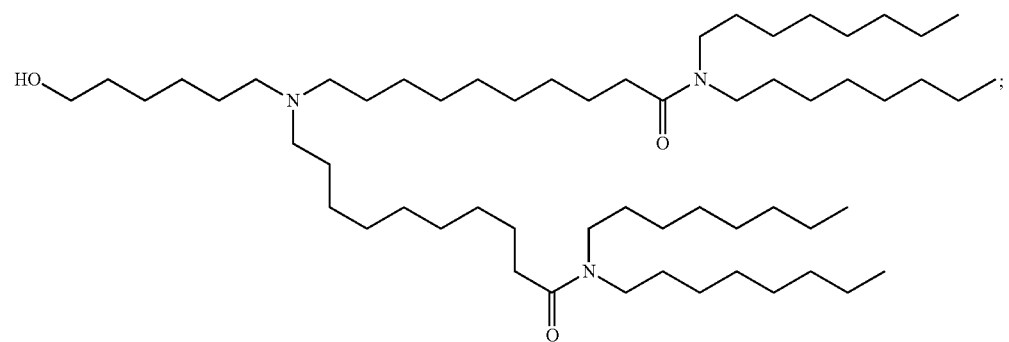
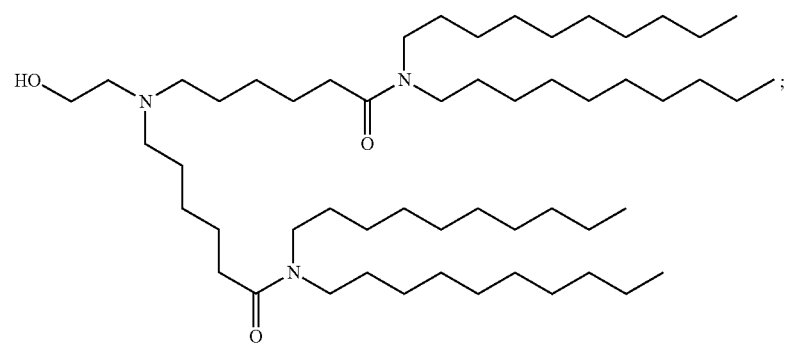

-continued
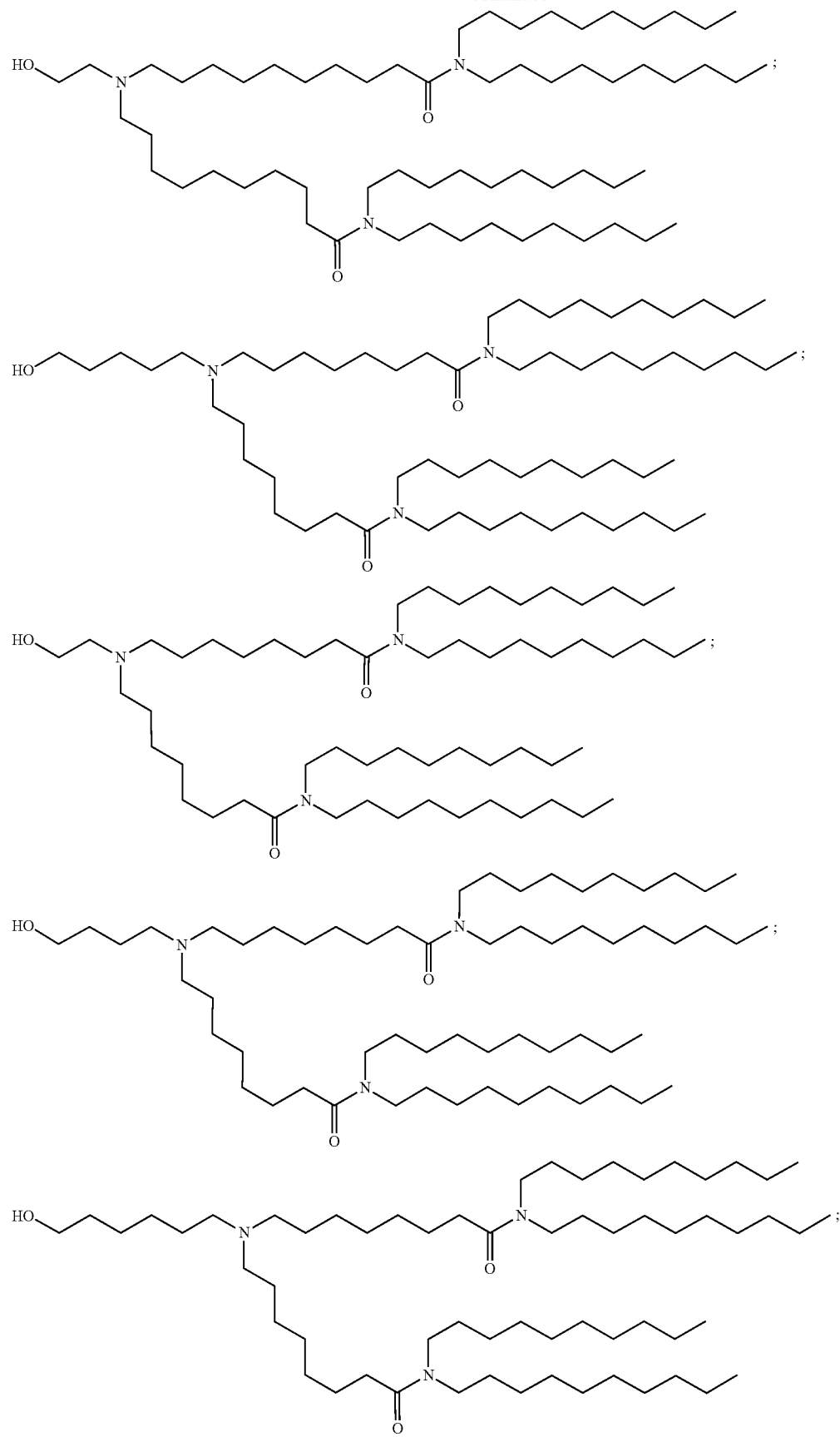

-continued
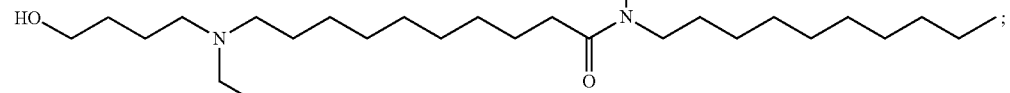
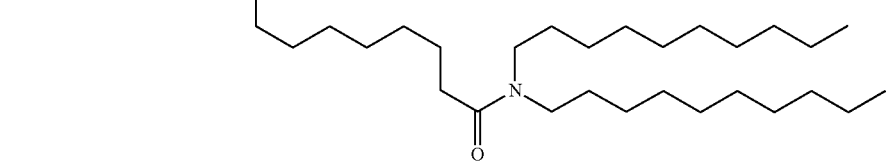
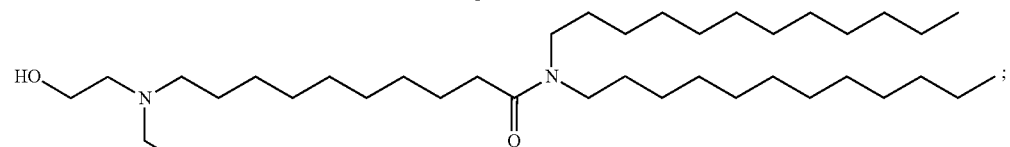
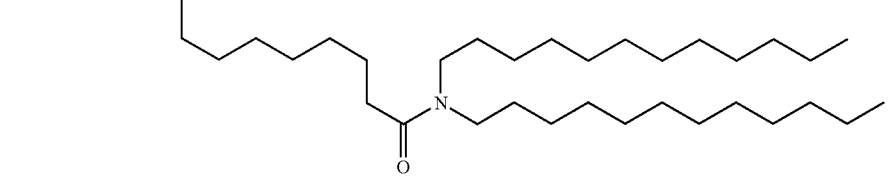
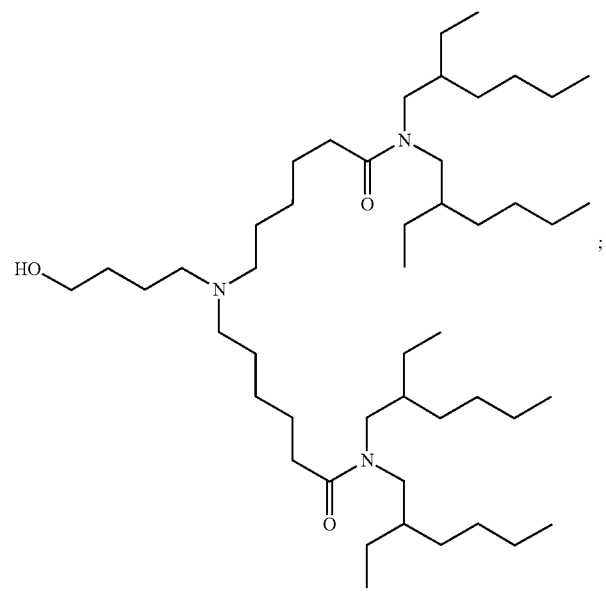
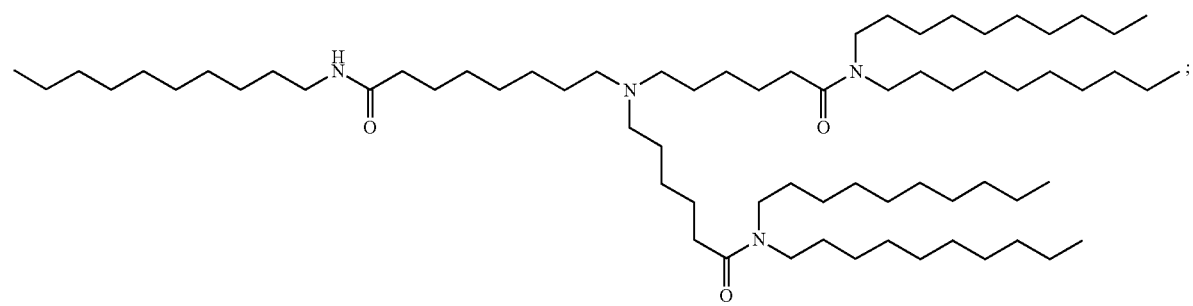

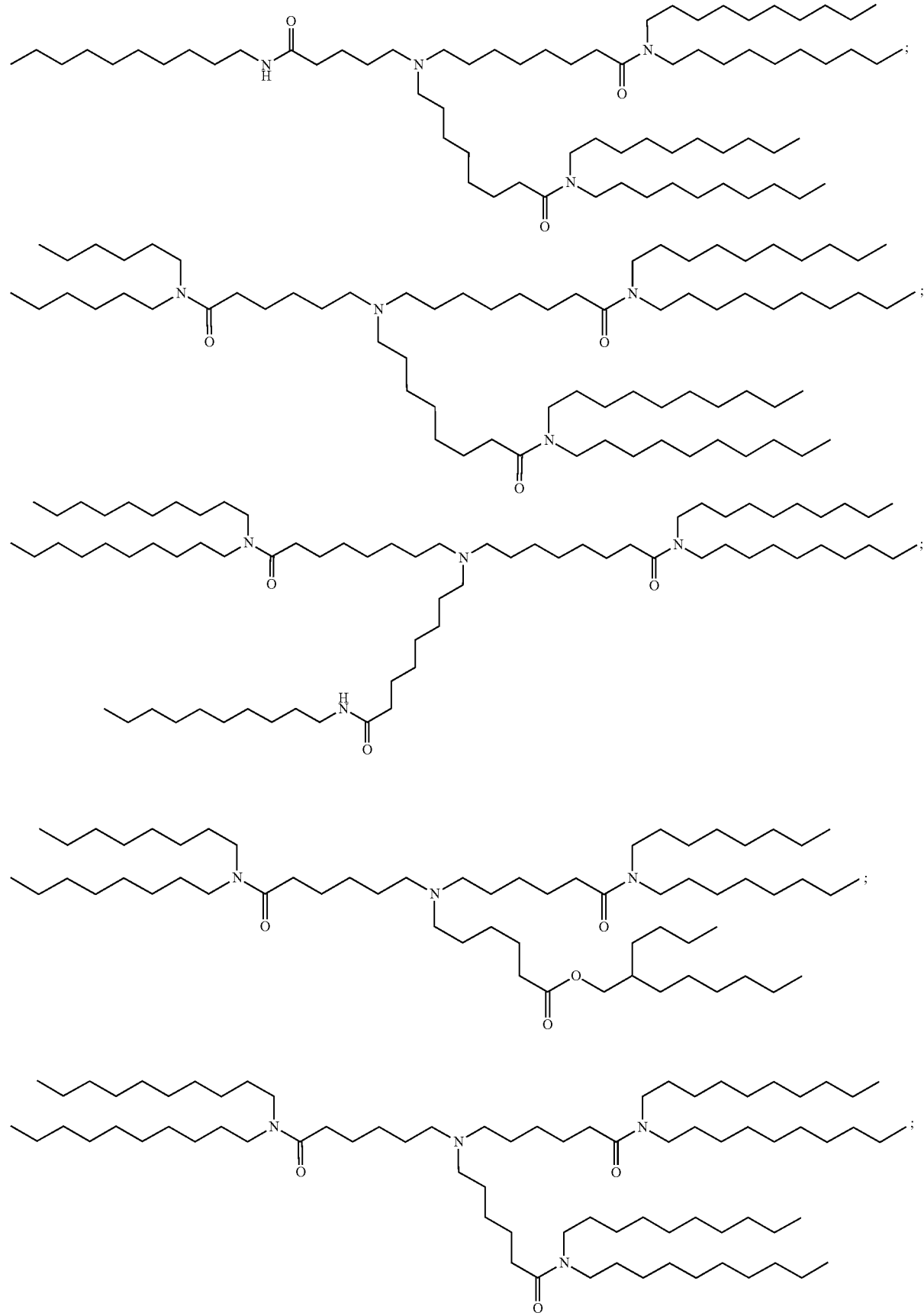

-continued
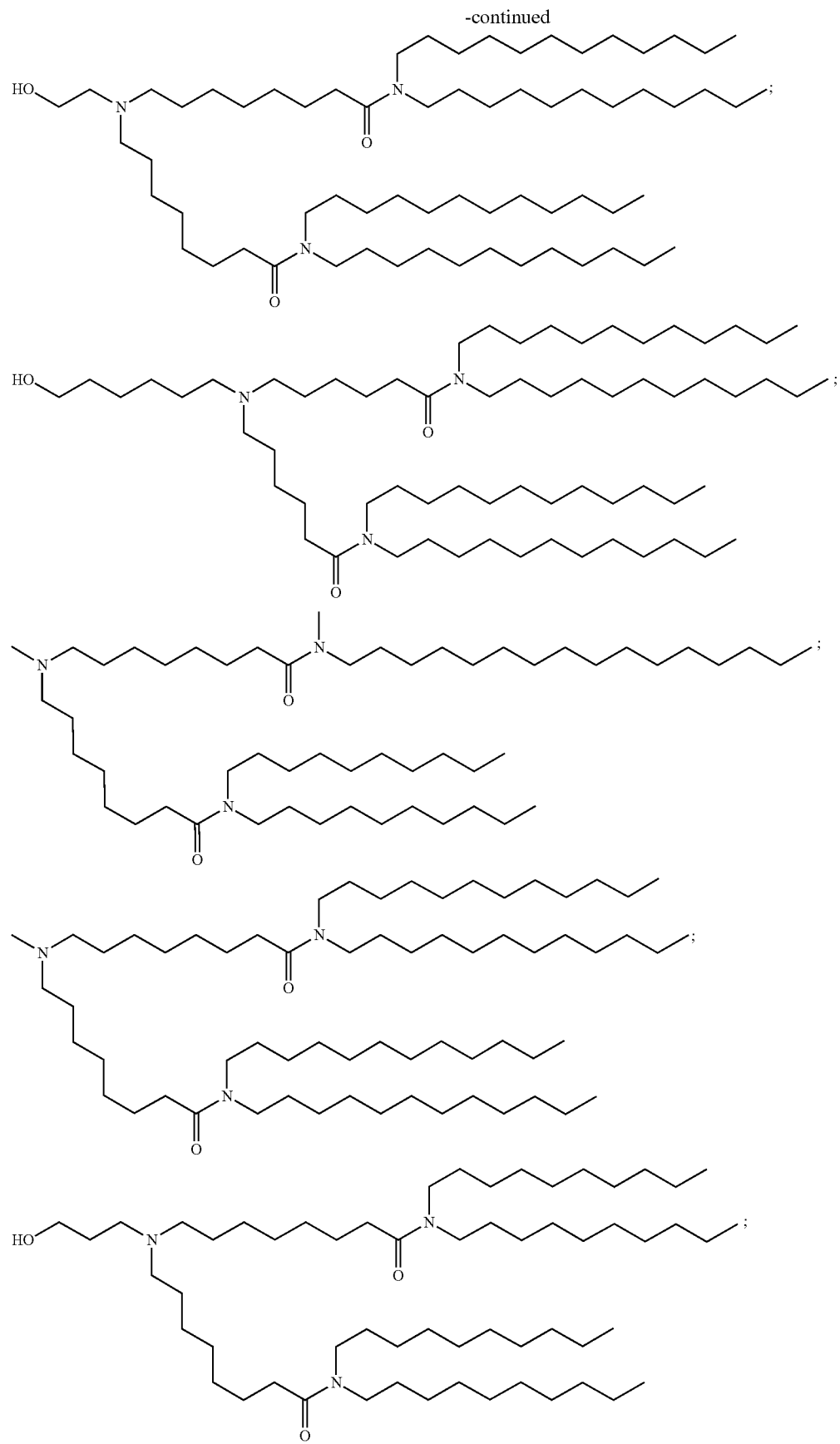

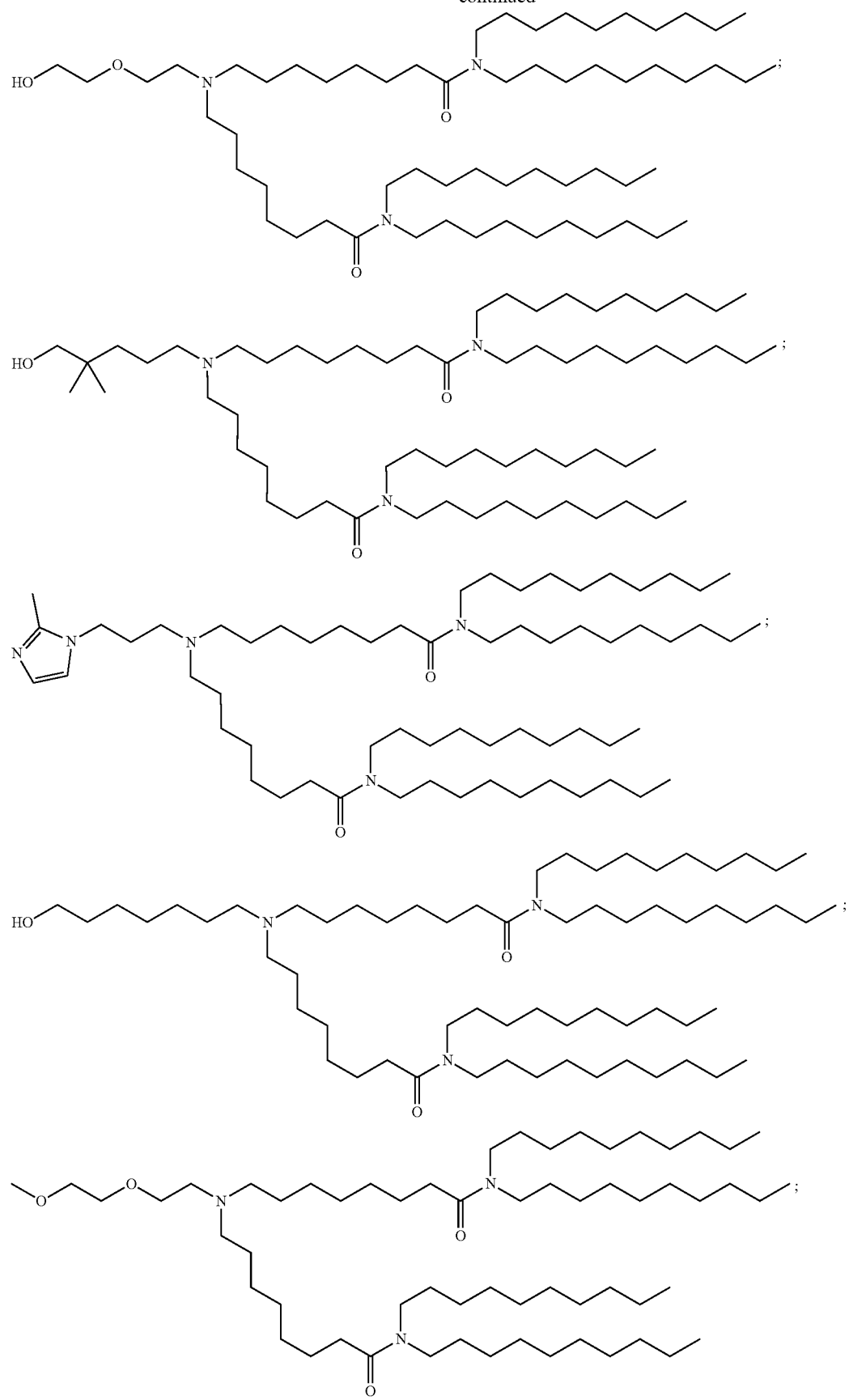

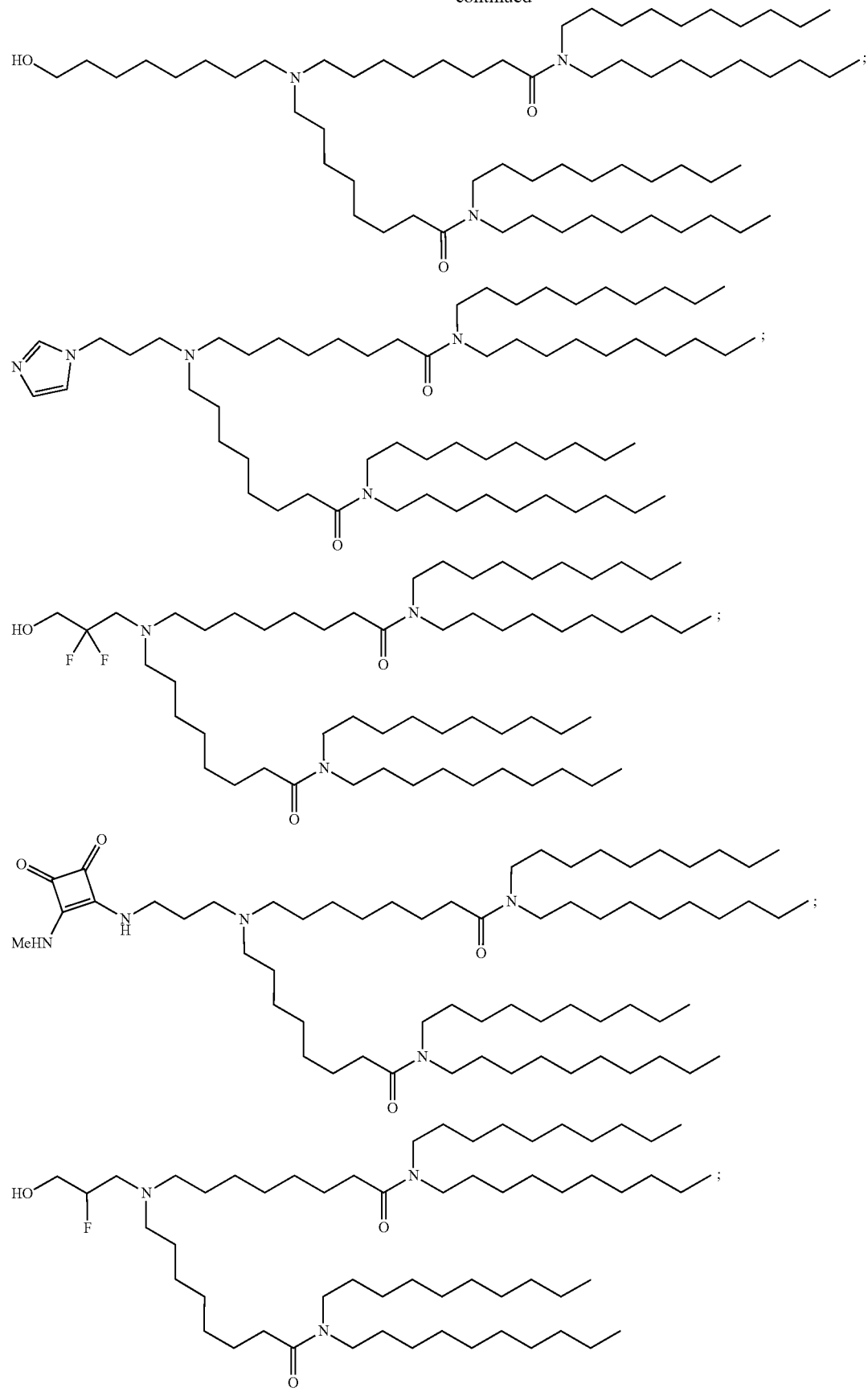

-continued
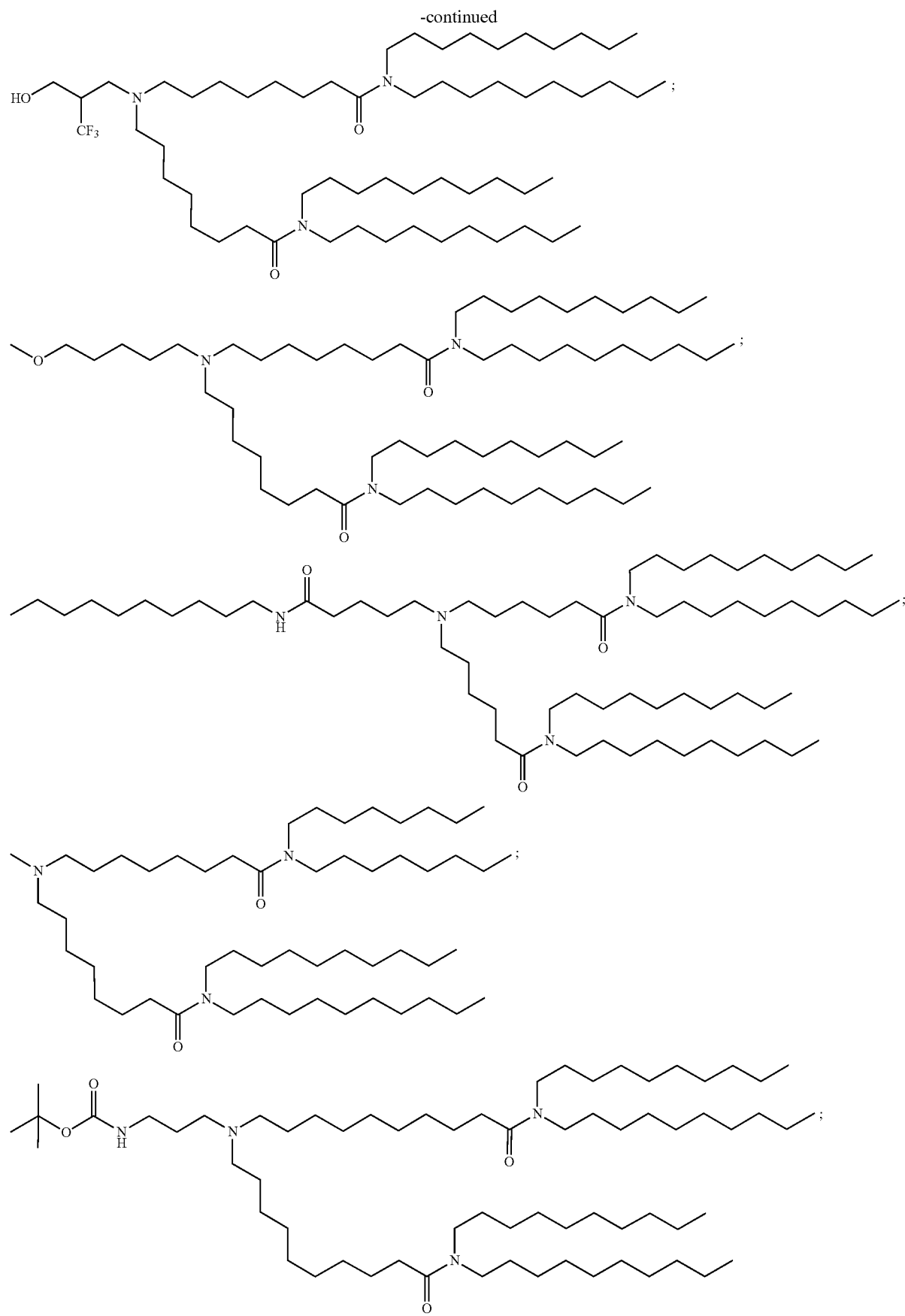

-continued
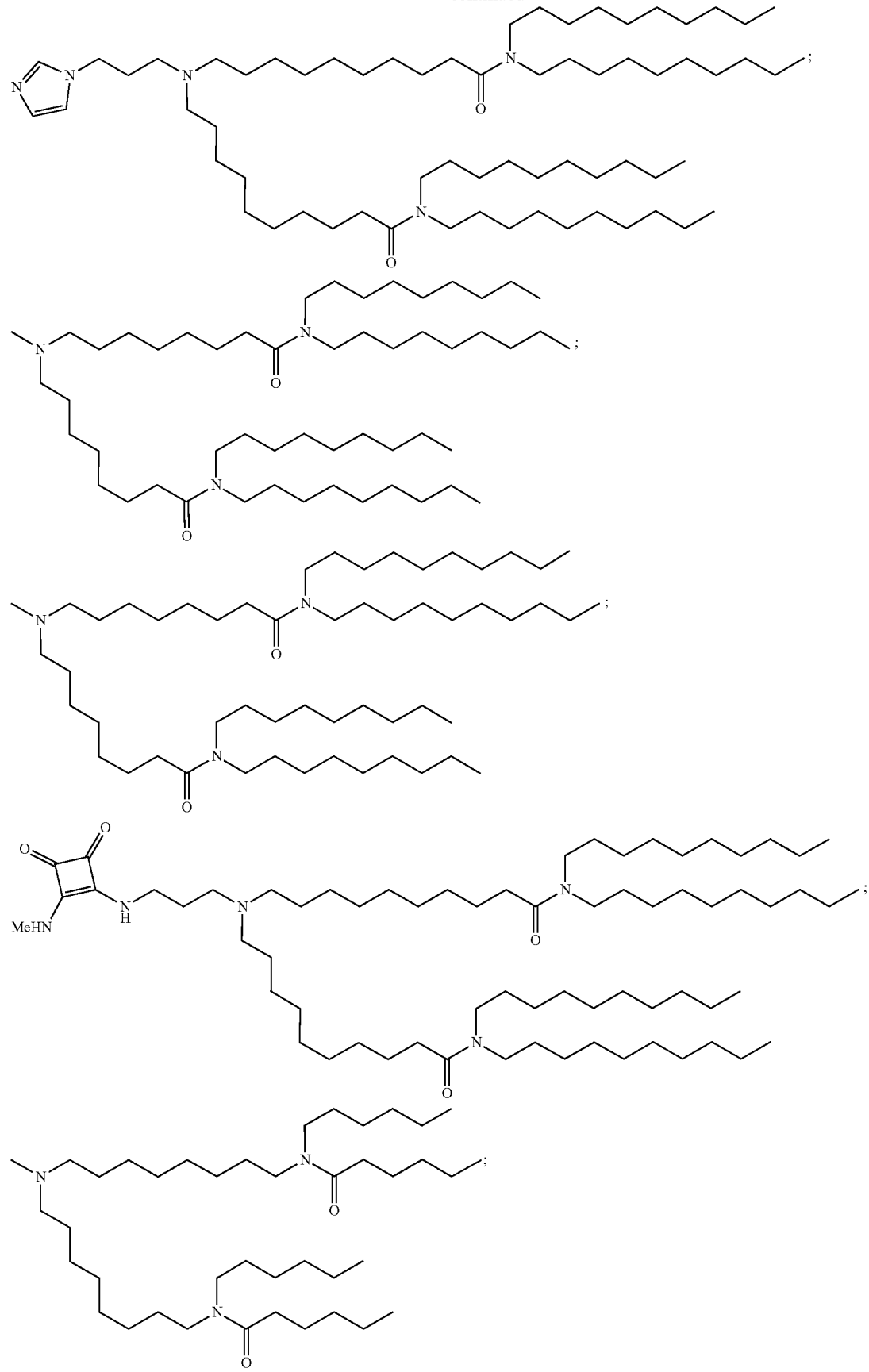

-continued
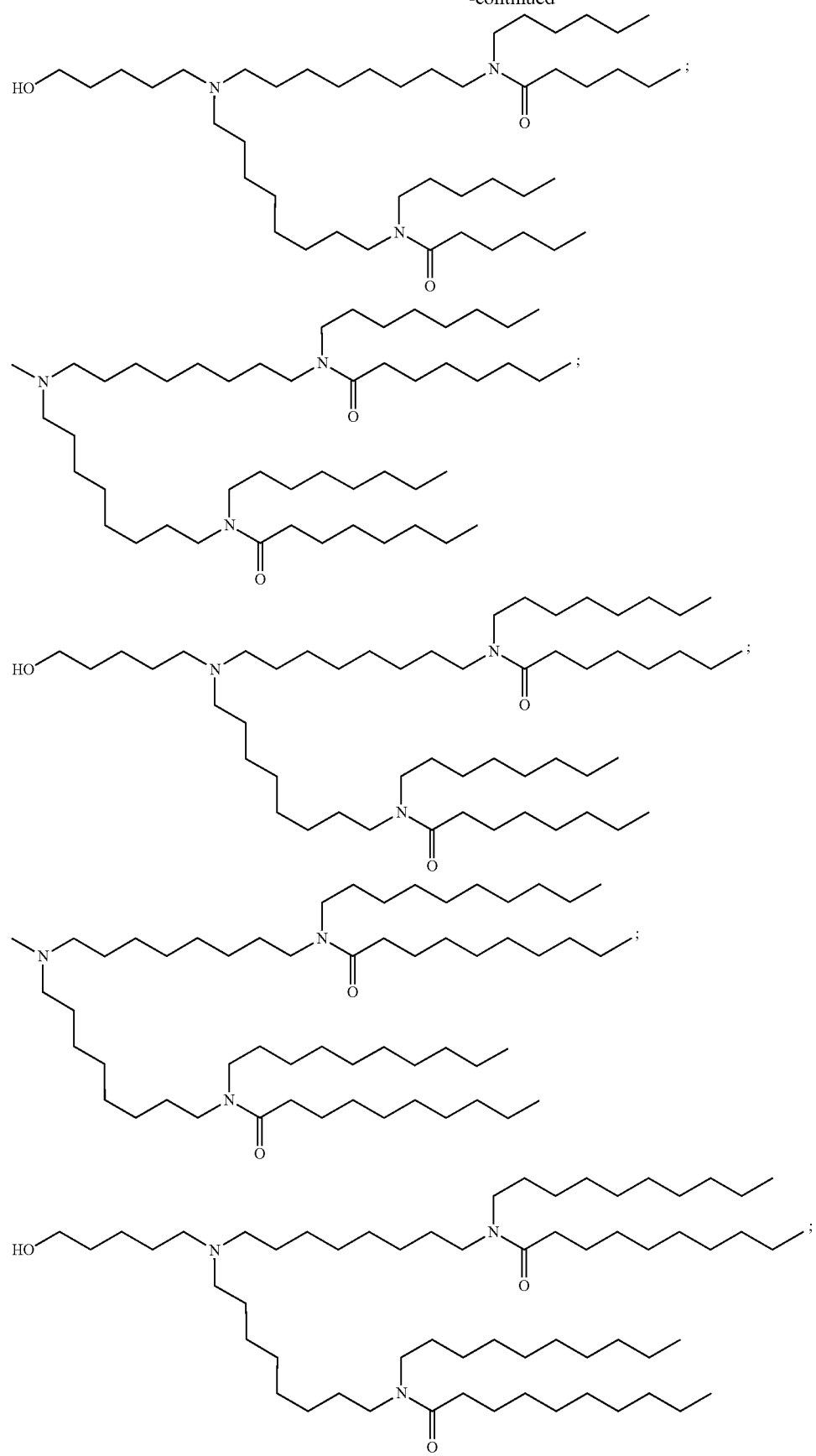

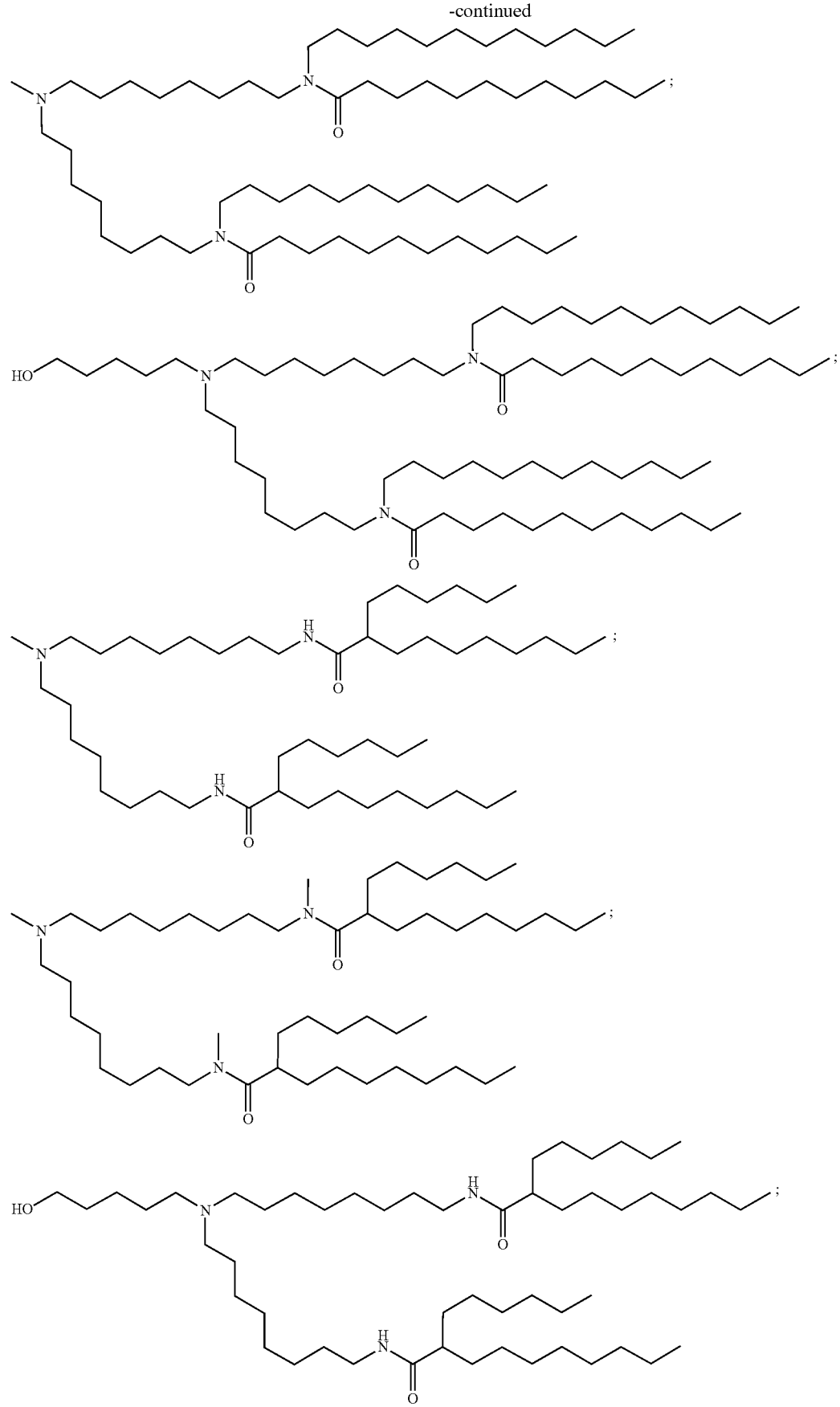

-continued
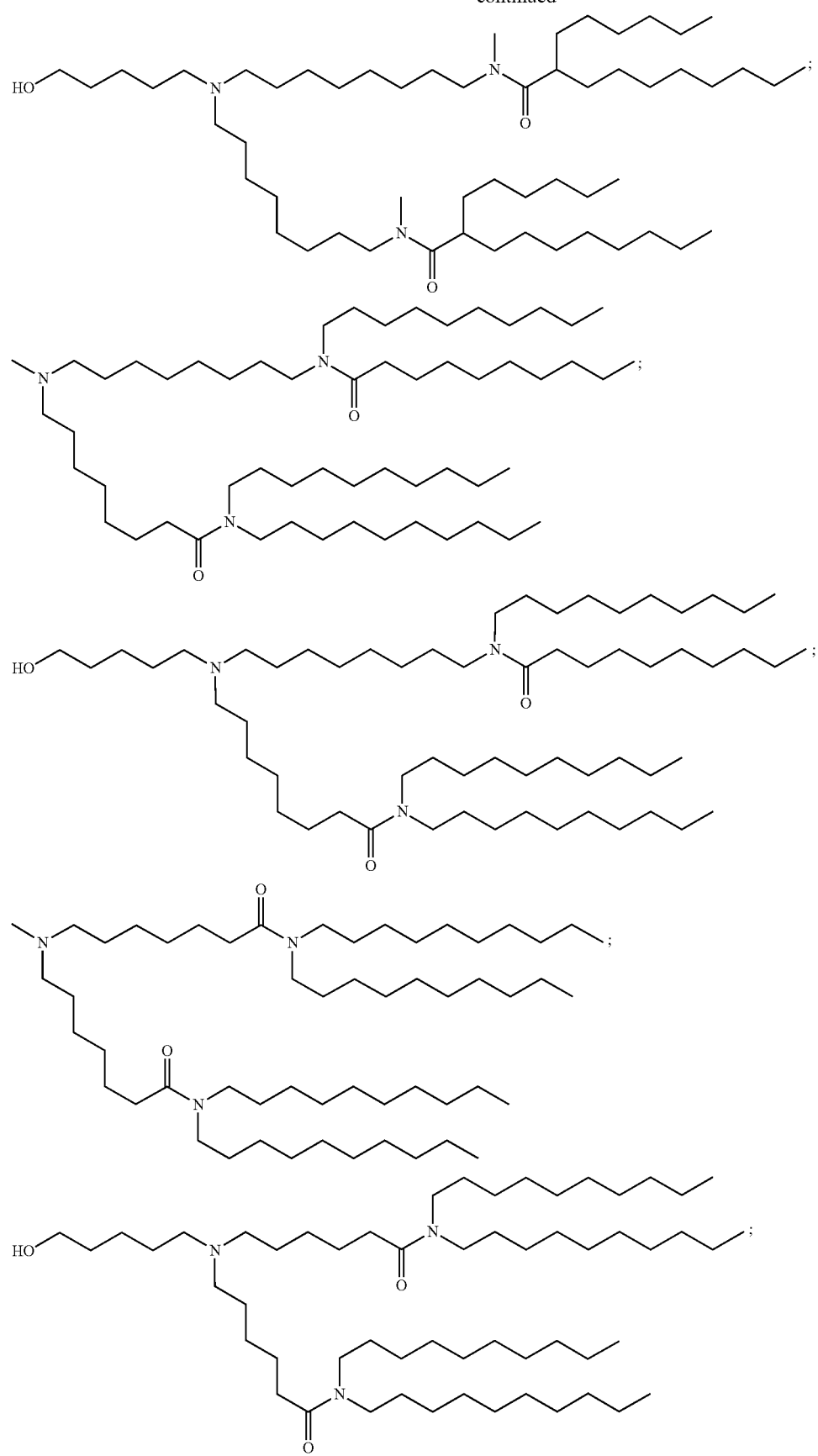

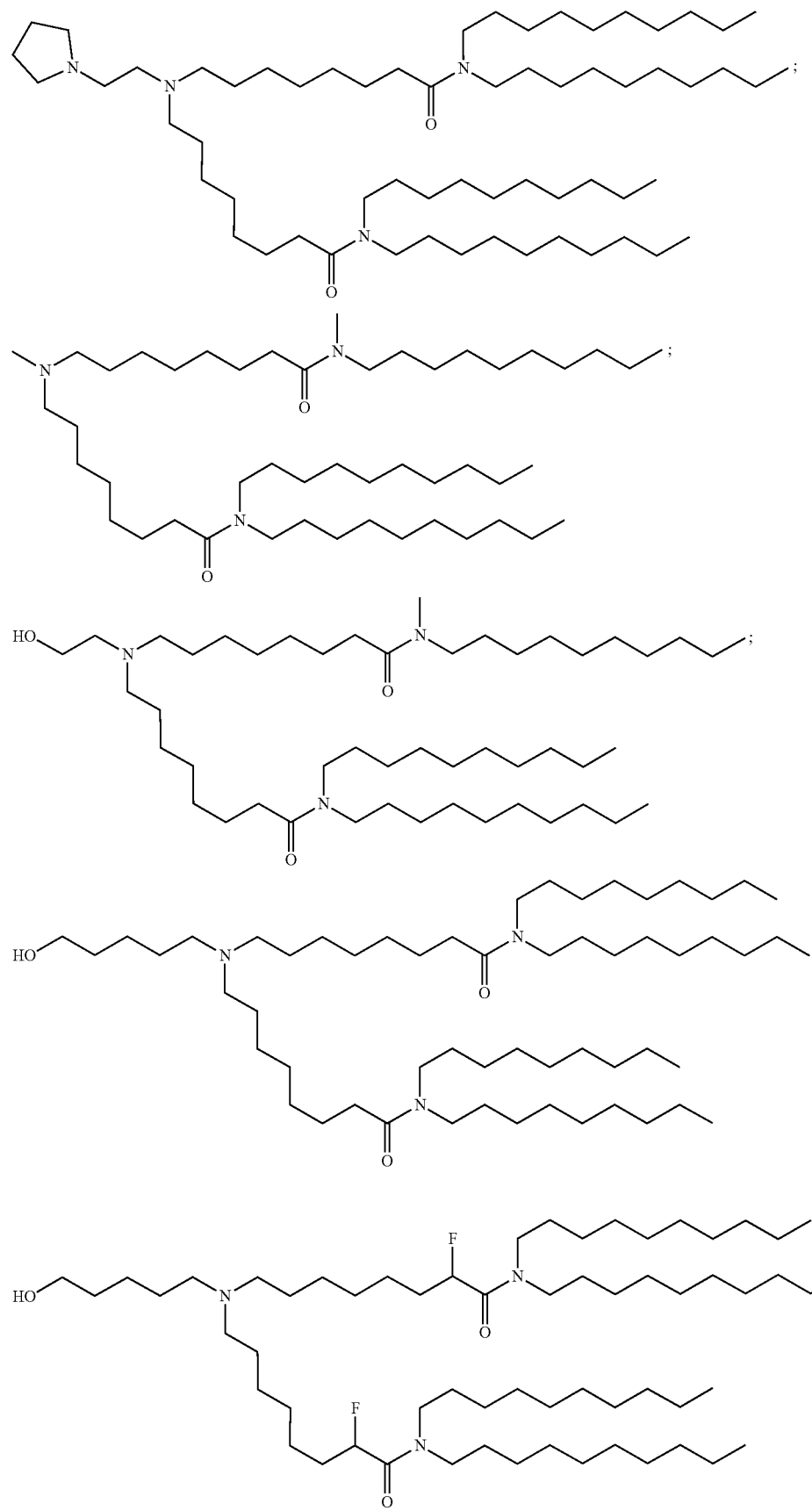

-continued

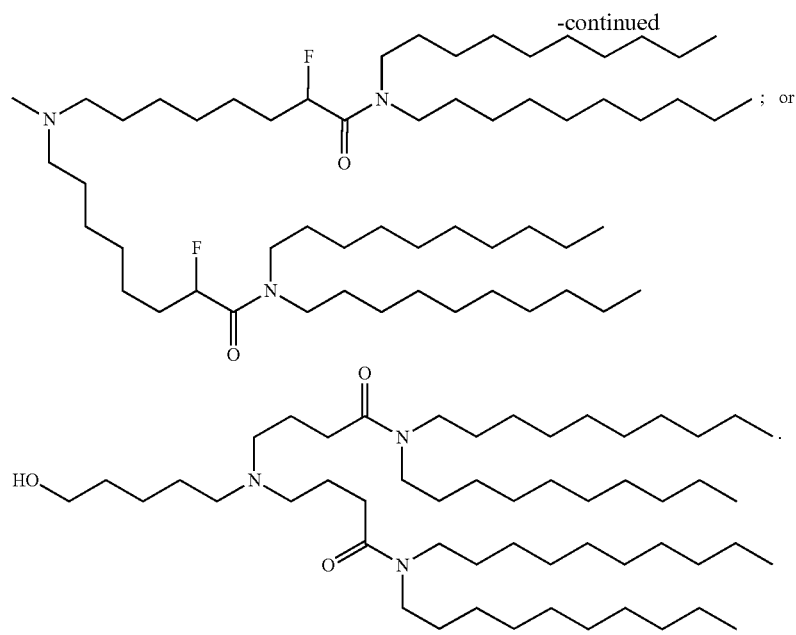

21. A lipid nanoparticle comprising the compound of claim 1 and a therapeutic agent.

22. A composition comprising the compound of claim 1 and a therapeutic agent.

23. The lipid nanoparticle of claim 21, wherein the therapeutic agent comprises a nucleic acid.

24. The lipid nanoparticle of claim 23, wherein the nucleic acid is selected from antisense and messenger RNA.

25. A method for administering a therapeutic agent to a patient in need thereof, the method comprising preparing or providing the lipid nanoparticle of claim 21, and administering the lipid nanoparticle to the patient.

26. A pharmaceutical composition comprising the lipid nanoparticle of claim 21 and a pharmaceutically acceptable diluent or excipient.

* * * * *